(12) United States Patent
Jarvi et al.

(10) Patent No.: US 9,040,464 B2
(45) Date of Patent: May 26, 2015

(54) MARKERS OF THE MALE UROGENITAL TRACT

(75) Inventors: Keith Jarvi, Toronto (CA); Eleftherios P. Diamandis, Toronto (CA); Andrei Drabovich, Toronto (CA)

(73) Assignee: Mount Sinai Hosptial, Toronto (CA)

( * ) Notice: Subject to any disclaimer, the term of this patent is extended or adjusted under 35 U.S.C. 154(b) by 0 days.

(21) Appl. No.: 13/814,959

(22) PCT Filed: Aug. 16, 2011

(86) PCT No.: PCT/CA2011/000925
§ 371 (c)(1),
(2), (4) Date: Feb. 8, 2013

(87) PCT Pub. No.: WO2012/021969
PCT Pub. Date: Feb. 23, 2012

(65) Prior Publication Data
US 2013/0210666 A1 Aug. 15, 2013

Related U.S. Application Data

(60) Provisional application No. 61/374,030, filed on Aug. 16, 2010.

(51) Int. Cl.
*G01N 33/68* (2006.01)
*C12Q 1/68* (2006.01)

(52) U.S. Cl.
CPC ............ *G01N 33/689* (2013.01); *C12Q 1/6883* (2013.01); *G01N 33/68* (2013.01); *C12Q 2600/158* (2013.01); *G01N 2333/78* (2013.01); *G01N 2800/367* (2013.01); *C12Q 2600/136* (2013.01)

(58) Field of Classification Search
CPC ...................... G01N 2800/367; G01N 33/543
USPC ........................................................... 506/9
See application file for complete search history.

(56) References Cited

FOREIGN PATENT DOCUMENTS

| CN | 101435820 A * | 5/2009 |
|---|---|---|
| WO | WO 2006/046108 A2 | 5/2006 |
| WO | WO 2009/059289 A2 | 5/2009 |
| WO | WO 2009/107122 A2 | 9/2009 |

OTHER PUBLICATIONS

Thimon et al., Biology of Reproduction, vol. 79, 23, Apr. 2008, pp. 262-273.*
Avellar, M. C. et al, Differential expression and antibacterial activity of epididymis protein 2 isoforms in the male reproductive tract of human and rhesus monkey (*Macaca mulatta*). Biol Reprod Nov. 2004, 71, (5), 1453-60.

(Continued)

*Primary Examiner* — Larry Riggs
*Assistant Examiner* — Karla Dines
(74) *Attorney, Agent, or Firm* — Howson & Howson LLP

(57) ABSTRACT

Methods for detecting urogenital conditions or urogenital status in a subject are described comprising measuring urogenital markers or polynucleotides encoding the markers in a sample from the subject. The invention also provides localization or imaging methods for urogenital conditions, and kits for carrying out the methods of the invention. The invention also contemplates therapeutic applications for urogenital conditions employing urogenital markers, polynucleotides encoding the markers, and/or binding agents for the markers.

11 Claims, 9 Drawing Sheets

(56) References Cited

OTHER PUBLICATIONS

Basciani, S. et al, Expression of platelet-derived growth factor-A (PDGF-A), PDGF-B, and PDGF receptor-alpha and -beta during human testicular development and disease. J. Clin. Endocrinol. Metab May 2002, 87 (5), 2310-2319.

Bowles, J. et al, Male-specific expression of Aldh1a1 in mouse and chicken fetal testes: implications for retinoid balance in gonad development. Developmental Dynamics, Aug. 2009, 238 (8), 2073-2080.

Busso, D. et al, Human testicular protein TPX1/CRISP-2: localization in spermatozoa, fate after capacitation and relevance for gamete interaction. Mol. Hum. Reprod., Apr. 2005, 11 (4), 299-305 (epublished Feb. 2005).

Cao, W. et al, Sorbitol can fuel mouse sperm motility and protein tyrosine phosphorylation via sorbitol dehydrogenase. Biol. Reprod. Jan. 2009, 80 (1), 124-133.

Cao, W., et al, Adenylate kinases 1 and 2 are part of the accessory structures in the mouse sperm flagellum. Biol. Reprod. Oct. 2006, 75 (4), 492-500.

Cho-Vega, J.H.,et al., Dicarbonyl/L-xylulose reductase: a potential biomarker identified by laser-capture microdissection-micro serial analysis of gene expression of human prostate adenocarcinoma. Cancer Epidemiol.Biomarkers Prev., Dec. 2007, 16:2615-2622.

Christopoulos, T.K., Diamandis, E.P., Enzymatically amplified time-resolved fluorescence immunoassay with terbium chelates. Anal. Chem. Feb. 1992, 64:342-346.

Cohen, D. J.; et al, Participation of epididymal cysteine-rich secretory proteins in sperm-egg fusion and their potential use for male fertility regulation. Asian J. Andrology, Jul. 2007, 9(4):528-532.

Cornwall, G. A.; Hsia, N., ADAM7, a member of the ADAM (a disintegrin and metalloprotease) gene family is specifically expressed in the mouse anterior pituitary and epididymis. Endocrinology, Oct. 1997, 138(10):4262-72.

Da Ros, V. G.; et al, Impaired sperm fertilizing ability in mice lacking Cysteine-RIch Secretory Protein 1 (CRISP1). Dev. Biol., Aug. 2008, 320(1):12-18.

Davies, B.; et al, Targeted deletion of the epididymal receptor HE6 results in fluid dysregulation and male infertility. Mol. Cell Biol. Oct. 2004, 24 (19), 8642-8648.

Deutsch, E. W.; et al, PeptideAtlas: a resource for target selection for emerging targeted proteomics workflows. EMBO Rep, May 2008, 9(5):429-34.

Dube, E.; et al, Alterations in gene expression in the caput epididymides of nonobstructive azoospermic men. Biol Reprod, Feb. 2008, 78(2): 342-51 (Epub Oct. 2007).

Edwards, J. J.; et al, Proteins of human semen. I. Two-dimensional mapping of human seminal fluid. Clin. Chem., Aug. 1981, 27(8):1335-1340.

Eguchi, Y.; et al, Expression of lipocalin-type prostaglandin D synthase (beta-trace) in human heart and its accumulation in the coronary circulation of angina patients. Proc Natl Acad Sci U S A, Dec. 1997, 94, (26), 14689-94.

Feig, C.; et al, A new paradigm for profiling testicular gene expression during normal and disturbed human spermatogenesis. Mol. Hum. Reprod. Jan. 2007, 13 (1), 33-43.

Gao, F., et al., Extracellular superoxide dismutase inhibits inflammation by preventing oxidative fragmentation of hyaluronan. J. Biol. Chem. Mar. 2008, 283, 6058-6066 (Epub Dec. 2007).

Gineitis, A. A.et al, Human sperm telomere-binding complex involves histone H2B and secures telomere membrane attachment. *J. Cell Biol*. Dec. 2000, 151 (7), 1591-1598.

Glander, H. J.et al, Insulin-like growth factor-I and alpha 2-macroglobulin in seminal plasma correlate with semen quality. *Hum. Reprod*. Nov. 1996, 11 (11), 2454-2460.

Goldberg, E.et al, LDHC: the ultimate testis-specific gene. J Androl Jan.-Feb. 2010, 31, (1), 86-94. (Epub Oct. 2009).

Gonzalez-Fernandez, L.et al, Identification of protein tyrosine phosphatases and dual-specificity phosphatases in mammalian spermatozoa and their role in sperm motility and protein tyrosine phosphorylation. Biol. Reprod. Jun. 2009, 80(6):1239-1252 (epub Feb. 2009).

Held, T.et al, Hspa4l-deficient mice display increased incidence of male infertility and hydronephrosis development. *Mol. Cell Biol*. Nov. 2006;26(21):8099-108. Epub Aug. 21, 2006.

Hoffhines, A. J.et al, Tyrosylprotein sulfotransferase-2 expression is required for sulfation of RNase 9 and Mfge8 in vivo. *J. Biol. Chem.* Jan. 30, 2009;284(5):3096-105. Epub Dec. 1, 2008.

Huang, J.et al, Overexpression of MUC15 activates extracellular signal-regulated kinase 1/2 and promotes the oncogenic potential of human colon cancer cells. Carcinogenesis Aug. 2009;30(8):1452-8. Epub Jun. 11, 2009.

Jamsai, D. et al, Polymorphisms in the human cysteine-rich secretory protein 2 (CRISP2) gene in Australian men. Hum. Reprod. Sep. 2008;23(9):2151-9. Epub Jun. 10, 2008.

Kaneko, T. et al, The expression of glutathione reductase in the male reproductive system of rats supports the enzymatic basis of glutathione function in spermatogenesis. Eur. J. Biochem. Mar. 2002, 269 (5), 1570-1578.

Kanters, E., et al., Filamin B mediates ICAM-1-driven leukocyte transendothelial migration. J. Biol. Chem. Nov. 14, 2008;283(46):31830-9. Epub Sep. 22, 2008.

Kaunisto, K. et al, Regional expression and androgen regulation of carbonic anhydrase IV and II in the adult rat epididymis. Biol. Reprod. Dec. 1999, 61 (6), 1521-1526.

Kiyonami, R. et al, Increased selectivity, analytical precision, and throughput in targeted proteomics. Mol Cell Proteomics Feb. 2011;10(2):M110.002931. Epub Jul. 27, 2010.

Klys, H. S et al, Glutathione S-transferase expression in the human testis and testicular germ cell neoplasia. Br. J. Cancer Sep. 1992, 66 (3), 589-593.

Krisfalusi, M. et al, Multiple glycolytic enzymes are tightly bound to the fibrous sheath of mouse spermatozoa. *Biol. Reprod.* Aug. 2006;75(2):270-8. Epub May 10, 2006.

Kyriakides, T. R. et al, The distribution of the matricellular protein thrombospondin 2 in tissues of embryonic and adult mice. *J. Histochem. Cytochem*. Sep. 1998, 46 (9), 1007-1015.

Lee, C. Het al, Gene copy number variations in Asian patients with congenital bilateral absence of the vas deferens. Hum. Reprod. Mar. 2009;24(3):748-55. Epub Dec. 17, 2008.

Lefebvre, J. et al, Recombinant expression and affinity purification of a novel epididymal human sperm-binding protein, BSPH1. Mol. Hum. Reprod. Feb. 2009;15(2):105-14. Epub Dec. 17, 2008.

Legare, C. et al, HE1/NPC2 status in human reproductive tract and ejaculated spermatozoa: consequence of vasectomy. *Mol. Hum. Reprod.* Jul. 2006;12(7):461-8. Epub Jun. 13, 2006.

Levitin, F. et al, PATE gene clusters code for multiple, secreted TFP/Ly-6/uPAR proteins that are expressed in reproductive and neuron-rich tissues and possess neuromodulatory activity. J Biol Chem Jun. 13, 2008;283(24):16928-39. Epub Apr. 3, 2008.

Li, J. Y. et al, Transcriptome analysis of a cDNA library from adult human epididymis. DNA Res Jun. 30, 2008;15(3):115-22. Epub Apr. 4, 2008.

Li, Y. et al, Cystatin E1 and E2, new members of male reproductive tract subgroup within cystatin type 2 family. Biol. Reprod. Aug. 2003;69(2):489-500. Epub Apr. 16, 2003.

Lilja, H. et al, Seminal vesicle-secreted proteins and their reactions during gelation and liquefaction of human semen. *J. Clin. Invest*, Aug. 1987, 80 (2), 281-285.

Lin, Y. N. et al, Loss of zona pellucida binding proteins in the acrosomal matrix disrupts acrosome biogenesis and sperm morphogenesis. *Mol. Cell Biol*. Oct. 2007;27(19):6794-805. Epub Jul. 30, 2007.

Loveland, K. et al, Developmental changes in the basement membrane of the normal and hypothyroid postnatal rat testis: segmental localization of fibulin-2 and fibronectin. Biol. Reprod. May 1998, 58 (5), 1123-1130.

Maillard, M. et al., Differential expression of the ccn3 (nov) proto-oncogene in human prostate cell lines and tissues. Mol. Pathol. Aug. 2001;54(4):275-80.

(56) References Cited

OTHER PUBLICATIONS

Mandal, A. et al, SLLP1, a unique, intra-acrosomal, non-bacteriolytic, c lysozyme-like protein of human spermatozoa. *Biol. Reprod.* May 2003;68(5):1525-37. Epub Nov. 27, 2002.
Miki, K. et al, Glyceraldehyde 3-phosphate dehydrogenase-S, a sperm-specific glycolytic enzyme, is required for sperm motility and male fertility. *Proc. Natl. Acad. Sci. U. S. A* Nov. 23, 2004;101(47):16501-6. Epub Nov. 16, 2004.
Odet, F. et al, Expression of the gene for mouse lactate dehydrogenase C (Ldhc) is required for male fertility. *Biol. Reprod.* Jul. 2008; 79(1):26-34. Epub Mar. 26, 2008.
Okada, H. et al, Genome-wide expression of azoospermia testes demonstrates a specific profile and implicates ART3 in genetic susceptibility. PLoS. Genet. Feb. 2008, 4 (2), e26.
Pilch, B.; Mann, M. Large-scale and high-confidence proteomic analysis of human seminal plasma. *Genome Biol.* May 2006, 7 (5), R40.
Piludu, M.et al, Ultrastructural localization of glycodelin oligosaccharides Le-x and Le-y in human seminal vesicles by immunogold staining J Anat. Mar. 2007, 210 (3), 352-356.
Ryu, O.H., et al, Identification of parotid salivary biomarkers in Sjogren's syndrome by surface-enhanced laser desorption/ionization time-of-flight mass spectrometry and two-dimensional difference gel electrophoresis. Rheumatology (Oxford) Sep. 2006;45(9):1077-86. Epub Mar. 7, 2006.
Sakata, A., et al., Acid sphingomyelinase inhibition suppresses lipopolysaccharide-mediated release of inflammatory cytokines from macrophages and protects against disease pathology in dextran sulphate sodium-induced colitis in mice. Immunology Sep. 2007;122(1):54-64. Epub Apr. 23, 2007.
Sarkar, O.et al, Interleukin 1 alpha (IL1A) is a novel regulator of the blood-testis barrier in the rat. *Biol. Reprod.* Mar. 2008;78(3):445-54. Epub Dec. 5, 2007.
Saxena, D. K. et al, Behaviour of a sperm surface transmembrane glycoprotein basigin during epididymal maturation and its role in fertilization in mice. *Reproduction.* Mar. 2002, 123 (3), 435-444.
Shinozaki, S. et al., Upregulation of Reg 1alpha and GW112 in the epithelium of inflamed colonic mucosa. Gut. May 2001, 48, 623-629.
Sullivan, R.et al, Epididymosomes are involved in the acquisition of new sperm proteins during epididymal transit. *Asian J. Androl* Jul. 2007, 9 (4), 483-491.
Szabo, Z.et al, Sorbitol dehydrogenase expression is regulated by androgens in the human prostate. Oncol. Rep. May 2010, 23 (5), 1233-1239.
Takayama, T et al, Sexually dimorphic expression of the novel germ cell antigen TEX101 during mouse gonad development. *Biol. Reprod.* Jun. 2005;72(6):1315-23. Epub Feb. 2, 2005.
Thimon, V.et al, Protein composition of human epididymosomes collected during surgical vasectomy reversal: a proteomic and genomic approach. *Hum. Reprod.* Aug. 2008;79(2):262-73. Epub Apr. 23, 2008.
Tokugawa, Y. et al, Lipocalin-type prostaglandin D synthase in human male reproductive organs and seminal plasma. *Biol. Reprod.* Feb. 1998, 58 (2), 600-607.
Vernon, R. B.; Sage, H. The calcium-binding protein SPARC is secreted by Leydig and Sertoli cells of the adult mouse testis. Biol. Reprod. Jun. 1989, 40 (6), 1329-1340.
von Horsten, H. H. et al, Novel antimicrobial peptide of human epididymal duct origin. Biol Reprod Sep. 2002, 67, (3), 804-13.
Wang, T. J. et al, PSA concentrations in seminal plasma. Clin Chem Apr. 1998, 44, (4), 895-6.
Williams, K., et al., Expression of extracellular superoxide dismutase in the human male reproductive tract, detected using antisera raised against a recombinant protein. Mol. Hum. Reprod. Mar. 1998, 4, 235-242.
Xiong, W. et al, Gas6 and the Tyro 3 receptor tyrosine kinase subfamily regulate the phagocytic function of Sertoli cells. Reproduction. Jan. 2008, 135 (1), 77-87.
Yoshioka, H. et al, In vivo analysis of developmentally and evolutionarily dynamic protein-DNA interactions regulating transcription of the Pgk2 gene during mammalian spermatogenesis. *Mol. Cell Biol.* Nov. 2007;27(22):7871-85. Epub Sep. 17, 2007.
Zalensky, A.O. et al, Human testis/sperm-specific histone H2B (hTSH2B). Molecular cloning and characterization. *J. Biol. Chem.* Nov. 8, 2002;277(45):43474-80. Epub Sep. 3, 2002.
Zhang, L. et al, Baculo-expression and enzymatic characterization of CES7 esterase. Acta Biochim. Biophys. Sin. (Shanghai) Sep. 2009, 41 (9), 731-736.
Ali, M., Nasosinus mucin expression in normal and inflammatory conditions. Curr. Opin Allergy Clin. Immunol. Feb. 2009, 9, 10-15.
Baldi, E. et al, Signal transduction pathways in human spermatozoa. J. Reprod. Immunol. Jan. 2002, 53 (1-2), 121-131.
Birkenmeier, G. et al, Prostate-specific antigen triggers transformation of seminal alpha2-macroglobulin (alpha2-M) and its binding to alpha2-macroglobulin receptor/low-density lipoprotein receptor-related protein (alpha2-M-R/LRP) on human spermatozoa. Prostate, Sep. 1998, 36 (4), 219-225.
Bush, L. A. et al, A novel asparaginase-like protein is a sperm autoantigen in rats. Mol. Reprod. Dev., Jun. 2002, 62 (2), 233-247.
Chemes, H. The phagocytic function of Sertoli cells: a morphological, biochemical, and endocrinological study of lysosomes and acid phosphatase localization in the rat testis. Endocrinology, Oct. 1986, 119 (4), 1673-1681.
Cheng, C. Y et al, Sertoli cell synthesizes and secretes a protease inhibitor, alpha 2-macroglobulin. Biochemistry, Jan. 1990, 29 (4), 1063-1068.
Chin, K.L.,et al., the regulation of OLFM4 expression in myeloid precursor cells relies on NF-kappaB transcription factor. Br. J. Haematol. Nov. 2008, 143, 421-432.
Choi, H.; Nesvizhskii, A. I. False discovery rates and related statistical concepts in mass spectrometry-based proteomics. J. Proteome. Res., Jan. 2008, 7 (1), 47-50.
Cohen, D. J.; et al, Relationship between the association of rat epididymal protein "DE" with spermatozoa and the behavior and function of the protein. Mol. Reprod. Dev., Jun. 2000, 56(2):180-188.
Dhundee, J., Maciver, A.G., An immunohistological study of granulomatous prostatitis. Histopathology, May 1991, 18:435-441.
Diamandis, E. P.; et al, Seminal plasma biochemical markers and their association with semen analysis findings. Urology, Mar. 1999, 53(3):596-603.
Dickinson, D.P., et al, Expression of type 2 cystatin genes CST1-CST5 in adult human tissues and the developing submandibular gland. DNA Cell. Biol., Jan. 2002, 21:47-65.
Doble, a., et al, Intraprostatic antibody deposition in chronic abacterial prostatitis. Br. J. Urol., Jun. 1990, 65:598-605.
Duncan, M. W. et al, the pros and cons of peptide-centric proteomics. Nat. Biotechnol. Jul. 2010, 28(7):659-664.
Dunkelberger, J.R., Song, W.C., Complement and its role in innate and adaptive immune responses. Cell Res., Jan. 2010, 20:34-50.
Ekhlasi-Hundrieser, M.;et al, Sperm-binding fibronectin type II-module proteins are genetically linked and functionally related. Gene, May 2007, 392 (1-2), 253-265.
Ekstedt, E.; et al, Carbonic anhydrase in mouse testis and epididymis; transfer of isozyme IV to spermatozoa during passage. J. Mol. Histol. Feb. 2004, 35 (2), 167-173.
Elias, J. E.; Gygi, S. P. Target-decoy search strategy for increased confidence in large-scale protein identifications by mass spectrometry. Nat. Methods Mar. 2007, 4 (3), 207-214.
Everaert, K., et al., Urinary plasma protein patterns in acute prostatitis. Clin. Chem.Lab. Med. Jan. 2003, 41, 79-84.
Foell, J. L.; et al, Membrane-associated phospholipase Al beta (LIPI) Is an Ewing tumour-associated disease/testis antigen. Pediatr. Blood Disease Aug. 2008, 51 (2), 228-234.
Fox, M. S.; et al, Feasibility of global gene expression analysis in testicular biopsies from infertile men. Mol. Reprod. Dev. Dec. 2003, 66 (4), 403-421.
Frenette, G.et al, Polyol pathway along the bovine epididymis. Mol. Reprod. Dev. Dec. 2004, 69 (4), 448-456.
Fung, K. Y.et al, A comprehensive characterization of the peptide and protein constituents of human seminal fluid. Prostate Oct. 2004, 61 (2), 171-181.

(56) References Cited

OTHER PUBLICATIONS

Gaboriau, D.et al, Binding of sperm proacrosin/beta-acrosin to zona pellucida glycoproteins is sulfate and stereodependent. Synthesis of a novel fertilization inhibitor. Dev. Biol. Jun. 2007, epub Apr. 6, 2007, 306 (2), 646-657.
Gibbs, G. M.; O'Bryan, M. K. Cysteine rich secretory proteins in reproduction and venom. Soc. Reprod. Fertil. Suppl 2007, 65 261-267.
Heshmat, S. M.et al, Seminal plasma lipocalin-type prostaglandin D synthase: a potential new marker for the diagnosis of obstructive azoospermia. J. Urol. Mar. 2008, 179 (3), 1077-1080.
Howe, C. C.et al, Expression of SPARC/osteonectin transcript in murine embryos and gonads. Differentiation May 1988, 37 (1), 20-25.
Igakura, T.et al, a null mutation in basigin, an immunoglobulin superfamily member, indicates its important roles in peri-implantation development and spermatogenesis. Dev. Biol. Feb. 1998, 194 (2), 152-165.
Kato, T., et al, Salivary cystatins induce interleukin-6 expression via cell surface molecules in human gingival fibroblasts. Mol. Immunol. Nov. 2002, 39, 423-430.
Kirchhoff, C. et al, Major human epididymis-specific gene product, HE3, is the first representative of a novel gene family. Mol Reprod Dev Feb. 1994, 37, (2), 130-7.
Lasserre, A. et al, Human epididymal proteins and sperm function during fertilization: un update. Biol Res 2001, 34, (3-4), 165-78.
Leone, M. G. et al, Changes of lipocalin type prostaglandin D-synthase in the seminal plasma of subfertile man. Res Commun Mol Pathol Pharmacol Jul. 2001, 110, (1-2), 17-25.
Liu, H., et al, A model for random sampling and estimation of relative protein abundance in shotgun proteomics. Anal. Chem. Jul. 2004, 76, 4193-4201.
Lu, Q. et al, Tyro-3 family receptors are essential regulators of mammalian spermatogenesis. Nature Apr. 1999, 398 (6729), 723-728.
Lu, S. C. Regulation of glutathione synthesis. Curr. Top. Cell Regul. 2000, 36 95-116.
Ludwig, M. et al, Evaluation of seminal plasma parameters in patients with chronic prostatitis or leukocytospermia. Andrologia Dec. 1998, 30, Suppl 1:41-47.
Mallick, P.; Kuster, B. Proteomics: a pragmatic perspective. Nat. Biotechnol. Jul. 2010, 28 (7), 695-709.
Miething, A. Germ-cell death during prespermatogenesis in the testis of the golden hamster. Cell Tissue Res. Mar. 1992, 267 (3), 583-590.
Miki, K. et al, Targeted disruption of the Akap4 gene causes defects in sperm flagellum and motility. Dev. Biol. Aug. 2002, 248 (2), 331-342.
Mitchell, P., Proteomics retrenches. Nat. Biotechnol. Jul. 2010, 28, 665-670.
Nata, K. et al, Molecular cloning, expression and chromosomal localization of a novel human REG family gene, REG III. Gene Sep. 2004, 340 (1), 161-170.
Nickel, J.C., et al, Prevalence of prostatitis-like symptoms in a population based study using the National Institutes of Health chronic prostatitis symptom index. J. Urol. Mar. 2001, 165, 842-845.
Nonoguchi, K. et al, Expression of Apg-1, a member of the Hsp110 family, in the human testis and sperm. Int. J. Urol. Jun. 2001, 8 (6), 308-314.
Oh, J. S. et al, ADAM7 is associated with epididymosomes and integrated into sperm plasma membrane. Mol Cells Nov. 2009, 28, (5), 441-6. Epub Oct. 21, 2009.
Oh, J. et al, Molecular, biochemical, and cellular characterization of epididymal ADAMs, ADAM7 and ADAM28. Biochem. Biophys. Res. Commun. Jun. 2005, 331 (4), 1374-1383.
Osterhoff, et al, Cloning of a human epididymis-specific mRNA, HE6, encoding a novel member of the seven transmembrane-domain receptor superfamily. DNA Cell Biol. Apr. 1997, 16 (4), 379-389.
Ota, T.; et al, Complete sequencing and characterization of 21,243 full-length human cDNAs. Nat Genet Jan. 2004, 36, (1), 40-5. Epub Dec. 21, 2003.

Pang, W.W., et al, Can the acute-phase reactant proteins be used as cancer biomarkers? Int. J. Biol. Markers Jan.-Mar. 2010, 25, 1-11.
Picotti, P. et al, High-throughput generation of selected reaction-monitoring assays for proteins and proteomes. Nat Meth Jan. 2009, 7, (1), 43-46. Epub Dec. 6, 2009.
Pineau, C. et al, Study in vitro of the phagocytic function of Sertoli cells in the rat. Cell Tissue Res. Jun. 1991, 264 (3), 589-598.
Poliakov, A. et al, Structural heterogeneity and protein composition of exosome-like vesicles (prostasomes) in human semen. Prostate Feb. 2009, 69 (2), 159-167.
Redl, B., Human tear lipocalin. Biochim. Biophys. Acta Oct. 2000, 1482, 241-248.
Robert, M.; Gagnon, C. Sperm motility inhibitor from human seminal plasma: presence of a precursor molecule in seminal vesicle fluid and its molecular processing after ejaculation. Int. J. Androl Oct. 1994, 17 (5), 232-240.
Rockett, J. C. et al, Gene expression patterns associated with infertility in humans and rodent models. Mutat. Res. May 2004, 549 (1-2), 225-240.
Russell, L. D.; Clermont, Y. Degeneration of germ cells in normal, hypophysectomized and hormone treated hypophysectomized rats. Anat. Rec. Mar. 1977, 187 (3), 347-366.
Russo, C. L.; et al, Mucin gene expression in human male urogenital tract epithelia. Hum. Reprod. 2006, 21 (11), 2783-2793.
Sahin, E.et al Fibronectin type II-module proteins in the bovine genital tract and their putative role in cell volume control during sperm maturation. Reprod. Feral. Dev. Mar. 4, 2009, 21 (3), 479-488.
Sardana, G.et al, Proteomic analysis of conditioned media from the PC3, LNCaP, and 22Rv1 prostate disease cell lines: discovery and validation of candidate prostate disease biomarkers. J. Proteome. Res. Aug. 2008, 7 (8), 3329-3338. Epub Jun. 26, 2008.
Sawane, M. V.et al, Seminal LDH-C4 isoenzyme and sperm mitochondrial activity: a study in male partners of infertile couples. Indian J. Med. Sci. Nov. 2002, 56 (11), 560-566.
Schill, W. B. Quantitative determination of high molecular weight serum proteinase inhibitors in human semen. Andrologia Oct. 1976, 8 (4), 359-364.
Searle, B. C. et al, Improving sensitivity by probabilistically combining results from multiple MS/MS search methodologies. J. Proteome. Res. Jan. 2008, 7 (1), 245-253.
Sies, H. Glutathione and its role in cellular functions. Free Radic. Biol. Med. Nov. 1999, 27 (9-10), 916-921.
Takayama, T.et al, TEX101 is shed from the surface of sperm located in the caput epididymidis of the mouse. Zygote. Nov. 2005, 13 (4), 325-333.
Uhlen, M. et al, Towards a knowledge-based Human Protein Atlas. Nat Biotechnol Dec. 2010, 28, (12), 1248-50.
Urade, Y.; Hayaishi, O., Biochemical, structural, genetic, physiological, and pathophysiological features of lipocalin-type prostaglandin D synthase. Biochim Biophys Acta Oct. 2000, 1482, (1-2), 259-71.
VandeBerg, J. L. et al, Mammalian testis phosphoglycerate kinase. Nat. New Biol. May 1973, 243 (123), 48-50.
Virji, N.; Naz, R. K. The role of lactate dehydrogenase-C4 in testicular function and infertility. Int. J. Androl Feb. 1995, 18 (1), 1-7.
Viswanathan, H. et al, MUC5B secretion is up-regulated in sinusitis compared with controls. Am. J. Rhinol Sep.-Oct. 2006, 20, 554-557.
Watanabe, H. et al., Expression of mesothelin mRNA in pure pancreatic juice from patients with pancreatic carcinoma, intraductal papillary mucinous neoplasm of the pancreas, and chronic pancreatitis. Pancreas May 2005, 30, 349-354.
Wilson, M. J.; et al, The matricellular protein SPARC is internalized in Sertoli, Leydig, and germ cells during testis differentiation. Mol. Reprod. Dev. May 2006, 73 (5), 531-539.
Wojnar, P., et al, The N-terminal part of recombinant human tear lipocalin/von Ebner's gland protein confers cysteine proteinase inhibition depending on the presence of the entire cystatin-like sequence motifs. Biol. Chem. Oct. 2001, 382, 1515-1520.
Wu, X.; Freeze, H. H. GLUT14, a duplicon of GLUT3, is specifically expressed in testis as alternative splice forms. Genomics Dec. 2002, 80 (6), 553-557.
Yeung, W. S. et al, Roles of glycodelin in modulating sperm function. Mol. Cell Endocrinol. May 2006, 250 (1-2), 149-156. Epub Jan. 2006.

(56) References Cited

OTHER PUBLICATIONS

Yin, L. et al, A sperm GPI-anchored protein elicits sperm-cumulus cross-talk leading to the acrosome reaction. Cell Mol Life Sci Mar. 2009, 66, (5), 900-8.

Yoshitake, H. et al, Molecular diversity of TEX101, a marker glycoprotein for germ cells monitored with monoclonal antibodies: variety of the molecular characteristics according to subcellular localization within the mouse testis. J. Reprod. Immunol. Oct. 2008, 79 (1), 1-11.

Zeeuwen, P.L., et al, Cystatin M / E expression in inflammatory and neoplastic skin disorders. Br. J. Dermatol. Jul. 2002, 147, 87-94.

Cox, J.; Mann, M. MaxQuant enables high peptide identification rates, individualized p.p.b.-range mass accuracies and proteome-wide protein quantification. Nat. Biotechnol. Dec. 2008, 26 (12), 1367-1372.

Cox, J.; et al, Andromeda: A Peptide Search Engine Integrated into the MaxQuant Environment. J. Proteome. Res. Jan. 2011, 10(4), 1794-805.

Craig, R.; et al, Open source system for analyzing, validating, and storing protein identification data. J Proteome Res Oct. 2004, 3, (6), 1234-42.

Heshmat et al, "Seminal Plasma Lipocalin-Type Prostaglandin D Synthase: A Potential New Marker for the Diagnosis of Obstructive Azoospermia", J of Urology, vol. 179(3) pp. 1077-1080 (Jan. 18, 2008).

Nadler et al, "IL-1beta and TNF-alpha in Prostatic Secretions are Indicators in the Evaluation of Men with Chronic Prostatitis", J of Urology, vol. 164(1) pp. 214-218 (Jul. 1, 2000).

Office Action issued in European Patent Application No. 11817602.3-1403 dated Jan. 29, 2014.

Han, Extracellular matrix protein 1 (ECM1) has angiogenic properties and is expressed by breast tumor cells. FASEB J., 15:988-994 (Apr. 2001).

Thimon, Effects of vasectomy on gene expression profiling along the human epididymis. Biol. Repro., 79:262-273 (epub Apr. 2008).

Wang, Proteomic analysis of seminal plasma from asthenozoospermia patients reveals proteins that affect oxidative stress responses and semen quality. Asian J. Androl., 11:484-491 (May 2009).

Yamakawa, Comparative analysis of interindividual variations in the seminal plasma proteome of fertile men with identification of potential markers for azoospermia in infertile patients. J. Androl., 28(6):858-865 (Nov. 2007).

Drabovich, Verification of male infertility biomarkers in seminal plasma by multiplex selected reaction monitoring assay. Molecular and Cellular Proteomics, epub Sep. 20, 2011.

Martinez-Heredia, Identification of proteomic differences in asthenozoospermic sperm samples. Human Reproduction. 23(4): 783-791 (Epub Feb. 2008).

International Search Report of corresponding PCT/CA2011/000925, issued Nov. 28, 2011.

Written Opinion of the International Search Authority of corresponding PCT/CA2011/000925, issued Nov. 28, 2011.

* cited by examiner (a)

(b)

a)

b)

SEQUENCE LISTING

```
<160> NUMBER OF SEQ ID NOS: 42

<210> SEQ ID NO 1
<211> LENGTH: 12
<212> TYPE: PRT
<213> ORGANISM: Homo sapiens

<400> SEQUENCE: 1

Leu Ser Glu Pro Ala Glu Leu Thr Asp Ala Val Lys
1               5                   10

<210> SEQ ID NO 2
<211> LENGTH: 14
<212> TYPE: PRT
<213> ORGANISM: Homo sapiens

<400> SEQUENCE: 2

Asp Pro Val Gln Glu Ala Trp Ala Glu Asp Val Asp Leu Arg
1               5                   10

<210> SEQ ID NO 3
<211> LENGTH: 6
<212> TYPE: PRT
<213> ORGANISM: Homo sapiens

<400> SEQUENCE: 3

Glu Asp Val Asp Leu Arg
1               5

<210> SEQ ID NO 4
<211> LENGTH: 16
<212> TYPE: PRT
```

<213> ORGANISM: Homo sapiens

<400> SEQUENCE: 4

Val Thr Ile Pro Thr Asp Leu Ile Ala Ser Ser Gly Asp Ile Ile Lys
1               5                   10                  15

<210> SEQ ID NO 5
<211> LENGTH: 13
<212> TYPE: PRT
<213> ORGANISM: Homo sapiens

<400> SEQUENCE: 5

Thr Leu Tyr Leu Ala Asp Thr Phe Pro Thr Asn Phe Arg
1               5                   10

<210> SEQ ID NO 6
<211> LENGTH: 15
<212> TYPE: PRT
<213> ORGANISM: Homo sapiens

<400> SEQUENCE: 6

Glu Leu Gly Ile Cys Pro Asp Asp Ala Ala Val Ile Pro Ile Lys
1               5                   10                  15

<210> SEQ ID NO 7
<211> LENGTH: 13
<212> TYPE: PRT
<213> ORGANISM: Homo sapiens

<400> SEQUENCE: 7

Glu Glu Leu Phe Leu Ser Ile Pro Cys Val Leu Gly Arg
1               5                   10

<210> SEQ ID NO 8
<211> LENGTH: 9
<212> TYPE: PRT
<213> ORGANISM: Homo sapiens

<400> SEQUENCE: 8

Ile Cys Val Asp Phe Leu Gly Pro Arg
1               5

<210> SEQ ID NO 9
<211> LENGTH: 14
<212> TYPE: PRT
<213> ORGANISM: Homo sapiens

<400> SEQUENCE: 9

Leu Met Ser Gly Ile Leu Ala Val Gly Pro Met Phe Val Arg
1               5                   10

<210> SEQ ID NO 10
<211> LENGTH: 12
<212> TYPE: PRT
<213> ORGANISM: Homo sapiens

<400> SEQUENCE: 10

Asp Gly Ile Pro Met Asp Asp Ile Pro Pro Leu Arg
1               5                   10

<210> SEQ ID NO 11
<211> LENGTH: 12
<212> TYPE: PRT
<213> ORGANISM: Homo sapiens

```
<400> SEQUENCE: 11

Asp Ala Gly Ala Pro Val Tyr Phe Tyr Glu Phe Arg
1               5                  10

<210> SEQ ID NO 12
<211> LENGTH: 17
<212> TYPE: PRT
<213> ORGANISM: Homo sapiens

<400> SEQUENCE: 12

Ala Gln Gly Phe Thr Glu Asp Thr Ile Val Phe Leu Pro Gln Thr Asp
1               5                  10                  15

Lys

<210> SEQ ID NO 13
<211> LENGTH: 10
<212> TYPE: PRT
<213> ORGANISM: Homo sapiens

<400> SEQUENCE: 13

Glu Leu Leu Ala Leu Ile Gln Leu Glu Arg
1               5                  10

<210> SEQ ID NO 14
<211> LENGTH: 10
<212> TYPE: PRT
<213> ORGANISM: Homo sapiens

<400> SEQUENCE: 14

Ala Tyr Val Ala Phe Pro Asp Phe Phe Arg
1               5                  10

<210> SEQ ID NO 15
<211> LENGTH: 12
<212> TYPE: PRT
<213> ORGANISM: Homo sapiens

<400> SEQUENCE: 15

Leu Gly Leu Leu Gly Asp Ser Val Asp Ile Phe Lys
1               5                  10

<210> SEQ ID NO 16
<211> LENGTH: 9
<212> TYPE: PRT
<213> ORGANISM: Homo sapiens

<400> SEQUENCE: 16

Phe Ala Leu Leu Gly Asp Phe Phe Arg
1               5

<210> SEQ ID NO 17
<211> LENGTH: 11
<212> TYPE: PRT
<213> ORGANISM: Homo sapiens

<400> SEQUENCE: 17

Thr Tyr Glu Glu Glu Leu Leu Tyr Glu Ile Lys
1               5                  10

<210> SEQ ID NO 18
<211> LENGTH: 11
<212> TYPE: PRT
<213> ORGANISM: Homo sapiens
```

<400> SEQUENCE: 18

Asn Ala Tyr Val Trp Val Gln Asn Pro Leu Lys
1               5                   10

<210> SEQ ID NO 19
<211> LENGTH: 12
<212> TYPE: PRT
<213> ORGANISM: Homo sapiens

<400> SEQUENCE: 19

Tyr Cys Asp Met Thr Glu Ser Asn Pro Leu Glu Arg
1               5                   10

<210> SEQ ID NO 20
<211> LENGTH: 12
<212> TYPE: PRT
<213> ORGANISM: Homo sapiens

<400> SEQUENCE: 20

Glu Asn Glu Leu Cys Ser Thr Thr Ala Tyr Phe Arg
1               5                   10

<210> SEQ ID NO 21
<211> LENGTH: 13
<212> TYPE: PRT
<213> ORGANISM: Homo sapiens

<400> SEQUENCE: 21

Asp Leu Leu Pro Asn Val Cys Ala Phe Pro Met Glu Lys
1               5                   10

<210> SEQ ID NO 22
<211> LENGTH: 9
<212> TYPE: PRT
<213> ORGANISM: Homo sapiens

<400> SEQUENCE: 22

Gly Glu Ile Met Phe Gln Tyr Asp Lys
1               5

<210> SEQ ID NO 23
<211> LENGTH: 13
<212> TYPE: PRT
<213> ORGANISM: Homo sapiens

<400> SEQUENCE: 23

Thr Ile Pro Ile Asp Gly Asn Phe Phe Thr Tyr Thr Arg
1               5                   10

<210> SEQ ID NO 24
<211> LENGTH: 15
<212> TYPE: PRT
<213> ORGANISM: Homo sapiens

<400> SEQUENCE: 24

Ala Ser Ile Ser Gly Gly Gly Leu Pro Ala Pro Tyr Gln Ala Lys
1               5                   10                  15

<210> SEQ ID NO 25
<211> LENGTH: 11
<212> TYPE: PRT
<213> ORGANISM: Homo sapiens

<400> SEQUENCE: 25

```
Leu Val Val Glu Trp Gln Leu Gln Asp Asp Lys
1               5                   10

<210> SEQ ID NO 26
<211> LENGTH: 10
<212> TYPE: PRT
<213> ORGANISM: Homo sapiens

<400> SEQUENCE: 26

Gly Gly Phe Asn Phe Tyr Ala Gly Leu Lys
1               5                   10

<210> SEQ ID NO 27
<211> LENGTH: 13
<212> TYPE: PRT
<213> ORGANISM: Homo sapiens

<400> SEQUENCE: 27

Ser Asp Leu Ala Val Pro Ser Glu Leu Ala Leu Leu Lys
1               5                   10

<210> SEQ ID NO 28
<211> LENGTH: 16
<212> TYPE: PRT
<213> ORGANISM: Homo sapiens

<400> SEQUENCE: 28

Val Thr Ile Pro Thr Asp Leu Ile Ala Ser Ser Gly Asp Ile Ile Lys
1               5                   10                  15

<210> SEQ ID NO 29
<211> LENGTH: 8
<212> TYPE: PRT
<213> ORGANISM: Homo sapiens

<400> SEQUENCE: 29

Leu Val Ala Glu Phe Asp Phe Arg
1               5

<210> SEQ ID NO 30
<211> LENGTH: 12
<212> TYPE: PRT
<213> ORGANISM: Homo sapiens

<400> SEQUENCE: 30

Asn Gln Cys Leu Cys Pro Pro Asp Phe Thr Gly Arg
1               5                   10

<210> SEQ ID NO 31
<211> LENGTH: 10
<212> TYPE: PRT
<213> ORGANISM: Homo sapiens

<400> SEQUENCE: 31

Ser Val Leu Gly Gln Leu Gly Ile Thr Lys
1               5                   10

<210> SEQ ID NO 32
<211> LENGTH: 9
<212> TYPE: PRT
<213> ORGANISM: Homo sapiens

<400> SEQUENCE: 32

Gly Gly Gly Ile Phe Ser Asn Leu Arg
1               5
```

```
<210> SEQ ID NO 33
<211> LENGTH: 15
<212> TYPE: PRT
<213> ORGANISM: Homo sapiens

<400> SEQUENCE: 33

Leu Asp Leu Asp Phe Pro Asn Leu Pro Tyr Leu Leu Asp Gly Lys
1               5                   10                  15

<210> SEQ ID NO 34
<211> LENGTH: 11
<212> TYPE: PRT
<213> ORGANISM: Homo sapiens

<400> SEQUENCE: 34

Ala Cys Cys Ile Pro Ser Asn Glu Asp His Arg
1               5                   10

<210> SEQ ID NO 35
<211> LENGTH: 10
<212> TYPE: PRT
<213> ORGANISM: Homo sapiens

<400> SEQUENCE: 35

Phe Ser Ile Leu Ser Ser Gly Trp Leu Arg
1               5                   10

<210> SEQ ID NO 36
<211> LENGTH: 12
<212> TYPE: PRT
<213> ORGANISM: Homo sapiens

<400> SEQUENCE: 36

Leu Ser Glu Pro Ala Glu Leu Thr Asp Ala Val Lys
1               5                   10

<210> SEQ ID NO 37
<211> LENGTH: 567
<212> TYPE: PRT
<213> ORGANISM: Homo sapiens
<300> PUBLICATION INFORMATION:
<308> DATABASE ACCESSION NUMBER: NP_001189787.1
<309> DATABASE ENTRY DATE: 2011-08-13
<313> RELEVANT RESIDUES IN SEQ ID NO: (1)..(567)

<400> SEQUENCE: 37

Met Gly Thr Thr Ala Arg Ala Ala Leu Val Leu Thr Tyr Leu Ala Val
1               5                   10                  15

Ala Ser Ala Ala Ser Glu Gly Gly Phe Thr Ala Thr Gly Gln Arg Gln
                20                  25                  30

Leu Arg Pro Glu His Phe Gln Glu Val Gly Tyr Ala Ala Pro Pro Ser
            35                  40                  45

Pro Pro Leu Ser Arg Ser Leu Pro Met Asp His Pro Asp Ser Ser Gln
        50                  55                  60

His Gly Pro Pro Phe Glu Gly Gln Ser Gly Lys Glu Gly Arg Gly Pro
65                  70                  75                  80

Arg Pro His Ser Gln Pro Trp Leu Gly Glu Arg Val Gly Cys Ser His
                85                  90                  95

Ile Pro Pro Ser Ile Val Gln Pro Pro Ser Gln Glu Ala Thr Pro
            100                 105                 110

Leu Gln Gln Glu Lys Leu Leu Pro Ala Gln Leu Pro Ala Glu Lys Glu
```

```
            115                 120                 125
Val Gly Pro Pro Leu Pro Gln Glu Ala Val Pro Leu Gln Lys Glu Leu
    130                 135                 140
Pro Ser Leu Gln His Pro Asn Glu Gln Lys Glu Gly Thr Pro Ala Pro
145                 150                 155                 160
Phe Gly Asp Gln Ser His Pro Glu Pro Glu Ser Trp Asn Ala Ala Gln
                165                 170                 175
His Cys Gln Gln Asp Arg Ser Gln Gly Gly Trp Gly His Arg Leu Asp
            180                 185                 190
Gly Phe Pro Pro Gly Arg Pro Ser Pro Asp Asn Leu Asn Gln Ile Cys
        195                 200                 205
Leu Pro Asn Arg Gln His Val Val Tyr Gly Pro Trp Asn Leu Pro Gln
210                 215                 220
Ser Ser Tyr Ser His Leu Thr Arg Gln Gly Glu Thr Leu Asn Phe Leu
225                 230                 235                 240
Glu Ile Gly Tyr Ser Arg Cys Cys His Cys Arg Ser His Thr Asn Arg
                245                 250                 255
Leu Glu Cys Ala Lys Leu Val Trp Glu Glu Ala Met Ser Arg Phe Cys
            260                 265                 270
Glu Ala Glu Phe Ser Val Lys Thr Arg Pro His Trp Cys Cys Thr Arg
        275                 280                 285
Gln Gly Glu Ala Arg Phe Ser Cys Phe Gln Glu Ala Pro Gln Pro
290                 295                 300
His Tyr Gln Leu Arg Ala Cys Pro Ser His Gln Pro Asp Ile Ser Ser
305                 310                 315                 320
Gly Leu Glu Leu Pro Phe Pro Pro Gly Val Pro Thr Leu Asp Asn Ile
                325                 330                 335
Lys Asn Ile Cys His Leu Arg Arg Phe Arg Ser Val Pro Arg Asn Leu
            340                 345                 350
Pro Ala Thr Asp Pro Leu Gln Arg Glu Leu Leu Ala Leu Ile Gln Leu
        355                 360                 365
Glu Arg Glu Phe Gln Arg Cys Cys Arg Gln Gly Asn Asn His Thr Cys
370                 375                 380
Thr Trp Lys Ala Trp Glu Asp Thr Leu Asp Lys Tyr Cys Asp Arg Glu
385                 390                 395                 400
Tyr Ala Val Lys Thr His His Leu Cys Cys Arg His Pro Pro Ser
                405                 410                 415
Pro Thr Arg Asp Glu Cys Phe Ala Arg Arg Ala Pro Tyr Pro Asn Tyr
            420                 425                 430
Asp Arg Asp Ile Leu Thr Ile Asp Ile Gly Arg Val Thr Pro Asn Leu
        435                 440                 445
Met Gly His Leu Cys Gly Asn Gln Arg Val Leu Thr Lys His Lys His
    450                 455                 460
Ile Pro Gly Leu Ile His Asn Met Thr Ala Arg Cys Cys Asp Leu Pro
465                 470                 475                 480
Phe Pro Glu Gln Ala Cys Cys Ala Glu Glu Lys Leu Thr Phe Ile
                485                 490                 495
Asn Asp Leu Cys Gly Pro Arg Arg Asn Ile Trp Arg Asp Pro Ala Leu
            500                 505                 510
Cys Cys Tyr Leu Ser Pro Gly Asp Glu Gln Val Asn Cys Phe Asn Ile
        515                 520                 525
Asn Tyr Leu Arg Asn Val Ala Leu Val Ser Gly Asp Thr Glu Asn Ala
    530                 535                 540
```

```
Lys Gly Gln Gly Glu Gln Gly Ser Thr Gly Gly Thr Asn Ile Ser Ser
545                 550                 555                 560

Thr Ser Glu Pro Lys Glu Glu
                565

<210> SEQ ID NO 38
<211> LENGTH: 540
<212> TYPE: PRT
<213> ORGANISM: Homo sapiens
<300> PUBLICATION INFORMATION:
<308> DATABASE ACCESSION NUMBER: NP_004416.2
<309> DATABASE ENTRY DATE: 2011-08-14
<313> RELEVANT RESIDUES IN SEQ ID NO: (1)..(540)

<400> SEQUENCE: 38

Met Gly Thr Thr Ala Arg Ala Ala Leu Val Leu Thr Tyr Leu Ala Val
1               5                   10                  15

Ala Ser Ala Ala Ser Glu Gly Gly Phe Thr Ala Thr Gly Gln Arg Gln
                20                  25                  30

Leu Arg Pro Glu His Phe Gln Glu Val Gly Tyr Ala Ala Pro Pro Ser
            35                  40                  45

Pro Pro Leu Ser Arg Ser Leu Pro Met Asp His Pro Asp Ser Ser Gln
        50                  55                  60

His Gly Pro Pro Phe Glu Gly Gln Ser Gln Val Gln Pro Pro Pro Ser
65                  70                  75                  80

Gln Glu Ala Thr Pro Leu Gln Gln Glu Lys Leu Leu Pro Ala Gln Leu
                85                  90                  95

Pro Ala Glu Lys Glu Val Gly Pro Leu Pro Gln Glu Ala Val Pro
            100                 105                 110

Leu Gln Lys Glu Leu Pro Ser Leu Gln His Pro Asn Glu Gln Lys Glu
        115                 120                 125

Gly Thr Pro Ala Pro Phe Gly Asp Gln Ser His Pro Glu Pro Glu Ser
130                 135                 140

Trp Asn Ala Ala Gln His Cys Gln Gln Asp Arg Ser Gln Gly Gly Trp
145                 150                 155                 160

Gly His Arg Leu Asp Gly Phe Pro Pro Gly Arg Pro Ser Pro Asp Asn
                165                 170                 175

Leu Asn Gln Ile Cys Leu Pro Asn Arg Gln His Val Val Tyr Gly Pro
            180                 185                 190

Trp Asn Leu Pro Gln Ser Ser Tyr Ser His Leu Thr Arg Gln Gly Glu
        195                 200                 205

Thr Leu Asn Phe Leu Glu Ile Gly Tyr Ser Arg Cys Cys His Cys Arg
210                 215                 220

Ser His Thr Asn Arg Leu Glu Cys Ala Lys Leu Val Trp Glu Ala
225                 230                 235                 240

Met Ser Arg Phe Cys Glu Ala Glu Phe Ser Val Lys Thr Arg Pro His
                245                 250                 255

Trp Cys Cys Thr Arg Gln Gly Glu Ala Arg Phe Ser Cys Phe Gln Glu
            260                 265                 270

Glu Ala Pro Gln Pro His Tyr Gln Leu Arg Ala Cys Pro Ser His Gln
        275                 280                 285

Pro Asp Ile Ser Ser Gly Leu Glu Leu Pro Phe Pro Pro Gly Val Pro
290                 295                 300

Thr Leu Asp Asn Ile Lys Asn Ile Cys His Leu Arg Arg Phe Arg Ser
305                 310                 315                 320
```

```
Val Pro Arg Asn Leu Pro Ala Thr Asp Pro Leu Gln Arg Glu Leu Leu
            325                 330                 335

Ala Leu Ile Gln Leu Glu Arg Glu Phe Gln Arg Cys Cys Arg Gln Gly
        340                 345                 350

Asn Asn His Thr Cys Thr Trp Lys Ala Trp Glu Asp Thr Leu Asp Lys
            355                 360                 365

Tyr Cys Asp Arg Glu Tyr Ala Val Lys Thr His His Leu Cys Cys
        370                 375                 380

Arg His Pro Pro Ser Pro Thr Arg Asp Glu Cys Phe Ala Arg Arg Ala
385                 390                 395                 400

Pro Tyr Pro Asn Tyr Asp Arg Asp Ile Leu Thr Ile Asp Ile Gly Arg
                405                 410                 415

Val Thr Pro Asn Leu Met Gly His Leu Cys Gly Asn Gln Arg Val Leu
            420                 425                 430

Thr Lys His Lys His Ile Pro Gly Leu Ile His Asn Met Thr Ala Arg
        435                 440                 445

Cys Cys Asp Leu Pro Phe Pro Glu Gln Ala Cys Cys Ala Glu Glu Glu
    450                 455                 460

Lys Leu Thr Phe Ile Asn Asp Leu Cys Gly Pro Arg Arg Asn Ile Trp
465                 470                 475                 480

Arg Asp Pro Ala Leu Cys Cys Tyr Leu Ser Pro Gly Asp Glu Gln Val
                485                 490                 495

Asn Cys Phe Asn Ile Asn Tyr Leu Arg Asn Val Ala Leu Val Ser Gly
            500                 505                 510

Asp Thr Glu Asn Ala Lys Gly Gln Gly Glu Gln Gly Ser Thr Gly Gly
        515                 520                 525

Thr Asn Ile Ser Ser Thr Ser Glu Pro Lys Glu Glu
    530                 535                 540

<210> SEQ ID NO 39
<211> LENGTH: 415
<212> TYPE: PRT
<213> ORGANISM: Homo sapiens
<300> PUBLICATION INFORMATION:
<308> DATABASE ACCESSION NUMBER: NP_073155.2
<309> DATABASE ENTRY DATE: 2011-08-14
<313> RELEVANT RESIDUES IN SEQ ID NO: (1)..(415)

<400> SEQUENCE: 39

Met Gly Thr Thr Ala Arg Ala Ala Leu Val Leu Thr Tyr Leu Ala Val
1               5                   10                  15

Ala Ser Ala Ala Ser Glu Gly Gly Phe Thr Ala Thr Gly Gln Arg Gln
            20                  25                  30

Leu Arg Pro Glu His Phe Gln Glu Val Gly Tyr Ala Ala Pro Pro Ser
        35                  40                  45

Pro Pro Leu Ser Arg Ser Leu Pro Met Asp His Pro Asp Ser Ser Gln
    50                  55                  60

His Gly Pro Pro Phe Glu Gly Gln Ser Gln Val Gln Pro Pro Pro Ser
65                  70                  75                  80

Gln Glu Ala Thr Pro Leu Gln Gln Glu Lys Leu Leu Pro Ala Gln Leu
                85                  90                  95

Pro Ala Glu Lys Glu Val Gly Pro Pro Leu Pro Gln Glu Ala Val Pro
            100                 105                 110

Leu Gln Lys Glu Leu Pro Ser Leu Gln His Pro Asn Glu Gln Lys Glu
        115                 120                 125

Gly Thr Pro Ala Pro Phe Gly Asp Gln Ser His Pro Glu Pro Glu Ser
```

```
                130             135             140
Trp Asn Ala Ala Gln His Cys Gln Gln Asp Arg Ser Gln Gly Gly Trp
145                 150                 155                 160

Gly His Arg Leu Asp Gly Phe Pro Pro Gly Arg Pro Ser Pro Asp Asn
                165                 170                 175

Leu Asn Gln Ile Cys Leu Pro Asn Arg Gln His Val Val Tyr Gly Pro
            180                 185                 190

Trp Asn Leu Pro Gln Ser Ser Tyr Ser His Leu Thr Arg Gln Gly Glu
        195                 200                 205

Thr Leu Asn Phe Leu Glu Ile Gly Tyr Ser Arg Cys Cys His Cys Arg
210                 215                 220

Ser His Thr Asn Arg Leu Glu Cys Ala Lys Leu Val Trp Glu Asp Thr
225                 230                 235                 240

Leu Asp Lys Tyr Cys Asp Arg Glu Tyr Ala Val Lys Thr His His His
                245                 250                 255

Leu Cys Cys Arg His Pro Pro Ser Pro Thr Arg Asp Glu Cys Phe Ala
            260                 265                 270

Arg Arg Ala Pro Tyr Pro Asn Tyr Asp Arg Asp Ile Leu Thr Ile Asp
        275                 280                 285

Ile Gly Arg Val Thr Pro Asn Leu Met Gly His Leu Cys Gly Asn Gln
290                 295                 300

Arg Val Leu Thr Lys His Lys His Ile Pro Gly Leu Ile His Asn Met
305                 310                 315                 320

Thr Ala Arg Cys Cys Asp Leu Pro Phe Pro Glu Gln Ala Cys Cys Ala
                325                 330                 335

Glu Glu Glu Lys Leu Thr Phe Ile Asn Asp Leu Cys Gly Pro Arg Arg
            340                 345                 350

Asn Ile Trp Arg Asp Pro Ala Leu Cys Cys Tyr Leu Ser Pro Gly Asp
        355                 360                 365

Glu Gln Val Asn Cys Phe Asn Ile Asn Tyr Leu Arg Asn Val Ala Leu
370                 375                 380

Val Ser Gly Asp Thr Glu Asn Ala Lys Gly Gln Gly Glu Gln Gly Ser
385                 390                 395                 400

Thr Gly Gly Thr Asn Ile Ser Ser Thr Ser Glu Pro Lys Glu Glu
                405                 410                 415

<210> SEQ ID NO 40
<211> LENGTH: 249
<212> TYPE: PRT
<213> ORGANISM: Homo sapiens
<300> PUBLICATION INFORMATION:
<308> DATABASE ACCESSION NUMBER: NP_001123483.1
<309> DATABASE ENTRY DATE: 2011-08-15
<313> RELEVANT RESIDUES IN SEQ ID NO: (1)..(249)

<400> SEQUENCE: 40

Met Gly Thr Pro Arg Ile Gln His Leu Leu Ile Leu Val Leu Val Gly
1               5                   10                  15

Ala Ser Leu Leu Thr Ser Gly Leu Glu Leu Tyr Cys Gln Lys Gly Leu
                20                  25                  30

Ser Met Thr Val Glu Ala Asp Pro Ala Asn Met Phe Asn Trp Thr Thr
            35                  40                  45

Glu Glu Val Glu Thr Cys Asp Lys Gly Ala Leu Cys Gln Glu Thr Ile
        50                  55                  60

Leu Ile Ile Lys Ala Gly Thr Glu Thr Ala Ile Leu Ala Thr Lys Gly
65                  70                  75                  80
```

-continued

```
Cys Ile Pro Glu Gly Glu Ala Ile Thr Ile Val Gln His Ser Ser
                85                  90                  95

Pro Pro Gly Leu Ile Val Thr Ser Tyr Ser Asn Tyr Cys Glu Asp Ser
            100                 105                 110

Phe Cys Asn Asp Lys Asp Ser Leu Ser Gln Phe Trp Glu Phe Ser Glu
        115                 120                 125

Thr Thr Ala Ser Thr Val Ser Thr Thr Leu His Cys Pro Thr Cys Val
    130                 135                 140

Ala Leu Gly Thr Cys Phe Ser Ala Pro Ser Leu Pro Cys Pro Asn Gly
145                 150                 155                 160

Thr Thr Arg Cys Tyr Gln Gly Lys Leu Glu Ile Thr Gly Gly Ile
                165                 170                 175

Glu Ser Ser Val Glu Val Lys Gly Cys Thr Ala Met Ile Gly Cys Arg
                180                 185                 190

Leu Met Ser Gly Ile Leu Ala Val Gly Pro Met Phe Val Arg Glu Ala
                195                 200                 205

Cys Pro His Gln Leu Leu Thr Gln Pro Arg Lys Thr Glu Asn Gly Ala
            210                 215                 220

Thr Cys Leu Pro Ile Pro Val Trp Gly Leu Gln Leu Leu Pro Leu
225                 230                 235                 240

Leu Leu Pro Ser Phe Ile His Phe Ser
                245

<210> SEQ ID NO 41
<211> LENGTH: 267
<212> TYPE: PRT
<213> ORGANISM: Homo sapiens
<300> PUBLICATION INFORMATION:
<308> DATABASE ACCESSION NUMBER: NP_113639.4
<309> DATABASE ENTRY DATE: 2011-08-15
<313> RELEVANT RESIDUES IN SEQ ID NO: (1)..(267)

<400> SEQUENCE: 41

Met Gly Ala Arg Gln Ile Gln Thr Ser Ser Gln Thr Ser Pro Glu
1               5                   10                  15

Glu Ala Met Gly Thr Pro Arg Ile Gln His Leu Leu Ile Leu Leu Val
                20                  25                  30

Leu Gly Ala Ser Leu Leu Thr Ser Gly Leu Glu Leu Tyr Cys Gln Lys
            35                  40                  45

Gly Leu Ser Met Thr Val Glu Ala Asp Pro Ala Asn Met Phe Asn Trp
        50                  55                  60

Thr Thr Glu Glu Val Glu Thr Cys Asp Lys Gly Ala Leu Cys Gln Glu
65                  70                  75                  80

Thr Ile Leu Ile Ile Lys Ala Gly Thr Glu Thr Ala Ile Leu Ala Thr
                85                  90                  95

Lys Gly Cys Ile Pro Glu Gly Glu Ala Ile Thr Ile Val Gln His
            100                 105                 110

Ser Ser Pro Pro Gly Leu Ile Val Thr Ser Tyr Ser Asn Tyr Cys Glu
        115                 120                 125

Asp Ser Phe Cys Asn Asp Lys Asp Ser Leu Ser Gln Phe Trp Glu Phe
    130                 135                 140

Ser Glu Thr Thr Ala Ser Thr Val Ser Thr Thr Leu His Cys Pro Thr
145                 150                 155                 160

Cys Val Ala Leu Gly Thr Cys Phe Ser Ala Pro Ser Leu Pro Cys Pro
                165                 170                 175
```

```
Asn Gly Thr Thr Arg Cys Tyr Gln Gly Lys Leu Glu Ile Thr Gly
            180                 185                 190

Gly Ile Glu Ser Ser Val Glu Val Lys Gly Cys Thr Ala Met Ile Gly
        195                 200                 205

Cys Arg Leu Met Ser Gly Ile Leu Ala Val Gly Pro Met Phe Val Arg
    210                 215                 220

Glu Ala Cys Pro His Gln Leu Leu Thr Gln Pro Arg Lys Thr Glu Asn
225                 230                 235                 240

Gly Ala Thr Cys Leu Pro Ile Pro Val Trp Gly Leu Gln Leu Leu Leu
            245                 250                 255

Pro Leu Leu Leu Pro Ser Phe Ile His Phe Ser
            260                 265

<210> SEQ ID NO 42
<211> LENGTH: 332
<212> TYPE: PRT
<213> ORGANISM: Homo sapiens
<300> PUBLICATION INFORMATION:
<308> DATABASE ACCESSION NUMBER: NP_002292.1
<309> DATABASE ENTRY DATE: 2011-08-13
<313> RELEVANT RESIDUES IN SEQ ID NO: (1)..(332)
<300> PUBLICATION INFORMATION:
<308> DATABASE ACCESSION NUMBER: NP_059144.1
<309> DATABASE ENTRY DATE: 2011-08-13
<313> RELEVANT RESIDUES IN SEQ ID NO: (1)..(332)

<400> SEQUENCE: 42

Met Ser Thr Val Lys Glu Gln Leu Ile Glu Lys Leu Ile Glu Asp Asp
1               5                   10                  15

Glu Asn Ser Gln Cys Lys Ile Thr Ile Val Gly Thr Gly Ala Val Gly
            20                  25                  30

Met Ala Cys Ala Ile Ser Ile Leu Leu Lys Asp Leu Ala Asp Glu Leu
        35                  40                  45

Ala Leu Val Asp Val Ala Leu Asp Lys Leu Lys Gly Glu Met Met Asp
50                  55                  60

Leu Gln His Gly Ser Leu Phe Phe Ser Thr Ser Lys Ile Thr Ser Gly
65                  70                  75                  80

Lys Asp Tyr Ser Val Ser Ala Asn Ser Arg Ile Val Ile Val Thr Ala
                85                  90                  95

Gly Ala Arg Gln Gln Glu Gly Glu Thr Arg Leu Ala Leu Val Gln Arg
            100                 105                 110

Asn Val Ala Ile Met Lys Ser Ile Ile Pro Ala Ile Val His Tyr Ser
        115                 120                 125

Pro Asp Cys Lys Ile Leu Val Val Ser Asn Pro Val Asp Ile Leu Thr
130                 135                 140

Tyr Ile Val Trp Lys Ile Ser Gly Leu Pro Val Thr Arg Val Ile Gly
145                 150                 155                 160

Ser Gly Cys Asn Leu Asp Ser Ala Arg Phe Arg Tyr Leu Ile Gly Glu
                165                 170                 175

Lys Leu Gly Val His Pro Thr Ser Cys His Gly Trp Ile Gly Glu
            180                 185                 190

His Gly Asp Ser Ser Val Pro Leu Trp Ser Gly Val Asn Val Ala Gly
        195                 200                 205

Val Ala Leu Lys Thr Leu Asp Pro Lys Leu Gly Thr Asp Ser Asp Lys
210                 215                 220

Glu His Trp Lys Asn Ile His Lys Gln Val Ile Gln Ser Ala Tyr Glu
225                 230                 235                 240
```

-continued

```
Ile Ile Lys Leu Lys Gly Tyr Thr Ser Trp Ala Ile Gly Leu Ser Val
            245                 250                 255

Met Asp Leu Val Gly Ser Ile Leu Lys Asn Leu Arg Arg Val His Pro
            260                 265                 270

Val Ser Thr Met Val Lys Gly Leu Tyr Gly Ile Lys Glu Glu Leu Phe
            275                 280                 285

Leu Ser Ile Pro Cys Val Leu Gly Arg Asn Gly Val Ser Asp Val Val
            290                 295                 300

Lys Ile Asn Leu Asn Ser Glu Glu Glu Ala Leu Phe Lys Lys Ser Ala
305                 310                 315                 320

Glu Thr Leu Trp Asn Ile Gln Lys Asp Leu Ile Phe
                325                 330
```

MARKERS OF THE MALE UROGENITAL TRACT

CROSS-REFERENCE TO RELATED APPLICATIONS

This application is a national stage of International Patent Application No. PCT/CA2011/000925, filed Aug. 16, 2011, which claims the benefit of the priority of US Provisional Patent Application No. 61/374,030, filed Aug. 16, 2010 (expired), which applications are incorporated herein by reference.

FIELD OF THE INVENTION

The invention relates to markers associated with the male urogenital tract, compositions and kits comprising the markers and methods for the detection, diagnosis, prediction and/or characterization of the male urogenital tract or a condition of the male urogenital tract, and therapy of conditions of the male urogenital tract, in particular infertility.

BACKGROUND OF THE INVENTION

Human infertility affects around 15% of couples, and the male contribution to it is found in near 50% of all cases [Pilch, B.; Mann, M., 2006; Robert, M.; Gagnon, C., 1994]. One of the medical conditions of male infertility is azoospermia, which is characterized by a non-measurable level of sperm in the semen [Edwards, J. J. et al, 1981]. Azoospermia is diagnosed in 20% of non-fertile men and has two forms: obstructive azoospermia (OA) and non-obstructive azoospermia (NOA). OA is caused by a physical obstruction in the male reproductive tract. The biological outcome of OA is thus identical to that of vasectomy, which is a surgical severance of vas deference. NOA is a more complicated infertility syndrome that can be classified as maturation arrest, Sertoli-cell-only syndrome and hypospermatogenesis [Martinez-Heredia, J. et al, 2008].

The only currently used method to definitively distinguish between OA and NOA syndromes is a testicular biopsy, which is an invasive surgical procedure [Fung, K. Y., 2004; Yamakawa, K. et al, 2007]. Thus, there is an urgent need for alternative non-invasive approaches with better diagnostic potential. Differential diagnosis of normal, NOA, and OA (or post-vasectomy, PV) conditions is required for the following reasons: (i) in infertile patients, use of molecular markers capable of differentiating NOA and OA may eliminate the need for a diagnostic testicular biopsy; (ii) in healthy individuals that underwent vasectomy, markers capable of differentiating normal and PV seminal plasma will reveal if vasectomy was successful.

Proteins are considered as promising biomarkers for clinical diagnostics. However, no biomarkers currently exist to definitively diagnose OA or NOA. Blood plasma levels of inhibin B or FSH were proposed for NOA diagnosis, but these molecules had poor specificity and sensitivity [Wang, J. et al, 2009; Lilja, H.; et al, 1987]. Protein levels in local fluids, such as seminal plasma, may have a better potential for diagnostics [Searle, B. C. et al, 2008]. For example, PTGDS protein has been recently proposed as a seminal plasma biomarker for diagnosis of OA [Elias, J. E. and Gygi, S. P., 2007]. However, PTGDS could not distinguish NOA from normal and OA (PV) groups with high confidence.

Recent progress in biological mass spectrometry facilitated identification of several thousand proteins in biological fluids [Choi, H. and Nesvizhskii, A., 20; Sardana, G. et al, 2008]. While identification of proteins is successfully used in biomedical research, routine quantification of proteins by mass spectrometry is still a challenge that requires considerable methodological and instrumental advances. Quantitative selected reaction monitoring (SRM) assays [Poliakov, A. et al, 2009; Thimon, V. et al, 2008] were introduced as mass spectrometry means to compete with antibody-based ELISAs that were widely used for verification of biomarkers in large numbers of clinical samples. Verification of biomarkers by SRM assays is an emerging field of proteomics with just several studies to date [Sullivan, R. et al, 2007; Virji, N. and Naz, R. K., 1995; Odet, F. et al, 2008]. The proteome of seminal plasma is as complex as the proteome of blood serum and contains large amounts of semenogelin, kallikrein 3, and other high-abundance proteins [Sawane, M. V. et al, 2002; Takayama, T. et al, 2005a, Takayama, T. et al, 2005b].

SUMMARY OF THE INVENTION

Applicants have developed methods to identify markers of the male urogenital tract. In particular, Applicants compared the proteomes of seminal plasma of normal fertile controls, men with NOA, men with prostatitis, and men who have undergone a vasectomy. Proteins were distinguished based on whether they originated proximal or distal to the site of ligation of the vas deferens. In particular, Applicants identified over 2000 proteins in seminal plasma from normal and post-vasectomy (PV) individuals. A group of proteins was found under-expressed more than 2-fold in PV samples based on semi-quantitative spectral counting comparison.

To verify obstructive azoospermia (OA) post-vasectomy candidate biomarkers, a multiplex selected reaction monitoring (SRM) assay was developed. With the SRM assay, relative abundances of proteins in normal, NOA and PV (OA) seminal plasma samples was measured. Biomarkers for differential diagnosis of azoospermia with high specificity and sensitivity were identified.

Thus, the invention relates to a method of characterizing or classifying a biological sample in particular a tissue or semen sample, from the male urogenital tract by detecting or quantitating in the sample one or more polypeptides extracted from the sample that are characteristic of the male urogenital tract or condition of the male urogenital tract, the method comprising assaying for differential expression of polypeptides or polynucleotides in the sample, for example, by mass spectroscopy of proteins extracted from the sample or using antibodies or polynucleotides (e.g. mRNA). In an embodiment, differential expression of proteins is carried out using mass spectroscopy, in particular surface enhanced laser desorption/ionization (SELDI-TOF MS). The invention includes polypeptides identified using a method of the invention.

In an embodiment, the invention provides a method for identifying markers associated with a tissue or organ of the male urogenital tract or a condition of the male urogenital tract comprising:

(a) obtaining a sample from the male urogenital tract from a post-vasectomy subject;

(b) extracting proteins from the sample and producing a profile of the proteins by subjecting the proteins to mass spectrometry; and (c) identifying the markers by comparing the profile with a profile of proteins from a similar sample from the male urogenital tract of a normal subject.

In another aspect, the invention is directed to bioinformatic methods for analyzing differential expression data generated from a method of the invention to identify further markers associated with a tissue or organ of the male urogenital tract, or a condition of the male urogenital tract.

The invention relates to novel markers for the male urogenital tract and conditions of the male urogenital tract, and in particular markers of infertility, more particularly NOA and OA, and PV markers, and compositions comprising same.

The invention provides marker sets that distinguish a tissue of the male urogenital tract or a condition of the male urogenital tract and uses thereof. A marker set may comprise a plurality of polypeptides and/or polynucleotides encoding such polypeptides, comprising or consisting of at least 2, 3, 4, 5, 6, 7, 8, 9, 10, 11, 12, 13, 14, 15, 20 or 25 of the markers of Table 1, 2, 3, 4, 5, 6, 7, 8, 9, 10, 11, 12 or 13. In specific aspects, the markers consist of at least 5, 6, 7, 8, 9, or polypeptides of Table 1, 2, 3, 4, 5, 6, 7, 8, 9, 10, 11, 12 or 13. In an aspect, the protein marker sets comprise or consist of protein clusters, or proteins in pathways comprising markers of Table 1, 2, 3, 4, 5, 6, 7, 8, 9, 10, 11, 12 or 13.

In embodiments of the invention, a marker is provided which is selected from the group consisting of the polypeptides set forth in Table 1, 2, 3, 4, 5, 6, 7, 8, 9, 10, 11, 12 or 13, which polypeptides are up-regulated biomarkers in a condition of the male urogenital tract.

In embodiments of the invention, a marker is provided which is selected from the group consisting of the polypeptides set forth in Table 1, 2, 3, 4, 5, 6, 7, 8, 9, 10, 11, 12 or 13, which polypeptides are down-regulated biomarkers in a tissue of the urogenital tract or a condition of the urogenital tract.

The markers identified in accordance with a method of the invention, in particular the markers identified in Table 1, 2, 3, 4, 5, 6, 7, 8, 9, 10, 11, 12 or 13, including but not limited to native-sequence polypeptides, isoforms, chimeric polypeptides, all homologs, fragments, and precursors of the markers, including modified forms of the polypeptides and derivatives, are referred to herein as "urogenital marker(s)". Polynucleotides encoding urogenital markers are referred to herein as "urogenital polynucleotide marker(s)", "polynucleotides encoding urogenital markers", or "polynucleotides encoding the marker(s)". The urogenital markers and urogenital polynucleotide markers are sometimes collectively referred to herein as "marker(s)". Markers of a urogenital condition are also sometimes referred to herein as "urogenital disease markers", "urogenital disease polynucleotide markers", and "polynucleotides encoding urogenital disease markers".

Urogenital markers identified in accordance with a method of the invention, (including the markers of Table 1, 2, 3, 4, 5, 6, 7, 8, 9, 10, 11, 12 or 13), and polynucleotides encoding the markers, have application in the determination of the status of a urogenital tissue, in the detection of a urogenital condition such as infertility, and in determining or monitoring the success of a vasectomy. Thus, the markers can be used for diagnosis, monitoring (i.e. monitoring progression or therapeutic treatment), prognosis, treatment (e.g. guiding treatment), or classification of a urogenital condition or as markers before and after surgery. The invention also contemplates methods for assessing the status of a urogenital tissue, and methods for the diagnosis and therapy of a urogenital condition.

In accordance with methods of the invention, a urogenital tissue can be assessed or characterized, for example, by detecting the presence in the sample of (a) a urogenital marker or fragment thereof; (b) a metabolite which is produced directly or indirectly by a urogenital marker; (c) a transcribed nucleic acid or fragment thereof having at least a portion with which a urogenital polynucleotide marker is substantially identical; and/or (c) a transcribed nucleic acid or fragment thereof, wherein the nucleic acid hybridizes with a urogenital polynucleotide marker.

The levels of urogenital markers or urogenital polynucleotide markers in a sample may be determined by methods as described herein and generally known in the art. The expression levels may be determined by isolating and determining the level of nucleic acids transcribed from each urogenital polynucleotide marker. Alternatively or additionally, the levels of urogenital markers translated from mRNA transcribed from a urogenital polynucleotide marker may be determined.

In an aspect, the invention provides a method for characterizing or classifying a urogenital sample comprising detecting a difference in the expression of a first plurality of urogenital markers or urogenital polynucleotide markers relative to a control, the first plurality of markers consisting of at least 2, 3, 4, 5, 6, 7, 8, 9, 10, 11, 12, 13, 14, 15, 20 or 25 of the markers corresponding to the markers of any one of Tables 1 to 13. In specific aspects, the plurality of markers consists of at least 2, 3, 4, 5, 8 or 10 of the markers of any one of Tables 1 to 13.

In an aspect, a method is provided for characterizing a male urogenital tissue or organ by detecting urogenital markers or urogenital polynucleotide markers associated with a urogenital tissue or organ, or urogenital condition in a patient comprising:
(a) obtaining a sample from a subject;
(b) detecting or identifying in the sample urogenital markers or urogenital polynucleotide markers; and
(c) characterizing the tissue or organ by comparing the detected amount with an amount detected for a standard.

One aspect of the invention provides a method for detecting a urogenital condition in a patient comprising determining the status of urogenital markers or polynucleotides encoding the markers in a sample obtained from the patient, wherein an abnormal status in the sample indicates the presence of the condition.

Urogenital markers may be correlated with specific urogenital conditions (e.g., infertility, in particular NOA and OA, or prostatitis). Thus, another aspect of the invention provides a method of diagnosing a urogenital condition in a patient comprising determining the status of a urogenital marker or polynucleotide encoding a urogenital marker in a sample obtained from the patient, wherein an abnormal status of the urogenital marker or polynucleotide indicates the presence of a specific urogenital condition.

Another aspect of the invention provides a method of screening for a urogenital condition in a patient comprising identifying a patient at risk of having the condition or in need of screening and determining the status of urogenital markers or polynucleotides encoding the markers in a sample obtained from the patient, wherein an abnormal status of the markers or polynucleotides encoding the markers indicates the presence of the condition. In some embodiments, the patient is at risk of developing a specific type of condition (e.g. OA, NOA or prostatitis) and the abnormal status indicates the presence of the specific type of condition.

Another aspect of the invention provides a method for diagnosis of a urogenital condition in a subject comprising: (a) obtaining a sample from the subject; (b) subjecting the sample to a procedure to detect one or more urogenital marker or polynucleotide encoding the urogenital marker in the sample; (c) diagnosing the urogenital condition by comparing the amount or status of urogenital marker or polynucleotide encoding the urogenital marker to the amount or status of the urogenital marker or polynucleotide encoding the urogenital marker obtained from a control subject who does not suffer from the urogenital condition, a post-vasectomy subject or the subject taken at a different time. In an embodiment, the urogenital condition is non-obstructive azoospermia or obstructive azoospermia and the urogenital marker is ECM1, and optionally TEX101 and/or LDHC. In embodiments, the method distinguishes NOA and OA.

The invention provides a method for assessing infertility in a subject, the method comprising: conducting an assay to determine presence or absence of urogenital markers or polynucleotides encoding the markers in a sample obtained from the subject and assessing infertility based on results of the assay. The assay may comprise determining an amount of urogenital markers or polynucleotides encoding the markers and comparing the determined amount to a reference or standard.

In an embodiment, the invention provides a method for diagnosis of azoospermia in a subject comprising determining the status of urogenital markers or polynucleotides encoding the markers in a sample obtained from the subject, wherein an abnormal status in the sample indicates the presence of azoospermia.

In an embodiment, the invention provides a method for diagnosis of NOA in a subject comprising determining the status of urogenital markers or polynucleotides encoding the markers in a sample obtained from the subject, wherein an abnormal status in the sample indicates the presence of NOA.

In an embodiment, the invention provides a method for diagnosis of OA in a subject comprising determining the status of urogenital markers or polynucleotides encoding the markers in a sample obtained from the subject, wherein an abnormal status in the sample indicates the presence of OA.

The present invention also relates to a method for identifying potentially infertile males or evaluating male fertility following an event which may influence the subject's fertility comprising determining the status of urogenital markers or polynucleotides encoding the markers in a sample obtained from the subject.

In an embodiment, the invention provides a method for assessing the success of a vasectomy in a subject comprising determining the status of urogenital markers or polynucleotides encoding the markers in a sample obtained from the subject, wherein the status is indicative of the success of the vasectomy.

Another aspect provides a diagnostic method comprising identifying a patient who is a candidate for treatment for a urogenital condition and determining the status of urogenital markers in a sample obtained from the patient, wherein an abnormal status of the markers in the sample indicates that treatment is desirable or necessary.

In aspects of the invention, the abnormal status can be an elevated status, low status or negative status. In an embodiment of the invention for detecting or diagnosing a urogenital condition the abnormal status is an elevated status. In an embodiment of the invention for detecting or diagnosing a urogenital condition the abnormal status is a low status.

In an embodiment of the invention, a method is provided for detecting urogenital disease markers or urogenital disease polynucleotide markers associated with a urogenital condition in a patient comprising:
(a) obtaining a sample from a patient;
(b) detecting in the sample urogenital disease markers or urogenital disease polynucleotide markers; and
(c) comparing the detected amount with an amount detected for a standard.

The term "detect" or "detecting" includes assaying, imaging or otherwise establishing the presence or absence of the target urogenital markers or polynucleotides encoding the markers, subunits thereof, or combinations of reagent bound targets, and the like, or assaying for, imaging, ascertaining, establishing, or otherwise determining one or more factual characteristics of a urogenital tissue or organ or urogenital condition. The term encompasses diagnostic, prognostic, and monitoring applications for the urogenital markers and polynucleotides encoding the markers.

The invention also provides a method of assessing whether a patient is afflicted with or has a pre-disposition for a urogenital condition, in particular male infertility, the method comprising comparing:
(a) levels of urogenital markers or polynucleotides encoding urogenital markers associated with the urogenital condition in a sample from the patient; and
(b) control levels of urogenital markers or polynucleotides encoding urogenital markers associated with the urogenital condition in samples of the same type obtained from control patients (e.g. patients not afflicted with the condition or in some embodiments post-vasectomy patients), wherein altered levels of the urogenital markers or the polynucleotides relative to the corresponding control levels of urogenital markers or polynucleotides is an indication that the patient is afflicted with the urogenital condition.

In an aspect of a method of the invention for assessing whether a patient is afflicted with or has a pre-disposition for a urogenital condition, higher levels of urogenital disease markers in a sample relative to the corresponding control levels is an indication that the patient is afflicted with the urogenital condition.

In another aspect of a method of the invention for assessing whether a patient is afflicted with or has a pre-disposition for urogenital condition, lower levels of urogenital disease markers in a sample relative to the corresponding control levels is an indication that the patient is afflicted with the urogenital condition.

In a further aspect, a method for screening a subject for a urogenital condition is provided comprising (a) obtaining a biological sample from a subject; (b) detecting the amount of urogenital markers associated with the condition in said sample; and (c) comparing said amount of urogenital markers detected to a predetermined standard, where detection of a level of urogenital markers that differs from the standard indicates the urogenital condition.

In an embodiment, a significant difference between the levels of urogenital marker levels in a patient and standard levels is an indication that the patient is afflicted with or has a predisposition to a urogenital condition.

In a particular embodiment the amount of urogenital marker(s) detected is greater than that of a standard and is indicative of a urogenital condition, in particular male infertility. In another particular embodiment the amount of urogenital marker(s) detected is lower than that of a standard and is indicative of a urogenital condition, in particular male infertility.

In aspects of the methods of the invention, the methods are non-invasive for detecting a urogenital condition which in turn allows for diagnosis of a variety of conditions or diseases associated with the urogenital tract.

The invention provides a non-invasive non-surgical method for detection, diagnosis or prediction of a urogenital condition in a subject comprising: obtaining a sample of a biological fluid or a tissue sample from the subject; subjecting the sample to a procedure to detect urogenital markers or urogenital polynucleotide markers in the sample; detecting, diagnosing, and predicting the urogenital condition by comparing the levels of urogenital markers or urogenital polynucleotide markers to the levels of marker(s) or polynucleotide(s) obtained from a control subject with no urogenital condition or a different stage of condition, or obtained from samples of the subject taken at a different time.

In an embodiment, the urogenital condition is detected, diagnosed, or predicted by determination of increased levels of markers when compared to such levels obtained from the control.

In another embodiment, the urogenital condition is detected, diagnosed, or predicted by determination of decreased levels of markers when compared to such levels obtained from the control.

The invention also provides a method for assessing the aggressiveness or indolence of a urogenital condition the method comprising comparing:
(a) levels of urogenital markers or polynucleotides encoding urogenital markers associated with the urogenital condition in a patient sample; and
(b) control levels of the urogenital markers or the polynucleotides in a control sample.

In an embodiment, a significant difference between the levels in the sample and the control levels is an indication that the urogenital condition is aggressive or indolent. In a particular embodiment, the levels of markers are higher than the control levels. In another particular embodiment, the levels of markers are lower than the control levels.

In another aspect, the invention provides a method for monitoring the progression of a urogenital condition in a patient the method comprising:
(a) detecting urogenital markers or polynucleotides encoding the markers associated with the condition in a sample from the patient at a first time point;
(b) repeating step (a) at a subsequent point in time; and
(c) comparing the levels detected in (a) and (b), and therefrom monitoring the progression of the urogenital condition.

The invention contemplates a method for determining the effect of an environmental factor on the urogenital tract or a urogenital condition comprising comparing urogenital polynucleotide markers or urogenital markers in the presence and absence of the environmental factor.

The invention also provides a method for assessing the potential efficacy of a test agent for inhibiting a urogenital condition, and a method of selecting an agent for inhibiting a urogenital condition.

The invention contemplates a method of assessing the potential of a test compound to contribute to a urogenital condition comprising:
(a) maintaining separate aliquots of urogenital diseased cells in the presence and absence of the test compound; and
(b) measuring the levels of urogenital markers or polynucleotides encoding the markers associated with the condition in each of the aliquots.

A significant difference between the levels of urogenital markers or polynucleotides encoding the markers in an aliquot maintained in the presence of (or exposed to) the test compound relative to the aliquot maintained in the absence of the test compound, indicates that the test compound potentially contributes to a urogenital condition.

The invention further relates to a method of assessing the efficacy of a therapy for inhibiting a urogenital condition in a patient. A method of the invention comprises comparing: (a) levels of urogenital markers or polynucleotides encoding the markers associated with the condition in a first sample from the patient obtained from the patient prior to providing at least a portion of the therapy to the patient; and (b) levels of urogenital markers or polynucleotides encoding the markers associated with the condition in a second sample obtained from the patient following therapy.

In an embodiment, a significant difference between the levels of urogenital markers or polynucleotides encoding the markers in the second sample relative to the first sample or an abnormal state is an indication that the therapy is efficacious for inhibiting a urogenital condition.

In a particular embodiment, the method is used to assess the efficacy of a therapy for inhibiting a urogenital condition where lower levels of urogenital markers or polynucleotides encoding same in the second sample relative to the first sample, is an indication that the therapy is efficacious for inhibiting the condition.

In a particular embodiment, the method is used to assess the efficacy of a therapy for inhibiting a urogenital condition where higher levels of urogenital markers or polynucleotides encoding same in the second sample relative to the first sample, is an indication that the therapy is efficacious for inhibiting the condition.

The "therapy" may be any therapy for treating a urogenital condition including but not limited to therapeutics, gene therapy, and surgery. Therefore, the method can be used to evaluate a patient before, during, and after therapy.

Certain methods of the invention employ binding agents (e.g. antibodies) that specifically recognize urogenital markers. In an embodiment, the invention provides methods for determining the presence or absence of a urogenital condition in a patient, comprising the steps of (a) contacting a biological sample obtained from a patient with one or more binding agent that specifically binds to one or more urogenital markers associated with the condition; and (b) detecting in the sample an amount of marker that binds to the binding agent, relative to a predetermined standard or cut-off value, and therefrom determining the presence or absence of the urogenital condition in the patient.

In another embodiment, the invention relates to a method for diagnosing and monitoring a urogenital condition in a subject by quantitating one or more urogenital markers associated with the condition in a biological sample from the subject comprising (a) reacting the biological sample with one or more binding agent specific for the urogenital markers (e.g. an antibody) that are directly or indirectly labeled with a detectable substance; and (b) detecting the detectable substance.

In another aspect the invention provides a method for using an antibody to detect expression of one or more urogenital marker in a sample, the method comprising: (a) combining antibodies specific for one or more urogenital marker with a sample under conditions which allow the formation of antibody:marker complexes; and (b) detecting complex formation, wherein complex formation indicates expression of the marker in the sample. Expression may be compared with standards and is diagnostic of a urogenital condition.

Embodiments of the methods of the invention involve (a) reacting a biological sample from a subject with antibodies specific for one or more urogenital markers which are directly or indirectly labeled with an enzyme; (b) adding a substrate for the enzyme wherein the substrate is selected so that the substrate, or a reaction product of the enzyme and substrate forms fluorescent complexes; (c) quantitating one or more urogenital markers in the sample by measuring fluorescence of the fluorescent complexes; and (d) comparing the quantitated levels to levels obtained for other samples from the subject patient, or control subjects.

In another embodiment, the quantitated levels are compared to levels quantitated for control subjects (e.g. normal)

without a urogenital condition wherein an increase in urogenital marker levels compared with the control subjects is indicative of the urogenital condition.

In a further embodiment, the quantitated levels are compared to levels quantitated for control subjects (e.g. normal) without a urogenital condition wherein a decrease in urogenital marker levels compared with the control subjects is indicative of the urogenital condition.

A particular embodiment of the invention comprises the following steps
 (a) incubating a biological sample with first antibodies specific for one or more urogenital disease markers which are directly or indirectly labeled with a detectable substance, and second antibodies specific for the one or more urogenital disease markers which are immobilized;
 (b) detecting the detectable substance thereby quantitating urogenital disease markers in the biological sample; and
 (c) comparing the quantitated urogenital disease markers with levels for a predetermined standard.

The standard or control may correspond to levels quantitated for samples from control subjects without a urogenital condition (normal), with a different disease stage, from other samples of the subject, or from samples from post-vasectomy subjects. In an embodiment, increased levels of urogenital disease markers as compared to the standard may be indicative of a urogenital condition. In another embodiment, lower levels of urogenital disease markers as compared to a standard may be indicative of a urogenital condition.

Urogenital marker levels can be determined by constructing an antibody microarray in which binding sites comprise immobilized, preferably monoclonal, antibodies specific to a substantial fraction of marker-derived urogenital marker proteins of interest.

Other methods of the invention employ one or more polynucleotides capable of hybridizing to one or more polynucleotides encoding urogenital markers. Thus, methods of the invention can be used to monitor a urogenital condition by detecting urogenital polynucleotide markers associated with the condition.

Thus, the present invention relates to a method for diagnosing and monitoring a urogenital condition in a sample from a subject comprising isolating nucleic acids, preferably mRNA, from the sample; and detecting urogenital marker polynucleotides associated with the condition in the sample. The presence of different levels of urogenital marker polynucleotides in the sample compared to a standard or control may be indicative of presence or absence of disease, disease stage, and/or a positive prognosis i.e. longer progression-free and overall survival.

In embodiments of the invention, urogenital disease marker polynucleotide positive samples (e.g. higher levels of the polynucleotides compared to a control normal) are a negative diagnostic indicator. Positive samples can be indicative of a urogenital condition, advanced stage disease, lower progression-free survival, and/or overall survival.

In other embodiments of the invention, urogenital disease marker polynucleotide negative samples (e.g. lower levels of the polynucleotides compared to a control normal) are a negative diagnostic indicator. Negative samples can be indicative of a urogenital condition, advanced stage disease, lower progression-free survival, and/or overall survival.

The invention provides methods for determining the presence or absence of a urogenital condition in a subject comprising detecting in the sample levels of nucleic acids that hybridize to one or more polynucleotides encoding urogenital markers associated with the condition, comparing the levels with a predetermined standard or cut-off value, and therefrom determining the presence or absence of the urogenital condition in the subject. In an embodiment, the invention provides methods for determining the presence or absence of a urogenital condition in a subject comprising (a) contacting a sample obtained from the subject with oligonucleotides that hybridize to one or more polynucleotides encoding urogenital disease markers; and (b) detecting in the sample a level of nucleic acids that hybridize to the polynucleotides relative to a predetermined cut-off value, and therefrom determining the presence or absence of the urogenital condition in the subject.

Within certain embodiments, the amount of polynucleotides that are mRNA are detected via polymerase chain reaction using, for example, oligonucleotide primers that hybridize to one or more polynucleotides encoding urogenital markers, or complements of such polynucleotides. Within other embodiments, the amount of mRNA is detected using a hybridization technique, employing oligonucleotide probes that hybridize to one or more polynucleotides encoding urogenital markers, or complements thereof.

When using mRNA detection, the method may be carried out by combining isolated mRNA with reagents to convert to cDNA according to standard methods; treating the converted cDNA with amplification reaction reagents (such as cDNA PCR reaction reagents) in a container along with an appropriate mixture of nucleic acid primers; reacting the contents of the container to produce amplification products; and analyzing the amplification products to detect the presence of one or more urogenital polynucleotide markers in the sample. For mRNA the analyzing step may be accomplished using Northern Blot analysis to detect the presence of urogenital polynucleotide markers. The analysis step may be further accomplished by quantitatively detecting the presence of urogenital polynucleotide markers in the amplification product, and comparing the quantity of markers detected against a panel of expected values for the known presence or absence of the markers in normal and disease tissue derived using similar primers.

Therefore, the invention provides a method wherein mRNA is detected by (a) isolating mRNA from a sample and combining the mRNA with reagents to convert it to cDNA; (b) treating the converted cDNA with amplification reaction reagents and nucleic acid primers that hybridize to one or more urogenital polynucleotide markers to produce amplification products; (d) analyzing the amplification products to detect an amount of mRNA encoding the urogenital markers; and (e) comparing the amount of mRNA to an amount detected against a panel of expected values for a standard or control derived using similar nucleic acid primers.

A method for diagnosing a urogenital condition in a subject comprising a) contacting a sample from a subject with a diagnostic reagent that measures urogenital markers or urogenital polynucleotide markers in the sample; and b) diagnosing the urogenital condition in the subject based upon the level of urogenital markers or urogenital polynucleotide markers in the sample from the subject over that of (i) a control level of urogenital markers or urogenital polynucleotide markers obtained from samples of the same type of sample from a subject who does not have the condition; or (ii) an earlier sample level of urogenital markers or urogenital polynucleotide markers obtained from samples of the same type taken from the same subject at a different time.

In an aspect, the levels of urogenital markers are measured and the markers are detected, directly or indirectly, by the interaction of the markers with an antibody specific for the urogenital markers. In an embodiment an antibody is labeled with an enzyme, fluorescent, luminescent or radioactive material. In an aspect, this method of the invention comprises performing a step selected from the group consisting of a counter immuno-electrophoresis, a radioimmunoassay, radioimmunoprecipitation assay, an enzyme-linked immunosorbent assay, a dot blot assay or an inhibition of competition assay and a sandwich assay using the antibody. In an embodiment of this method of the invention, step (b) the contacting comprises forming a complex in the sample comprising an antibody specific for one or more urogenital marker and the urogenital marker in the sample. Step (b) may further comprise measuring a level of the complex in a suitable assay.

In an aspect, the levels of urogenital polynucleotide markers are measured and the markers are detected using a nucleotide probe that hybridizes to the polynucleotide markers in the sample or by selective amplification of the polynucleotide markers in the sample using polymerase chain reaction.

In particular embodiments of the invention, the methods described herein utilize the urogenital polynucleotide markers placed on a microarray so that the expression status of each of the markers is assessed simultaneously.

In a particular aspect, the invention provides a urogenital microarray comprising a defined set of genes whose expression is significantly altered by a urogenital condition or procedure. The invention further relates to the use of the microarray as a prognostic tool to predict a urogenital condition or status of a urogenital organ or tissue. In an embodiment, the urogenital microarray discriminates between urogenital conditions resulting from different etiologies.

In an embodiment, the invention provides for oligonucleotide arrays comprising marker sets described herein. The microarrays provided by the present invention may comprise probes to markers able to distinguish urogenital tissues or organs or conditions. In particular, the invention provides oligonucleotide arrays comprising probes to a subset or subsets of at least 5 or 10 gene markers up to a full set of markers which distinguish urogenital tissues or organs, or urogenital conditions.

The invention also contemplates a method comprising administering to cells or tissues imaging agents that carry labels for imaging and bind to urogenital markers or polynucleotides encoding the markers, and optionally other markers of a urogenital condition, and then imaging the cells or tissues.

In an aspect, the invention provides an in vivo method comprising administering to a subject an agent that has been constructed to target one or more urogenital markers or polynucleotides encoding the markers. In a particular embodiment, the invention contemplates an in vivo method comprising administering to a mammal one or more agent that carries a label for imaging and binds to one or more urogenital marker or polynucleotide encoding the marker, and then imaging the mammal.

According to a particular aspect of the invention, an in vivo method for imaging a urogenital condition is provided comprising:
(a) injecting a patient with an agent that binds to one or more urogenital disease marker, the agent carrying a label for imaging the urogenital condition;
(b) allowing the agent to incubate in vivo and bind to one or more urogenital disease marker associated with the urogenital condition; and
(c) detecting the presence of the label localized to the urogenital condition.

In an embodiment of the invention, the agent is an antibody which recognizes a urogenital disease marker. In another embodiment of the invention the agent is a chemical entity which recognizes a urogenital disease marker.

The invention also contemplates the localization or imaging methods described herein using multiple markers.

An agent carries a label to image a urogenital marker and optionally other markers. Examples of labels useful for imaging are radiolabels, fluorescent labels (e.g. fluorescein and rhodamine), nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes can also be employed.

The invention also relates to kits for carrying out the methods of the invention. In an embodiment, a kit is for assessing whether a patient is afflicted with a urogenital condition and it comprises reagents for assessing one or more urogenital markers or polynucleotides encoding the markers.

The invention further provides kits comprising marker sets described herein. The invention also provides a diagnostic composition comprising a urogenital marker or a polynucleotide encoding the marker. A composition is also provided comprising a probe that specifically hybridizes to a urogenital polynucleotide marker, or a fragment thereof, or an antibody specific for a urogenital marker or a fragment thereof. In another aspect, a composition is provided comprising one or more urogenital polynucleotide marker specific primer pairs capable of amplifying the polynucleotides using polymerase chain reaction methodologies. The probes, primers or antibodies can be labeled with a detectable substance.

Still further, the invention relates to therapeutic applications for urogenital conditions, employing urogenital markers and polynucleotides encoding the markers, and/or binding agents for the markers.

The invention contemplates the methods, compositions, and kits described herein using additional markers associated with the urogenital tract or a urogenital condition. The methods described herein may be modified by including reagents to detect the additional markers, or polynucleotides for the markers.

In particular, the invention contemplates the methods described herein using multiple markers for a urogenital condition. Therefore, the invention contemplates a method for analyzing a biological sample for the presence of urogenital disease markers and polynucleotides encoding the markers, and other markers that are specific indicators of a urogenital condition. The methods described herein may be modified by including reagents to detect the additional markers, or nucleic acids for the additional markers.

In embodiments of the invention the methods, compositions and kits use one or more of the markers of any one of Tables 1 to 13. In another embodiment, the method uses a panel of markers selected from the markers of any one of Tables 1 to 13, in particular a panel comprising two, three or more of the markers in any one of Tables 1 to 13.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will now be described in relation to the drawings in which.

DETAILED DESCRIPTION OF THE INVENTION

Figure 1:
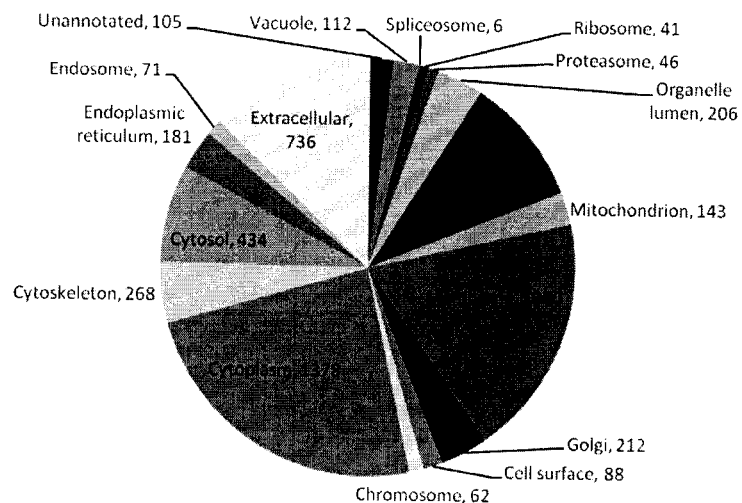
FIG. 1 shows the distribution of cellular components of proteins identified in (a) Control and (b) post-vasectomy (PV) seminal plasma samples.
Figure 1:
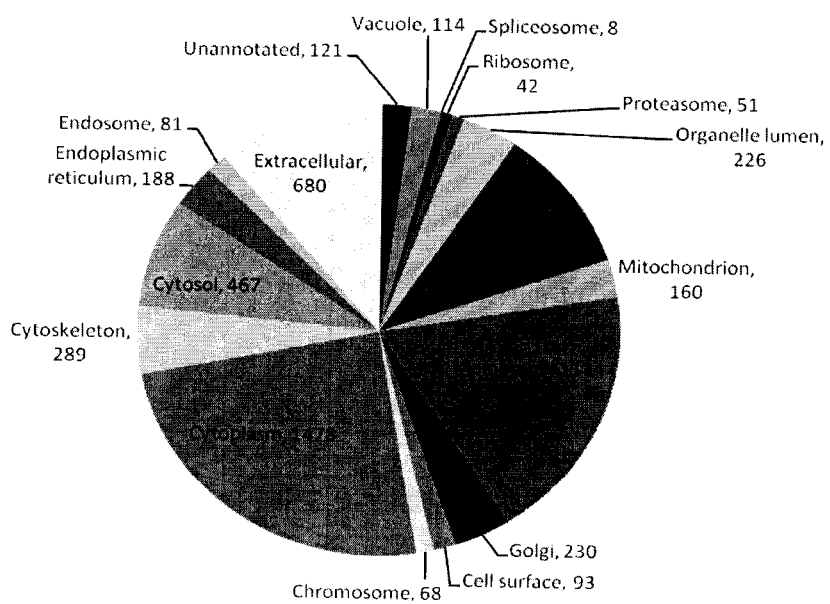

Methods are provided for characterizing a tissue or organ or status of the urogenital tract or a condition of the urogenital tract in a sample, the absence of a condition in a sample, the stage of a condition, and other characteristics of conditions of the urogenital tract that are relevant to prevention, diagnosis, characterization, and therapy of conditions of the urogenital tract in a patient. Methods are also provided for assessing the efficacy of one or more test agents for inhibiting or altering a condition of the urogenital tract, assessing the efficacy of a therapy for a condition of the urogenital tract, monitoring the progression of a condition of the urogenital tract, selecting an agent or therapy for inhibiting a condition of the urogenital tract, treating a patient afflicted with a condition of the urogenital tract, inhibiting a condition of the urogenital tract in a patient, and assessing the disease potential of a test compound.

Unless defined otherwise, all technical and scientific terms used herein have the same meaning as commonly understood by one of ordinary skill in the art to which this invention belongs. The following definitions supplement those in the art and are directed to the present application and are not to be imputed to any related or unrelated case. Generally, nomenclatures used in connection with, and techniques of, molecular biology, immunology, microbiology, genetics, protein and nucleic acid chemistry and hybridization described herein are those well known and commonly used in the art. Methods and techniques employed in the present invention are generally performed according to conventional methods known in the art and as described, for example, in general references such as Sambrook et al, Molecular Cloning: A Laboratory Manual, $2^{nd}$ ed., Cold Spring Harbor Laboratory Press, Cold Spring Harbor, N.Y. (1989) and Ausubel et al, Current Protocols in Molecular Biology, Greene Publishing Associates (1992) and Harlow and Lane, Antibodies: A Laboratory Manual, Cold Spring Harbor Laboratory Press, Cold Spring Harbor, to N.Y., (1990). Although any methods and materials similar or equivalent to those described herein can be used in the practice of the invention, particular materials and methods are described herein.

A "condition(s) of the urogenital tract" or "urogenital condition(s)" refers to any disease, disorder, syndrome or combination of manifestations or symptoms recognized or diagnosed as a disorder of the male urogenital tract, including but not limited to reproductive disorders and male infertility or pathological conditions associated with male infertility. Examples of such conditions include without limitation acute prostatitis, chronic prostatitis, prostatosis, benign hypertrophy of the prostate, prostatic carcinoma, acute epididymitis, azoospermia, partial obstruction of the male reproductive tract, and partial or incomplete testicular failure.

In aspects of the invention, pathological conditions associated with male infertility are conditions of spermatogenetic failure. These conditions may be histologically classified using a scoring system such as the Johnsen scoring system. [For a description of the system see, for example, Johnsen (1970), Hormones, 1, 2-25; de Kretser, D. and Holstein, A. F. Testicular biopsy and abnormal germ cells. In: Hafez, E. S. E. (ed.) Human semen and fertility regulation in men (1976).]

Pathological conditions associated with male infertility which can be diagnosed, detected or treated by the methods of the invention may comprise: a) post-testicular obstruction conditions associated with complete spermatogenesis, late spermatids per seminiferous tubule cross-section and repeated occurrence of residual bodies; b) conditions associated with severe hypospermatogenesis in all areas of the testis parenchyma with only few late spermatids; c) conditions associated with meiotic arrest of germ cells showing many spermatocytes and no spermatids; and d) conditions associated with Sertoli-cell-only syndrome (SCOS) and no germ cells.

In aspects of the invention, conditions which can be diagnosed or treated by the methods of the invention may comprise: a) conditions having a Johnsen count of 10; b) conditions having a Johnsen score of 8; c) conditions having a Johnsen score count of 5; or d) conditions having a Johnsen score of 2.

In embodiments of the invention the condition is azoospermia. Azoospermia includes the following categories:
1) testicular failure or non-obstructive azoospermia (NOA) generally characterized by either reduced spermatogenesis (hypo-spermatogenesis), maturation arrest at either an early or late stage of spermatogenesis or a complete failure of spermatogenesis noted with Sertoli-cell only syndrome [Yamakawa, K. et al, 2007; Wang, J. et al, 2009; Lilja, H. et al, 1987; Searle, B. C. et al, 2008; Elias, J. E. and Gygi, S., 2007].
2) post-testicular obstruction or obstructive azoospermia (OA) characterized by normal spermatogenesis but obstructive azoospermia due to blockage of the male reproductive tract [Yamakawa, K. et al, 2007; Wang, J. et al, 2009; Lilja, H. et al, 1987; Searle, B. C. et al, 2008; Elias, J. E. and Gygi, S., 2007].

In embodiments of the invention, the condition is a partial obstruction of the male reproductive tract. Partial obstruction may lead to infertility with reduced sperm counts or quality of the sperm. The present invention may be used to diagnose the etiology of the reduced sperm quality or counts, guide therapy and monitor the results of the therapy used.

In embodiments of the invention, the condition is partial or incomplete testicular failure. The present invention may be used to diagnose, guide therapy and monitor therapy for men with infertility due to reduced sperm counts or quality of the sperm which is secondary to testicular dysfunction identified by the markers.

In particular embodiments of the invention, the condition is NOA. In other particular embodiments, the condition is OA. In other particular embodiments, the methods of the invention are used to distinguish NOA and OA. In further particular embodiments of the invention, the condition is partial obstruction of the male reproductive tract or incomplete NOA.

In embodiments of the invention, the condition is male infertility.

In embodiments, the subject has components of obstruction and testicular failure and optionally a component of prostatitis.

In embodiments of the invention, the condition is prostatitis, in particular acute prostatitis, chronic prostatitis or prostatosis.

In embodiments of the invention, the prostatitis is one of the following:
1) acute bacterial prostatitis characterized by fever and acute symptoms of prostatitis;
2) chronic bacterial prostatitis characterized by symptoms of chronic prostatitis with a proven bacterial infection;
3) chronic prostatitis/chronic pelvic pain syndrome (chronic pelvic pain with no evidence of infection); and
4) asymptomatic inflammatory prostatitis.

In embodiments of the invention, the condition is prostate cancer.

The terms "sample", "biological sample", and the like mean a material known or suspected of expressing or containing one or more urogenital markers or polynucleotides encoding urogenital markers. A test sample can be used directly as obtained from the source or following a pretreatment to modify the character of the sample. The sample can be derived from any biological source, such as tissues, extracts, or cell cultures, including cells, cell lysates, and physiological fluids, such as, for example, seminal plasma, seminal fluid, whole blood, plasma, serum, saliva, ocular lens fluid, cerebral spinal fluid, sweat, urine, ascites fluid, synovial fluid, peritoneal fluid, lavage fluid, and the like. The sample can be obtained from animals, preferably mammals, most preferably humans. The sample can be treated prior to use, such as preparing plasma from blood, diluting viscous fluids, and the like. Methods of treatment can involve filtration, distillation, extraction, concentration, inactivation of interfering components, the addition of reagents, and the like.

In embodiments of the invention the sample is a mammalian tissue sample. In a particular embodiment, the tissue is a urogenital tissue sample.

In another embodiment the sample is a human physiological fluid. In a particular embodiment, the sample is a seminal plasma sample.

The samples that may be analyzed in accordance with the invention include polynucleotides from clinically relevant sources, preferably expressed RNA or a nucleic acid derived therefrom (cDNA or amplified RNA derived from cDNA that incorporates an RNA polymerase promoter). The target polynucleotides can comprise RNA, including, without limitation total cellular RNA, poly(A)$^+$ messenger RNA (mRNA) or fraction thereof, cytoplasmic mRNA, or RNA transcribed from cDNA (i.e., cRNA; see, for example., Linsley & Schelter, U.S. patent application Ser. No. 09/411,074, or U.S. Pat. No. 5,545,522, 5,891,636 or 5,716,785). Methods for preparing total and poly(A)$^+$ RNA are well known in the art, and are described generally, for example, in Sambrook et al., (1989, Molecular Cloning—A Laboratory Manual (2$^{nd}$ Ed.), Vols. 1-3, Cold Spring Harbor Laboratory, Cold Spring Harbor, N.Y.) and Ausubel et al, eds. (1994, Current Protocols in Molecular Biology, vol. 2, Current Protocols Publishing, New York). RNA may be isolated from eukaryotic cells by procedures involving lysis of the cells and denaturation of the proteins contained in the cells. Additional steps may be utilized to remove DNA. Cell lysis may be achieved with a nonionic detergent, followed by microcentrifugation to remove the nuclei and hence the bulk of the cellular DNA. (See Chirgwin et al., 1979, Biochemistry 18:5294-5299). Poly(A)+RNA can be selected using oligo-dT cellulose (see Sambrook et al., 1989, *Molecular Cloning—A Laboratory Manual* (2nd Ed.), Vols. 1-3, Cold Spring Harbor Laboratory, Cold Spring Harbor, N.Y.). In the alternative, RNA can be separated from DNA by organic extraction, for example, with hot phenol or phenol/chloroform/isoamyl alcohol.

It may be desirable to enrich mRNA with respect to other cellular RNAs, such as transfer RNA (tRNA) and ribosomal RNA (rRNA). Most mRNAs contain a poly(A) tail at their 3' end allowing them to be enriched by affinity chromatography, for example, using oligo(dT) or poly(U) coupled to a solid support, such as cellulose or Sephadex™ (see Ausubel et al., eds., 1994, *Current Protocols in Molecular Biology*, vol. 2, Current Protocols Publishing, New York). Bound poly(A)+ mRNA is eluted from the affinity column using 2 mM EDTA/ 0.1% SDS.

Target polynucleotides can be detectably labeled at one or more nucleotides using methods known in the art. The label or detectable substance or agent is preferably uniformly incorporated along the length of the RNA, and more preferably, is carried out at a high degree of efficiency. The detectable label, substance or agent can be a luminescent label, fluorescent label, bio-luminescent label, chemi-luminescent label, radio-label, and colorimetric label. In a particular embodiment, the label is a fluorescent label, such as a fluorescein, a phosphor, a rhodamine, or a polymethine dye derivative. Commercially available fluorescent labels include, for example, fluorescent phosphoramidites such as FluorePrime (Amersham Pharmacia, Piscataway, N.J.), Fluoredite (Millipore, Bedford, Mass.), FAM (ABI, Foster City, Calif.), and Cy3 or Cy5 (Amersham Pharmacia, Piscataway, N.J.).

Target polynucleotides from a patient sample can be labeled differentially from polynucleotides of a standard. The standard can comprise target polynucleotides from normal individuals (i.e., those not afflicted with or pre-disposed to a urogenital condition), in particular pooled from samples from normal individuals. The target polynucleotides can be derived from the same individual, but taken at different time points, and thus may indicate the efficacy of a treatment by a change in expression of the markers, or lack thereof, during and after the course of treatment.

The terms "subject", "individual" or "patient" refer to a warm-blooded animal such as a mammal. In particular, the terms refer to a human. A subject, individual or patient may be afflicted with, at risk for, or suspected of having or being pre-disposed to a urogenital condition. The term also includes domestic animals bred for food or as pets, including horses, cows, sheep, pigs, cats, dogs, and zoo animals. Typical subjects for treatment include persons susceptible to, suffering from or that have suffered a condition or disease described herein. In particular, suitable subjects for treatment in accordance with the invention are persons that are susceptible to, suffering from or that have suffered a urogenital condition.

A subject at risk for a condition disclosed herein includes a subject with one or more risk factors for developing the condition. As used herein, the term "characterizing a condition in a subject" refers to the identification of one or more properties of a sample in a subject, including but not limited to the subject's prognosis. A condition may be characterized by the identification of the expression of one or more urogenital markers or polynucleotides encoding urogenital markers.

As used herein, the term "treat" or "treating" refers to any method used to partially or completely alleviate, ameliorate, relieve, inhibit, prevent, delay onset of, reduce severity of and/or reduce incidence of one or more symptoms or features of a particular condition. Treatment may be administered to a subject who does not exhibit signs of a condition and/or exhibits only early signs of the condition for the purpose of decreasing the risk of developing pathology associated with the condition. Thus, depending on the state of the subject, the term in some aspects of the invention may refer to preventing a condition, and includes preventing the onset, or preventing the symptoms associated with a condition. The term also includes maintaining the condition and/or symptom such that the condition and/or symptom do not progress in severity. A treatment may be either performed in an acute or chronic way. The term also refers to reducing the severity of a condition or symptoms associated with such condition prior to affliction with the condition. Such prevention or reduction of the severity of a condition prior to affliction refers to administration of a therapy to a subject that is not at the time of administration afflicted with the condition. Preventing also includes preventing the recurrence of a condition, or of one or more symptoms associated with such condition. The terms "treatment" and "therapeutically" refer to the act of treating, as "treating" is defined above. The purpose of intervention is to combat the condition and includes the administration of therapy to prevent or delay the onset of the symptoms or complications, or alleviate the symptoms or complications, or eliminate the condition. For example, a treatment may be used to ameliorate symptoms associated with a urogenital condition.

The term "urogenital marker" includes a polypeptide marker associated with normal urogenital tissue or a condition of the urogenital tract identified using a method of the invention. The term includes native-sequence polypeptides isoforms, chimeric polypeptides, complexes, all homologs, fragments, precursors, and modified forms and derivatives of the markers.

A urogenital marker may be associated with a urogenital condition, in particular it may be a urogenital disease marker. The term "urogenital disease marker" includes a marker associated with urogenital condition identified using a method of the invention, in particular a marker of any one of Tables 1 to 13.

A "native-sequence polypeptide" comprises a polypeptide having the same amino acid sequence of a polypeptide derived from nature. Such native-sequence polypeptides can be isolated from nature or can be produced by recombinant or synthetic means. The term specifically encompasses naturally occurring truncated or secreted forms of a polypeptide, polypeptide variants including naturally occurring variant forms (e.g. alternatively spliced forms or splice variants), and naturally occurring allelic variants.

The term "variant" means a polypeptide having at least about 45%, 50%, 55%, 60%, 65%, 70%, 75%, 80%, 85%, 90%, 95%, 97%, 98%, or 99% amino acid sequence identity, particularly at least about 70-80%, more particularly at least about 85%, still more particularly at least about 90%, most particularly at least about 95% amino acid sequence identity with a native-sequence polypeptide. Such variants include, for instance, polypeptides wherein one or more amino acid residues are added to, or deleted from, the N- or C-terminus of the full-length or mature sequences of the polypeptide, including variants from other species, but excludes a native-sequence polypeptide. In aspects of the invention variants retain the immunogenic activity of the corresponding native-sequence polypeptide.

Percent identity of two amino acid sequences, or of two nucleic acid sequences, is defined as the percentage of amino acid residues or nucleotides in a candidate sequence that are identical with the amino acid residues in a polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various conventional ways, for instance, using publicly available computer software including the GCG program package (Devereux J. et al., Nucleic Acids Research 12(1): 387, 1984); BLASTP, BLASTN, and FASTA (Atschul, S. F. et al. J. Molec. Biol. 215: 403-410, 1990). The BLAST X program is publicly available from NCBI and other sources (BLAST Manual, Altschul, S. et al. NCBI NLM NIH Bethesda, Md. 20894; Altschul, S. et al. J. Mol. Biol. 215: 403-410, 1990). Skilled artisans can determine appropriate parameters for measuring alignment, including any algorithms needed to achieve maximal alignment over the full length of the sequences being compared. Methods to determine identity and similarity are codified in publicly available computer programs.

An allelic variant may also be created by introducing substitutions, additions, or deletions into a polynucleotide encoding a native polypeptide sequence such that one or more amino acid substitutions, additions, or deletions are introduced into the encoded protein. Mutations may be introduced by standard methods, such as site-directed mutagenesis and PCR-mediated mutagenesis. In an embodiment, conservative substitutions are made at one or more predicted non-essential amino acid residues. A "conservative amino acid substitution" is one in which an amino acid residue is replaced with an amino acid residue with a similar side chain. Amino acids with similar side chains are known in the art and include amino acids with basic side chains (e.g. Lys, Arg, His), acidic side chains (e.g. Asp, Glu), uncharged polar side chains (e.g. Gly, Asp, Glu, Ser, Thr, Tyr and Cys), nonpolar side chains (e.g. Ala, Val, Leu, Iso, Pro, Trp), beta-branched side chains (e.g. Thr, Val, Iso), and aromatic side chains (e.g. Tyr, Phe, Trp, H is). Mutations can also be introduced randomly along part or all of the native sequence, for example, by saturation mutagenesis. Following mutagenesis the variant polypeptide can be recombinantly expressed and the activity of the polypeptide may be determined.

Polypeptide variants include polypeptides comprising amino acid sequences sufficiently identical to or derived from the amino acid sequence of a native polypeptide which include fewer amino acids than the full length polypeptides. A portion of a polypeptide can be a polypeptide which is for example, 10, 15, 20, 25, 30, 35, 40, 45, 50, 60, 70, 80, 90, 100 or more amino acids in length. Portions in which regions of a polypeptide are deleted can be prepared by recombinant techniques and can be evaluated for one or more functional activities such as the ability to form antibodies specific for a polypeptide.

A naturally occurring allelic variant may contain conservative amino acid substitutions from the native polypeptide sequence or it may contain a substitution of an amino acid from a corresponding position in a polypeptide homolog, for example, a murine polypeptide.

Urogenital markers include chimeric or fusion proteins. A "chimeric protein" or "fusion protein" comprises all or part (preferably biologically active) of a urogenital marker operably linked to a heterologous polypeptide (i.e., a polypeptide other than a urogenital marker). Within the fusion protein, the term "operably linked" is intended to indicate that a urogenital marker and the heterologous polypeptide are fused in-frame to each other. The heterologous polypeptide can be fused to the N-terminus or C-terminus of a urogenital marker. A useful fusion protein is a GST fusion protein in which a urogenital marker is fused to the C-terminus of GST sequences. Another example of a fusion protein is an immunoglobulin fusion protein in which all or part of a urogenital marker is fused to sequences derived from a member of the immunoglobulin protein family. Chimeric and fusion proteins can be produced by standard recombinant DNA techniques.

A modified form of a polypeptide referenced herein includes modified forms of the polypeptides and derivatives of the polypeptides, including post-translationally modified forms such as glycosylated, phosphorylated, acetylated, methylated or lapidated forms of the polypeptides.

In an aspect of the invention, the urogenital marker is extracellular matrix protein 1 (ECM1), including without limitation, human ECM1, in particular the native-sequence polypeptide, isoforms, chimeric polypeptides, all homologs, fragments, precursors, complexes, and modified forms and derivatives of human ECM1. The amino acid sequence for native human ECM1 includes the amino acid sequences referenced in NCBI Gene ID: 1893, including GenBank Accession Nos. $NP_{13}$ 001189787.1, $NP_{13}$ 004416.2 and $NP_{13}$ 073155.2 (see SEQ ID NO:37,38, and 39).

In an aspect of the invention, the urogenital marker is testis expressed 101 (TEX101), including without limitation, human TEX101, in particular the native-sequence polypeptide, isoforms, chimeric polypeptides, all homologs, fragments, precursors, complexes, and modified forms and derivatives of human TEX101. The amino acid sequence for native human TEX101 includes the amino acid sequences referenced in NCB I Gene ID: 83639, including GenBank Accession Nos. $NP_{13}$ 001123483.1 and $NP_{13}$ 113639.4 (see SEQ ID NO: 40 and 41). In an aspect, the urogenital marker is isoform 2 of testis-expressed protein 101 [SEQ ID NO: 40].

In an aspect of the invention, the urogenital marker is lactate dehydrogenase (LDHC), including without limitation, human LDHC, in particular the native-sequence polypeptide, isoforms, chimeric polypeptides, all homologs, fragments, precursors, complexes, and modified forms and derivatives of human LDHC. The amino acid sequence for native human LDHC includes the amino acid sequences referenced in NCBI Gene ID: 3948, including GenBank Accession Nos. $NP_{13}$ 002292 and $NP_{13}$ 059144 (see SEQ ID NO. 42).

In an aspect of the invention, the urogenital marker is sperm associated antigen 11B (SPAG11B), including without limitation, human SPAG11B, in particular the native-sequence polypeptide, isoforms, chimeric polypeptides, all homologs, fragments, precursors, complexes, and modified forms and derivatives of human SPAG11B. The amino acid sequence for native human SPAG11B includes the amino acid sequences referenced in NCBI Gene ID: 10407.

In an aspect of the invention, the urogenital marker is sorbital dehydrogenase (SORD), including without limitation, human SORD, in particular the native-sequence polypeptide, isoforms, chimeric polypeptides, all homologs, fragments, precursors, complexes, and modified forms and derivatives of human SORD. The amino acid sequence for native human SORD includes the amino acid sequences referenced in NCBI Gene ID: 6652, including GenBank Accession Nos. NP_003095.2.

In an aspect of the invention, the urogenital marker is gamma-glutamyltransferase 7 (GGT7), including without limitation, human GGT7, in particular the native-sequence polypeptide, isoforms, chimeric polypeptides, all homologs, fragments, precursors, complexes, and modified forms and derivatives of human GGT7. The amino acid sequence for native human GGT7 includes the amino acid sequences referenced in NCBI Gene ID: 2686, including GenBank Accession Nos. NP_821158.2.

Urogenital markers identified in accordance with a method of the invention may be prepared by recombinant or synthetic methods, or isolated from a variety of sources, or by any combination of these and similar techniques.

"Urogenital polynucleotide marker(s)", polynucleotides encoding the marker(s)", and "polynucleotides encoding urogenital markers" refer to polynucleotides that encode urogenital markers including native-sequence polypeptides, polypeptide variants including a portion of a polypeptide, an isoform, homolog, precursor, complex, a chimeric polypeptide, or modified forms and derivatives of the polypeptides. A urogenital polynucleotide marker includes the polynucleotides encoding the polypeptides of any one of Tables 1 to 13.

Urogenital polynucleotide markers include complementary nucleic acid sequences, and nucleic acids that are substantially identical to these sequences (e.g. having at least about 45%, 50%, 55%, 60%, 65%, 70%, 75%, 80%, 85%, 90%, 95%, 97%, 98%, or 99% sequence identity).

Urogenital polynucleotide markers also include sequences that differ from a native sequence due to degeneracy in the genetic code. As one example, DNA sequence polymorphisms within the nucleotide sequence of a urogenital marker may result in silent mutations that do not affect the amino acid sequence. Variations in one or more nucleotides may exist among individuals within a population due to natural allelic variation. DNA sequence polymorphisms may also occur which lead to changes in the amino acid sequence of a polypeptide.

Urogenital polynucleotide markers also include nucleic acids that hybridize under stringent conditions, preferably high stringency conditions, to a urogenital polynucleotide marker, in particular a urogenital disease polynucleotide marker. Appropriate stringency conditions which promote DNA hybridization are known to those skilled in the art, or can be found in Current Protocols in Molecular Biology, John Wiley & Sons, N.Y. (1989), 6.3.1-6.3.6. For example, 6.0× sodium chloride/sodium citrate (SSC) at about 45° C., followed by a wash of 2.0×SSC at 50° C. may be employed. The stringency may be selected based on the conditions used in the wash step. By way of example, the salt concentration in the wash step can be selected from a high stringency of about 0.2×SSC at 50° C. In addition, the temperature in the wash step can be at high stringency conditions, at about 65° C.

Urogenital polynucleotide markers also include truncated nucleic acids or nucleic acid fragments and variant forms of the nucleic acids that arise by alternative splicing of an mRNA corresponding to a DNA.

The urogenital polynucleotide markers are intended to include DNA and RNA (e.g. mRNA) and can be either double stranded or single stranded. A polynucleotide may, but need not, include additional coding or non-coding sequences, or it may, but need not, be linked to other molecules and/or carrier or support materials. The polynucleotides for use in the methods of the invention may be of any length suitable for a particular method. In certain applications the term refers to antisense polynucleotides (e.g. mRNA or DNA strand in the reverse orientation to sense disease polynucleotide markers).

In an aspect, a polynucleotide urogenital marker encodes ECM1 more particularly a polynucleotide sequence referenced in NCBI Gene ID. 1893, or a fragment thereof, including GenBank Accession Nos. NM_001202858.1, NM_004425.3 and NM_022664.2.

In an aspect, a polynucleotide urogenital marker encodes TEX101 more particularly a polynucleotide sequence referenced in NCBI Gene ID. 83639, or a fragment thereof, including GenBank Accession Nos. NM_001130011.1 and NM_031451.4.

In an aspect, a polynucleotide urogenital marker encodes LDHC more particularly a polynucleotide sequence referenced in NCBI Gene ID. 3948, or a fragment thereof, including GenBank Accession Nos. NM_002301.4 and NM_017448.3.

In an aspect, a polynucleotide urogenital marker encodes SPAG11B more particularly a polynucleotide sequence referenced in NCBI Gene ID. 10407, or a fragment thereof.

In an aspect, a polynucleotide urogenital marker encodes SORD more particularly a polynucleotide sequence referenced in NCBI Gene ID. 6652, or a fragment thereof.

In an aspect, a polynucleotide urogenital marker encodes GGT7 more particularly a polynucleotide sequence referenced in NCBI Gene ID. 2686, or a fragment thereof.

"Statistically different levels", "significantly altered", or "significant difference" in levels of markers in a patient sample compared to a control or standard (e.g. normal levels or levels in other samples from a patient) may represent levels that are higher or lower than the standard error of the detection assay. In particular embodiments, the levels may be 1.5, 2, 3, 4, 5, or 6 times higher or lower than the control or standard.

"Microarray" and "array" refer to nucleic acid or nucleotide arrays or protein or peptide arrays that can be used to detect biomolecules associated with the urogenital tract or a urogenital condition, for instance to measure gene expression. A variety of arrays are made in research and manufacturing facilities worldwide, some of which are available commercially. By way of example, spotted arrays and in situ synthesized arrays are two kinds of nucleic acid arrays that differ in the manner in which the nucleic acid materials are placed onto the array substrate. A widely used in situ synthesized oligonucleotide array is GeneChip™ made by Affymetrix, Inc. Oligonucleotide probes that are 20- or 25-base long can be synthesized in silico on the array substrate. These arrays can achieve high densities (e.g., more than 40,000 genes per $cm^2$). Generally spotted arrays have lower densities, but the probes, typically partial cDNA molecules, are much longer than 20- or 25-mers. Examples of spotted cDNA arrays include LifeArray made by Incyte Genomics and DermArray made by IntegriDerm (or Invitrogen). Pre-synthesized and amplified cDNA sequences are attached to the substrate of spotted arrays. Protein and peptide arrays also are known [see for example, Zhu et al., *Science* 293:2101 (2001)].

The preparation, use, and analysis of microarrays are well known to a person skilled in the art. (See, for example, Brennan, T. M. et al. (1995) U.S. Pat. No. 5,474,796; Schena, et al. (1996) Proc. Natl. Acad. Sci. 93:10614-10619; Baldeschweiler et al. (1995), PCT Application WO95/251116; Shalon, D. et al. (I 995) PCT application WO95/35505; Heller, R. A. et al. (1997) Proc. Natl. Acad. Sci. 94:2150-2155; and Heller, M. J. et al. (1997) U.S. Pat. No. 5,605,662.)

"Binding agent" refers to a substance such as a polypeptide or antibody that specifically binds to one or more urogenital markers. A binding agent, in particular an antibody, that "specifically binds" or "binds" (used interchangeably herein) to a target or an antigen or epitope is a term well understood in the art, and methods to determine specific binding are also well known in the art. A binding agent "specifically binds" to a target if it binds with greater affinity, avidity, more readily, and/or with greater duration than it binds to other substances. It will be appreciated that an antibody that specifically binds to a first target may or may not specifically or preferentially bind to a second target. Thus, "specific binding" does not necessarily require (although it can include) exclusive binding but generally refers to preferential binding. Binding properties may be assessed using an ELISA, which may be readily performed by those skilled in the art (see for example, Newton et al, Develop. Dynamics 197: 1-13, 1993). In an embodiment of the invention, antibodies are reactive against a polypeptide marker if they bind with a $K_a$ of greater than or equal to $10^{-7}$ M.

A binding agent may be a ribosome, with or without a peptide component, an aptamer, an RNA molecule, or a polypeptide. A binding agent may be a polypeptide that comprises one or more urogenital marker sequence, a peptide variant thereof, or a non-peptide mimetic of such a sequence. By way of example, a SPAG11B or MUC15 sequence may be a peptide portion of a SPAG11B or MUC15 that is capable of modulating a function mediated by SPAG11B or MUC15.

An aptamer includes a DNA or RNA molecule that binds to nucleic acids and proteins. An aptamer that binds to a protein (or binding domain) of a urogenital marker or a urogenital polynucleotide marker can be produced using conventional techniques, without undue experimentation. [For example, see the following publications describing in vitro selection of aptamers: Klug et al., Mol. Biol. Reports 20:97-107 (1994); Wallis et al., Chem. Biol. 2:543-552 (1995); Ellington, Curr. Biol. 4:427-429 (1994); Lato et al., Chem. Biol. 2:291-303 (1995); Conrad et al., Mol. Div. 1:69-78 (1995); and Uphoff et al., Curr. Opin. Struct. Biol. 6:281-287 (1996)].

Antibodies for use in the present invention include but are not limited to synthetic antibodies, monoclonal antibodies, polyclonal antibodies, recombinant antibodies, antibody fragments (such as Fab, Fab', F(ab')2), dAb (domain antibody; see Ward, et al, 1989, Nature, 341:544-546), antibody heavy chains, intrabodies, humanized antibodies, human antibodies, antibody light chains, single chain $F_{vs}$ (scFv) (e.g., including monospecific, bispecific etc), anti-idiotypic (ant-Id) antibodies, proteins comprising an antibody portion, chimeric antibodies (for example, antibodies which contain the binding specificity of murine antibodies, but in which the remaining portions are of human origin), derivatives, such as enzyme conjugates or labeled derivatives, diabodies, linear antibodies, disulfide-linked Fvs (sdFv), multispecific antibodies (e.g., bispecific antibodies), epitope-binding fragments of any of the above, and any other modified configuration of an immunoglobulin molecule that comprises an antigen recognition site of the required specificity. An antibody includes an antibody of any type (e.g. IgA, IgD, IgE, IgG, IgM and IgY), any class (e.g. IgG1, IgG2, IgG3, IgG4, IgA1 and IgA2), or any subclass (e.g. IgG2a and IgG2b), and the antibody need not be of any particular type, class or subclass. In certain embodiments of the invention the antibodies are IgG antibodies or a class or subclass thereof. An antibody may be from any animal origin including birds and mammals (e.g. human, murine, donkey, sheep, rabbit, goat, guinea pig, camel, horse, or chicken).

A "recombinant antibody" includes antibodies that are prepared, expressed, created or isolated by recombinant means, such as antibodies expressed using a recombinant expression vector transfected into a host cell, antibodies isolated from recombinant, combinatorial antibody libraries, antibodies isolated from an animal (e.g. a mouse or cow) that is transgenic and/or transchromosomal for human immunoglobin genes, or antibodies prepared, expressed, created or isolated by any other means that involves slicing of immunoglobulin gene sequences to other DNA sequences.

A "monoclonal antibody" refers to an antibody obtained from a population of homogenous or substantially homogenous antibodies. Generally each monoclonal antibody recognizes a single epitope on an antigen. In aspects of the invention, a monoclonal antibody is an antibody produced by a single hybridoma or other cell, and it specifically binds to only a urogenital marker as determined, for example by ELISA or other antigen-binding or competitive binding assay known in the art. The term is not limited to a particular method for making the antibody and for example they may be produced by the hybridoma method or isolated from phage libraries using methods known in the art.

Antibodies, including monoclonal and polyclonal antibodies, fragments and chimeras, may be prepared using methods well known to those skilled in the art. Isolated native or recombinant polypeptides may be utilized to prepare antibodies. See, for example, Kohler et al. (1975) Nature 256:495-497; Kozbor et al. (1985) J. Immunol. Methods 81:31-42; Cote et al. (1983) Proc Natl Acad Sci 80:2026-2030; and Cole et al. (1984) Mol Cell Biol 62:109-120 for the preparation of monoclonal antibodies; Huse et al. (1989) Science 246:1275-1281 for the preparation of monoclonal Fab fragments; and, Pound (1998) Immunochemical Protocols, Humana Press, Totowa, N.J. for the preparation of phagemid or B-lymphocyte immunoglobulin libraries to identify antibodies. Antibodies specific for polypeptide markers may also be obtained from scientific or commercial sources.

The "status" of a marker refers to the presence, absence or extent/level of the marker or some physical, chemical or genetic characteristic of the marker. Such characteristics include without limitation, expression level, activity level, structure (sequence information), copy number, post-translational modification etc. The status of a marker may be directly or indirectly determined. In some embodiments status is determined by determining the level of a marker in the sample. The "level" of an element in a sample has its conventional meaning in the art, and includes quantitative determinations (e.g. mg/mL, fold change, etc) and qualitative determinations (e.g. determining the presence or absence of a marker or determining whether the level of the marker is high, low or even present relative to a standard).

The term "abnormal status" means that a marker's status in a sample is different from a reference status for the marker. A reference status may be the status of the marker in samples from normal subjects, averaged samples from subjects with the condition or sample(s) from the same subject taken at different times. An abnormal status includes an elevated, decreased, present or absent marker(s). Determining the level of a marker in a sample may include determining the level of the marker in a sample and abnormal status could be either lower levels (including undetectable levels) or higher levels (including any amount over zero) compared to a standard. A subject may have an increased likelihood of a condition disclosed herein if the status of a marker in the subject's sample is correlated with the condition (e.g. a level of the marker is closer to a standard or reference or is present in levels that exceed some threshold value where exceeding that value is correlated with the condition). A subject with an increased likelihood of a condition disclosed herein includes a subject with an abnormal status for a marker and as such the subject has a higher likelihood of the condition than if the subject did not have that status.

An "elevated status" means one or more characteristics of a marker are higher than a standard. In aspects of the invention, the term refers to an increase in a characteristic as compared to a standard. A "low status" means one or more characteristics of a marker are lower than a standard. In aspects of the invention, the term refers to a decrease in a characteristic as compared to a standard. A "negative status" means that one or more characteristic of a marker is absent or undetectable.

Markers

The invention provides a set of markers correlated with the male urogenital tract or a urogenital condition. A subset of these markers identified as useful for detection, diagnosis, prevention and therapy of a urogenital condition is one, two or more markers of any one of Tables 1 to 13. The invention also provides a method of using these markers to distinguish or determine the status of organs and tissues of the urogenital tract or to distinguish a urogenital condition.

The invention provides marker sets that distinguish organs and tissues of the urogenital tract or a urogenital condition and uses therefor. In an aspect, the invention provides a marker set for classifying an organ or tissue of the urogenital tract or a urogenital condition comprising a first plurality of urogenital markers or urogenital polynucleotide markers, the first plurality of urogenital markers or urogenital polynucleotide markers consisting of at least 2, 3, 4, 5, 8, 10, 20 or 25 of the markers of any one of Tables 1 to 13 or polynucleotides encoding the markers.

In an aspect, the invention provides markers that distinguish a urogenital condition identified by assaying for differential expression of polypeptides in seminal plasma samples from normal subjects and post-vasectomy subjects.

Any of the markers provided herein may be used alone or with other markers of organs and tissues of the urogenital tract or a urogenital condition, or with markers for other phenotypes or conditions.

Identification of Urogenital Markers

The invention relates to a method for identifying markers associated with the organs and tissues of the urogenital tract, or associated with a condition of the urogenital tract comprising:

(a) obtaining a sample of seminal fluid from a normal subject or a subject with a urogenital condition (e.g. vasectomy);
(b) extracting proteins from the sample and producing a profile of the proteins by subjecting the proteins to mass spectrometry; and
(c) comparing the profile with a profile for a reference to identify to proteins associated with organs and tissues of the urogenital tract or a urogenital condition.

Proteins may be extracted from the samples in a manner known in the art. For example, proteins may be extracted by ultra-centrifugation or other standard techniques.

The separated proteins may be digested into peptides, in particular using proteolytic enzymes such as trypsin, pepsin, subtilisin, and proteinase. For example, proteins may be treated with trypsin which cleaves at the sites of lysine and arginine, to provide doubly-charged peptides with a length of from about 5 to 50 amino acids. Such peptides may be particularly appropriate for mass spectrometry analysis, especially electrospray ionization mass spectrometry. Chemical reagents including cyanogen bromide may also be utilized to digest proteins.

Mass spectrometers that may be used to analyze the peptides or proteins include a Matrix-Assisted Laser Desorption/Ioniation Time-of-Flight Mass Spectrometer ("MALDI-TOF") (e.g. from PerSeptive Biosystems, Framingham, Mass.); an Electrospray Ionization ("ESI") ion trap spectrometer, (e.g. from Finnigan MAT, San Jose, Calif.), an ESI quadrupole mass spectrometer (e.g. from Finnigan or Perkin-Elmer Corporation, Foster City, Calif.), a quadrupole/TOF hybrid tandem mass spectrometer, QSTAR XL (Applied Biosystems/MDS Sciex), or a Surface Enhanced Laser Desorption/Ionization (SELDI-TOF) Mass Spectrometer (e.g. from Ciphergen Biosystems Inc.).

Comparing the profile with a profile for a reference may include using a statistical method to calculate a significance value for each of the markers in the profile, and data having a significance value within a predetermined range may identify markers associated with organs and tissues of the urogenital tract or a urogenital condition.

Markers associated with the organs and tissues of the urogenital tract, or associated with a condition of the urogenital tract, can also be identified by detecting and comparing markers expressed in samples (e.g. semen or tissues) from normal subjects or subjects with a urogenital condition (e.g. vasectomy) using antibodies and polynucleotides (e.g. mRNA) using methods described herein or known in the art.

Detection Methods

A variety of methods can be employed for the diagnostic and prognostic evaluation of a urogenital condition or urogenital status involving one or more urogenital markers and polynucleotides encoding the markers, and the identification of subjects with a predisposition to urogenital conditions. Such methods may, for example, utilize urogenital polynucleotide markers, and fragments thereof, and binding agents (e.g. antibodies) against one or more urogenital markers, including peptide fragments. In particular, the polynucleotides and antibodies may be used, for example, for (1) the detection of the presence of urogenital polynucleotide marker mutations, or the detection of either over- or under-expression of urogenital polynucleotide markers relative to a non-disorder state or different urogenital status, or the qualitative or quantitative detection of alternatively spliced forms of urogenital polynucleotide marker transcripts which may correlate with certain conditions or susceptibility toward such conditions; and (2) the detection of either an over- or an under-abundance of one or more urogenital markers relative to a non-disorder state or a different urogenital status or the presence of a modified (e.g., less than full length) urogenital marker which correlates with a disorder state or a progression toward a disorder state, or a particular urogenital state.

The methods described herein can be adapted for diagnosing and monitoring urogenital status or a urogenital condition by detecting one or more urogenital markers or polynucleotides encoding the markers in biological samples from a subject. These applications can require that the amount of markers or polynucleotides quantitated in a sample from a subject being tested be compared to a control, predetermined standard, reference or cut-off value. The standard may correspond to levels quantitated for another sample or an earlier sample from the subject, or levels quantitated for a control sample. Levels for control samples from healthy subjects, different urogenital status, or subjects with a urogenital condition may be established by prospective and/or retrospective statistical studies. Healthy subjects who have no clinically evident disease or abnormalities may be selected for statistical studies. Diagnosis may be made by a finding of statistically different levels of detected urogenital markers associated with a condition or polynucleotides encoding same, compared to a control sample or previous levels quantitated for the same subject.

The invention contemplates a method for detecting the status of a urogenital tissue or organ comprising producing a profile of levels of one or more urogenital marker associated with a known urogenital state and/or polynucleotides encoding the markers, and optionally other markers associated with the urogenital state in samples from a patient, and comparing the profile with a reference to identify a profile for the samples indicative of the urogenital status. Comparing the profile with a reference may include using a statistical method to calculate a significance value for each of the markers in the profile, and data having a significance value within a predetermined range may identify markers or a profile of markers indicative of the urogenital status.

In an aspect the markers are specific for testis and/or epididymis, in particular the markers comprise the markers of Table 1.

In an aspect the markers are specific for regions of the male reproductive tract other than testis and/or epididymis, in particular the markers comprise the markers of Table 2.

The invention also contemplates a method for detecting a urogenital condition comprising producing a profile of levels of one or more urogenital marker associated with the urogenital condition and/or polynucleotides encoding the urogenital markers, and other markers associated with the urogenital condition in samples from a patient, and comparing the profile with a reference to identify a profile for the test cells indicative of the condition. Comparing the profile with a reference may include using a statistical method to calculate a significance value for each of the markers in the profile, and data having a significance value within a predetermined range may identify markers or a profile of markers diagnostic of the urogenital condition.

In an aspect, the invention contemplates a method for diagnosis of a urogenital condition in a subject comprising: (a) obtaining a sample from the subject; (b) subjecting the sample to a procedure to detect urogenital markers or polynucleotides encoding the urogenital markers in the sample; (c) diagnosing the condition by comparing the amount or status of urogenital markers or polynucleotides to the amount or status of markers or polynucleotides obtained from a control subject who does not suffer from the condition or the subject taken at a different time. The procedure may comprise: (a) contacting the sample with antibodies that specifically bind to the urogenital markers under conditions effective to bind the antibodies and form complexes; and (b) measuring the amount of urogenital markers present in the sample by quantitating the amount of the complexes, wherein a change or significant difference in the amount of urogenital markers in the sample compared with the amount obtained from a control subject who does not suffer from the condition or the subject taken at a different time is indicative of the condition. The procedure may comprise detecting one or more polynucleotides encoding the urogenital markers in the sample by contacting the sample with oligonucleotides that hybridize to the polynucleotides; and detecting in the sample the amount or status of nucleic acids that hybridize to the polynucleotides relative to the amount or status from a control subject or the subject taken at a different time, wherein a change or significant difference in the amount or status of urogenital markers in the sample compared with the amount from the control or subject taken at a different time is indicative of the condition.

In an aspect, the urogenital markers are one or more of the markers of Table 1, 2, 3, 4, 5, 6, 7, 8, 9, 10, 11, 12 or 13. In an aspect, the urogenital markers are one or more of the markers of Table 12.

In an embodiment the condition is infertility and the urogenital markers are the markers of Table 1, 2, 3, 4, 7, 10, 11, 12 or 13. In an embodiment the condition is infertility and the urogenital markers are the markers of Table 6 or 7. In an embodiment the condition is infertility and the urogenital markers are the markers of Table 12 or 13.

In an embodiment the condition is infertility and the urogenital markers are ECM1, TEX101 and/or LDHC.

In an embodiment the condition is infertility and the urogenital markers are selected from the group consisting of HIST1H4H, DPEP3, TEX101, CEL, PGK2, PRKACA, PGAM2, SLC2A14, CDH2 and ASRGLI.

In an embodiment the condition is infertility and the urogenital markers are selected from the group consisting of TEX101, PGK2, HIST1H4H, SLC2A14, SPACA3, GAPDHS and AKAP4.

In an embodiment the condition is infertility and the urogenital markers are one, two, three or more, or all of the markers in Table 5.

In an embodiment the condition is infertility and the urogenital markers are one, two, three or more, or all of the markers in Table 12.

In an embodiment the condition is infertility and the urogenital markers are selected from the group consisting of CAMP, ECM1, CRISP1, PTGDS, MGAM, SPINT3, GPR64, NPC2, CD177, FAM12B, LDHC, CEL, ADAM7, CES7, ALDH1A1, TEX101, MUC15, CA4 and SPAG11B.

In an embodiment the condition is azoospermia and the urogenital markers are the markers of Table 7 or 13.

In an embodiment the condition is azoospermia and the urogenital markers are the markers selected from the group consisting of SPAG11B, TEX101, MUC15, FAM12B, LDHC, ECM1, ADAM7, CEL, SPINT3, CRISP1, CAMP, CES7, MGAM, GPR64, CA4, and PTGDS.

In an embodiment the condition is azoospermia and the urogenital markers are the markers selected from the group consisting of LDHC, SPAG11B, TEX101, MUC15, FAM12B, ECM1, ADAM7, CEL, SPINT3, CRISP1, CAMP, CES7, MGAM, GPR64, CA4, NPC2, ALDH1A1 and PTGDS.

In an embodiment the condition is azoospermia and the urogenital markers are the markers of Table 7.

In an embodiment, the condition is azoospermia and the urogenital markers are at least one, two, three or more of SPAG11B, TEX101, MUC15, FAM12B, LDHC, ECM1, ADAM7, CEL, SPINT3, CRISP1, PATE4, and PTGDS.

In an embodiment the condition is azoospermia and the urogenital markers are at least one, two, three or more of SPAG11B, TEX101, MUC15, ECM1, ADAM7, LDHC, and PTGDS.

In an embodiment the condition is azoospermia and the urogenital markers are TEX101, LDHC and CEL.

In an embodiment the condition is azoospermia and the urogenital markers are ECM1, TEX101 and LDHC.

In an embodiment the condition is azoospermia and the urogenital markers are the markers selected from the group consisting of LDHC, ELSPBP1, CES7, A2M, OVCH2, PTGDS, GPR64 and ALDH1A1.

In an embodiment the condition is NOA and the urogenital markers are selected from the group consisting of MUC15, SPAG11B, FAM12B, ADAM7, CEL, ALDH1A1, PATE4, and PTGDS more particularly at least one, two or more of TEX101, LDHC, CEL, ALDH1A1, PATE4 and PTGDS.

In an embodiment the condition is NOA and the urogenital markers are selected from the group consisting of TEX101, LDHC, CEL, ECM1, CAMP, MGAM, MUC15, CES7, SPINT3, FAM12B, CRISP1, SPAG11B, ADAM7 and GPR64.

In an embodiment the condition is NOA and the urogenital markers are selected from the group consisting of ECM1, CAMP, MGAM, MUC15, CES7, SPINT3, FAM12B, CRISP1, SPAG11B, ADAM7 and GPR64.

In an embodiment the condition is NOA and the urogenital markers are the markers of Table 7, in particular TEX101, LDHC, MUC15, SPAG11B, FAM12B, ADAM7, CEL, ALDH1A1, PATE4, and PTGDS, more particularly at least one, two or more of TEX101, LDHC, CEL, ALDH1A1, PATE4 and PTGDS.

In an embodiment the condition is NOA and the urogenital markers are the markers of Table 13, in particular, LDHC, TEX101, PTGDS, CEL, MUC15, SPAG11B, ALDH1A1, GPR64, CA4, ADAM7, ECM1, CRISP1, FAM12B, SPINT3, CAMP, CES7, MGAM, and NPC2, more particularly at least one, two or more or all of LDHC, TEX101, PTGDS, CEL, MUC15, SPAG11B, ALDH1A1, GPR64, CA4, and ADAM7, most particularly LDHC, TEX101, ECM1, CRISP1, CAMP and MGAM.

In an embodiment the condition is NOA and the urogenital markers are LDHC, TEX101, PTGDS, CEL, MUC15, SPAG11B, ALDH1A1, GPR64, CA4 and ADAM7.

In an embodiment the condition is NOA and the urogenital markers are LDHC, TEX101, PTGDS, CEL, MUC15, SPAG11B, ALDH1A1, GPR64, CA4, ADAM7 and CES7.

In an embodiment the condition is NOA and the urogenital markers are ECM1, CRISP1, FAM12B, SPINT3, CAMP, PTGDS, CES7, ADAM7, MGAM, SPAG11B, MUC15, CEL, NPC2, CA4, and GPR64.

In an embodiment the condition is NOA and the urogenital markers are ECM1, CAMP, MGAM, MUC15, CES7, SPINT3, FAM12B, CRISP1, SPAG11B, ADAM7 and GPR64.

In an embodiment the condition is NOA and the urogenital markers are TEX101, LDHC and CEL.

In a particular embodiment the condition is NOA and the urogenital markers are TEX101, LDHC and SPAG11B.

In a particular embodiment the condition is NOA and the urogenital markers are TEX101, LDHC, SPAG11B and PTGDS.

In an embodiment the condition is NOA and the urogenital markers are LDHC, AKAP4 and MGAM.

In a particular embodiment the condition is NOA and the urogenital markers are ECM1, TEX101 and LDHC.

In a particular embodiment the condition is NOA and the urogenital markers are ECM1, TEX101 and LDHC, and a decrease in levels of the markers relative to a control or standard or lower status are indicative of NOA.

In an embodiment the condition is NOA and the urogenital markers are ZPBP, ELSBPB1, PGAM2, SPAC3, GPR64 and SLC2A14. In a particular embodiment the condition is NOA and the urogenital markers are ZPBP, ELSBPB1, PGAM2, SPAC3, GPR64 and SLC2A14, and a decrease in levels of the markers relative to a control or standard or lower status are indicative of NOA.

In an embodiment the condition is NOA and the urogenital markers are CD177, WFDC2 and MPO.

In an embodiment the condition is NOA and the urogenital markers are LDHC, ELSPBP1, CES7, A2M, OVCH2, PTGDS, GPR64 and ALDH1A1.

In an embodiment the condition is NOA and the urogenital markers are LDHC, PTGDS, CA4 and GPR64.

In an embodiment the condition is NOA and the urogenital markers are the markers of Table 10.

In an embodiment the condition is NOA and the urogenital markers are selected from the group consisting of SORD, GGT7, STOM, OVCH2, PTGDS, CRISP2, LIPI, LDHC, SERPINA6, CA4, HISTIH2BA, MPO, VAV2, TGM2, SPARC, KIAA0368, EPS8L2, SPARCLI, COL6A2, DDX1, CST2 and CST4.

In an embodiment the condition is NOA and the urogenital markers are sorbital dehydrogenase (SORD) and GGT7.

In an embodiment the condition is NOA and the urogenital markers are selected from the group consisting of STOM, OVCH2, PTGDS, CRISP2, LIPI, LDHC, SERPINA6, CA4, HISTIH2BA and MPO, and a decrease in levels of the markers relative to a control or standard or lower status are indicative of NOA.

In an embodiment the condition is NOA and the urogenital markers are selected from the group consisting of VAV2, TGM2, SPARC, KIAA0368, EPS8L2, SPARCL1, COL6A2, DDX1, CST2 and CST4, and an increase in levels of the markers relative to a control or standard or elevated status are indicative of NOA.

In an embodiment the condition is NOA and the urogenital markers are the markers of Table 11.

In an embodiment the condition is NOA and the urogenital markers are selected from the group consisting of LDHC, BSPH1, ADAM7, MFGE8, REG3G, MFAP4, AKAP4, SORD, MUC5B, CPVL, CRIM2, SLC2A5, ELSPBP1, PATE4, LOC642103, SPINT3, COL18A1, BGN, HIST1H2BL, FGG, AZU1, GSTM2, PRELP, ORM1, FLJ11151, GFB, and PAEP.

In an embodiment the condition is NOA and the urogenital markers are LDHC, BSPH1, ADAM7, MFGE8, REG3G, MFAP4, AKAP and SORD.

In an embodiment the condition is NOA and the urogenital markers are selected from the group consisting of HIST1H2BL, FGG, AZU1, GSTM2, PRELP, ORM1, FLJ11151, GFB, MPO and PAEP, and a decrease in levels of the markers relative to a control or standard or lower status are indicative of NOA.

In an embodiment the condition is NOA and the urogenital markers are selected from the group consisting of MUC5B, CPVL, CRIM2, SLC2A5, ELSPBP1, PATE4, LOC642103, SPINT3, COL18A1 and BGN, and an increase in levels of the markers relative to a control or standard or elevated status are indicative of NOA.

In an embodiment, the condition is OA and the urogenital markers are the markers of Table 1.

In an embodiment the condition is OA and the urogenital markers are the markers of Table 2. In an embodiment the condition is OA and the urogenital markers are the markers of Table 2 and lower levels of the markers relative to a control or standard or low status of the markers is indicative of OA.

In an embodiment the condition is OA and the urogenital markers are the markers in Table 3. In an embodiment the condition is OA and the urogenital markers are the markers of Table 3 and elevated levels of the markers relative to a control or standard or elevated status of the markers is indicative of OA.

In an embodiment the condition is OA and the urogenital markers are the markers in Table 4. In an embodiment the condition is OA and the urogenital markers are selected from the group consisting of TEX101, PGK2, HISTIH2BA, SLC2A14, SPACA3, GAPDHS and AKAP4.

In an embodiment the condition is OA and the urogenital markers are selected from the group consisting of PTGDS, ELSPBP1, SPINT3, CRISP2, FAM12B, PATE4, NPC2 and CRISP1. In an embodiment the condition is OA and the urogenital markers are selected from the group consisting of PTGDS, ELSPBP1, SPINT3, CRISP2, FAM12B, PATE4, NPC2 and CRISP1 and lower levels of the markers relative to a control or standard or low status of the markers is indicative of OA.

In an embodiment the condition is OA and the urogenital markers are the markers in Table 7. In an embodiment the condition is OA and the urogenital markers are selected from the group consisting of LDHC, SPAG11B, TEX101, MUC15, PTGDS, ECM1, CEL, FAM12B, CAMP, SPINT3, CES7, MGAM, ADAM7, CRISP1, GPR64 and CA4. In another embodiment the condition is OA and the urogenital markers are selected from the group consisting of ECM1, CAMP, MGAM, MUC15, CES7, SPINT3, FAM12B, CRISP1, SPAG11B, ADAM7 and GPR64.

In an embodiment the condition is OA and the urogenital markers at least one, two or more of SPAG11B, TEX101, MUC15, FAM12B, LDHC, ECM1, MGAM, CAMP, CRISP1 and GPR64.

In an embodiment the condition is OA and the urogenital markers at least one, two or more of LDHC, SPAG11B, TEX101, MUC15, PTGDS, ECM1, CEL and FAM12B.

In an embodiment the condition is OA and the urogenital markers at least one, two or more of ECM1, CAMP, MGAM, MUC15, CES7, SPINT3, FAM12B, CRISP1, SPAG11B, ADAM7 and GPR64.

In an embodiment the condition is OA and the urogenital markers are the markers in Table 11. In an embodiment the condition is OA and the urogenital markers are selected from the group consisting of HIST1H4H, ELA2, MMP9, CORO1A, SAA2 and SAA1.

In an embodiment the condition is OA and the urogenital markers are the markers of Table 13, in particular LDHC, TEX101, PTGDS, ECM1, MUC15, FAM12B, SPAG11B, CEL, SPINT3, ADAM7, CAMP, CES7, MGAM, GPR64, CA4, NPC2 and ALDH1A1, more particularly LDHC, TEX101, PTGDS, ECM1, MUC15, FAM12B, SPAG11B, CEL, SPINT3, ADAM7 and CAMP.

In an embodiment the condition is OA and the urogenital markers are selected from the group consisting of ECM1, CRISP1, FAM12B, SPINT3, CAMP, PTDGS, CES7, ADAM7, MGAM, SPAG11B, MUC15, CEL, NPC2, CA4 and GPR64.

In an embodiment the condition is OA and the urogenital markers are selected from the group consisting of ECM1, CRISP1, FAM12B, SPINT3, CAMP, PTDGS, CES7, ADAM7, MGAM and SPAG11B, more particularly ECM1, CRISP1, FAM12B, SPINT3, CAMP, PTDGS and CES7.

In an embodiment, the condition is OA and the urogenital markers are at least one, two or more of SPAG11B, TEX101, MUC15, FAM12B, LDHC, ECM1, MGAM, CAMP, CRISP1 and GPR64.

In an embodiment the condition is OA and the urogenital markers are selected from the group consisting of LDHC, SPAG11B, TEX101, MUC15, PTGDS, CEL, ECM1, FAM12B, CAMP, MGAM, CES7, SPINT3, CRISP1, CA4, ADAM7, and GPR64.

In an embodiment the condition is OA and the urogenital markers are selected from the group consisting of ECM1, CAMP, MGAM, MUC15, CES7, SPINT3, FAM12B, CRISP1, SPAG11B, ADAM7 and GPR64.

In embodiments of the invention, methods are provided for distinguishing NOA and OA comprising detecting levels of urogenital markers selected from the group consisting of ECM1, CAMP, MGAM, MUC15, CES7, SPINT3, FAM12B, CRISP1, SPAG11B, ADAM7 and GPR64.

In embodiments of the invention, methods are provided for distinguishing NOA and OA comprising detecting levels of urogenital markers of Table 11.

In embodiments of the invention, methods are provided for distinguishing NOA and OA comprising detecting levels of MUC5B, CPVL, CRIM2, SLC2A5, ELSPBP1, PATE4, LOC642103, SPINT3, COL18A1, BGN, HISTIH2BL, FGG, AZU1, MPO, PRELP, ORM1, FLJ11151, FGB, GSTM2 and PAEP.

In embodiments of the invention, methods are provided for distinguishing NOA and OA comprising detecting levels of MUC5B, CPVL, CRIM2, SLC2A5, ELSPBP1, PATE4, LOC642103, SPINT, COL18A1 and BGN.

In embodiments of the invention, methods are provided for distinguishing NOA and OA comprising detecting levels of HISTIH2BL, FGG, AZU1, MPO, PRELP, ORM1, FLJ11151, FGB, GSTM2 and PAEP.

In embodiments of the invention, methods are provided for distinguishing NOA and OA comprising detecting levels of MFGE8, BSPH1, COL18A1, GAS6, LDHC, AKAP4, CD177, WFDC2, MPO, and/or MGAM.

In embodiments of the invention, methods are provided for distinguishing NOA and OA comprising detecting levels of urogenital markers selected from the group consisting of ECM1, CRISP1, FAM12B, SPINT3, CAMP, PTDGS, CES7, ADAM7, MGAM, SPAG11B, MUC15, CEL, MPC2, CA4, and GPR64.

In embodiments of the invention, methods are provided for distinguishing NOA and OA comprising detecting levels of LDHC.

In embodiments of the invention, methods are provided for distinguishing NOA and OA comprising detecting levels of TEX101.

In embodiments of the invention, methods are provided for distinguishing NOA and OA comprising detecting levels of ECM1.

In embodiments of the invention, methods are provided for distinguishing NOA and OA comprising detecting levels of the urogenital markers ECM1, TEX101 and LDHC.

In an embodiment the condition is prostatitis and the urogenital markers are the markers of Table 8. In an embodiment the condition is prostatitis and the urogenital markers are selected from the group consisting of ALB, SERPINA1, CST4, CST3, PAEP, C4A, A2M, SERPINA5, C3, LPL, IGHG2, A1BG, MSLN, SERPING1, GLA, OLFM4, SMPD1, CTSF, SERPINF1, MINPP1, CFI, CTSC, CST6, TXNDC16, LCN1, COL6A2, A4GALT, PATE4, TIMP3, CST2, FGB, and COMP. In an embodiment the condition is prostatitis and the urogenital markers are selected from the group consisting of ALB, SERPINA1, CST4, CST3, PAEP, C4A, A2M, SERPINA5, C3, LPL, IGHG2, A1BG, MSLN, SERPING1, GLA, OLFM4, SMPD1, CTSF, SERPINF1, MINPP1, CFI, CTSC, CST6, TXNDC16, LCN1, COL6A2, A4GALT, PATE4, TIMP3, CST2, FGB, and COMP, and an increase in levels of the markers relative to a control or standard or elevated status are indicative of prostatitis.

In an embodiment the condition is prostatitis and the urogenital markers are the markers of Table 9. In an embodiment the condition is prostatitis and the urogenital markers are selected from the group consisting of CPM, DYNC1H1, MUC5B, RAB27B, PHGDH, CA2, AC01, ANXA6, CACNA2D1, FAM129A, CDC42, RHOC, HGD, RAB2A, DCXR, LAMP1, ALDH9A1, COMPK1, NOV, NAPA, SOD3, LIFR, RNPEP, FLNB, DDAH1 and KIF5B. In an embodiment the condition is prostatitis and the urogenital markers are selected from the group consisting of CPM, DYNC1H1, MUC5B, RAB27B, PHGDH, CA2, AC01, ANXA6, CACNA2D1, FAM129A, CDC42, RHOC, HGD, RAB2A, DCXR, LAMP1, ALDH9A1, COMPK1, NOV, NAPA, SOD3, LIFR, RNPEP, FLNB, DDAH1 and KIF5B, and a decrease in levels of the markers relative to a control or standard or elevated status are indicative of prostatitis.

In an embodiment the condition is prostatitis and the urogenital markers are one or more of PTGDS, PATE4 and OR51E2.

In an embodiment the condition is prostatitis and the urogenital markers are one or more of cystatin-S, cystatin-SA, cystatin-C and lipocalin-1.

In an embodiment the condition is prostate cancer and the urogenital marker is anti-coagulant factor, Protein S (PROS 1).

In an embodiment the condition is a prostate specific condition, such as prostate cancer or prostatitis, and the urogenital markers include or comprise one or more of prostatic acid phosphatase (ACPP) (NCBI Gene ID: 55); aldehyde dehydrogenase 1 family, member A3 (ALDH1A3) (NCBI Gene ID: 220); ATP-binding cassette, sub-family C (CFTR/MRP) member 4 (ABCC4) (NCBI Gene ID: 10257); Arachidonate 15-lipoxygenase type II (ALOX15B) (NCBI Gene ID: 247); breast carcinoma amplified sequence 1 (BCAS1) (NCBI Gene ID: 8537); CD177 antigen; folate hydrolase 1 (FOLH1) (NCBI Gene ID: 2346); homeobox B13 (HOXB13) (NCBI Gene ID: 10481); N-acetylneuraminic acid synthase (NANS) (NCBI Gene ID: 54187); neuropeptide Y (NPY) (NCBI Gene ID: 4852); neural proliferation differentiation and control protein 1 (NPDC1) (NCBI Gene ID: 56654); lipid phosphate phosphohydrolase 1 (PPAP2A) (NCBI Gene ID: 8611); prostate stem cell antigen (PSCA) (NCBI Gene ID: 8000); SEC16 homolog A (*S. cerevisiae*) (SEC16A) (NCBI Gene ID: 9919); solute carrier family 44, member 4 (SLC44A4) (NCBI Gene ID: 80736); sorbitol dehydrogenase (SORD) (NCBI Gene ID: 6652); ST6 beta-galactosamide alpha-2,6-sialyltransferase 1 (ST6GAL1) (NCBI Gene ID: 6480); protein-glutamine gamma-glutamyltransferase 4 (TGM4) (NCBI Gene ID: 7047); Transmembrane serine protease 2 (TMPRSS2) (NCBI Gene ID: 7113); Six transmembrane epithelial antigen of the prostate 1 (STEAP1) (NCBI Gene ID: 26872); TCR gamma alternate reading frame protein (TARP) (NCBI Gene ID: 445347); TIMP metallopeptidase inhibitor 1 (TIMP1) (NCBI Gene ID: 7076); Trefoil factor 1 (TFF1) (NCBI Gene ID: 7031); and (TGM4) (NCBI Gene ID: 7051).

In an embodiment the condition is a prostate specific condition, such as prostate cancer or prostatitis and the urogenital markers include or comprise one or more of prostatic acid phosphatase (ACPP) (NCBI Gene ID: 55); Arachidonate 15-lipoxygenase type II (ALOX15B) (NCBI Gene ID: 247); breast carcinoma amplified sequence 1 (BCAS1) (NCBI Gene ID: 8537); CD177 antigen; folate hydrolase 1 (FOLH1) (NCBI Gene ID: 2346); N-acetylneuraminic acid synthase (NANS) (NCBI Gene ID: 54187); neural proliferation differentiation and control protein 1 (NPDC1) (NCBI Gene ID: 56654); lipid phosphate phosphohydrolase 1 (PPAP2A) (NCBI Gene ID: 8611); prostate stem cell antigen (PSCA) (NCBI Gene ID: 8000); solute carrier family 44, member 4 (SLC44A4) (NCBI Gene ID: 80736); sorbitol dehydrogenase (SORD) (NCBI Gene ID: 6652); ST6 beta-galactosamide alpha-2,6-sialyltranferase 1 (ST6GAL1) (NCBI Gene ID: 6480); protein-glutamine gamma-glutamyltransferase 4 (TGM4) (NCBI Gene ID: 7047); TIMP metallopeptidase inhibitor 1 (TIMP1) (NCBI Gene ID: 7076); Trefoil factor 1 (TFF1) (NCBI Gene ID: 7031); and (TGM4) (NCBI Gene ID: 7051).

The invention provides a method for assessing risk of prostate cancer in a patient which comprises measuring levels of Prostate Specific Antigen (PSA), kallikrein 2, kallikrein 3, and/or kallikrein 11, and one or more urogenital marker of Table 8 or 9 in the patient, analyzing a risk associated with the level of PSA kallikrein 2, kallikrein 3, and/or kallikrein 11, and a risk associated with the level of the urogenital marker, and using the combined risks to assess the risk of prostate cancer in the patient.

The methods can be used to detect the presence of a condition, as well as confirm the absence or removal of diseased tissues following surgery and/or therapy. They can further be used to monitor disease therapy, guide disease therapy, and disease recurrence or remission.

The present invention also relates to a method for identifying potentially infertile males or evaluating male fertility following an event which may influence the subject's fertility comprising determining the status of urogenital markers or polynucleotides encoding the markers in a sample obtained from the subject. An event which may influence fertility includes, without limitation, radiation therapy, vasectomy, injury to reproduction organ, age, general medical condition, and other events identified by a medical practitioner.

In an aspect, the invention provides a method for assessing the success of a vasectomy in a subject comprising determining the status of urogenital markers or polynucleotides encoding the markers in a sample obtained from the subject, wherein the status is indicative of the success of the vasectomy. In embodiments of this method of the invention the urogenital markers are the markers of Table 1, 2, 3 or 7. In embodiments of this method of the invention the urogenital markers are TEX101, PGK2, HISTIH2BA, SLCA14, SPAC3, GAPDHS and/or AKAP4. In embodiments of this method of the invention the urogenital markers are TEX101, PGK2, HISTIH2BA, SLCA14, SPAC3, GAPDHS and/or AKAP4, and the absence of the markers is indicative of a successful vasectomy. In embodiments of this method of the invention the urogenital markers are PTGDS, ELSPBP1, SPINT3, CRISP2, FAM12B, PATE4, NPC2, and CRISP1. In embodiments of this method of the invention the urogenital markers are PTGDS, ELSPBP1, SPINT3, CRISP2, FAM12B, PATE4, NPC2, and CRISP1, and a decrease in levels of the markers relative to a control or low levels of the markers is indicative of a successful vasectomy. In embodiments of this method of the invention the urogenital markers are LDHC, SPAG11B, TEX101, MUC15, PTGDS, ECM1, CEL, FAM12B, CAMP, SPINT3, CES7, MGAM, ADAM7, CRISP1, GPR64 and/or CA4.

In an aspect the invention provides a method for assessing the success of a vasectomy reversal in a subject comprising determining the status of urogenital markers or polynucleotides encoding the markers in a sample obtained from the subject, wherein the status is indicative of the success of the vasectomy reversal. In embodiments of this method of the invention the urogenital markers are the markers of Table 1, 2, 3, 7, 12 or 13. In embodiments of this method of the invention the urogenital markers are TEX101, PGK2, HISTIH2BA, SLCA14, SPAC3, GAPDHS and/or AKAP4. In embodiments of this method of the invention the urogenital markers are TEX101, PGK2, HISTIH2BA, SLCA14, SPAC3, GAPDHS and/or AKAP4, and the presence of the markers is indicative of a successful vasectomy reversal. In embodiments of this method of the invention the urogenital markers are PTGDS, ELSPBP1, SPINT3, CRISP2, FAM12B, PATE4, NPC2, and CRISP1. In embodiments of this method of the invention the urogenital markers are PTGDS, ELSPBP1, SPINT3, CRISP2, FAM12B, PATE4, NPC2, and CRISP1, and an increase in levels of the markers relative to a control or elevated levels of the markers is indicative of a successful vasectomy reversal. In embodiments of this method of the invention the urogenital markers are LDHC, SPAG11B, TEX101, MUC15, PTGDS, ECM1, CEL, FAM12B, CAMP, SPINT3, CES7, MGAM, ADAM7, CRISP1, GPR64 and/or CA4.

The methods described herein may also use multiple markers for a urogenital condition. Therefore, the invention contemplates a method for analyzing a biological sample for the presence of one or more urogenital markers and polynucleotides encoding the markers, and other markers that are specific indicators of a urogenital condition. The methods described herein may be modified by including reagents to detect the additional markers, or polynucleotides for the markers.

In aspects of methods of the invention, the amount or levels of one, two three or more urogenital markers may be mathematically combined. In an embodiment, the amount or levels of SORD and GGT7, or polynucleotides encoding same, are combined. In another embodiment, the amount of LDHC, TEX101 and SPAG11B, or polynucleotides encoding same, are combined. In another embodiment, the amount of LDHC, TEX101 and ECM1, or polynucleotides encoding same, are combined. In another embodiment, the amount of LDHC, BSPH1, ADAM7, MFGE8, REG3G, MFAP4, AKAP4 and SORD, or polynucleotides encoding same, are combined.

In a particular embodiment the invention provides a method for detecting or diagnosing a urogenital condition or status, in particular infertility, more particularly NOA, in a subject comprising:
  (a) determining the amount of SORD or polynucleotide encoding SORD in a sample from the subject;
  (b) determining the amount of GGT7 or polynucleotide encoding GGT7 in the sample;
  (c) mathematically combining the results of step (a) and step (b) to provide a mathematical combination; and
  (d) comparing or correlating the mathematical combination to the presence of the urogenital condition or status.

In a particular embodiment the invention provides a method for detecting or diagnosing a urogenital condition or status in particular infertility, more particularly NOA, in a subject comprising:
  (a) determining the amount of LDHC or polynucleotide encoding LDHC in a sample from the subject;
  (b) determining the amount of TEX101 or polynucleotide encoding TEX101 in the sample;

(c) determining the amount of SPAG11B or polynucleotide encoding SPAG11B in the sample;
(d) mathematically combining the results of step (a), step (b) and step (c) to provide a mathematical combination; and
(e) comparing or correlating the mathematical combination to the presence of the urogenital condition or status.

In a particular embodiment the invention provides a method for detecting or diagnosing a urogenital condition or status in particular infertility, more particularly NOA, in a subject comprising:
(a) determining the amount of LDHC or polynucleotide encoding LDHC in a sample from the subject;
(b) determining the amount of TEX 101 or polynucleotide encoding TEX101 in the sample;
(c) determining the amount of ECM1 or polynucleotide encoding ECM1 in the sample;
(d) mathematically combining the results of step (a), step (b) and step (c) to provide a mathematical combination; and
(e) comparing or correlating the mathematical combination to the presence of the urogenital condition or status.

The combination is preferably compared to a mathematical combination for a predetermined standard. The term "mathematical combination" or "mathematically combining" as used herein refers to any mathematical calculation of the amount of the one, two, three or more selected urogenital markers. The combinations of markers may be analyzed with the aid of a ROC curve.

Nucleic Acid Methods/Assays

As noted herein a urogenital condition or urogenital status may be detected based on the level of urogenital polynucleotide markers in a sample. Techniques for detecting polynucleotides such as polymerase chain reaction (PCR) and hybridization assays are well known in the art.

Probes may be used in hybridization techniques to detect urogenital polynucleotide markers. The technique generally involves contacting and incubating nucleic acids (e.g. recombinant DNA molecules, cloned genes) obtained from a sample from a patient or other cellular source with a probe under conditions favorable for the specific annealing of the probes to complementary sequences in the nucleic acids. After incubation, the non-annealed nucleic acids are removed, and the presences of nucleic acids that have hybridized to the probe if any are detected.

The probes may comprise DNA or DNA mimics (e.g., derivatives and analogues) corresponding to a portion of an organism's genome, or complementary RNA or RNA mimics. Mimics are polymers comprising subunits capable of specific, Watson-Crick-like hybridization with DNA, or of specific hybridization with RNA. The nucleic acids can be modified at the base moiety, at the sugar moiety, or at the phosphate backbone. DNA can be obtained using standard methods such as polymerase chain reaction (PCR) amplification of genomic DNA or cloned sequences. (See, for example, in Innis et al., eds., 1990, PCR Protocols: A Guide to Methods and Applications, Academic Press Inc., San Diego, Calif.). Computer programs known in the art can be used to design primers with the required specificity and optimal amplification properties, such as Oligo version 5.0 (National Biosciences). Controlled robotic systems may be useful for isolating and amplifying nucleic acids.

A nucleotide probe may be labeled with a detectable substance or detection agent such as a radioactive label that provides for an adequate signal and has sufficient half-life such as $^{32}$P, $^3$H, $^{14}$C or the like. Other detectable substances that may be used include antigens that are recognized by a specific labeled antibody, fluorescent compounds, enzymes, antibodies specific for a labeled antigen, and luminescent compounds. An appropriate label may be selected having regard to the rate of hybridization and binding of the probe to the nucleotide to be detected and the amount of nucleotide available for hybridization. Labeled probes may be hybridized to nucleic acids on solid supports such as nitrocellulose filters or nylon membranes as generally described in Sambrook et al, 1989, Molecular Cloning, A Laboratory Manual (2nd ed.). The nucleic acid probes may be used to detect urogenital polynucleotide markers, preferably in human cells. The nucleotide probes may also be useful in the diagnosis of a urogenital condition involving one or more urogenital polynucleotide markers, in monitoring the progression of such disorder, or monitoring or guiding a therapeutic treatment.

The detection of urogenital polynucleotide markers may involve the amplification of specific gene sequences using an amplification method such as polymerase chain reaction (PCR), followed by the analysis of the amplified molecules using techniques known to those skilled in the art. Suitable primers can be routinely designed by one of skill in the art.

By way of example, at least two oligonucleotide primers may be employed in a PCR based assay to amplify a portion of a polynucleotide encoding one or more urogenital marker derived from a sample, wherein at least one of the oligonucleotide primers is specific for (i.e. hybridizes to) a polynucleotide encoding the urogenital marker. The amplified cDNA is then separated and detected using techniques well known in the art, such as gel electrophoresis.

In order to maximize hybridization under assay conditions, primers and probes employed in the methods of the invention generally have at least about 60%, preferably at least about 75%, and more preferably at least about 90% identity to a portion of a polynucleotide encoding a urogenital marker; that is, they are at least 10 nucleotides, and preferably at least 20 nucleotides in length. In an embodiment the primers and probes are at least about 10-40 nucleotides in length.

Hybridization and amplification techniques described herein may be used to assay qualitative and quantitative aspects of urogenital polynucleotide marker expression. For example, RNA may be isolated from a cell type or tissue known to express a urogenital polynucleotide marker and tested utilizing the hybridization (e.g. standard Northern analyses) or PCR techniques referred to herein.

The primers and probes may be used in the above-described methods in situ i.e. directly on tissue sections (fixed and/or frozen) of patient tissue obtained from biopsies or resections.

In an aspect of the invention, a method is provided employing reverse transcriptase-polymerase chain reaction (RT-PCR), in which PCR is applied in combination with reverse transcription. Generally, RNA is extracted from a sample tissue using standard techniques (for example, guanidine isothiocyanate extraction as described by Chomcynski and Sacchi, Anal. Biochem. 162:156-159, 1987) and is reverse transcribed to produce cDNA. The cDNA is used as a template for a polymerase chain reaction. The cDNA is hybridized to a set of primers, at least one of which is specifically designed against a urogenital marker sequence. Once the primer and template have annealed a DNA polymerase is employed to extend from the primer, to synthesize a copy of the template. The DNA strands are denatured, and the procedure is repeated many times until sufficient DNA is generated to allow visualization by ethidium bromide staining and agarose gel electrophoresis.

Amplification may be performed on samples obtained from a subject with a suspected urogenital condition and an individual who is not afflicted with a urogenital condition. The reaction may be performed on several dilutions of cDNA spanning at least two orders of magnitude. A statistically significant difference in expression in several dilutions of the subject sample as compared to the same dilutions of the non-disease sample may be considered positive for the presence of a urogenital condition.

In an embodiment, the invention provides methods for determining the presence or absence of a urogenital condition in a subject comprising (a) contacting a sample obtained from the subject with oligonucleotides that hybridize to urogenital polynucleotide markers; and (b) detecting in the sample a level of nucleic acids that hybridize to the polynucleotides relative to a predetermined cut-off value, and therefrom determining the presence or absence of a urogenital condition in the subject.

The invention provides a method wherein a urogenital marker mRNA is detected by (a) isolating mRNA from a sample and combining the mRNA with reagents to convert it to cDNA; (b) treating the converted cDNA with amplification reaction reagents and nucleic acid primers that hybridize to one or more urogenital marker polynucleotides, to produce amplification products; (c) analyzing the amplification products to detect amounts of mRNA encoding urogenital polynucleotide markers; and (d) comparing the amount of mRNA to an amount detected against a panel of expected values for samples from healthy subjects derived using similar nucleic acid primers.

Urogenital disease marker-positive samples or alternatively higher levels in patients compared to a control (e.g. non-diseaseous tissue) may be indicative of late stage disease, and/or that the patient is not responsive to therapy. Alternatively, negative samples or lower levels compared to a control (e.g. non-diseaseous tissue or negative samples) may also be indicative of progressive disease and shorter overall survival.

In another embodiment, the invention provides methods for determining the presence or absence of a urogenital condition in a subject comprising (a) contacting a sample obtained from the subject with oligonucleotides that hybridize to one or more urogenital disease marker polynucleotides; and (b) detecting in the sample levels of nucleic acids that hybridize to the polynucleotides relative to a predetermined cut-off value, and therefrom determining the presence or absence of a urogenital condition in the subject. In an embodiment, the urogenital disease polynucleotide markers encode one or more polypeptides of Table 1, 2, 3, 4, 5, 6, 7, 8, 9, 10, 11, 12 or 13, in particular, the urogenital markers are one or more of SPAG11B, TEX101, LDHC, PTGDS, FAM12B, and MUC15.

Oligonucleotides or longer fragments derived from a urogenital disease polynucleotide marker may be used as targets in a microarray. The microarray can be used to simultaneously monitor the expression levels of large numbers of genes and to identify genetic variants, mutations, and polymorphisms. The information from the microarray may be used to determine gene function, to understand the genetic basis of a disorder, to diagnose a disorder, and to develop and monitor the activities of therapeutic agents.

Thus, the invention also includes an array comprising one, two, three, four or five or more urogenital polynucleotide markers (in particular the markers of any one of Tables 1 to 11) and optionally other markers. The array can be used to assay expression of urogenital polynucleotide markers in the array. The invention allows the quantitation of expression of one or more urogenital polynucleotide markers.

Microarrays typically contain at separate sites nanomolar quantities of individual genes, cDNAs, or ESTs on a substrate (e.g., nitrocellulose or silicon plate), or photolithographically prepared glass substrate. The arrays are hybridized to cDNA probes using conventional techniques with gene-specific primer mixes. The target polynucleotides to be analyzed are isolated, amplified and labeled, typically with fluorescent labels, radiolabels or phosphorous label probes. After hybridization is completed, the array is inserted into the scanner, where patterns of hybridization are detected. Data are collected as light emitted from the labels incorporated into the target, which becomes bound to the probe array. Probes that completely match the target generally produce stronger signals than those that have mismatches. The sequence and position of each probe on the array are known, and thus by complementarity, the identity of the target nucleic acid applied to the probe array can be determined.

Microarrays are prepared by selecting polynucleotide probes and immobilizing them to a solid support or surface. The probes may comprise DNA sequences, RNA sequences, copolymer sequences of DNA and RNA, DNA and/or RNA analogues, or combinations thereof. The probe sequences may be full or partial fragments of genomic DNA, or they may be synthetic oligonucleotide sequences synthesized either enzymatically in vivo, enzymatically in vitro (e.g., by PCR), or non-enzymatically in vitro.

The probe or probes used in the methods of the invention can be immobilized to a solid support or surface which may be either porous or non-porous. For example, the probes can be attached to a nitrocellulose or nylon membrane or filter covalently at either the 3' or the 5' end of the polynucleotide probe. The solid support may be a glass or plastic surface. In an aspect of the invention, hybridization levels are measured to microarrays of probes consisting of a solid support on the surface of which are immobilized a population of polynucleotides, such as a population of DNA or DNA mimics, or, alternatively, a population of RNA or RNA mimics. A solid support may be a nonporous or, optionally, a porous material such as a gel.

In accordance with embodiments of the invention, a microarray is provided comprising a support or surface with an ordered array of hybridization sites or "probes" each representing one of the markers described herein. The microarrays can be addressable arrays, and in particular positionally addressable arrays. Each probe of the array is typically located at a known, predetermined position on the solid support such that the identity of each probe can be determined from its position in the array. In preferred embodiments, each probe is covalently attached to the solid support at a single site.

Microarrays used in the present invention are preferably (a) reproducible, allowing multiple copies of a given array to be produced and easily compared with each other; (b) made from materials that are stable under hybridization conditions; (c) small, (e.g., between 1 cm$^2$ and 25 cm$^2$, between 12 cm$^2$ and 13 cm$^2$, or 3 cm$^2$; and (d) comprise a unique set of binding sites that will specifically hybridize to the product of a single gene in a cell (e.g., to a specific mRNA, or to a specific cDNA derived therefrom). However, it will be appreciated that larger arrays may be used particularly in screening arrays, and other related or similar sequences will cross hybridize to a given binding site.

In accordance with an aspect of the invention, the microarray is an array in which each position represents one of the markers described herein. Each position of the array can comprise a DNA or DNA analogue based on genomic DNA to which a particular RNA or cDNA transcribed from a genetic marker can specifically hybridize. A DNA or DNA analogue can be a synthetic oligomer or a gene fragment. In an embodiment, probes representing at least 5, 10, or 15 of the urogenital markers and urogenital polynucleotide markers is present on the array. In a preferred embodiment, the array comprises all of the urogenital polynucleotide markers.

Probes for the microarray can be synthesized using N-phosphonate or phosphoramidite chemistries (Froehler et al., 1986, Nucleic Acid Res. 14:5399-5407; McBride et al., 1983, Tetrahedron Lett. 24:246-248). Synthetic sequences are typically between about 10 and about 500 bases, 20-100 bases, or 40-70 bases in length. Synthetic nucleic acid probes can include non-natural bases, such as, without limitation, inosine. Nucleic acid analogues such as peptide nucleic acid may be used as binding sites for hybridization. (see, e.g., Egholm et al., 1993, Nature 363:566-568; U.S. Pat. No. 5,539,083).

Probes can be selected using an algorithm that takes into account binding energies, base composition, sequence complexity, cross-hybridization binding energies, and secondary structure (see Friend et al., International Patent Publication WO 01/05935, published Jan. 25, 2001).

Positive control probes, (e.g., probes known to be complementary and hybridize to sequences in the target polynucleotides), and negative control probes, (e.g., probes known to not be complementary and hybridize to sequences in the target polynucleotides) are typically included on the array. Positive controls can be synthesized along the perimeter of the array or synthesized in diagonal stripes across the array. A reverse complement for each probe can be next to the position of the probe to serve as a negative control.

The probes can be attached to a solid support or surface, which may be made from glass, plastic (e.g., polypropylene, nylon), polyacrylamide, nitrocellulose, gel, or other porous or nonporous material. The probes can be printed on surfaces such as glass plates (see Schena et al., 1995, Science 270: 467-470). This method may be particularly useful for preparing microarrays of cDNA (See also, DeRisi et al., 1996, Nature Genetics 14:457-460; Shalon et al., 1996, Genome Res. 6:639-645; and Schena et al., 1995, Proc. Natl. Acad. Sci. U.S.A. 93:10539-11286).

High-density oligonucleotide arrays containing thousands of oligonucleotides complementary to defined sequences, at defined locations on a surface can be produced using photolithographic techniques for synthesis in situ (see, Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; and 5,510,270) or other methods for rapid synthesis and deposition of defined oligonucleotides (Blanchard et al., Biosensors & Bioelectronics 11:687-690). Using these methods oligonucleotides (e.g., 60-mers) of known sequence are synthesized directly on a surface such as a derivatized glass slide. The array produced may be redundant, with several oligonucleotide molecules per RNA.

Microarrays can be made by other methods including masking (Maskos and Southern, 1992, Nuc. Acids. Res. 20:1679-1684). In an embodiment, microarrays of the present invention are produced by synthesizing polynucleotide probes on a support wherein the nucleotide probes are attached to the support covalently at either the 3' or the 5' end of the polynucleotide.

The invention provides microarrays comprising a disclosed marker set. In one embodiment, the invention provides a microarray for distinguishing urogenital disease samples comprising a positionally-addressable array of polynucleotide probes bound to a support, the polynucleotide probes comprising a plurality of polynucleotide probes of different nucleotide sequences, each of the different nucleotide sequences comprising a sequence complementary and hybridizable to a plurality of genes, the plurality consisting of at least 2, 3, 4, 5, 6, 7, 8, 9, 10, 11, 12, 13, 14, or 15 of the genes corresponding to the markers of any one or more of Tables 1 to 13. An aspect of the invention provides microarrays comprising at least 5, 10, or 15 of the polynucleotides encoding the markers of any one or more of Tables 1 to 13.

In an aspect, the invention provides a method for classifying urogenital status or conditions comprising detecting a difference in the expression of a first plurality of genes relative to a control, the first plurality of genes consisting of at least 2, 3, 4, or 5 of the genes encoding the markers of Table 1, 2, 3, 4, 5, 6, 7, 8, 9, 10, 11, 12 or 13. In specific aspects, the plurality of genes consists of at least 10 or 15 of the genes encoding the markers of any one or more of Tables 1 to 13. In another specific aspect, the control comprises nucleic acids derived from a pool of samples from individual control patients.

The invention provides a method for classifying a urogenital tissue or organ or urogenital condition by calculating the similarity between the expression of at least 2, 3, 4 or 5 polynucleotides encoding markers of any of Tables 1 to 13 in a sample to the expression of the same markers in a control pool, comprising the steps of:

(a) labeling nucleic acids derived from a sample, with a first fluorophore to obtain a first pool of fluorophore-labeled nucleic acids;

(b) labeling with a second fluorophore a first pool of nucleic acids derived from two or more samples from subjects with a urogenital condition, and a second pool of nucleic acids derived from two or more control samples;

(c) contacting the first fluorophore-labeled nucleic acid and the first pool of second fluorophore-labeled nucleic acid with a first microarray under conditions such that hybridization can occur, and contacting the first fluorophore-labeled nucleic acid and the second pool of second fluorophore-labeled nucleic acid with a second microarray under conditions such that hybridization can occur, detecting at each of a plurality of discrete loci on the first microarray a first fluorescent emission signal from the first fluorophore-labeled nucleic acid and a second fluorescent emission signal from the first pool of second fluorophore-labeled genetic matter that is bound to the first microarray and detecting at each of the marker loci on the second microarray the first fluorescent emission signal from the first fluorophore-labeled nucleic acid and a third fluorescent emission signal from the second pool of second fluorophore-labeled nucleic acid;

(d) determining the similarity of the sample to patient and control pools by comparing the first fluorescence emission signals and the second fluorescence emission signals, and the first emission signals and the third fluorescence emission signals; and (e) classifying the sample as a urogenital condition where the first fluorescence emission signals are more similar to the second fluorescence emission signals than to the third fluorescent emission signals, and classifying the sample as a non-urogenital condition where the first fluorescence emission signals are more similar to the third fluorescence emission signals than to the second fluorescent emission signals, wherein the first microarray and the second microarray are similar to each other, exact replicas of each other, or are identical, and wherein the similarity is defined by a statistical method such that the cell sample and control are similar where the p value of the similarity is less than 0.01.

In an embodiment, the array can be used to monitor the time course of expression of one or more urogenital polynucleotide markers in the array. This can occur in various biological contexts such as disease progression.

The array is also useful for ascertaining differential expression patterns of urogenital polynucleotide markers, and optionally other markers, in normal and abnormal cells. This may provide a battery of nucleic acids that could serve as molecular targets for diagnosis or therapeutic intervention.

Protein Methods

Binding agents may be used for a variety of diagnostic and assay applications. There are a variety of assay formats known to the skilled artisan for using a binding agent to detect a target molecule in a sample. (For example, see Harlow and Lane, Antibodies: A Laboratory Manual, Cold Spring Harbor Laboratory, 1988). In general, the presence or absence of a urogenital condition or a urogenital state in a subject may be determined by (a) contacting a sample from the subject with a binding agent; (b) detecting in the sample a level of polypeptide that binds to the binding agent; and (c) comparing the level of polypeptide with a predetermined standard, reference or cut-off value.

In particular embodiments of the invention, the binding agent is an antibody. Antibodies specifically reactive with one or more urogenital marker, or derivatives, such as enzyme conjugates or labeled derivatives, may be used to detect one or more urogenital marker in various samples (e.g. biological samples). They may be used as diagnostic or prognostic reagents and they may be used to detect abnormalities in the level of expression of one or more urogenital marker, or abnormalities in the structure, and/or temporal, tissue, cellular, or subcellular location of one or more urogenital marker. Antibodies may also be used to screen potentially therapeutic compounds in vitro to determine their effects on disorders (e.g. a urogenital condition) involving one or more urogenital markers, and other conditions. In vitro immunoassays may also be used to assess or monitor the efficacy of particular therapies.

In an aspect, the invention provides a method for monitoring or diagnosing a urogenital condition in a subject by quantitating one or more urogenital markers in a biological sample from the subject comprising reacting the sample with antibodies specific for one or more urogenital markers, which are directly or indirectly labeled with detectable substances or agents and detecting the detectable substances or agents. In a particular embodiment of the invention, urogenital markers are quantitated or measured.

In an aspect of the invention, a method for detecting a urogenital condition is provided comprising:
(a) obtaining a sample suspected of containing one or more urogenital markers associated with a urogenital condition;
(b) contacting said sample with antibodies that specifically bind to the urogenital markers under conditions effective to bind the antibodies and form complexes;
(c) measuring the amount of urogenital markers present in the sample by quantitating the amount of the complexes; and
(d) comparing the amount of urogenital markers present in the samples with the amount of urogenital markers in a control, wherein a change or significant difference in the amount of urogenital markers in the sample compared with the amount in the control is indicative of the urogenital condition.

In an embodiment, the invention contemplates a method for monitoring the progression of a urogenital condition in an individual, comprising:
(a) contacting antibodies which bind to one or more urogenital markers with a sample from the individual so as to form complexes comprising the antibodies and one or more urogenital markers in the sample;
(b) determining or detecting the presence or amount of complex formation in the sample;
(c) repeating steps (a) and (b) at a point later in time; and
(d) comparing the result of step (b) with the result of step (c), wherein a difference in the amount of complex formation is indicative of disease, disease stage, and/or progression of the disease in said individual.

The amount of complexes may also be compared to a value representative of the amount of the complexes from an individual not at risk of, or afflicted with, a urogenital condition at different stages. A significant difference in complex formation may be indicative of advanced disease e.g. advanced urogenital condition, or an unfavourable prognosis.

In aspects of the invention for diagnosis and monitoring of a urogenital condition, the urogenital markers are one or more of SPAG11B, TEX101, MUC15, FAM12B, and PTGDS, or fragments thereof.

In aspects of the invention for guiding or monitoring therapy of a urogenital condition, the urogenital markers are one or more of SPAG11B, TEX101, MUC15, FAM12B, and PTGDS, or fragments thereof.

In aspects of the invention for the diagnosis and monitoring of a urogenital condition, the urogenital markers are one or more of SPAG11B, TEX101, and LDHC, or fragments thereof.

In aspects of the invention for guiding or monitoring therapy of a urogenital condition, the urogenital markers are SORD and GGT7, or fragments thereof.

In aspects of the invention for the diagnosis and monitoring of a urogenital condition, the urogenital markers are LDHC, PSPH1, ADAM7, MFGE8, REG3G, MFAP4, AKAP4, and SORD, or fragments thereof.

In aspects of the invention for diagnosis and monitoring of a urogenital condition the amounts or levels of one, two, three or more selected urogenital markers are mathematically combined. In an embodiment, the amount of SORD and GGT7 are combined. In another embodiment, the amount of LDHC, TEX101 and SPAG11B are combined. In another embodiment, the amount of LDHC, BSPH1, ADAM7, MFGE8, REG3G, MFAP4, AKAP4 and SORD are combined.

Accordingly, an aspect of the present invention provides a method for determining the presence of a urogenital condition or status in particular infertility, more particularly NOA, in a subject comprising the steps of:
(a) providing a first antibody that specifically binds to SORD;
(b) providing a second antibody that specifically binds to GGT7;
(c) contacting the first and second antibody with a sample from the subject under conditions that allow formation of a first complex comprising the first antibody and SORD and a second complex comprising the second antibody and GGT7;
(d) detecting or determining the presence or amount of the first and second complexes;
(e) mathematically combining the amount of the complexes or the amount of SORD and GGT7; and
(f) comparing the mathematically combined amount with a standard to determine the presence of the urogenital condition or status in the subject.

Accordingly, an aspect of the present invention provides a method for determining the presence of a urogenital condition or status in particular infertility, more particularly NOA, in a subject comprising the steps of:
  (a) providing a first antibody that specifically binds to LDHC;
  (b) providing a second antibody that specifically binds to TEX101;
  (c) providing a third antibody that specifically binds to SPAG11B;
  (d) contacting the first, second and third antibody with a sample from the subject under conditions that allow formation of a first complex comprising the first antibody and LDHC, a second complex comprising the second antibody and TEX101, and a third complex comprising the third antibody and SPAG11B;
  (e) detecting or determining the presence or amount of the first, second and third complexes;
  (f) mathematically combining the amount of the complexes or the amount of LDHC, TEX101 and SPAG11B; and
  (g) comparing the mathematically combined amount with a standard to determine the presence of the urogenital condition or status in the subject.

Antibodies may be used in any known immunoassays that rely on the binding interaction between antigenic determinants of one or more urogenital marker and the antibodies. Immunoassay procedures for in vitro detection of antigens in fluid samples are also well known in the art. [See for example, Paterson et al., Int. J. Can. 37:659 (1986) and Burchell et al., Int. J. Can. 34:763 (1984) for a general description of immunoassay procedures]. Qualitative and/or quantitative determinations of one or more urogenital marker in a sample may be accomplished by competitive or non-competitive immunoassay procedures in either a direct or indirect format. Detection of one or more urogenital marker using antibodies can be done utilizing immunoassays which are run in either the forward, reverse or simultaneous modes. Examples of immunoassays are radioimmunoassays (RIA), enzyme immunoassays (e.g. ELISA), immunofluorescence, immunoprecipitation, latex agglutination, hemagglutination, histochemical tests, and sandwich (immunometric) assays. These terms are well understood by those skilled in the art. A person skilled in the art will know, or can readily discern, other immunoassay formats without undue experimentation.

According to an embodiment of the invention, an immunoassay for detecting one or more urogenital markers in a biological sample comprises contacting binding agents that specifically bind to urogenital markers in the sample under conditions that allow the formation of first complexes comprising a binding agent and urogenital markers and determining the presence or amount of the complexes as a measure of the amount of urogenital markers contained in the sample. In a particular embodiment, the binding agents are labeled differently or are capable of binding to different labels.

Antibodies may be used to detect and quantify one or more urogenital markers in a sample in order to diagnose and treat pathological states. In particular, the antibodies may be used in immunohistochemical analyses, for example, at the cellular and sub-subcellular level, to detect one or more urogenital markers, to localize them to particular urogenital cells and tissues, and to specific subcellular locations, and to quantitate the level of expression.

Immunohistochemical methods for the detection of antigens in tissue samples are well known in the art. For example, immunohistochemical methods are described in Taylor, Arch. Pathol. Lab. Med. 102:112 (1978). Briefly, in the context of the present invention, a tissue sample obtained from a subject suspected of having a urogenital condition is contacted with antibodies, preferably monoclonal antibodies recognizing one or more urogenital markers. The site at which the antibodies are bound is determined by selective staining of the sample by standard immunohistochemical procedures. The same procedure may be repeated on the same sample using other antibodies that recognize one or more urogenital markers. Alternatively, a sample may be contacted with antibodies against one or more urogenital markers simultaneously, provided that the antibodies are labeled differently or are able to bind to a different label. The tissue sample may be normal urogenital tissue or a disease tissue.

An antibody microarray in which binding sites comprise immobilized, preferably monoclonal, antibodies specific to a substantial fraction of marker-derived urogenital markers of interest can be utilized in the present invention. Antibody arrays can be prepared using methods known in the art [(see for example, Zhu et al., *Science* 293:2101 (2001) and reference 20].

Antibodies specific for one or more urogenital marker may be labeled with a detectable substance or detection agent and localised in biological samples based upon the presence of the detectable substance or agent. Examples of detectable substances or agents include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or colorimetric methods), and predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualised by electron microscopy.

One of the ways an antibody can be detectably labeled is to link it directly to an enzyme. The enzyme when later exposed to its substrate will produce a product that can be detected. Examples of detectable substances or agents that are enzymes are horseradish peroxidase, beta-galactosidase, luciferase, alkaline phosphatase, acetylcholinesterase, malate dehydrogenase, ribonuclease, urease, catalase, glucose-6-phosphate, staphylococcal nuclease, delta-5-steroid isomerase, yeast alcohol dehydrogenase, alpha-glycerophosphate, triose phosphate isomerase, asparaginase, glucose oxidase, and acetylcholine esterase.

For increased sensitivity in an immunoassay system a fluorescence-emitting metal atom such as Eu (europium) and other lanthanides can be used. These can be attached to the desired molecule by means of metal-chelating groups such as DTPA or EDTA.

A bioluminescent compound may also be used as a detectable substance. Bioluminescence is a type of chemiluminescence found in biological systems where a catalytic protein increases the efficiency of the chemiluminescent reaction. The presence of a bioluminescent molecule is determined by detecting the presence of luminescence. Examples of bioluminescent detectable substances are luciferin, luciferase and aequorin.

Indirect methods may also be employed in which the primary antigen-antibody reaction is amplified by the introduction of a second antibody, having specificity for the antibody reactive against one or more urogenital markers. By way of example, if the antibody having specificity against one or more urogenital markers is a rabbit IgG antibody, the second antibody may be goat anti-rabbit gamma-globulin labeled with a detectable substance or agent as described herein.

Methods for conjugating or labeling the antibodies discussed above may be readily accomplished by one of ordinary skill in the art. (See for example Inman, Methods In Enzymology, Vol. 34, Affinity Techniques, Enzyme Purification: Part B, Jakoby and Wichek (eds.), Academic Press, New York, p. 30, 1974; and Wilchek and Bayer, "The Avidin-Biotin Complex in Bioanalytical Applications," Anal. Biochem. 171:1-32, 1988 re methods for conjugating or labeling the antibodies with enzyme or ligand binding partner).

Cytochemical techniques known in the art for localizing antigens using light and electron microscopy may be used to detect one or more urogenital markers. Generally, antibodies may be labeled with detectable substances and one or more urogenital markers may be localised in tissues and cells based upon the presence of the detectable substances.

In the context of the methods of the invention, the sample, binding agents (e.g. antibodies specific for one or more urogenital markers), or one or more urogenital markers may be immobilized on a carrier or support. Examples of suitable carriers or supports are agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinyl-ether-maleic acid copolymer, amino acid copolymer, ethylene-maleic acid copolymer, nylon, silk, etc. The support material may have any possible configuration including spherical (e.g. bead), cylindrical (e.g. inside surface of a test tube or well, or the external surface of a rod), or flat (e.g. sheet, test strip). Thus, the carrier may be in the shape of, for example, a tube, test plate, well, beads, disc, sphere, etc. The immobilized antibody may be prepared by reacting the material with a suitable insoluble carrier using known chemical or physical methods, for example, cyanogen bromide coupling. An antibody may be indirectly immobilized using a second antibody specific for the antibody. For example, mouse antibody specific for a urogenital marker may be immobilized using sheep anti-mouse IgG Fc fragment specific antibody coated on the carrier or support.

Where a radioactive label is used as a detectable substance, one or more urogenital marker may be localized by radioautography. The results of radioautography may be quantitated by determining the density of particles in the radioautographs by various optical methods, or by counting the grains.

Time-resolved fluorometry may be used to detect a signal. For example, the method described in Christopoulos T K and Diamandis E P in Anal Chem 1992:64:342-346 may be used with a conventional time-resolved fluorometer.

In accordance with an embodiment of the invention, a method is provided wherein one or more urogenital marker antibodies are directly or indirectly labeled with enzymes and substrates for the enzymes are added wherein the substrates are selected so that the substrates, or a reaction product of an enzyme and substrate, form fluorescent complexes with a lanthanide metal (e.g. europium, terbium, samarium, and dysprosium, preferably europium and terbium). A lanthanide metal is added and one or more urogenital disease markers are quantitated in the sample by measuring fluorescence of the fluorescent complexes. Enzymes are selected based on the ability of a substrate of the enzyme, or a reaction product of the enzyme and substrate, to complex with lanthanide metals such as europium and terbium.

Examples of enzymes and substrates for enzymes that provide such fluorescent complexes are described in U.S. Pat. No. 5,312,922 to Diamandis, for example, alkaline phosphatase and β-galactosidase. Preferably, the enzyme is alkaline phosphatase. By way of example, when the antibody is directly or indirectly labeled with alkaline phosphatase the substrate employed in the method may be 4-methylumbelliferyl phosphate, 5-fluorosalicyl phosphate, or diflunisal phosphate. The fluorescence intensity of the complexes is typically measured using a time-resolved fluorometer e.g. a CyberFluor 615 Immunoanalyzer (Nordion International, Kanata, Ontario).

One or more urogenital marker antibodies may also be indirectly labeled with an enzyme. For example, the antibodies may be conjugated to one partner of a ligand binding pair, and the enzyme may be coupled to the other partner of the ligand binding pair. Representative examples include avidin-biotin, and riboflavin-riboflavin binding protein. In an embodiment, the antibodies are biotinylated, and the enzyme is coupled to streptavidin. In another embodiment, an antibody specific for a urogenital marker antibody is labeled with an enzyme.

In accordance with an embodiment, the present invention provides means for determining one or more urogenital markers in a sample by measuring one or more urogenital markers by immunoassay. It will be evident to a skilled artisan that a variety of immunoassay methods can be used to measure one or more urogenital markers. In general, an immunoassay method may be competitive or noncompetitive. Competitive methods typically employ an immobilized or immobilizable antibody to one or more urogenital marker and a labeled form of one or more urogenital marker. Sample urogenital markers and labeled urogenital markers compete for binding to antibodies to urogenital markers. After separation of the resulting labeled urogenital markers that have become bound to antibodies (bound fraction) from that which has remained unbound (unbound fraction), the amount of the label in either bound or unbound fraction is measured and may be correlated with the amount of urogenital markers in the test sample in any conventional manner, e.g., by comparison to a standard curve.

In an aspect, a non-competitive method is used for the determination of one or more urogenital markers, with the most common method being the "sandwich" method. In this assay, two antibodies to urogenital markers are employed. One of the antibodies to urogenital markers is directly or indirectly labeled (sometimes referred to as the "detection antibody") and the other is immobilized or immobilizable (sometimes referred to as the "capture antibody"). The capture and detection antibodies can be contacted simultaneously or sequentially with the test sample. Sequential methods can be accomplished by incubating the capture antibody with the sample, and adding the detection antibody at a predetermined time thereafter (sometimes referred to as the "forward" method); or the detection antibody can be incubated with the sample first and then the capture antibody added (sometimes referred to as the "reverse" method). After the necessary incubation(s) have occurred, to complete the assay, the capture antibody is separated from the test mixture, and the label is measured in at least a portion of the separated capture antibody phase or the remainder of the test mixture. Generally it is measured in the capture antibody phase since it comprises urogenital disease markers bound by ("sandwiched" between) the capture and detection antibodies. In an embodiment, the label may be measured without separating the capture antibodies and liquid test mixture.

In a typical two-site immunometric assay for urogenital markers, one or both of the capture and detection antibodies are polyclonal antibodies or one or both of the capture and detection antibodies are monoclonal antibodies (i.e. polyclonal/polyclonal, monoclonal/monoclonal, or monoclonal/polyclonal). The label used in the detection antibody can be selected from any of those known conventionally in the art. The label may be an enzyme or a chemiluminescent moiety, but it can also be a radioactive isotope, a fluorophor, a detectable ligand (e.g., detectable by a secondary binding by a labeled binding partner for the ligand), and the like. In a particular aspect, the antibody is labeled with an enzyme which is detected by adding a substrate that is selected so that a reaction product of the enzyme and substrate forms fluorescent complexes. The capture antibody may be selected so that it provides a means for being separated from the remainder of the test mixture. Accordingly, the capture antibody can be introduced to the assay in an already immobilized or insoluble form, or can be in an immobilizable form, that is, a form which enables immobilization to be accomplished subsequent to introduction of the capture antibody to the assay. An immobilized capture antibody may comprise an antibody covalently or noncovalently attached to a solid phase such as a magnetic particle, a latex particle, a microtiter plate well, a bead, a cuvette, or other reaction vessel. An example of an immobilizable capture antibody is antibody which has been chemically modified with a ligand moiety, e.g., a hapten, biotin, or the like, and which can be subsequently immobilized by contact with an immobilized form of a binding partner for the ligand, e.g., an antibody, avidin, or the like. In an embodiment, the capture antibody may be immobilized using a species specific antibody for the capture antibody that is bound to the solid phase.

The above-described immunoassay methods and formats are intended to be exemplary and are not limiting.

Computer Systems

Analytic methods contemplated herein can be implemented by use of computer systems and methods described below and known in the art. Thus, the invention provides computer readable media comprising one or more urogenital markers, and/or polynucleotides encoding one or more urogenital markers, and optionally other markers of a urogenital condition. "Computer readable media" refers to any medium that can be read and accessed directly by a computer, including but not limited to magnetic storage media, such as floppy discs, hard disc storage medium, and magnetic tape; optical storage media such as CD-ROM; electrical storage media such as RAM and ROM; and hybrids of these categories such as magnetic/optical storage media. Thus, the invention contemplates computer readable medium having recorded thereon markers identified for patients and controls.

"Recorded" refers to a process for storing information on computer readable medium. The skilled artisan can readily adopt any of the presently known methods for recording information on computer readable medium to generate manufactures comprising information on one or more urogenital markers, and optionally other markers.

A variety of data processor programs and formats can be used to store information on one or more urogenital markers, and/or polynucleotides encoding one or more urogenital markers, and other markers on computer readable medium. For example, the information can be represented in a word processing text file, formatted in commercially-available software such as WordPerfect and MicroSoft Word, or represented in the form of an ASCII file, stored in a database application, such as DB2, Sybase, Oracle, or the like. Any number of dataprocessor structuring formats (e.g., text file or database) may be adapted in order to obtain computer readable medium having recorded thereon the marker information.

By providing the marker information in computer readable form, one can routinely access the information for a variety of purposes. For example, one skilled in the art can use the information in computer readable form to compare marker information obtained during or following therapy with the information stored within the data storage means.

The invention provides a medium for holding instructions for performing a method for determining whether a patient has a urogenital condition or a pre-disposition to a urogenital condition, comprising determining the presence or absence of one or more urogenital markers, and/or polynucleotides encoding one or more urogenital markers, and optionally other markers, and based on the presence or absence of the one or more urogenital markers, and/or polynucleotides encoding one or more urogenital markers, and optionally other markers, determining a urogenital condition, or a pre-disposition to a urogenital condition, and optionally recommending a procedure or treatment.

The invention also provides in an electronic system and/or in a network, a method for determining whether a subject has a urogenital condition or a pre-disposition to a urogenital condition comprising determining the presence or absence of one or more urogenital markers, and/or polynucleotides encoding one or more urogenital markers, and optionally other markers, and based on the presence or absence of the one or more urogenital markers, and/or polynucleotides encoding one or more urogenital markers, and optionally other markers, determining whether the subject has a urogenital condition or a pre-disposition to a urogenital condition, and optionally recommending a procedure or treatment.

The invention further provides in a network, a method for determining whether a subject has a urogenital condition or a pre-disposition to a urogenital condition comprising: (a) receiving phenotypic information on the subject and information on one or more urogenital markers, and/or polynucleotides encoding one or more urogenital markers, and optionally other markers associated with samples from the subject; (b) acquiring information from the network corresponding to the one or more urogenital markers, and/or polynucleotides encoding one or more urogenital markers, and optionally other markers; and (c) based on the phenotypic information and information on the one or more urogenital markers, and/or polynucleotides encoding one or more urogenital markers, and optionally other markers, determining whether the subject has a urogenital condition or a pre-disposition to a urogenital condition; and (d) optionally recommending a procedure or treatment.

The invention still further provides a system for identifying selected records that identify a diseased urogenital cell or tissue or urogenital state. A system of the invention generally comprises a digital computer; a database server coupled to the computer; a database coupled to the database server having data stored therein, the data comprising records of data comprising one or more urogenital markers, and/or polynucleotides encoding one or more urogenital markers, and optionally other urogenital markers, and a code mechanism for applying queries based upon a desired selection criteria to the data file in the database to produce reports of records which match the desired selection criteria.

In an aspect of the invention a method is provided for detecting urogenital disease tissue or cells using a computer having a processor, memory, display, and input/output devices, the method comprising the steps of:

(a) creating records of one or more urogenital disease markers, and/or polynucleotides encoding one or more urogenital disease markers, and optionally other markers of disease identified in a sample suspected of containing urogenital disease cells or tissue;

(b) providing a database comprising records of data comprising one or more urogenital disease markers, and/or polynucleotides encoding one or more urogenital disease markers, and optionally other markers of disease; and (c) using a code mechanism for applying queries based upon a desired selection criteria to the data file in the database to produce reports of records of step (a) which provide a match of the desired selection criteria of the database of step (b) the presence of a match being a positive indication that the markers of step (a) have been isolated from cells or tissue that are urogenital disease cells or tissue.

The invention contemplates a business method for determining whether a subject has a urogenital condition or a pre-disposition to a urogenital condition comprising: (a) receiving phenotypic information on the subject and information on one or more urogenital markers, and/or polynucleotides encoding the markers, and optionally other markers, associated with samples from the subject; (b) acquiring information from a network corresponding to one or more urogenital markers, and/or polynucleotides encoding the markers, and optionally other markers; and (c) based on the phenotypic information, information on one or more urogenital markers, and/or polynucleotides encoding the markers, and optionally other markers, and acquired information, determining whether the subject has a urogenital condition or a pre-disposition to a urogenital condition; and (d) optionally recommending a procedure or treatment.

In an aspect of the invention, the computer systems, components, and methods described herein are used to monitor a condition, guide or monitor therapy or determine the stage of disease.

Imaging Methods

Binding agents, in particular antibodies, specific for one or more urogenital markers may also be used in imaging methodologies in the management of a urogenital condition or assessing the status or state of a urogenital tissue or organ.

In an aspect, the invention provides a method for imaging tissues or organs associated with one or more urogenital disease markers.

The invention also contemplates imaging methods described herein using multiple markers for a urogenital condition or urogenital tissue or organ. Preferably each agent is labeled so that it can be distinguished during the imaging.

In an embodiment the method is an in vivo method and a subject or patient is administered one or more agents that carry an imaging label and that are capable of targeting or binding to one or more urogenital markers. The agent is allowed to incubate in vivo and bind to the urogenital markers associated with urogenital cells or tissues or associated with diseased cells or tissues. The presence of the label is localized to the urogenital cells or tissues, and the localized label is detected using imaging devices known to those skilled in the art.

The agent may be an antibody or chemical entity that recognizes the urogenital markers. In an aspect of the invention the agent is a polyclonal antibody or monoclonal antibody, or fragments thereof or constructs thereof including but not limited to, single chain antibodies, bifunctional antibodies, molecular recognition units, and peptides or entities that mimic peptides. The antibodies specific for the urogenital markers used in the methods of the invention may be obtained from scientific or commercial sources, or isolated native urogenital markers or recombinant urogenital markers may be utilized to prepare antibodies etc. as described herein.

An agent may be a peptide that mimics the epitope for an antibody specific for a urogenital marker and binds to the marker. The peptide may be produced on a commercial synthesizer using conventional solid phase chemistry. By way of example, a peptide may be prepared that includes tyrosine, lysine, or phenylalanine to which $N_2S_2$ chelate is complexed (See U.S. Pat. No. 4,897,255). An anti-urogenital marker peptide conjugate is then combined with a radiolabel (e.g. sodium $^{99m}$Tc pertechnetate or sodium $^{188}$Re perrhenate) and it may be used to locate a urogenital marker producing cell or tissue.

The agent carries a label to image the urogenital markers. The agent may be labeled for use in radionuclide imaging. In particular, the agent may be directly or indirectly labeled with a radioisotope. Examples of radioisotopes that may be used in the present invention are the following: $^{277}$Ac, $^{211}$At, $^{128}$Ba, $^{131}$Ba, $^{7}$Be, $^{204}$Bi, $^{205}$Bi, $^{206}$Bi, $^{76}$Br, $^{77}$Br, $^{82}$Br, $^{109}$Cd, $^{47}$Ca, $^{11}$C, $^{14}$C, $^{36}$Cl, $^{48}$Cr, $^{51}$Cr, $^{62}$Cu, $^{64}$Cu, $^{67}$Cu, $^{165}$Dy, $^{155}$Eu, $^{18}$F, $^{153}$Gd, $^{66}$Ga, $^{67}$Ga, $^{68}$Ga, $^{72}$Ga, $^{198}$Au, $^{3}$H, $^{166}$Ho, $^{111}$In, $^{113m}$In, $^{115m}$In, $^{123}$I, $^{125}$I, $^{131}$I, $^{189}$Ir, $^{191m}$Ir, $^{192}$Ir, $^{194}$Ir, $^{52}$Fe, $^{55}$Fe, $^{59}$Fe, $^{177}$Lu, $^{15}$O, $^{191m-191}$Os, $^{109}$Pd, $^{32}$P, $^{33}$P, $^{42}$K, $^{226}$Ra, $^{186}$Re, $^{188}$Re, $^{82m}$Rb, $^{153}$Sm, $^{46}$Sc, $^{47}$Sc, $^{72}$Se, $^{75}$Se, $^{105}$Ag, $^{22}$Na, $^{24}$Na, $^{89}$Sr, $^{35}$S, $^{38}$S, $^{177}$Ta, $^{96}$Tc, $^{99m}$Tc, $^{201}$Tl, $^{202}$Tl, $^{113}$Sn, $^{117m}$Sn, $^{121}$Sn, $^{166}$Yb, $^{169}$Yb, $^{175}$Yb, $^{88}$Y, $^{90}$Y, $^{62}$Zn, and $^{65}$Zn. Preferably the radioisotope is $^{131}$I, $^{125}$I, $^{123}$I, $^{111}$I, $^{99m}$Tc, $^{90}$Y, $^{186}$Re, $^{32}$P, $^{153}$Sm, $^{67}$Ga, $^{201}$Tl $^{77}$Br, or $^{18}$F, which is imaged with a photoscanning device.

Procedures for labeling biological agents with the radioactive isotopes are generally known in the art. U.S. Pat. No. 4,302,438 describes tritium labeling procedures. Procedures for iodinating, tritium labeling, and $^{35}$S labeling especially adapted for murine monoclonal antibodies are described by Goding, J. W. (supra, pp 124-126) and the references cited therein. Other procedures for iodinating biological agents, such as antibodies, binding portions thereof, probes, or ligands, are described in the scientific literature (see Hunter and Greenwood, Nature 144:945 (1962), David et al., Biochemistry 13:1014-1021 (1974), and U.S. Pat. Nos. 3,867, 517 and 4,376,110). Iodinating procedures for agents are described by Greenwood, F. et al., Biochem. J. 89:114-123 (1963); Marchalonis, J., Biochem. J. 113:299-305 (1969); and Morrison, M. et al., Immunochemistry, 289-297 (1971). $^{99m}$Tc-labeling procedures are described by Rhodes, B. et al. in Burchiel, S. et al. (eds.), Tumor Imaging: The Radioimmunochemical Detection of Disease, New York: Masson 111-123 (1982) and the references cited therein. Labeling of antibodies or fragments with technetium-99m are also described for example in U.S. Pat. Nos. 5,317,091, 4,478,815, 4,478, 818, 4,472,371, 32,417, and 4,311,688. Procedures suitable for $^{111}$In-labeling biological agents are described by Hnatowich, D. J. et al., J. Immul. Methods, 65:147-157 (1983), Hnatowich, D. et al., J. Applied Radiation, 35:554-557 (1984), and Buckley, R. G. et al., F.E.B.S. 166:202-204 (1984).

An agent may also be labeled with a paramagnetic isotope for purposes of an in vivo method of the invention. Examples of elements that are useful in magnetic resonance imaging include gadolinium, terbium, tin, iron, or isotopes thereof (See, for example, Schaefer et al., (1989) JACC 14, 472-480; Shreve et al., (1986) Magn. Reson. Med. 3, 336-340; Wolf, G L., (1984) Physiol. Chem. Phys. Med. NMR 16, 93-95; Wesbey et al., (1984) Physiol. Chem. Phys. Med. NMR 16, 145-

155; Runge et al., (1984) Invest. Radiol. 19, 408-415 for discussions on in vivo nuclear magnetic resonance imaging.)

In the case of a radiolabeled agent, the agent may be administered to the patient, it is localized to the cell or tissue having a urogenital marker with which the agent binds, and is detected or "imaged" in vivo using known techniques such as radionuclear scanning using e.g., a gamma camera or emission tomography. [See for example, A. R. Bradwell et al., "Developments in Antibody Imaging", Monoclonal Antibodies for Disease Detection and Therapy, R. W. Baldwin et al., (eds.), pp. 65-85 (Academic Press 1985)]. A positron emission transaxial tomography scanner, such as designated Pet VI located at Brookhaven National Laboratory, can also be used where the radiolabel emits positrons (e.g., $^{11}C$, $^{18}F$, $^{15}O$, and $^{13}N$).

Whole body imaging techniques using radioisotope labeled agents can be used for locating diseased cells and tissues. Antibodies specific for urogenital markers or fragments thereof having the same epitope specificity, are bound to a suitable radioisotope, or a combination thereof, and administered parenterally. Administration is preferably intravenous. The bio-distribution of the label can be monitored by scintigraphy, and accumulations of the label is related to the presence of disease cells. Whole body imaging techniques are described in U.S. Pat. Nos. 4,036,945 and 4,311,688. Other examples of agents useful for diagnosis and therapeutic use that can be coupled to antibodies and antibody fragments include metallothionein and fragments (see, U.S. Pat. No. 4,732,864). These agents are useful in diagnosis staging and visualization of disease, in particular a urogenital condition, so that surgical and/or treatment protocols can be used more efficiently.

An imaging agent may carry a bioluminescent or chemiluminescent label. Such labels include polypeptides known to be fluorescent, bioluminescent or chemiluminescent, or, that act as enzymes on a specific substrate (reagent), or can generate a fluorescent, bioluminescent or chemiluminescent molecule. Examples of bioluminescent or chemiluminescent labels include luciferases, aequorin, obelin, mnemiopsin, berovin, a phenanthridinium ester, and variations thereof and combinations thereof. A substrate for the bioluminescent or chemiluminescent polypeptide may also be utilized in a method of the invention. For example, the chemiluminescent polypeptide can be luciferase and the reagent luciferin. A substrate for a bioluminescent or chemiluminescent label can be administered before, at the same time (e.g., in the same formulation), or after administration of the agent.

An imaging agent may comprise a paramagnetic compound, such as a polypeptide chelated to a metal, e.g., a metalloporphyrin. The paramagnetic compound may also comprise a monocrystalline nanoparticle, e.g., a nanoparticle comprising a lanthanide (e.g., Gd) or iron oxide; or, a metal ion comprising a lanthanide. "Lanthanides" refers to elements of atomic numbers 58 to 70, a transition metal of atomic numbers 21 to 29, 42 or 44, a Gd(III), a Mn(II), or an element comprising a Fe element. Paramagnetic compounds can also comprise a neodymium iron oxide ($NdFeO_3$) or a dysprosium iron oxide ($DyFeO_3$). Examples of elements that are useful in magnetic resonance imaging include gadolinium, terbium, tin, iron, or isotopes thereof. (See, for example, Schaefer et al., (1989) JACC 14, 472-480; Shreve et al., (1986) Magn. Reson. Med. 3, 336-340; Wolf, G L., (1984) Physiol. Chem. Phys. Med. NMR 16, 93-95; Wesbey et al., (1984) Physiol. Chem. Phys. Med. NMR 16, 145-155; Runge et al., (1984) Invest. Radiol. 19, 408-415, for discussions on in vivo nuclear magnetic resonance imaging.)

An image can be generated in a method of the invention by computer assisted tomography (CAT), magnetic resonance spectroscopy (MRS) image, magnetic resonance imaging (MRI), positron emission tomography (PET), single-photon emission computed tomography (SPECT), bioluminescence imaging (BLI) or equivalent, or computerized axial tomography (CAT) systems and devices well known in the are. (See, for example, U.S. Pat. Nos. 6,151,377; 5,946,371; 5,446,799; 5,406,479; 5,208,581; 5,109,397). The invention may also utilize animal imaging modalities, such as MicroCAT™ (Im-Tek, Inc.).

Screening Methods

The invention also contemplates methods for evaluating test agents or compounds for their ability to inhibit a urogenital condition, potentially contribute to a urogenital condition, or inhibit or enhance a urogenital state. Test agents and compounds include but are not limited to peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), antibodies [e.g. polyclonal, monoclonal, humanized, anti-idiotypic, chimeric, single chain antibodies, fragments, (e.g. Fab, $F(ab)_2$, and Fab expression library fragments, and epitope-binding fragments thereof)], and small organic or inorganic molecules. The agents or compounds may be endogenous physiological compounds or natural or synthetic compounds.

The invention provides a method for assessing the potential efficacy of a test agent for inhibiting a urogenital condition in a patient, the method comprising comparing:
  (a) levels of one or more urogenital markers, and/or polynucleotides encoding urogenital markers, and optionally other markers in a first sample obtained from a patient and exposed to the test agent; and
  (b) levels of one or more urogenital markers and/or polynucleotides encoding urogenital markers, and optionally other markers, in a second sample obtained from the patient, wherein the sample is not exposed to the test agent, wherein a significant difference in the levels of expression of one or more urogenital markers, and/or polynucleotides encoding one or more urogenital markers, and optionally the other markers, in the first sample, relative to the second sample, is an indication that the test agent is potentially efficacious for inhibiting a urogenital condition in the patient.

The first and second samples may be portions of a single sample obtained from a patient or portions of pooled samples obtained from a patient.

In an aspect, the invention provides a method of selecting an agent for inhibiting a urogenital condition in a patient comprising:
  (a) obtaining a sample from the patient;
  (b) separately maintaining aliquots of the sample in the presence of a plurality of test agents;
  (c) comparing one or more urogenital markers, and/or polynucleotides encoding urogenital markers, and optionally other markers, in each of the aliquots; and
  (d) selecting one of the test agents which alters the levels of one or more urogenital markers, and/or polynucleotides encoding urogenital markers, and optionally other markers in the aliquot containing that test agent, relative to other test agents.

Still another aspect of the present invention provides a method of conducting a drug discovery business comprising:

(a) providing one or more methods or assay systems for identifying agents that inhibit a urogenital condition or affect the status of a urogenital tissue or organ in a patient;
(b) conducting therapeutic profiling of agents identified in step (a), or further analogs thereof, for efficacy and toxicity in animals; and
(c) formulating a pharmaceutical preparation including one or more agents identified in step (b) as having an acceptable therapeutic profile.

In certain embodiments, the subject method can also include a step of establishing a distribution system for distributing the pharmaceutical preparation for sale, and may optionally include establishing a sales group for marketing the pharmaceutical preparation.

The invention also contemplates a method of assessing the potential of a test compound to contribute to a urogenital condition comprising:
(a) maintaining separate aliquots of samples (e.g. seminal fluid, tissue) from a patient with a urogenital condition in the presence and absence of the test compound; and
(b) comparing one or more urogenital markers, and/or polynucleotides encoding urogenital markers, and optionally other markers in each of the aliquots.

A significant difference between the levels of the markers in the aliquot maintained in the presence of (or exposed to) the test compound relative to the aliquot maintained in the absence of the test compound, indicates that the test compound possesses the potential to contribute to a urogenital condition.

Kits

The invention also contemplates kits for carrying out the methods of the invention. Kits may typically comprise two or more components required for performing a diagnostic or screening assay. Components include but are not limited to compounds, reagents, containers, and/or equipment.

The methods described herein may be performed by utilizing pre-packaged diagnostic kits comprising one or more specific urogenital marker polynucleotide or binding agent (e.g. antibody) described herein, which may be conveniently used, e.g., in clinical settings to screen and diagnose patients and to screen and identify those individuals exhibiting a predisposition to developing a urogenital condition or that have a urogenital condition.

In an embodiment, a container with a kit comprises a binding agent as described herein. By way of example, the kit may contain antibodies or antibody fragments which bind specifically to epitopes of one or more urogenital markers and optionally other markers, antibodies against the antibodies labeled with an enzyme; and a substrate for the enzyme. The kit may also contain microtiter plate wells, standards, assay diluent, wash buffer, adhesive plate covers, and/or instructions for carrying out a method of the invention using the kit.

In an aspect of the invention, the kit includes antibodies or fragments of antibodies which bind specifically to an epitope of one or more urogenital marker of any Tables 1 to 13 and means for detecting binding of the antibodies to their epitope either as concentrates (including lyophilized compositions), which may be further diluted prior to use or at the concentration of use, where the vials may include one or more dosages. Where the kits are intended for in vivo use, single dosages may be provided in sterilized containers, having the desired amount and concentration of agents. Containers that provide a formulation for direct use usually do not require other reagents, as for example, where the kit contains a radiolabelled antibody preparation for in vivo imaging.

A kit may be designed to detect the level of polynucleotides encoding one or more urogenital polynucleotide markers in a sample. In an embodiment, the polynucleotides encode one or more polynucleotides encoding a urogenital marker of any Tables 1 to 13. Such kits generally comprise at least one oligonucleotide probe or primer, as described herein, that hybridizes to a polynucleotide encoding one or more urogenital disease markers. Such an oligonucleotide may be used, for example, within a PCR or hybridization procedure. Additional components that may be present within the kits include a second oligonucleotide and/or a diagnostic reagent or container to facilitate detection of a polynucleotide encoding one or more urogenital markers.

The invention provides a kit containing a microarray described herein ready for hybridization to target urogenital polynucleotide markers, plus software for the data analysis of the results. The software to be included with the kit comprises data analysis methods, in particular mathematical routines for marker discovery, including the calculation of correlation coefficients between clinical categories and marker expression. The software may also include mathematical routines for calculating the correlation between sample marker expression and control marker expression, using array-generated data, to determine the clinical classification of the sample.

The reagents suitable for applying the screening methods of the invention to evaluate compounds may be packaged into convenient kits described herein providing the necessary materials packaged into suitable containers.

The invention contemplates a kit for assessing the presence of urogenital diseased cells, wherein the kit comprises antibodies specific for one or more urogenital markers, or primers or probes for polynucleotides encoding same, and optionally probes, primers or antibodies specific for other markers associated with a urogenital condition.

The invention relates to a kit for assessing the suitability of each of a plurality of test compounds for inhibiting a urogenital condition in a patient. The kit comprises reagents for assessing one or more urogenital markers or polynucleotides encoding same, and optionally a plurality of test agents or compounds.

Additionally the invention provides a kit for assessing the potential of a test compound to contribute to a urogenital condition. The kit comprises urogenital diseased cells and reagents for assessing one or more urogenital markers, polynucleotides encoding same, and optionally other markers associated with a urogenital condition.

Therapeutic Applications

The invention relates to compositions comprising markers or parts thereof associated with a urogenital condition, or antibodies specific for urogenital markers associated with a urogenital condition, and a pharmaceutically acceptable carrier, excipient, or diluent. A method for treating or preventing a urogenital condition in a patient is also provided comprising administering to a patient in need thereof, markers or parts thereof associated with a urogenital condition, antibodies specific for urogenital markers associated with a urogenital condition, or a composition of the invention. In an aspect the invention provides a method of treating a patient afflicted with or at risk of developing a urogenital condition comprising inhibiting expression of urogenital markers.

The invention also contemplates a method of using urogenital markers or parts thereof, antibodies specific for urogenital markers, or polynucleotides encoding urogenital markers for the prevention or treatment of a urogenital condition, or in the preparation or manufacture of a medicament for the prevention or treatment of a urogenital condition.

One or more urogenital markers may be targets for immunotherapy. Immunotherapeutic methods include the use of antibody therapy, in vivo vaccines, and ex vivo immunotherapy approaches.

In an aspect, the invention provides antibodies specific for urogenital markers associated with a urogenital condition that can be used therapeutically to destroy or inhibit the disease, or to block urogenital marker activity associated with the condition.

In one aspect, the invention provides one or more urogenital marker antibodies that may be used to treat a urogenital condition associated with the marker. In particular, one or more urogenital marker antibodies may be used to treat a urogenital condition. Preferably antibodies are used that target the diseased cells/tissues but not the surrounding healthy cells and tissue.

Thus, the invention provides a method of treating a patient susceptible to, or having a disease that expresses one or more urogenital marker (in particular a marker up-regulated in a urogenital condition, for example, an up-regulated marker in any of Tables 1 to 13), comprising administering to the patient an effective amount of an antibody that binds specifically to one or more urogenital marker.

One or more urogenital marker antibodies may also be used in a method for selectively inhibiting the growth of, or killing a cell expressing one or more urogenital marker comprising reacting one or more urogenital marker antibody immunoconjugate or immunotoxin with the cell in an amount sufficient to inhibit the growth of, or kill the cell.

By way of example, unconjugated antibodies to urogenital disease markers may be introduced into a patient such that the antibodies bind to urogenital disease marker expressing disease cells and mediate growth inhibition of such cells (including the destruction thereof) by mechanisms which may include complement-mediated cytolysis, antibody-dependent cellular cytotoxicity, altering the physiologic function of one or more urogenital disease markers, and/or the inhibition of ligand binding or signal transduction pathways. In addition to unconjugated antibodies to urogenital disease markers, one or more urogenital disease marker antibodies conjugated to therapeutic agents (e.g. immunoconjugates) may also be used therapeutically to deliver the agent directly to one or more urogenital disease marker expressing cells. Examples of such agents include abrin, ricin A, *Pseudomonas* exotoxin, or diphtheria toxin; proteins such as tumor necrosis factor, alpha-interferon, beta-interferon, nerve growth factor, platelet derived growth factor, tissue plasminogen activator; and biological response modifiers such as lymphokines, interleukin-1, interleukin-2, interleukin-6, granulocyte macrophage colony stimulating factor, granulocyte colony stimulating factor, or other growth factors.

Disease immunotherapy using one or more urogenital disease marker antibodies may utilize the various approaches that have been successfully employed for diseases, including but not limited to colon cancer (Arlen et al., 1998, Crit Rev Immunol 18: 133-138), multiple myeloma (Ozaki et al., 1997, Blood 90: 3179-3186; Tsunenati et al., 1997, Blood 90: 2437-2444), gastric disease (Kasprzyk et al., 1992, Disease Res 52: 2771-2776), B-cell lymphoma (Funakoshi et al., 1996, J Immunther Emphasis Tumor Immunol 19: 93-101), leukemia (Zhong et al., 1996, Leuk Res 20: 581-589), colorectal disease (Moun et al., 1994, Disease Res 54: 6160-6166); Velders et al., 1995, Disease Res 55: 4398-4403), and breast disease (Shepard et al., 1991, J Clin Immunol 11: 117-127).

In the practice of a method of the invention, urogenital disease marker antibodies capable of inhibiting the growth of disease cells expressing urogenital disease markers are administered in a therapeutically effective amount to disease patients whose disease cells express or overexpress one or more urogenital disease markers. The invention may provide a specific and effective treatment for a urogenital condition. The antibody therapy methods of the invention may be combined with other therapies.

Patients may be evaluated for the presence and level of expression or overexpression of one or more urogenital markers in diseased cells and tissues, in particular using immunohistochemical assessments of tissue, quantitative imaging as described herein, or other techniques capable of reliably indicating the presence and degree of expression of one or more urogenital markers. Immunohistochemical analysis of biopsies or surgical specimens may be employed for this purpose.

The methods of the invention contemplate the administration of single urogenital marker antibodies as well as combinations, or "cocktails", of different individual antibodies such as those recognizing different epitopes of other markers. Such cocktails may have certain advantages inasmuch as they contain antibodies that bind to different epitopes of urogenital markers and/or exploit different effector mechanisms or combine directly cytotoxic antibodies with antibodies that rely on immune effector functionality. Such antibodies in combination may exhibit synergistic therapeutic effects. In addition, the administration of one or more urogenital marker specific antibodies may be combined with other therapeutic agents. The urogenital marker specific antibodies may be administered in their "naked" or unconjugated form, or may have therapeutic agents conjugated to them.

The urogenital marker specific antibodies used in the methods of the invention may be formulated into pharmaceutical compositions comprising a carrier suitable for the desired delivery method. Suitable carriers include any material which when combined with the antibodies retains the function of the antibody and is non-reactive with the subject's immune systems. Examples include any of a number of standard pharmaceutical carriers such as sterile phosphate buffered saline solutions, bacteriostatic water, and the like (see, generally, Remington's Pharmaceutical Sciences 16.sup.th Edition, A. Osal., Ed., 1980).

One or more urogenital marker specific antibody formulations may be administered via any route capable of delivering the antibodies to the disease site. Routes of administration include, but are not limited to, intravenous, intraperitoneal, intramuscular, intradermal, and the like. Preferably, the route of administration is by intravenous injection. Antibody preparations may be lyophilized and stored as a sterile powder, preferably under vacuum, and then reconstituted in bacteriostatic water containing, for example, benzyl alcohol preservative, or in sterile water prior to injection.

Treatment will generally involve the repeated administration of the antibody preparation via an acceptable route of administration such as intravenous injection (IV), at an effective dose. Dosages will depend upon various factors generally appreciated by those of skill in the art, including the type of condition and the severity, grade, or stage of the condition, the binding affinity and half life of the antibodies used, the degree of urogenital marker expression in the patient, the extent of circulating urogenital markers, the desired steady-state antibody concentration level, frequency of treatment, and the influence of any therapeutic agents used in combination with the treatment method of the invention. Daily doses may range from about 0.1 to 100 mg/kg. Doses in the range of 10-500 mg antibodies per week may be effective and well tolerated, although even higher weekly doses may be appropriate and/or well tolerated. A determining factor in defining the appropriate dose is the amount of a particular antibody necessary to be therapeutically effective in a particular context. Repeated administrations may be required to achieve disease inhibition or regression. Direct administration of one or more urogenital marker antibodies is also possible and may have advantages in certain situations.

Patients may be evaluated for urogenital disease markers in order to assist in the determination of the most effective dosing regimen and related factors. The urogenital condition assay methods described herein, or similar assays, may be used for quantitating circulating urogenital marker levels in patients prior to treatment. Such assays may also be used for monitoring throughout therapy, and may be useful to gauge therapeutic success in combination with evaluating other parameters such as serum levels of urogenital markers.

Another aspect of the invention is the use of urogenital markers, peptides derived therefrom, or chemically produced (synthetic) peptides, or any combination of these molecules, for use in the preparation of vaccines to prevent a urogenital condition and/or to treat a urogenital condition.

The invention contemplates vaccines for stimulating or enhancing in a subject to whom the vaccine is administered production of antibodies directed against one or more urogenital markers.

The invention also provides a method for stimulating or enhancing in a subject production of antibodies directed against one or more urogenital marker. The method comprises administering to the subject a vaccine of the invention in a dose effective for stimulating or enhancing production of the antibodies.

The invention further provides a method for treating, preventing, or delaying recurrence of a urogenital condition. The method comprises administering to the subject a vaccine of the invention in a dose effective for treating, preventing, or delaying recurrence of a urogenital condition.

The invention further provides vaccines formulated to contain one or more urogenital marker or fragment thereof. In an embodiment, the invention provides a method of vaccinating an individual against one or more urogenital marker of Table 1, 4, 6, 7, 8, 10, 11 12, or 13 comprising the step of inoculating the individual with the marker or fragment thereof that lacks activity, wherein the inoculation elicits an immune response in the individual thereby vaccinating the individual against the marker.

The methods can be practiced by employing one or more urogenital markers, or fragment thereof, or urogenital polynucleotide markers and recombinant vectors capable of expressing and appropriately presenting urogenital marker immunogens. By way of example, viral gene delivery systems may be used to deliver one or more urogenital polynucleotide markers. Various viral gene delivery systems which can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8: 658-663). Non-viral delivery systems may also be employed by using naked DNA encoding one or more urogenital disease marker or fragment thereof introduced into the patient (e.g., intramuscularly) to induce a therapeutic response.

Various ex vivo strategies may also be employed. One approach involves the use of cells to present one or more urogenital marker to a patient's immune system. For example, autologous dendritic cells which express MHC class I and II, may be pulsed with one or more urogenital marker or peptides thereof that are capable of binding to MHC molecules, to thereby stimulate the patients' immune systems (See, for example, Tjoa et al., 1996, Prostate 28: 65-69; Murphy et al., 1996, Prostate 29: 371-380).

Anti-idiotypic urogenital marker specific antibodies can also be used in therapy as a vaccine for inducing an immune response to cells expressing one or more urogenital marker. The generation of anti-idiotypic antibodies is well known in the art and can readily be adapted to generate anti-idiotypic urogenital disease marker specific antibodies that mimic an epitope on one or more urogenital disease markers (see, for example, Wagner et al., 1997, Hybridoma 16: 33-40; Foon et al., 1995, J Clin Invest 96: 334-342; Herlyn et al., 1996, Disease Immunol Immunother 43: 65-76). Such an antibody can be used in anti-idiotypic therapy as presently practiced with other anti-idiotypic antibodies directed against antigens associated with disease.

Genetic immunization methods may be utilized to generate prophylactic or therapeutic humoral and cellular immune responses directed against cells expressing one or more urogenital disease marker. One or more DNA molecules encoding urogenital markers, constructs comprising DNA encoding one or more urogenital markers/immunogens and appropriate regulatory sequences may be injected directly into muscle or skin of an individual, such that the cells of the muscle or skin take-up the construct and express the encoded urogenital markers/immunogens. The urogenital markers/immunogens may be expressed as cell surface proteins or be secreted. Expression of one or more urogenital markers results in the generation of prophylactic or therapeutic humoral and cellular immunity against the disease. Various prophylactic and therapeutic genetic immunization techniques known in the art may be used.

The invention further provides methods for inhibiting cellular activity (e.g., cell proliferation, activation, or propagation) of a cell expressing one or more urogenital marker. This method comprises reacting immunoconjugates of the invention (e.g., a heterogeneous or homogenous mixture) with the cell so that urogenital markers on the cell form complexes with the immunoconjugates. A subject with a urogenital condition can be treated when the inhibition of cellular activity results in cell death.

In another aspect, the invention provides methods for selectively inhibiting a cell expressing one or more urogenital marker by reacting any one or a combination of the immunoconjugates of the invention with the cell in an amount sufficient to inhibit the cell. Amounts include those that are sufficient to kill the cell or sufficient to inhibit cell growth or proliferation.

Vectors derived from retroviruses, adenovirus, herpes or vaccinia viruses, or from various bacterial plasmids, may be used to deliver polynucleotides encoding urogenital disease markers to a targeted organ, tissue, or cell population. Methods well known to those skilled in the art may be used to construct recombinant vectors that will express antisense polynucleotides for urogenital markers. (See, for example, the techniques described in Sambrook et al (supra) and Ausubel et al (supra)).

Methods for introducing vectors into cells or tissues include those methods discussed herein and which are suitable for in vivo, in vitro and ex vivo therapy. For ex vivo therapy, vectors may be introduced into stem cells obtained from a patient and clonally propagated for autologous transplant into the same patient (See U.S. Pat. Nos. 5,399,493 and 5,437,994). Delivery by transfection and liposome are well known in the art.

Genes encoding urogenital markers can be turned off by transfecting a cell or tissue with vectors that express high levels of a desired urogenital marker-encoding fragment.

Such constructs can inundate cells with untranslatable sense or antisense sequences. Even in the absence of integration into the DNA, such vectors may continue to transcribe RNA molecules until all copies are disabled by endogenous nucleases.

Modifications of gene expression can be obtained by designing antisense molecules, DNA, RNA or PNA, to the regulatory regions of a gene encoding a urogenital marker, i.e., the promoters, enhancers, and introns. Preferably, oligonucleotides are derived from the transcription initiation site, e.g. between −10 and +10 regions of the leader sequence. The antisense molecules may also be designed so that they block translation of mRNA by preventing the transcript from binding to ribosomes. Inhibition may also be achieved using "triple helix" base-pairing methodology. Triple helix pairing compromises the ability of the double helix to open sufficiently for the binding of polymerases, transcription factors, or regulatory molecules. Therapeutic advances using triplex DNA were reviewed by Gee J E et al (In: Huber B E and B I Carr (1994) Molecular and Immunologic Approaches, Futura Publishing Co, Mt Kisco N.Y.).

Ribozymes are enzymatic RNA molecules that catalyze the specific cleavage of RNA. Ribozymes act by sequence-specific hybridization of the ribozyme molecule to complementary target RNA, followed by endonucleolytic cleavage. The invention therefore contemplates engineered hammerhead motif ribozyme molecules that can specifically and efficiently catalyze endonucleolytic cleavage of sequences encoding a urogenital marker.

Specific ribozyme cleavage sites within any potential RNA target may initially be identified by scanning the target molecule for ribozyme cleavage sites which include the following sequences, GUA, GUU and GUC. Once the sites are identified, short RNA sequences of between 15 and 20 ribonucleotides corresponding to the region of the target gene containing the cleavage site may be evaluated for secondary structural features which may render the oligonucleotide inoperable. The suitability of candidate targets may also be determined by testing accessibility to hybridization with complementary oligonucleotides using ribonuclease protection assays.

One or more urogenital markers and polynucleotides encoding the markers, and fragments thereof, may be used in the treatment of a urogenital condition in a subject. In an aspect the urogenital markers and polynucleotides encoding the markers are urogenital disease markers that are down-regulated in urogenital condition, for example, a down-regulated marker in Table 1, 4, 8, 12 or 13. The markers or polynucleotides may be formulated into compositions for administration to subjects suffering from a urogenital condition. Therefore, the present invention also relates to a composition comprising one or more urogenital markers or polynucleotides encoding the markers, or a fragment thereof, and a pharmaceutically acceptable carrier, excipient or diluent. A method for treating or preventing a urogenital condition in a subject is also provided comprising administering to a patient in need thereof, one or more urogenital markers or polynucleotides encoding the markers, or a composition of the invention.

The invention further provides a method of inhibiting a urogenital condition in a patient comprising:
(a) obtaining a sample comprising diseased cells from the patient;
(b) separately maintaining aliquots of the sample in the presence of a plurality of test agents;
(c) comparing levels of one or more urogenital markers, and/or polynucleotides encoding one or more urogenital markers in each aliquot;
(d) administering to the patient at least one of the test agents which alters the levels of the urogenital markers, and/or polynucleotides encoding one or more urogenital markers in the aliquot containing that test agent, relative to the other test agents.

An active therapeutic substance described herein may be administered in a convenient manner such as by injection (subcutaneous, intravenous, etc.), oral administration, inhalation, transdermal application, or rectal administration. Depending on the route of administration, the active substance may be coated in a material to protect the substance from the action of enzymes, acids and other natural conditions that may inactivate the substance. Solutions of an active compound as a free base or pharmaceutically acceptable salt can be prepared in an appropriate solvent with a suitable surfactant. Dispersions may be prepared in glycerol, liquid polyethylene glycols, and mixtures thereof, or in oils.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the active substances in association with one or more pharmaceutically acceptable vehicles or diluents, and contained in buffered to solutions with a suitable pH and iso-osmotic with the physiological fluids.

The compositions are indicated as therapeutic agents either alone or in conjunction with other therapeutic agents or other forms of treatment. The compositions of the invention may be administered concurrently, separately, or sequentially with other therapeutic agents or therapies.

The therapeutic activity of compositions and agents/compounds identified using a method of the invention and may be evaluated in vivo using a suitable animal model.

The following non-limiting examples are illustrative of the present invention:

EXAMPLE 1

The proteomes of pooled seminal plasma from fertile control and post-vasectomy (PV) men were profiled. PV seminal plasma samples are void of proteins originating from the testis and the epididymis due to ligation of the vas deferens, hence, comparative analysis of control and PV datasets allows for identification of proteins originating from these tissues. Utilizing offline MudPIT and high-resolution mass spectrometry over 2000 proteins were identified in Control and PV pools each and over 2300 proteins all together. With semi-quantitative analysis using spectral counting 32 proteins unique to Control, 49 at lower abundance in PV, 3 unique to PV and 25 at higher abundance in PV were catalogued. Proteins unique to Control or at lower abundance in PV have their origin in the testis and the epididymis. Many of these proteins have been confirmed to originate from the testis and epididymis and to be linked to the reproductive tract.

The following materials and methods were used in the study.

Sample Collection and Processing. Semen from fertile men (controls) and post-vasectomy men (PV) was collected after a minimum of 3 days of sexual abstinence. Samples were allowed to liquefy for 2-3 hours at room temperature and centrifuged at 13,000×g for 10 minutes. The supernatant (seminal plasma) was aliquoted into 1.5 mL Eppendorf tubes and stored at −80° C. until further analysis. Total protein concentration was measured using the Biuret assay and ranged between 26-55 mg/mL. Five control and five post-vasectomy (PV) seminal plasma samples were combined to make 'Control' and 'PV' pools, such that each sample contributed an equivalent amount of protein to the 3 mg of total protein pool. Many aliquots of such pools were prepared to allow for repeated analysis, as necessary (see below).

Trypsin Digestion. Three Control and three PV pools were denatured with 8 M urea (7 M final), reduced with 200 mM dithiothreitol (15 mM final, Sigma) for 30 minutes at 50° C. and alkylated with 500 mM iodoacetamide (125 mM final, Sigma) in the dark, on a shaker at room temperature for 60 minutes. Next, samples were desalted using PD-10 columns (GE Healthcare) in 50 mM ammonium bicarbonate, frozen and partially lyophilized to reduce sample volume. The samples were left to digest overnight at 37° C. by addition of 400 µL of 50 mM ammonium bicarbonate (pH 8), 60 mg of sequencing grade modified porcine trypsin (1:50, trypsin:protein concentration, Promega) and 200 µL of methanol. To stop the digestion in the morning, the samples were acidified to pH 2 with 20 µL of formic acid.

Strong-Cation Exchange Liquid Chromatography. Each of the trypsin-digested Control and PV samples was diluted two-fold to 2.5 mL with mobile phase A (0.26 M formic acid in 10% acetonitrile) and loaded onto a strong-cation exchange (SCX) PolySULFOETHYL A column (The Nest Group, Inc.) connected to an Agilent 1100 HPLC system. A 60 minute method with an increasing mobile phase B (1 M ammonium formate, 0.26 M formic acid in 10% acetonitrile) gradient at a flow of 200 µL/min was used to elute the peptides. The peptide elution profile was monitored with absorbance at 280 nm and fractions were collected every minute, resulting in 60 fractions. Based on the absorbance elution profile, fractions 26-30 as well as 50-54 were pooled together, whereas fractions 31 to 49 were stored individually, all at −80° C.

Mass Spectrometry. A total of 21 SCX fractions from each of the three Control and PV were desalted and pre-concentrated using the Omix C18MB (Varian Inc.) tips and eluted with 5 µl of buffer A (0.1% formic acid and 0.02% trifluoroacetic acid in 65% acetonitrile). To each sample, 80 µL of buffer B (0.1% formic acid and 0.02% trifluoroacetic acid in 5% acetonitrile) was added, of which 40 µL was loaded from a 96-well microplate autosampler onto a $C_{18}$ trap column using the EASY-nLC system (Proxeon Biosystems, Odense, Denmark) and running Buffer C (0.1% formic acid in water). The trap column consisted of IntegraFrit capillary (inner diameter 150 µm, New Objective) cut to 3 cm in length and packed in-house with 5 µm Pursuit $C_{18}$ (Varian Inc.). Peptides were eluted from the trap column with an increasing concentration of Buffer D (0.1% formic acid in acetonitrile) onto a resolving 5 cm long PicoTip Emitter (75 µm inner diameter, 8 µm tip, New Objective) packed in-house with 3 µm Pursuit $C_{18}$ (Varian Inc.). Pooled fraction 26-30 and individual fractions 31 to 39 were subjected to an 88 min liquid chromatography gradient, whereas fractions 40 to 49 and pooled 50-54 were analyzed with a 55 min gradient at a flow of 400 nL/min. This liquid chromatography setup was coupled online to LTQ-Orbitrap XL (Thermo Fisher Scientific, San Jose, Calif.) mass spectrometer using a nanoelectrospray ionization source (Proxeon Biosystems, Odense, Denmark) with capillary temperature set to 160° C. and spray voltage of 2 kV. The full $MS^1$ scan from 450-1450 m/z was acquired in the Orbitrap at a resolution of 60,000 with subsequent $MS^2$ scans on the top six parent ions in the linear ion trap (LTQ) in data-dependent mode. Dynamic exclusion, monoisotopic precursor selection and charge state screening were enabled. Unassigned charge states as well as charges +1 and ≥+4 were rejected from $MS^2$ fragmentation.

Data analysis. XCalibur RAW files were uploaded into Mascot Daemon (v. 2.2) and Mascot Generic Files (MGF) were generated using extract_msn with the following parameters: minimum mass, 300 Da; maximum mass, 4000 Da; automatic precursor charge selection; minimum peaks, 10 per MS/MS scan for acquisition; and minimum scans per group, 1. MGF files were then searched with Mascot (Matrix Science, London, UK; version 2.2) and X!Tandem (Global Proteome Machine Manager, version 2006.06.01) against the non-redundant IPI.Human v.3.54 database containing 75,426 forward and 75,426 reverse protein sequences. Data was searched with one missed cleavage allowed, fixed carbamidomethylation of cysteines and the following variable modifications: oxidation of methionines, deamidation of asparagines and glutamines, cyclization of N-terminal glutamic and aspartic acids (pyroGlu-Asp), and protein N-terminal acetylation. A parent tolerance of 7 ppm and fragment tolerance of 0.4 Da were used for both search engines with trypsin as the digestion enzyme. The resulting Mascot DAT and X!Tandem XML search result files were all loaded into Scaffold (version 2.0, Proteome Software Inc., Portland, Oreg.) with 'MudPIT' (multidimensional protein identification technology) and 'Thinning on' options checked. Scaffold result data was filtered using the X!Tandem LogE filter and Mascot ion-score filters in order to achieve a protein false-positive rate (FPR) of ~1.1-1.5%. Scaffold protXML reports were exported and uploaded into Protein Center (Proxeon Biosystems, Odense, Denmark) to retrieve Genome Ontology annotations.

The following are the results of the study.

Sample preparation and LC-MS analysis. Collected ejaculate samples from healthy controls and post-vasectomy men were allowed to liquefy. To account for inter-individual variability, samples from five patients of the same diagnostic group were pooled together and then divided into three replicates, each containing 3 mg of protein. Following digestion, each replicate was fractionated using a strong-cation exchange liquid-chromatography to simplify the complexity of the peptide mixture, thereby increasing the depth of peptide identification. Control and PV groups were analyzed in triplicate in order to gauge reproducibility, increase protein identification and prediction confidence. The first 10 fractions were analyzed with an 88 min gradient versus 55 min for the remaining 11 fractions, as the former had greater sample complexity resulting in more peptide identifications.

Data Analysis.

Data was searched with Mascot and X!Tandem since use of multiple search engines increases protein sequence coverage and number of protein identifications. Search results from the two search engines were merged using Scaffold 2.0 in MudPit mode for analysis and visualization [Searle et al, 2008]. Mascot and X!Tandem filter settings were adjusted for individual Control and PV groups to achieve an FPR of 1.1-1.5%. FPR was computed as 2×FP/(TP+FP), where FP (false positive) is the number of spectra matching the reverse database and TP (true positive) is the number of spectra matching the forward database [Elias, J. E. and Gygi, S. P, 2007; Choi, H.; Nesvizhskii, A. I., 2008]. A triplicate sample dataset corresponding to Control and PV clinical diagnostic groups was uploaded into Scaffold and normalized according to the number of spectra in each sample. Cellular component and protein function from Genome Ontology for each clinical category was retrieved using Protein Center. Since one protein may have multiple functions and can be localized in several cellular compartments, many of the proteins have been annotated to more than one classification within the Genome Ontology.

Figure 2:
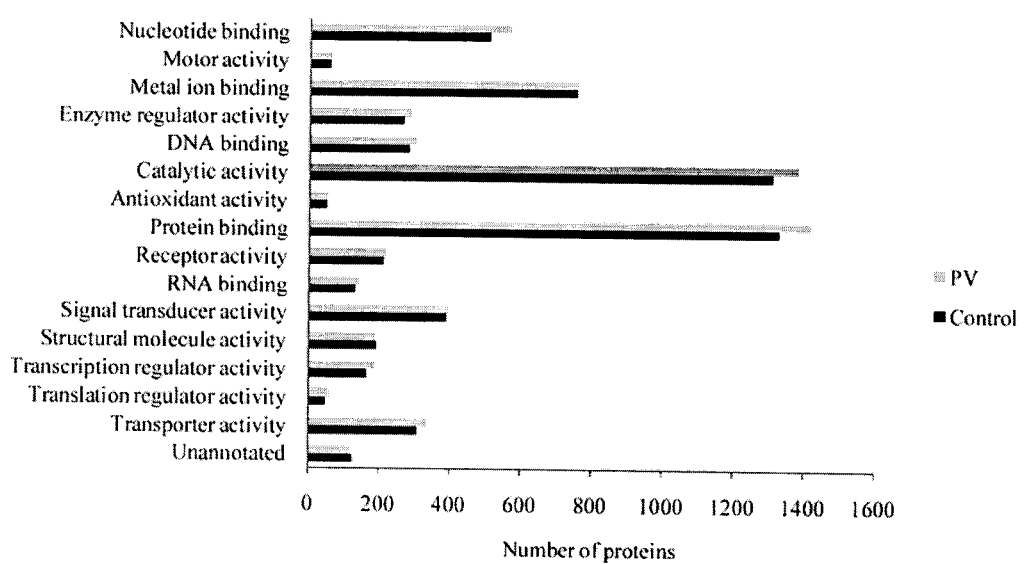
FIG. 2 shows the distribution of molecular function of proteins identified in Control and post-vasectomy (PV) seminal plasma samples.

Proteins identified in the Control and PV Groups. 1569, 1658 and 1657 proteins were identified in each replicate belonging to the Control group, with a total of 2022 proteins (including 15 proteins that matched reverse sequences) at FPR of 1.5%. Genome Ontology analysis shows that the majority of proteins have cytoplasmic, followed by membrane, extracellular and nuclear origin (FIG. 1a). The largest percentages of proteins are implicated in binding followed by catalytic function (FIG. 2).

In triplicate analysis of the PV group a total of 2096 proteins (including 12 proteins that matched reverse sequences) were found at FPR of 1.1% with 1411, 1599 and 1810 proteins in each replicate. Genome Ontology breakdown of cellular component and function illustrates that these proteins are distributed in the same manner as those in the Control group (FIG. 1b, FIG. 2).

Comparison of Control and PV protein lists. One objective was to identify the tissue of origin of proteins within the semen. Those proteins found exclusively, or more abundantly, in the Control group compared to the post-vasectomy group, are likely to have originated from the testis and/or the epididymis. Comparing Control and PV proteomes, there are 1662 proteins in common, 280 found only in Control and 418 found only in PV. In total, 2360 proteins (including 15 proteins that matched reverse sequences) were identified at FRP of 1.3% in the combined Control and PV groups. The common or unique proteins to each group include proteins that were identified by one peptide and/or in one replicate. Normalized spectral counts were used to identify proteins that were unique to one group or under-expressed in one group in comparison to the other. The following arbitrary criteria were used to select a high-confidence list of potential proteins originating from the testis and/or the epididymis or proteins with higher concentration in one of the groups (a) proteins that showed an average of at least 3 spectral counts in one group and zero in the other (b) fold changes ≥2 (c) fold changes ≥2 but <3 needed to have an average spectral count of at least 10 in one clinical group (d) fold changes ≥3 needed to have an average spectral count of at least 5 in one clinical group (e) spectral counts in each replicate (belonging to the same clinical group) for criteria a-d needed to be consistent. Selected proteins that had their spectral counts significantly elevated due to shared peptides with other proteins were removed from analysis. Applying the above mentioned selection criteria the following was found: 32 proteins uniquely present in the Controls; 49 present at lower abundance in PV; 3 uniquely present in the PV; 25 present at higher abundance in PV (Table 1, Table 2, Table 3). In the case of proteins at higher or lower concentration, the majority of the candidates have fold changes much greater than the cut-off of 2. Since the fold changes were calculated from averaged spectral counts, they may be overestimated, especially in cases where only one out of three replicates contains spectral counts.

The 109 proteins that are found uniquely or more abundantly in either of the two clinical groups were searched against UniProtKB, UniGene, BioGPS (formerly Novartis Gene Expression Atlas) and Human Protein Atlas databases for tissue specificity. Only proteins that showed restricted, dominant or above average expression in the testis, epididymis, seminal vesicle or prostate were annotated as expressed in these tissues. In order for proteins to be selected as being specific to the above mentioned tissues, in UniGene expression needed to be 'restricted' to the tissue of interest or the tissue had a dominant/major contribution, in BioGPS expression in the tissue of interest needed to be at least 3× the average expression, in Human Protein Atlas expression needed to be 'strong'. Because not all databases contained epididymis and seminal vesicle in their tissue list, and since epididymis is proximal to the site of ligation in post-vasectomy patients and would not contribute to the protein pool in PV samples, proteins expressed in the epididymis were grouped with testis as testis-specific. There are 14 proteins that show testicular/epididymal origin in three out of four databases, 7 are in the list of proteins unique to Control and 7 are in the list of proteins at lower abundance in PV (Table 4). When only two out of four databases are considered, then in addition to the 14 proteins above, there are 8 other proteins found in the testis/epididymis: 6 in the list of proteins unique to Control and 2 in the list of proteins at lower abundance in PV (Table 1, Table 2). There are also 2 proteins found in two out of four databases with expression in the prostate. 19 proteins were identified with 'restricted' expression in the testis, 15 according to UniGene and 16 according to BioGPS. Upon comparison of the 109 proteins to proteomic analysis of three prostate disease cell lines by Sardana et al., 2008, 29 proteins among all three cell lines are in common; 15 found in 22Rv1, 17 found in LNCaP and 20 in PC3.

2022 proteins were identified in pooled seminal plasma from 5 fertile (Control) men and 2096 proteins in men who had a vasectomy (PV). Currently, this is the most exhaustive list of proteins to be found in seminal plasma. Of the 923 seminal plasma proteins identified by Pilch et al., 2006, 699 are in common with this list. There were also 349 proteins in common between the list and that of Wang et al. 2009, where 625 proteins were identified in fertile patients. An indication of the tissues of origin of some of these proteins could be determined by comparing the protein lists with proteomic studies from other reproductive tract fluids. There has never been a proteomic study on prostatic fluid, but Poliakov et al., 2009 characterized the protein composition of membrane-bound vesicles (prostasomes) secreted by the prostate gland. Of the 440 proteins identified by Poliakov et al 2009, 316 are found in the Control list. No proteomic studies on whole epididymal fluid have been reported. In a study of membraneous vesicles secreted in the intraluminal compartment of the epididymis (epididymosomes), Thimon et al., 2008, identified 146 proteins. Epididymosomes are believed to be involved in the transfer of proteins to spermatozoa as they pass the epididymis, having an important role in sperm maturation [Sullivan, R, et al, 2007]. 112 of these epididymosomal proteins were identified in the Control list and 100 in the PV list. One epididymosomal protein, ARF5, was found in the PV list, but not in Control, whereas the 13 proteins: LDHC, TEX101, HSPA2, ADAM7, PGK2, PGAM2, GAPDHS, ZPBP, AKAP4, RUVBL1, HK1, NRAS and SDCBP2 were not identified in the PV group. Since LDHC, TEX101, ADAM7, PGK2, PGAM2, GAPDHS are in the list of 32 proteins unique to Control, it suggests their epididymal origin. All proteins other than PGAM2 were identified by two or more databases as being expressed in the testis. As vasectomy obstructs the passage of epididymal proteins into seminal plasma, a significantly lower number of epididymosomal proteins may be found in PV seminal plasma than in Control. This suggests that proteins which make up epididymosomes are not strictly found in the epididymis, but also in other regions of the reproductive tract.

Genome Ontology analysis shows that the majority of the proteins in Control and PV groups have cytoplasmic, followed by membrane, extracellular and nuclear origin. The possible explanation for the large portion of proteins being cytoplasmic (and intracellular) is due to the presence of prostasomes and epididymosomes in seminal plasma. Prostasomes, arising from the prostate, are exosome-like vesicles that form into vesicular bodies from intracellular membranes, taking up cytoplasmic and intracellular proteins in the process. Similarly, epididymosomes originate in the epididymis and are secreted into seminal plasma in an apocrine manner [Thimon, V et al, 2008]. Since prostasomes and epididymosomes have not been removed from seminal plasma in this study, many of these intracellular proteins would find their way into seminal plasma [Poliakov, A, et al, 2009].

Functionally, the majority of the proteins have been assigned a binding function, followed by catalytic activity. The binding category consists of many different subcategories of which protein binding is the largest. This is a very general protein designation category as protein binding functionality could be implicated in another function. A large proportion of seminal plasma proteins have been assigned a catalytic activity, consistent with many of the proteins being involved in semen coagulum liquefaction and sperm maturation.

Proteins unique to Control. Many of the proteins found to be unique to the Control group have been identified with one peptide and not in all three replicates. Therefore, in order to improve the confidence in recognition of proteins strictly found in the Control group, selection criteria described earlier were used to narrow the list of proteins down to 32 (Table 1). Proteins TEX101, PGK2, HIST1H2BA, SLC2A14, SPACA3, GAPDHS and AKAP4 are exclusively or mainly transcribed in the testis/epididymis in at least three out of four searched databases (Table 4), whereas LDHC, DPEP3, ADAM7, ACRBP, SLC1A1 and ZPBP are found in two out of four databases (Table 1). Note that proteins expressed in the epididymis were grouped as testis-specific since only two databases contained epididymis in their tissue list. The 19 remaining proteins: CEL, LIPI, BSPH1, OVCH2, MFGE8, PGAM2, CDH2, MFAP4, REG3G, PTPRG, HSPA4L, THBS2, RNASE13, VASN, LRRC37A3, SI, C16orf89, DEFB121 and BSG have not been identified as testis- or epididymis-specific by at least 2 databases. According to UniGene, proteins LDHC, DPEP3, ADAM7, PGK2, ACRBP2, SLC2A14, RNASE13, SPACA3, GAPDHS, ZBPB and AKAP4 are found to have 'restricted' expression in the testis. Similarly, in BioGPS, LDHC, DPEP3, TEX101, ADAM7, PGK2, HSPA4L, SPACA3, GAPDHS, ZPBP and AKAP4 are also exclusively expressed in the testis. Some of these proteins may have been identified as testis- or epididymis-specific by at least one database. The 32 proteins unique to the Control are mostly extracellular, followed by membrane and cytoplasmic or a combination thereof. Interestingly, whereas in the Control group the extracellular component was the third largest, amongst these Control-unique proteins the extracellular component dominates. In addition to proteins annotated as expressed in testis/epididymis, the remaining proteins on this list may potentially have their origin in the testis or the epididymis and may represent candidate markers of infertility.

According to the literature, many proteins that have testicular or epididymal tissue specificity have been shown to have a strong link to fertility. LDHC (L-lactate dehydrogenase C chain) is a testis-specific enzyme secreted into testicular or epididymal fluid from exfoliated postmeiotic germ cells [Virji, N. and Naz, R. K., 1995] that affects male fertility due to reduced sperm motility [Odet, F.; et al, 2008]. Absence of LDHC inhibits glycolysis which results in lower levels of ATP (adenosine triphosphate) required from movement of sperm flagellum [Odet, F.; et al, 2008]. The LDHC/sperm ratio is indicative of the status of the seminiferous epithelium [Virji, N. and Naz, R. K., 1995]. Measurement of LDH-C4 (homotetramer of LDHC) in semen samples of fertile and infertile men showed complete absence of LDH-C4 activity in all azoospermic samples except one, and all samples from men who underwent a vasectomy compared to fertile controls [Sawane, M. V., 2002]. In mouse, TEX101 is a germ cell marker glycoprotein during gametogenesis [Takayama, T., 2005a; Takayama, T., 2005b; Yoshitake, H., 2008]. It is later found on spermatocytes, spermatids and testicular sperm after the onset of puberty and is shed as sperm passes the caput epididymis [Takayama, T., 2005a; Takayama, T., 2005b]. In mouse studies, ADAM7 expressed in the epididymis is transferred to the sperm surface and during acrosome reaction it is redistributed to the posterior of the sperm head [Oh, J., et al, 2005]. It is possible that ADAM7 may play a critical role in sperm maturation. PGK2 is involved in glycolysis of spermatozoa as it activates phosphoglycerate-kinase, important for development of spermatozoa [Yoshioka, H., 2007]. PGK2 gene, along with LDHC and GAPDHS, are germ-cell specific genes [Yoshioka, H., 2007]. GAPDHS, being a glycolytic enzyme found in fibrous sheath of the sperm tail is involved in glycolysis, a process that produces ATP required for movement of sperm flagellum [Krisfalusi, M., 2006; Miki, K. et al, 2004] GAPDHS knock-out mice contain sperm that is immotile, suggesting importance of GAPDHS in male fertility. AKAP4 is another fibrous sheath protein that is involved in sperm motility. In AKAP4 null male mice, sperm numbers were not reduced, but sperm motility was diminished resulting in infertility [Miki, K. et al, 2002]. In these mice, sperm had morphological differences such as reduced sperm diameter, shortened flagellum and improper formation of the fibrous sheath. Mutant mice also showed lower GAPDHS expression levels, suggesting that AKAP4 is necessary for binding of GAPDHS to the fibrous sheath [Miki, K. et al, 2002]. This finding implies that in AKAP4 free sperm, glycolysis is inhibited. HIST1H2BA gene is expressed exclusively in the testis and also in sperm [Zalensky, A. et al, 2002]. The protein is found in the basal area of sperm nuclei [Zalensky, A., et al, 2002] and a variant of this protein is involved in the telomere-binding complex, suggesting its role in spermiogenesis and fertilization [Gineitis, A et al, 2000]. SLC2A14 gene is selectively expressed in the testis and the protein is involved in glucose transport [Wu, X. and Freeze, H. H., 2002]. SPACA3 gene encodes for a lysozyme protein localized on the acrosome of human spermatozoa and hence may serve as a receptor for egg membrane saccharide N-acetylglucosamine [Mandal, A., et al, 2003]. It may therefore be involved in sperm-egg interaction during fertilization. ZPBP is located on zona-pellucida (ZP), the outer region of the egg responsible for sperm binding and initiation of acrosome reaction that is required for sperm penetration [Lin, Y. et al, 2007]. Studies on ZPBP have shown that male mice lacking this gene are sterile as they have reduced sperm motility due to abnormal sperm morphology. Furthermore, these mice also suffer from improper acrosome biogenesis resulting in poor Sertoli-spermatid junctions. ACRBP is another acrosomal protein involved in binding of polysulfate groups on ZP glycoproteins in a stereodependent fashion [Gaboriau, D. et al, 2007]. ACRBP therefore mediates prolonged and proper interaction of sperm with ZP, thereby providing ample time for the sperm head to penetrate through the ZP.

Literature searches on proteins that show expression in only one database, or have not been shown to have expression in the testis or epididymis, indicate that many of these are also important in the well-being of the reproductive system. MFGE8, being expressed on sperm, is involved in sperm-egg adhesion and MFGE8 null mice are subfertile [Hoffhines, A. J. et al, 2009]. CDH2 is involved in rat blood-testis-barrier function [Sarkar, O., et al, 2008]. Studies of HSPA4L protein in mice show high expression in the testis and in spermatogenic cells [Held, T. et al, 2006]. In HSPA4L null male mice spermatogenesis is not disrupted, however, they are infertile and are more prone to osmotic stress. The disruption of fertility in mice may be due to an observed higher number of apoptotic spermatocytes and decreased sperm motility [Held, T. et al, 2006]. In a study conducted on gene expression patterns in infertile men and rodent models, HSPA4L gene was downregulated in the infertile male mouse compared to wild-type, but not in human males [Rockett, J. C. et al, 2004]. According to Nonoguchi et al., 2001, HSPA4L is expressed during and after the spermatocyte stage in germ cells and also in sperm [Nonoguchi, K. et al, 2001]. THBS2 was also detected in interstitial Leidig cells in mouse testis [Kyriakides, T. R. et al, 1998]. BSG is a highly glycosylated protein belonging to the Ig superfamily that is required for reproduction in both males and females [Igakura, T. et al, 1998]. BSG is initially localized on the principal piece of testicular spermatozoa, then in the middle region during epididymal maturation and finally on the head of the sperm after capacitation, suggesting its importance in sperm-ZP interaction [Saxena, D. K., et al, 2002]. During the capacitation process, BSG undergoes deglycosylation which may be required for sperm-egg fusion.

Many of the above mentioned proteins have their origin in the testis and/or epididymis and show a strong link to the male reproductive tract, despite not being annotated as epididymal or testicular by all four databases.

Proteins at lower abundance in PV patients. There are 49 proteins that according to spectral counting are at lower abundance in the PV group relative to the Control. These proteins may potentially be expressed in regions of the reproductive tract other than the testis or the epididymis; hence they are also found in the PV samples but at lower concentration levels. Proteins PTGDS, ELSPBP1, SPINT3, CRISP2, FAM12B, NPC2 and CRISP1 are expressed in the testis/epididymis in at least three out of four tissue databases, whereas GPR64 and RNASE1 are found in two out of four databases (Table 2, Table 4). PATE4 and PTGDS were also identified as having strong expression in the prostate in three out of four and two out of four databases, respectively (Table 2, Table 4). Proteins expressed in the epididymis were grouped as testis-specific since only two databases contained epididymis in their tissue list. PTGDS, FAM12B and NPC2 are also shown to be expressed in the epididymis by two out of four databases (Table 2). According to UniGene, proteins CRISP2, SPINT3, CRISP1 and FAM12B are found to have 'restricted' expression in the testis. Similarly, according to BioGPS, ELSPBP1, GPR64, SPINT3, CRISP2, FAM12B and CRISP1 are exclusively expressed in the testis. PATE4 also has 'restricted' and exclusive expression in the prostate according to UniGene and BioGPS, respectively. Genome Ontology identifies most of the proteins in this group as extracellular, membrane or cytoplasmic.

Several of the proteins at lower levels in PV pools have been previously investigated by looking at their concentration levels in semen from men with various reproductive abnormalities. These include PTGDS, A2M and NPC2. PTGDS (prostaglandin-H2 D-isomerase) is a secretory protein expressed by the Sertoli and Leydig cells as well as the epithelial cells of the prostate [Diamandis, E. P. et al, 1999; Tokugawa, Y. et al, 1998]. In previous studies of PTGDS in seminal plasma from men belonging to different fertility groups, median PTGDS levels in normal men was 800 µg/L, compared to 9.0 µg/L in men who have had a vasectomy, 11.0 µg/L in men with obstructive azoospermia and 18.5 µg/L in men with non-obstructive azoospermia [Heshmat, S. M. et al, 2008]. Clearly, PTGDS levels can potentially be used in differentiation of obstructive from non-obstructive azoospermia patients. These PTGDS values by ELISA corroborate quite well with the semi-quantitative results. A2M (alpha-2-macroglobulin) is a protease inhibitor produced in Sertoli cells that is modified and complexed by PSA, allowing it to bind with a receptor on spermatozoa [Birkenmeier, G., et al, 1998]. A2M is believed to have important implications in sperm motility. In a study of seminal plasma A2M concentrations, A2M levels have been reduced from 9.15 µg/L in normal to 0.74 µg/L in vasectomised men [Glander, H. J., et al, 1996]. NPC2 (epididymal secretory protein E1), an epididymal protein believed to be involved in transporting cholesterol during sperm maturation, is decreased by 40% in seminal plasma from vasectomised men compared to normal men [Legare, C., et al, 2006]. Following vasectomy reversal, NPC2 protein levels increased to those of normal men. In a proteomic analysis of seminal plasma samples from obstructive and non-obstructive azoospermia patients, NPC2 was not identified in the latter group [Yamakawa, K. et al, 2007].

Many of the remaining proteins that have their origins in the reproductive tract are associated with fertility. ELSPBP1 is present in caudal, corpus and caput regions of bull epididymis and binds to transiting spermatozoa [Sahin, E., et al, 2009]. In human and porcine sperm, it was found to be bound to the mid-piece region of the sperm [Ekhlasi-Hundrieser, M. et al, 2007]. GPR64 gene is found to be expressed in all regions of the epididymis with highest expression in the caput portion [Osterhoff, C.; et al, 1997]. Inhibition of GPR64 gene in mice models leads to dysregulation of fluid reabsorption within the efferent ductules, which leads to flow stagnation of spermatozoa in efferent ducts, resulting in infertility [Davies, B. et al, 2004]. CRISP1 and CRISP2 belong to the CRISP family which shows strong expression in the male reproductive tract [Gibbs, G. M.; and O'Bryan, M. K, 2007]. CRISP1 is a secreted epididymal protein that binds the post-acrosomal region of spermatozoa. CRISP 1 gene knockout mouse sperm showed reduced ability to fertilize ZP-intact and ZP-free eggs [Da Ros, V. G., 2008], suggesting the importance of CRISP 1 in the sperm-egg fusion processes [Cohen, D. J.; et al, 2007; Cohen, D. J. et al, 2000]. CRISP2 is believed to have a role in male fertility as it is an acrosomal and tail protein potentially involved in sperm motility and acrosomal reaction [Jamsai, D. et al, 2008]. It is also implicated in adhesion between spermatids and Sertoli cells and gamete interaction [Busso, D. et al, 2005]. In a proteomic analysis of seminal plasma from healthy and asthenoazoospermic (AS) men, Wang et al identified 100 proteins that were up- or down-regulated [Wang, J et al, 2009]. In that study, A2M, ABP1 and MXRA5 were up-regulated in healthy men, and these same proteins were also at higher concentration in our Control samples. CD 177 was up-regulated in AS, but was found to be at lower concentration in Controls in this study.

Literature searches on the remaining proteins on the list show that many of these belong to the reproductive tract and are believed to be involved in fertility (Table 2). The finding that proteins previously annotated as testicular or epididymal are found in the PV samples, suggests that they may not strictly be localized to these tissues, but could also be expressed in other regions of the reproductive tract. Contribution of proteins from testicular or epididymal tissue to Control seminal plasma samples and absence of such contribution to PV seminal plasma renders these proteins potential indicators of fertility status.

Proteins unique to PV and at higher abundance in PV patients. Three proteins, MMP9, FGG and SAA2 were found to be unique to the PV list. Furthermore, there are 25 proteins that are at higher abundance in PV relative to Control (Table 3). According to literature, PAEP and STAT3 seem to be implicated in fertility (Table 3). Six of the proteins, GSR, PYGB, ORM1, ORM2, MYH9 and MPO, were previously found to be differentially expressed in seminal plasma from healthy and AS men [Wang, J et al, 2009]. ORM1, ORM2 and MPO were also found to be up-regulated in AS samples. It has been previously shown that vasectomy alters the expression of epididymal proteins [Thimon, V. et al, 2008], hence it is also possible that proteins in other parts of the reproductive tract may also be prone to up- or down-regulation.

Seminal plasma is a highly complex fluid, with seminal proteins arising from all parts of the male genital tract. A list of over 2000 proteins have been identified in seminal plasma: thus far this is the largest list of proteins identified in this fluid. Upon spectral counting analysis of Control and PV protein lists, 81 proteins were catalogued at higher abundance and 28 were catalogued at lower abundance in Control relative to PV. The proteins unique to Control and those at significantly lower abundance in PV have their reproductive tract origin solely or principally in the testis or epididymis. Twenty-two of these proteins have been shown to be testis- or epididymis-specific by at least two out of four gene or protein databases; others are linked to reproductive biology, while others have not been annotated to be part of the urogenital system.

EXAMPLE 2

The strategy of step-wise elimination of poorly performing candidates was used to identify specific markers. Only those proteins which would be reproducibly quantified by SRM in the unfractionated digest of seminal plasma were analyzed. With the final multiplexed SRM assay, the concentration of 20 proteins in 30 normal, NOA and PV seminal plasma samples was measured. For the first time, a panel of biomarkers for the differential diagnosis of azoospermia with absolute or near-absolute specificities and sensitivities is proposed.

The following materials and methods were used in the study.

The following materials and chemicals were used: sequencing grade modified trypsin (Promega; Madison, Wis., USA), iodoacetamide, dithiothreitol (DTT) (Sigma-Aldrich; St. Louis, Mo., USA), Rapigest surfactant (Waters, Milford, Mass., USA). Heavy isotope-labeled peptides were obtained from Thermo Fisher Scientific Inc.

Patients and specimens. Seminal plasma samples were obtained by masturbation with informed consent and Mount Sinai Hospital IRB approval from normal fertile men about to undergo a vasectomy (n=12), infertile men with proven non-obstructive azoospermia (n=10) and previously fertile men who had undergone a vasectomy (n=8).

Sample preparation. Seminal fluid was allowed to liquefy at room temperature for 1 h, after collection. Seminal fluid was aliquoted in 1 mL portions and centrifuged at 13,000×g for 15 min at room temperature three times, to separate plasma from cells and cellular debris. The supernatant seminal plasma was then frozen at −80° C. until use.

Seminal plasma digestion for SRM assays. Ten microliters of seminal plasma were diluted 10-fold and subjected to trypsin digestion without prior purification or removal of high-abundance proteins. Proteins were denatured with 0.1% Rapigest at 60° C., and the disulfide bonds were reduced with 10 mM dithiothreitol. Following reduction, the samples were alkylated with 20 mM iodoacetamide. Samples were then trypsin-digested overnight at 37° C. One hundred femtomoles of heavy 13C6, 15N2 L-Lysine-labeled peptide LSEPAELT-DAVK* [SEQ ID NO: 1] of KLK3 protein or a mixture of 20 heavy isotope-labeled peptide standards was added to each digest. Rapigest was cleaved with 1% trifluoroacetic acid, and a 96-well plate with all samples was centrifuged at 4000×g for 20 min. Peptides were extracted with 10 µL OMIX C18 tips (Varian; Lake Forest, Calif., USA), eluted with 65% acetonitrile and diluted to 130 µL to provide three, 40 µL injections.

Peptide selection for SRM. Proteotypic peptides were manually chosen in Scaffold using Orbitrap identification data that included proteins identified with 1.1-1.5% false discovery rate (Example 1). Typical accuracy of peptide identification was 2-4 ppm. SRM candidate peptides that had clear and intense y-ion fragments (especially at proline residue) were selected. Peptides that had modifications and/or cysteine, methionine and tryptophan aminoacids were avoided, if possible. To confirm the choice of peptides, in silico digestions and fragmentations were performed using Pinpoint software (Thermo Fisher Scientific Inc.), which was also used to generate SRM methods for the triple quadrupole mass spectrometer.

LC conditions. Tryptic peptides were separated on a 2 cm C18 trap column with an inner diameter of 150 µm. The peptides were eluted from the trap column onto a resolving 5 cm analytical C18 column (inner diameter 75 µm) with a 15 µm tip (New Objective). The LC setup was coupled online to a triple-quadrupole mass spectrometer (TSQ Quantum Ultra or TSQ Vantage, Thermo Fisher Scientific Inc.) using a nano-electrospray ionization source (nano-ESI, Proxeon A/S). Buffer A contained 0.1% formic acid in water, and buffer B contained 0.1% formic acid in acetonitrile. A three-step gradient was used with an injection volume of 40 µL, which was loaded onto the column via an EASY-nLC pump (Proxeon A/S).

Verification of peptide identity by iSRM and SRM-Triggered MS/MS. Each iSRM method included 5 peptides in scheduled acquisition windows. Each peptide was monitored with two primary transitions that were selected based on LTQ-Orbitrap identification data (Example 1). A threshold of 500 was used to trigger an acquisition of 6 additional transitions with 0.1 s scan time each. Resulting raw files were uploaded to Pinpoint software, and an overlay of all individual transitions for each peptide was inspected manually. SRM-triggered MS/MS methods had 1 s full MS/MS scan. The MS/MS spectra were analyzed using Mascot (Matrix Science, London, UK; version 2.2) search engine on the non-redundant International Protein Index (IPI) human database (version 3.69, 10 Feb. 2010). Unfractionated digest of normal seminal plasma was used in all experiments.

Label-free SRM. For a label-free SRM assay, 32 peptides and 96 transitions representing 31 proteins were scheduled within 2-min intervals during a 60 min LC gradient (84 min method) and analyzed by TSQ Quantum Ultra in the positive-ion mode. SRM method had the following parameters: predicted CE values, 0.002 m/z scan width, 0.1 s scan time, 0.2 Q1, 0.7 Q3, 1.5 mTorr Q2 pressure, tuned tube lens values, 7 V skimmer offset. The three most intense and reproducible transitions for each peptide based on iSRM results were included in the SRM method. Spiked-in heavy-isotope labeled peptide of KLK3 was used as an internal standard to normalize relative abundances of all peptides and thus account for variations of the sample preparation protocol.

Stable-isotope dilution—SRM. Heavy isotope-labeled peptide standards were synthesized for 20 proteins. Twenty standard peptides were mixed and diluted to the final concentration of 18 fmol/µL. Ten micro litters of internal standard mixture were spiked into a digest of each seminal plasma sample (equivalent of 0.5 µL of original seminal plasma) prior to C18 micro extraction. Each seminal plasma sample (one normal, one NOA, and one PV) was digested in triplicate. Each digest was subjected to C18 micro extraction and finally analyzed by LC-SRM in duplicate. Forty peptides and 120 transitions representing 20 proteins were scheduled within 1.5-min intervals during a 30 min LC gradient (54 min method) and analyzed by TSQ Vantage in the positive-ion mode. SRM method had the following parameters: optimized CE values, 0.010 m/z scan width, 0.015-0.040 s scan time, 0.4 Q1, 0.7 Q3, 1.5 mTorr Q2 pressure, tuned S-lens values, +1 V Declustering voltage.

Data analysis. Raw files recorded for each sample were analyzed using LCquan (version 2.5.6). The peak areas were examined manually for verification and used for quantification. All areas were normalized by an internal standard to account for variation of sample preparation and mass spectrometry. For a stable-isotope dilution SRM method, Pinpoint was used to validate retention times and relative intensities of three transitions of both endogenous tryptic peptides and spiked-in standards. Pinpoint was also used to calculate light-to-heavy ratio and CVs for all peptides.

Statistical analysis. Three groups of samples were compared by GraphPad software using the nonparametric one-way ANOVA Kruskal-Wallis test, followed by Dunn's multiple-comparisons test for differences between groups. One-way test has been applied since protein concentrations were expected to decrease in PV due to physical obstruction. In all cases, a p-value <0.05 was considered significant. Receiver operating characteristic (ROC) area, sensitivity and specificity were calculated with GraphPad software.

The following are the results of the study.

Multi-step strategy for biomarker verification. The approach for biomarker discovery included a step-wise selection of candidates from the list of all identified proteins in seminal plasma. The initial list of candidate biomarkers was assembled based on at least 1.5-fold difference in spectral counts between normal and PV pools; some candidates were not detected at all in the PV pool. In total, 79 candidate proteins were selected for SRM assay development.

To verify a list of 79 candidate biomarkers, a multi-step strategy with sequential elimination of poorly performing peptides and proteins was designed and followed: (i) based on discovery data, choose proteins that have peptides suitable for SRM assay development (54 proteins); (ii) develop preliminary SRM assays (35 proteins); (iii) verify peptide identity (30 proteins); (iv) measure relative abundance of candidates in pools of 5 samples; (v) measure relative abundance in individual samples and select candidates that showed statistically significant difference between groups (18 proteins); (vi) using spiked-in synthetic heavy isotope-labeled peptide standards, measure concentration of proteins in seminal plasma. This strategy resulted in 16 biomarkers that will be further validated in hundreds of seminal plasma samples to provide 2-4 biomarkers for ELISA development and routine use in clinical practice.

Selection of proteotypic peptides and SRM transitions. In a typical SRM assay, a unique peptide is measured and its concentration is assumed to be equal to the concentration of its parent protein. In this work, proteotypic peptides and SRM transitions were chosen based on LTQ-Orbitrap identification data (Example 1).

The same nanoLC and electrospray sources and conditions used for identification (LTQ-Orbitrap) and quantification (triple quadrupole) assured identical efficiency of peptide ionization. Similar peptide fragmentation patterns in ion traps and quadrupoles [Pilch, B. and Mann, M, 2006] facilitated selection of SRM transitions. One to five peptides identified with LTQ-Orbitrap were chosen per protein. Doubly charged tryptic peptides that had 8 to 15 amino acids, had clear, intense and unambiguous y-ion fragments (especially at pro-line residue) were preferentially selected. Peptides that had cysteine (especially at the N-terminus) and/or modifications such as partially oxidized methionine, partially deamidated glutamine or asparagine were avoided, when possible. All candidate peptides were searched with Basic Local Alignment Search Tool (BLAST) [http://blast.ncbi.nlm.nih.gov/Blast.cgi) to ensure the uniqueness of each peptide sequence. Five transitions were chosen per peptide based on y-ion fragment intensities. Finally, 140 peptides, representing 54 proteins remained in the list.

Observing peptides with SRM. Two to four peptides with 5 transitions were grouped into 46 methods, and 700 transitions were measured. In total, 140 peptides were experimentally tested and manually inspected with Pinpoint software. Peptides that had multiple co-eluting peaks for individual SRM transitions were considered as positive hits. A significant number of low-abundance proteins failed at this step and were removed. As a result, 68 peptides representing 35 proteins remained.

Confirmation of peptide identities. Since SRM assays are prone to false positive quantification due to interfering ions, confirmation of the identity of observed peaks is required. The best means for such confirmation is the SRM analysis of synthetic peptides. Multiplex SRM development, however, requires several hundred synthetic peptides which is quite costly. Large libraries of unpurified synthetic peptides were proposed as an alternative [Picotti, P., et al, 2009]. Even though the latter approach allows for better tuning of instrumental parameters (collision energy, tube lens voltage), it is quite tedious, if optimization of hundreds of peptides is required. Ultimately, a digest of a suitable biological fluid represents the most complete library of peptides required for SRM development. The large number of peptides identified with LTQ-Orbitrap in the SCX-fractionated digest is typically suitable for SRM quantification with triple quadrupole in the unfractionated digest.

Figure 3:
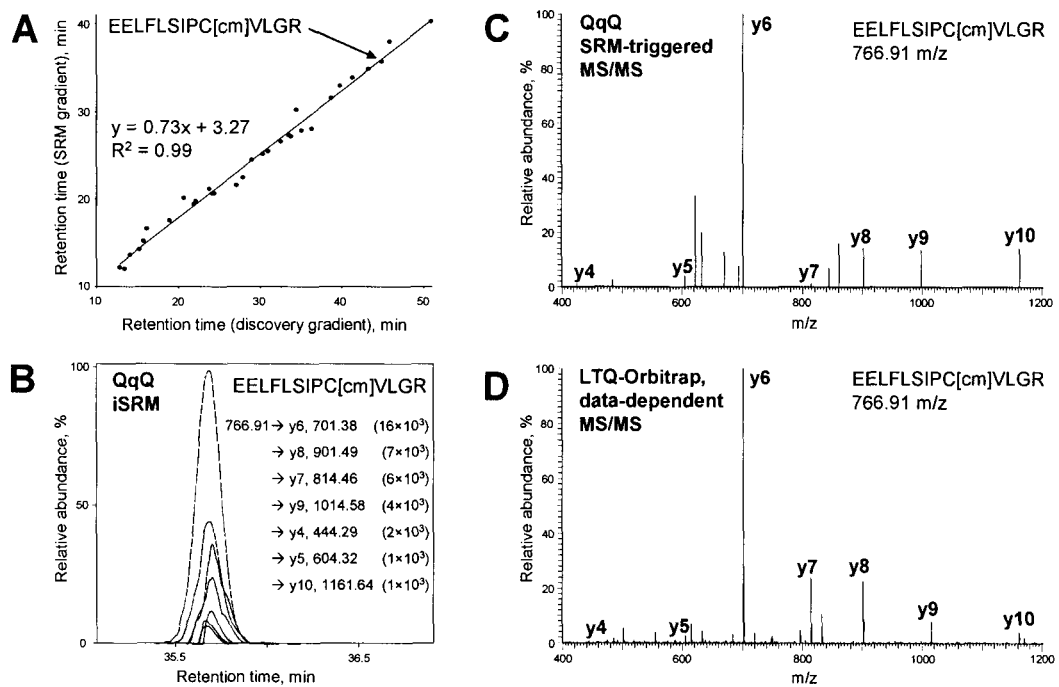
FIG. 3 shows the confirmation of the identity of proteotypic peptide FALLGDFFR of CAMP protein. (A) Correlation of retention time of 32 peptides representing all candidate biomarker proteins. Retention time of FALLGDFFR with a 60 min SRM gradient can be accurately predicted using linear regression and peptide's retention time with a 120 min identification gradient. (B) iSRM for y2-y8 fragment ions with intensity of each transition in brackets. Fragments y5 and y6 were used as the primary iSRM transitions. (C) SRM-triggered MS/MS fragmentation of FALLGDFFR in a triple quadrupole mass spectrometer. (D) MS/MS spectrum of FALLGDFFR acquired with LTQ-Orbitrap at 2 ppm resolution.

To confirm the identity of selected peptides, the following was used: (i) correlation of LC retention time between discovery and SRM gradients (FIG. 3A); (ii) intelligent SRM (iSRM) assays (FIG. 3B); (iii) SRM-triggered MS/MS fragmentation assays followed by Mascot database search and comparison to LTQ-Orbitrap MS/MS fragmentation (FIG. 3 C, D). First, correlation of retention times was a prompt method to test peptide identity since peptides typically elute within a narrow and specific range of acetonitrile gradient. Here, retention times of 31 peptides in the SRM LC gradient (60 min) were correlated to the retention times of the identification LC gradient (90 min) and correlation with $R^2=0.99$ was found. Identical nanoLC and nanoESI sources facilitated high coefficient of linear correlation. High resolution in the first quadrupole (Q1 0.2 FWHM) in SRM experiment ensured little or no interference, even in the complex matrix of the unfractionated digest.

Second, all peptides were confirmed with iSRM assays. Typically, iSRM assays are used to either reconstruct MS/MS spectra of peptides or to quantify peptides with 5-8 transitions [Kiyonami, R. et al, 2010]. In this work, iSRM was used to quickly acquire 8 transitions per peptide and this data was used to prove the identity of peptides, reconfirm the choice of most intensive transitions, and exclude transitions with significant interferences. Six or more co-eluting peaks corresponding to individual transitions ensured the identity of the peptides [Pilch, B and Mann, M, 2006]. Three most intense and selective transitions were chosen for the final SRM assay.

Third, 12 peptides representing 12 proteins were confirmed by an SRM-triggered MS/MS fragmentation assay followed by Mascot database search and also comparison to LTQ-Orbitrap MS/MS fragmentation. This approach, however, was applicable to high-abundance proteins only and was not efficient for medium- and low-abundance proteins.

Figure 4:
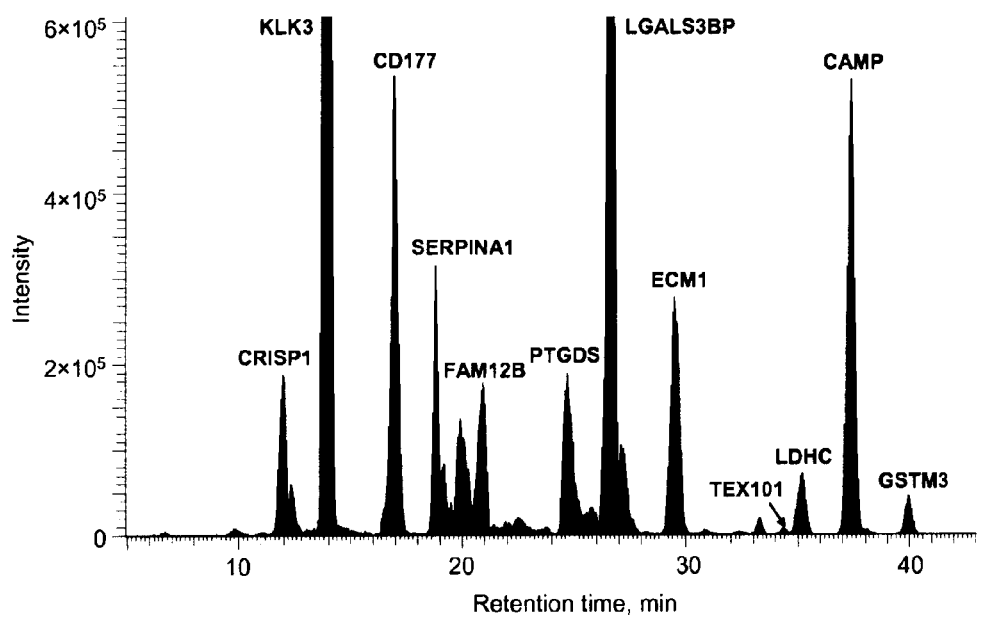
FIG. 4 shows the global profile of 32 peptides analyzed with a label-free SRM assay in the unfractionated digest of normal seminal plasma. Peptide abundances spanned 4 orders of magnitude. Peaks representing the most abundant proteins are indicated.

Finally, all ambiguous peptides were excluded and a single peptide for each protein was selected. Thirty one proteins, including KLK3, were used in the label-free assay (Table 5 and FIG. 4).

In silico assessment of selectivity of SRM transitions at high resolution in Q1. To inquire if higher resolution of the first quadrupole resulted in a lower number of potential interferences, in silica interferences at 0.2 FWHM in Q1 versus typical resolution of 0.7 FWHM were assessed. Since all peptide forms, fragments and all possible post-translational modifications cannot be considered, only unmodified peptides and b-and y-fragment ions were assessed. First, a database of all peptides identified in the seminal plasma digest was assembled; it included 12073 peptides (Example 1). Using Pinpoint, 32 peptides and 273 transitions corresponding to y-ions within the 300-1500 m/z range were evaluated. All transitions were matched against all possible combinations of band y-ions for 12073 peptides with +2, +3 and +4 charges. Surprisingly, at high resolution in the first quadrupole (0.2 Q1), only three interfering transitions were found for peptides of DAG 1 (y3), GPR64 (y9) and MUC15 (yI2) proteins. For example, transition DPVQEAWAEDVDLR [SEQ ID NO:2] (+2), 821.889 m/Z-7 EDVDLR [SEQ ID NO: 3] (+2), 373.687 m/z found for PKM2 protein interfered with transition VTIPTDLIASSGDI1K [SEQ ID NO: 4] (+2), 821.967 m/z -7 IIK (+2), 373.280 mlz for DAGI protein. These three interfering transitions were outside the typical range of transitions used in this assay (y4y10). Interestingly, at higher Q1 value (0.7), there were 9 interfering transitions. Such interferences could be discriminated based on peptide hydrophobicity and, if they still interfered in the LC dimension, could be excluded. Thus, higher resolution in Q1 indeed provided higher selectivity of SRM assay.

Recently, a useful database was built on the platform of the Global Proteome Machine at mrm.thegpm.org/thegpna-cgi/peaksearch.pl (available at mrm.thegpm.org/thegpcgi/peak search.pl). This database allows predicting isobaric interferences based on peptide m/z, hydrophobicity, and intensity of fragments in different biological matrices.

Sample preparation. Sample preparation protocols in quantitative proteomics typically include a set of physicochemical procedures (protein denaturation, C18 micro extraction), chemical reactions (DTT reduction, iodoacetamide alkylation) and enzymatic reactions (trypsin digestion). Each procedure has less than 100% yield, which can vary from day to day. From past experience, even the most optimal sample preparation protocol may have variability as high as 20%. If the reproducibility of each step of the protocol is slightly compromised, the whole quantification may be compromised (CV>>20%). To facilitate high reproducibility of analysis and accurate comparison of protein abundances in individual samples, all sample preparation steps in this work were performed on a single 96-well plate and no additional fractionation of seminal plasma was done prior to LC-SRM.

The efficiency of some critical steps of the sample preparation protocol, such as trypsin digestion, alkylation, and C18 micro extraction was evaluated. Three seminal plasma samples were trypsin-digested in duplicate, a known amount of a heavy peptide of KLK3 was spiked into each sample, each digest was subjected to C18 micro extraction, and each duplicate was analyzed three times with the SRM assay. While area values of light KLK3 peptide varied by about 20%, the coefficients of variation for the light-to-heavy ratio were 2.8, 3.0 and 1.8%. Thus, normalization of the area with an internal standard significantly reduced variability.

To estimate the efficiency of iodoacetamide alkylation, a ratio of alkylated over non-alkylated peptide ELGIC*PDDAAVIPIK [SEQ ID NO: 6] for a high-abundance protein (PIP) was measured by SRM. The yield of alkylated peptide was 99.8%.

Comparison of normal, PV and NOA pools of samples. A multiplex scheduled SRM assay was used to analyze 31 proteins, including KLK3, in pools of five normal, NOA and PV samples. Significant differences in abundances were found for the majority of proteins. Four proteins (LDHC, TEX101, MUC15 and SPAG11B) were not detected in PV samples, so their abundances were estimated using the level of background signal. The estimated relative abundance of some proteins between samples exceeded two or three orders of magnitude.

Label-free analysis of 31 proteins in 30 seminal plasma Samples. Individual seminal plasma samples (12 normal, 10 NOA, 8 PV) were analyzed in triplicate. Coefficients of variation for each of 30 proteins were less than 12%, 26% and 28% in Normal, NOA and PV samples, respectively. The concentration of KLK3 was measured with accuracy of around 3%. KLK3 concentration in normal seminal plasma was within the previously published range of 0.4-3 mg/Ml [Wang, T. J. et al, 1998]. The relative abundances for all proteins in individual samples (N=30) were subjected to nonparametric one-way ANOVA Kruskal-Wallis test. Eighteen proteins showed a statistically significant difference (p<0.05) in at least one of three groups.

Validation of SRM assay with heavy isotope-labeled peptide standards. To validate the SRM assay and to measure concentrations of proteins in seminal plasma samples, 20 heavy isotope-labeled peptide standards were synthesized: 18 peptides to quantify candidate biomarkers that showed statistically significant difference in PV samples in comparison to normals and 2 peptides to quantify prostate-specific proteins (KLK3 and CD177). One representative seminal plasma sample from each group (normal, NOA, and PV) was digested in triplicate, and each digest was analyzed in triplicate. As a result, retention times of all heavy-isotope labeled internal standards were found identical to those of the endogenous tryptic peptides. Relative intensities of three transitions per peptide were the same for both endogenous tryptic peptides and spiked-in standards. Variabilities of digestion of a normal seminal plasma sample were found less than 9% for each of the 20 proteins, with an average value of 5%. The variability of three LC-SRM injections was less than 6% for each of the 20 proteins, with an average value of 2%. Assuming a similar level of variability of the whole assay in the consecutive analyses, a single digestion and two SRM runs for the subsequent analysis of 30 seminal plasma samples was used. It should be mentioned that SRM analysis of other proteins in other biological fluids may require multiple digestions and MS injections per sample to ensure acceptable variability of SRM measurements. Finally, to demonstrate that label-free quantification using a single internal standard for normalization can be used to shorten the initial list of candidates, ratios of proteins in the same normal and PV samples measured with either a single or 20 internal standards were compared. Ratios calculated with both methods were in good agreement. This suggested that heavy isotope-labeled peptides could be synthesized and used at later steps of assay development and only for those proteins that performed well in the preliminary studies. To conclude, the use of heavy-isotope labeled internal standards unambiguously proved that this multi-step SRM development approach was valid, rigorous and fairly reproducible and could be used for SRM-based biomarker verification.

Measurement of concentrations of proteins in 30 seminal plasma samples. Using spiked-in heavy isotope-labeled internal standards, 30 seminal plasma samples were re-analyzed and concentrations of 20 proteins in 12 Normal, 10 NOA and 8 PV seminal plasma samples were calculated (Table 6). Concentrations of proteins were found in the range 0.1-1000 µg/mL, which corresponded to the range of medium abundance proteins and was near the limit of protein quantification by mass spectrometry. These findings were in good agreement with previous results and demonstrated that the lowest level of quantification of proteins with SRM assays in the unfractionated digest of seminal plasma was around 0.1 µg/mL. Since several proteins (TEX101, LDHC, etc.) were not detected in PV or NOA samples, limits of quantification of these proteins were determined by serial dilution analysis of heavy peptides in the seminal plasma digest.

Figure 5:
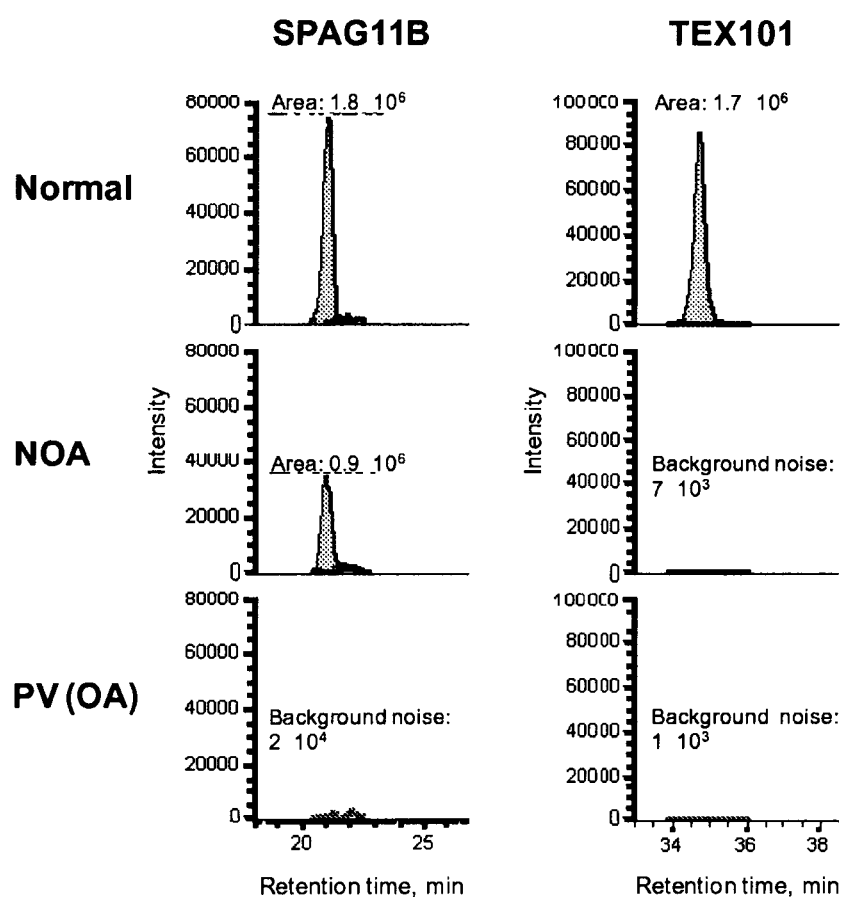
FIG. 5 shows the combination of two proteins SPAG11B and TEX101 can be used for differential diagnosis of azoospermia. In normal seminal plasma, both SPAG11B and TEX101 are abundant; in NOA, SPAG11B is abundant, while TEX101 is significantly decreased; in PV (OA), levels of both SPAG11B and TEX101 are significantly decreased (below LOQ of present SRM assay). For quantitative data, see also Table 6.

Selection of biomarkers for differential diagnosis of azoospermia. Concentrations of all proteins in individual samples (N=30) were subjected to nonparametric one-way ANOVA Kruskal-Wallis test with a statistical cut-off of $p<0.05$. Three groups of proteins were selected: (i) a group of 16 proteins to differentiate normal and PV seminal plasma; (ii) 3 proteins—normal and NOA (iii) 11 proteins—NOA and PV (Table 7). Some proteins discriminated groups with absolute or near-absolute specificities and sensitivities and the areas under the receiver operating characteristic (ROC) curves of 0.96-1.0. To distinguish between three groups of patients, combination of two markers from groups (ii) and (iii) is required (FIG. 5).

Figure 6:
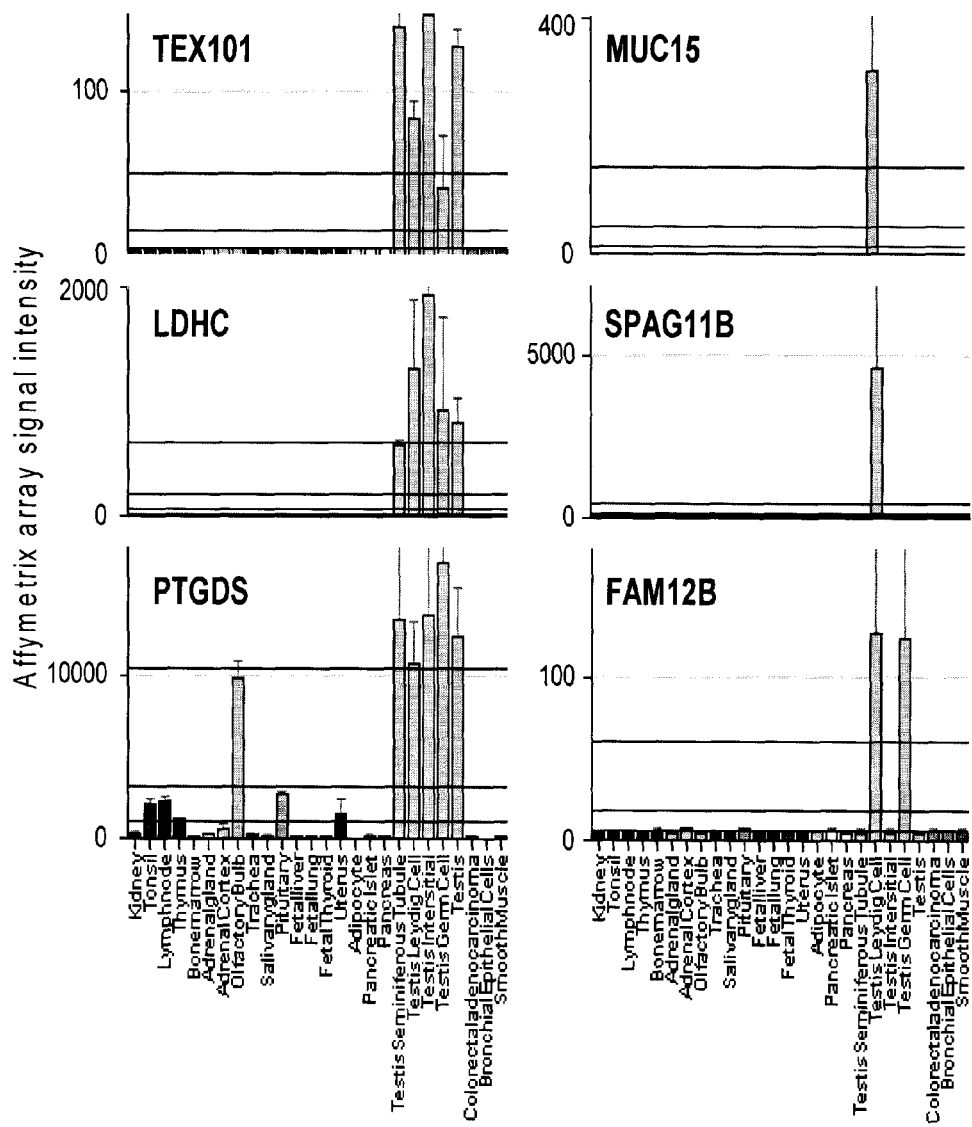
FIG. 6 shows that the tissue specificity of top candidates reveals cell expression specificity: Sertoli cells (seminiferous tubule), Leydig cells (testis intersitial), and germ cells. All six proteins shown are significantly decreased in PV seminal plasma samples. In NOA seminal plasma, Leydig cell proteins [MUC15, SPAG11B, FAM12B] are slightly decreased, while Sertoli and germ cell proteins [TEX101, LDHC and PTGDS] are significantly decreased. Thus, dysfunction of Sertoli or germ cells, but not Leydig, may be a possible reason of NOA.

Tissue specificity analysis. Tissue specificity analysis was performed using microarray mRNA expression profiles available at BioGPS (http://biogps.gnf.org), a "centralized gene portal for aggregating distributed gene annotation resources". Tissue specificity was a key parameter in predicting PV (OA) markers, since testis-specific proteins were absent in PV seminal plasma due to surgical severance of the vas deferens. All top candidates were highly specific to the testis. Cell specificity analysis of the top six candidates revealed that Leydig cell-specific proteins were only slightly decreased, while Sertoli cell-specific proteins and germ cell-specific proteins were significantly under-expressed in NOA (FIG. 6).

Development of SRM assays. The challenges of development of SRM assays include: (i) selection of proteotypic peptides; (ii) selection of transitions; (iii) optimization of MS and LC parameters; and (iv) multiplexing of dozens of peptides in a single assay.

Selection of proteotypic peptides for SRM is a critical step of assay development. It is hardly possible to predict prior to the experiment which peptide will be fairly separated in LC and efficiently ionized in electrospray, thus providing a stable and intense signal. Proteotypic peptides can be selected based on identification data or by searching publicly available databases, if the peptide of interest has previously been identified. In recent years, a large volume of identification data became available in public databases such as GPM Proteomics Database (available at mrm.thegpm.org) [Craig, R., et al., 2004] and Peptide Atlas (available at peptideatlas.org) [Deutsch, E.W., et al., 2008]. These databases, however, still lack high-quality data for many low- and medium-abundance proteins. Once proteotypic peptides are selected, optimization of SRM transitions and LC-MS parameters can be accomplished with SRM software such as Pinpoint (Thermo Fisher Scientific Inc.), MRMaid (www.mrmaid.info) or MRM Pilot (Applied Biosystems Inc.).

It should be noted that the sensitivity of SRM assays is still not sufficient to compete with ELISA. Proteins can be quantified with SRM assays in unfractionated digests of biological fluids if their lowest concentration is near 0.1 µg/mL. Furthermore, these levels are even higher for iSRM and SRM-triggered MS/MS assays. Such assays work well for high- and medium-abundance proteins, but do not provide any conclusive information for low-abundance proteins due to the increased level of interferences and distorted peak shapes for low-intensity transitions. iSRM and SRM-triggered MS/MS assays for proteins with concentrations in plasma lower than 1-10 ug/mL are not recommended. The use of synthetic peptide standards may be the most straightforward way to validate the identity of lower abundance peptides.

Relative abundance of proteins in pools and individual samples. The same pools of normal and PV seminal plasma samples were used for protein identification (Example 1) and SRM quantification, and relative abundances of proteins were compared. Interestingly, the relative abundances of proteins that were observed with more than 20-30 spectral counts in the PV pool correlated fairly well to the relative SRM abundances. Proteins with less than 20 spectral counts showed poor correlation between spectral counting and SRM data. Spectral counting, however, was a fair guide to filter over 2000 proteins and choose the initial list of 79 candidate biomarkers.

A relatively wide distribution of abundances in individual seminal plasma samples was found for some proteins. This finding might question the significance of 1.5-fold change used as a cut-off in this and other biomarker studies. The majority of proteins with such relatively small differences between groups would likely underperform in the verification phase. A striking example in the present work was PATE4 protein which showed high promise in the PV pool but failed when individual samples were tested, due to its extremely wide (more than 100-fold) distribution. Such outcome could be explained by possible intermittent secretion of PATE4 (prostate and testis expressed 4 protein) by both prostate and testis.

Biological function of promising candidates. TEX101 is a very specific marker for both male and female germ cells during gonadal development [Takayama, T., et al, 2005a]. TEX101 is a membrane glycoprotein expressed on the cell surface of germ cells during spermatogenesis but shed to the seminal plasma at the late stages of post-testicular sperm maturation [Takayama, T., et al 2005b]. The biological function of TEX101 still remains unknown although it may play a crucial role in the acrosome reaction [Yin, L. et al, 2009]. LDHC is testis-specific isozyme discovered in male germ cells and is critical for fertilization [Goldberg, E et al, 2010; Odet, F. et al, 2008]. PTGDS stands for lipocalin-type prostaglandin D synthase, which is expressed in Sertoli cells of the testis and in epithelial cells of the prostate and ductus epididymis [Tokugawa, Y, et al, 1998]. However, it is also significantly expressed in the central nervous system and found in cerebrospinal fluid [Urade, Y and Hayaishi, O. 2000], and in the heart [Eguchi, Y., et al, 1997]. PTGDS has been previously studied as a biomarker of azoospermia [Heshmat, S. M. et al, 2008; Leone, M. G., et al, 2001].

MUC15 is cell membrane-associated mucin. MUC15 overexpression in colorectal carcinoma cells enhances cell proliferation, cell-extracellular matrix adhesion, colony-forming ability and invasion [Huang, J., et al, 2009]. SPAG11B is a cationic secretory anti-microbial peptide expressed in human epididymis [von Horsten, H. H. et al, 2002; Avellar, M. C., et al, 2004]. FAM12B is an epididymal secretory protein [Kirchhoff, C, et al, 1994; Lasserre, A., et al, 2001] that has been found upregulated in epididymides of nonobstructive azoospermic men [Dube, E. et al, 2008]. ADAM7 is a membrane protein expressed specifically in the epididymis and localized to the sperm surface during epididymal transit [Oh, J. et al, 2009; Cornwall, G. A., and Hsia, N., 1997]. PATE4 is a hypothetical prostate and testis-expressed secreted protein that has never been previously studied. Its amino acid sequence was predicted based on the sequence of its mRNA transcript [Li, J. Y. et al, 2008; Ota, T. et al, 2004; Levitin, F., et al, 2008].

Tissue-specific proteins perform well as biomarkers. Previously published work aiming to identify azoospermia-specific biomarkers did not provide conclusive results [Yamakawa, K., et al, 2007]. Using 2D gel electrophoresis, four proteins (STAB2, CEP135, GNRP and PIP) were proposed as candidate NOA biomarkers. No verification was undertaken, so, the potential of the proposed proteins for NOA diagnosis was not clear. In the same work, NPC2, a protein with moderate testis specificity, was proposed as OA biomarker. The results of this study, however, demonstrated that NPC2 was a mediocre OA biomarker.

In general, proteins highly specific to testis should be absent in PV (OA) seminal plasma due to the physical obstruction and thus should perform as PV (OA) biomarkers with outstanding sensitivity and specificity. On the contrary, non-specific proteins may still be present in seminal plasma if produced by prostate gland or seminal vesicles. The sensitivity of such markers (NPC2, CA4, ALDH1A1) is typically low (Table 7).

Recently, expression profiles of many proteins (rather than mRNA) became available at the Human Protein Atlas (available at proteinatlas.org) [Uhlen, M., et al., 2010]. For example, two different antibodies were used for immunohistochemistry analysis of TEX101 protein. Both antibodies confirmed exclusive specificity of TEX101 to the cells in seminiferous ducts (Sertoli and germ cells) but not to Leydig cells.

Cell-specific proteins may reveal aspects of the molecular basis of NOA. Impaired maturation of sperm cells in NOA may originate from the failure of certain types of testis cells (Leydig, Sertoli or germ). Analysis shows that testis-specific proteins can be slightly or significantly affected in NOA. Cell-specific proteins differentially expressed in NOA may also shed some light on protein networks involved in NOA pathogenesis.

Using the BioGPS database of gene expression profiles (http://biogps.gnforg), the abundance of testis-specific proteins was correlated to the specificity of mRNA expression by three types of testis cells. As a result, in NOA conditions, the expression of Leydig cell-specific proteins (ADAM7, SPAG11B, MUC15, FAM12B) was slightly affected, while expression of germ cell and Sertoli cell (e.g. seminiferous tubule) proteins (TEX101, LDHC) decreased significantly (Table 7). Thus, Sertoli or germ cell dysfunction, but not Leydig cell dysfunction, may be associated with NOA. Such hypothesis was previously investigated using expression of inhibin B (Sertoli cell-specific protein), but the results were not clear-cut [Heshmat, S. M. et al, 2008]. The results of this study support this hypothesis. The large number of cell-specific proteins differentially expressed in normal, NOA and PV (OA) seminal plasma will facilitate identification of molecular pathways impaired in NOA.

A step-wise workflow to verify biomarkers for differential diagnosis of azoospermia by SRM was presented. A multiplex label-free SRM assay was used to measure the relative abundance of 31 proteins in the unfractionated digest of seminal plasma, verify 30 candidate proteins in 30 samples, and identify 18 promising biomarkers. To follow up on these candidates, heavy isotope-labeled peptides were used to re-measure concentrations of 20 proteins in the same cohort of samples. Concentrations of promising biomarkers were found in the range 0.1-1000 µg/mL and thus corresponded to medium abundance proteins in seminal plasma.

For the first time, a working panel of 16, 3 and 11 azoospermia biomarkers capable of differentiating three pairs of three biological conditions: normal, NOA and PV (OA), is proposed. The present panel of identified biomarkers has the potential to eliminate the need for testicular biopsy, providing significant benefits to patients at decreased costs. It is possible that an expanded panel (under development) may be capable of further classifying the three subgroups of the NOA syndrome. The current and expanded panels identified could also be examined for the diagnosis of other pathologies of the male reproductive tract such as prostatitis and prostate cancer.

EXAMPLE 3

By using a shotgun proteomic approach, the proteomes of seminal plasma from men with confirmed prostatitis to the proteomes of seminal plasma from fertile, healthy controls were compared. Seminal plasma samples from 5 individuals from each of the two diagnostic groups were pooled together to account for inter-individual variation in protein composition. Using this approach, a list of candidate prostatitis biomarkers was compiled and two of the biomarkers were validated using an ELISA assay.

The following materials and methods were used in the study.

Seminal plasma samples were collected, processed, and analyzed in accordance with the methods described above. A brief summary of the methods for the Prostatitis and Control samples is given below.

Sample Collection and Processing. Semen from men with prostatitis was collected after a minimum of 3 days of sexual abstinence. The 5 selected patients all had confirmed prostatitis, as diagnosed by the presence of lower urinary tract symptoms (frequency, urgency, dysuria), pain in the pelvic region, and prostatic tenderness on digital rectal examination. Samples were allowed to liquefy, centrifuged, and the supernatant (seminal plasma) was stored for further analysis. Total protein concentration was measured using the Biuret assay. Five prostatitis seminal plasma samples were combined to make a "Prostatitis" pool with 3 mg total protein per experiment. Each sample contributed an equivalent amount of protein to the total pooled protein.

Trypsin Digestion. Three "Prostatitis" replicate pools were denatured with urea, reduced with dithiothreitol and alkylated with iodoacetamide. Samples were then desalted, frozen and partially lyophilized. The samples were left to digest overnight using modified porcine trypsin (1:50, trypsin: protein concentration, Promega). Digestion was stopped the following morning by acidifying the solution with formic acid.

Strong-Cation Exchange Liquid Chromatography. Samples were fractionated using an Agilent 1100 High Performance Liquid Chromatography (HPLC) system equipped with a strong-cation exchange (SCX) PolySULFOETHYL A column (The Nest Group, Inc.). Sixty fractions were collected. Fractions 31 to 49 were stored individually, while fractions 26-30 and 50-54 were pooled together (total 21 fractions).

Mass Spectrometry. Twenty-one SCX fractions from each of the three Prostatitis replicates were further fractionated using nano-flow reverse-phase chromatography on a Proxeon EASY-nLC system, coupled online to a linear trap quadrupole (LTQ)-Orbitrap XL (Thermo Fisher Scientific, San Jose, Calif.). See Example 1 for more details of the method. The Orbitrap was used to acquire a full MS1 scan followed by six MS2 scans in the linear-ion trap (LTQ). Only charge states of 2+ and 3+ were subjected to fragmentation.

Data analysis. X!Calibur RAW files were uploaded into Mascot Daemon (Matrix Science, London, UK, v.2.2) to create Mascot Generic Files (MGF). These were then searched against a concatenated forward and reverse IPI.Human v.3.54 database with Mascot (v.2.2) and X!Tandem (Global Proteome Machine Manager, version 2006.06.01) with a parent tolerance of 7 ppm and fragment tolerance of 0.4 Da. The following modifications were used in searches: one missed cleavage allowed, fixed carbamidomethylation of cysteines and the following variable modifications: oxidation of methionines, deamidation of asparagines and glutamines, cyclization of N-terminal glutamic and aspartic acids (pyro-Glu-Asp), and protein N-terminal acetylation. Search result files from Mascot and X!Tandem were uploaded into Scaffold (Proteome Software, Portland, Oreg., v. 2.0) and filtered using peptide thresholds to achieve a false positive rate (FPR) of ~1.0-1.5%. FPR was calculated as follows: 2×FP/(FP+TP) where FP is the number of proteins matching the reverse database and TP is the number of proteins matching the forward database.

Candidate Validation: In order to validate the semi-quantitative data obtained from mass spectrometric analysis of the seminal plasma samples, 2 candidate proteins were arbitrarily selected for validation by enzyme-linked immunosorbent assay. The concentrations of cystatin-C and mesothelin isoform 2 were measured separately using specific sandwich immunoassays developed with DuoSet ELISA reagents (R&D Systems Inc., MN, USA). The cystatin-C assay employed two monoclonal antibodies, one for coating (Part 842942) and one for detection (Part 842943). Similarly, the mesothelin isoform 2 assay used two monoclonal antibodies, one for coating (Part 843359) and one for detection (Part 843360). All four antibodies were raised in mice. Both assays were conducted in a two-site sequential immunometric format with time-resolved fluorescence detection. Each assay has a detection limit of 0.1 µg/L and a dynamic range up to 10 µg/L. For each assay, within the measurement range, precision was <15%. All standards and samples for both assays were measured in duplicate.

Prior to analysis, samples analyzed for cystatin-C were diluted 10,000 times in a dilution buffer consisting of 1% bovine serum albumin (BSA) in phosphate-buffered saline (PBS) at pH=7.2. Samples analyzed for mesothelin isoform 2 were diluted 100 times in the same buffer.

Each well on the cystatin-C plate was incubated overnight at room temperature with 250 ng/100 µL monoclonal capture antibody in coating buffer (PBS, pH=7.2). Each well on the mesothelin isoform 2 plate was incubated overnight at room temperature with 400 ng/100 µL monoclonal capture antibody in coating buffer (PBS, pH=7.2). The next day each plate was washed 3 times with washing buffer (PBS with 0.05% Tween 20 at pH=7.4). Dilution buffer (1% BSA in PBS at pH=7.2) was then added to each well to block the plate for 1 hour. Each plate was then washed 6 times with washing buffer and then 100 µL of diluted samples or standards were added to each plate. Both plates were then incubated at room temperature for 90 minutes with gentle shaking. Each plate was then washed 6 times with washing buffer. To each well on the cystatin-C plate, 25 ng/100 µL of biotinylated detection antibody in dilution buffer was added. To each well on the mesothelin isoform 2 plate, 100 ng/100 µL of biotinylated monoclonal anti-human mesothelin isoform 2 detection antibody in dilution buffer was added. Both plates were then incubated for 1 hour at room temperature with gentle shaking, then washed 6 times with washing buffer. Five ng/well of alkaline phosphatase-conjugated streptavidin solution (Jackson ImmunoResearch) in sample buffer was added to each well, and allowed to incubate at room temperature for 15 minutes with gentle shaking. Each plate was then washed 6 times with washing buffer. To each well on both plates 100 µL of substrate buffer [0.1 mol/L Tris buffer (pH 9.1) containing 0.25 mmol/L diflunisal phosphate (DFP), 0.1 mol/L NaCl, and 1 mmol/L $MgCl_2$] was added. Both plates were then incubated at room temperature for 10 minutes with gentle shaking. To each well on both plates 100 µL of developing solution (1 mol/L Tris base, 0.15 mol/L NaOH, 2 mmol/L $TbCl_3$, 3 mmol/L EDTA) was added and allowed to incubate for 1 minute at room temperature with gentle shaking prior to measurement. Protein concentration was quantified by measuring fluorescence in each well with an Envision time-resolved fluorometer (Perkin Elmer) as previously described [Christopouolos, T. K. et al, 1992].

The following are the results of the study.

LC-MS analysis. Following trypsin digestion, each replicate was fractionated using SCX liquid-chromatography to increase the number of peptides identified in each fraction. Three replicates were analyzed in order to gauge reproducibility, as well as to increase protein identification and prediction confidence. The first 10 fractions from SCX were analyzed using an 88 min gradient and the next 11 fractions were analyzed using a 55 min gradient, since the first 10 fractions had greater sample complexity, allowing for more peptide identifications (data not shown).

Data analysis. Data was searched with Mascot and X!Tandem to increase sequence coverage and the number of proteins identified. Search results were merged using Scaffold 2.0 in MudPit mode for analysis and visualization. Mascot and X!Tandem filter settings were adjusted to achieve a FPR of 1.1-1.5%. A triplicate sample dataset was uploaded into Scaffold. The original Scaffold file (Prostatitis.sfd) can be downloaded from Tranche (available at ProteomeCommons.org; hash code:

```
AA1Px7YK40 + 62ODDQaBE2qOoMTkT7LqKHsEDFO/pc/WDtaIR
rYEn9bIEAtQ + 7q7WPGOGZhDmSebpgfJbUEdHg6pNUXQAAAAA
AAACjQ==).
```

In triplicate analysis of the Prostatitis group a total of 1708 proteins (including 9 proteins that matched reverse sequences) at a FPR of 1.1% with 1449, 1357 and 1157 proteins in each replicate were found.

Comparison of Control and Prostatitis protein lists. Comparing Control and Prostatitis proteomes, there are 1464 proteins in common, 413 found only in Control and 254 found only in Prostatitis. In total, 2131 proteins (including 12 proteins that matched reverse sequences) in the combined Control and Prostatitis groups with a FPR of 1.1% were identified.

Proteins that had their counts significantly affected due to shared peptides were carefully evaluated and removed from further analysis. Spectral counting is a semi-quantitative method with the advantage of having a linear dynamic range of several orders of magnitude [Mitchell, P., 2010]. Due to the inherent limitations of this quantitative method which include poor sensitivity to small changes in abundance (or sensitivity to fold changes greater than 100%) and diminished quantitative accuracy of proteins identified by very few counts [Mitchell, P., 2010; Liu, H., 2004], the following criteria were used to select a high-confidence list of potential proteins with significantly increased concentration in one of the groups: a) Fold differences must be greater than or equal to 2; b) The coefficient of variation (CV) for the 3 replicates must be less than 50%; c) If one clinical group average has 5 or less spectral counts, then accept CV less than 100% for that group; d) One clinical group must have an average >5 spectral counts; e) If one clinical group has an average <10 spectral counts, then the other must have an average >10 spectral counts. These selection criteria were based on the ability of spectral counting to accurately distinguish between large changes in protein concentration, and changes in concentration between abundant proteins, and the reduced accuracy associated with proteins with few spectral counts [Liu, H., 2004]. By applying the above mentioned selection criteria, it was found that: 33 proteins were significantly increased in prostatitis as compared to controls (Table 8), and 26 proteins were significantly increased in controls as compared to prostatitis (Table 9).

To identify the tissue specificity of the candidate prostatitis biomarkers, candidates were searched against UniGene, BioGPS, and Human Protein Atlas. According to UniGene, 18 proteins had "strong" expression in the prostate, 19 had "moderate" expression in the prostate, and 12 had "weak" expression in the prostate. According to Human Protein Atlas, 10 proteins had "strong" expression in the prostate, 11 proteins had "moderate" expression in the prostate, and 11 had "weak" expression in the prostate. According to BioGPS, 19 proteins have strong expression in the prostate, as defined by an expression of 3 times the average tissue expression.

The seminal plasma proteome of prostatitis patients was analyzed using ProteinCenter software to ascertain the Gene Ontology (GO) annotations for molecular functions, cellular components, and biological processes for the entire prostatitis proteome. The top 3 molecular functions were catalytic activity, protein binding, and metal ion binding. The top 3 cellular components were cytoplasm, membrane, and extracellular. The top 3 biological processes were metabolic processes, regulation of biological processes, and response to stimulus.

To better delineate the differences between the normal seminal plasma proteome and those of prostatitis patients, a comparison of GO annotations was performed using ProteinCenter in which the seminal plasma proteome of healthy fertile controls (see Example 1) was compared to the protein candidates found to be upregulated and downregulated in prostatitis. In comparing the upregulated prostatitis candidates to the normal seminal plasma proteome, the most striking differences were a 3-fold increase in the percentage of proteins involved in enzyme regulatory activity, a 2.5-fold increase in the percentage of extracellular proteins, and a 3-fold increase in the percentage of proteins involved in the defensive response. A comparison of the candidates downregulated in prostatitis to the normal seminal plasma proteome showed a moderate (10-15%) increase in the percentage of proteins involved in catalytic activity and protein binding, a moderate (10-15%) increase in the percentage of proteins found in the cytoplasm, Golgi apparatus, and membrane, and a significant (20-25%) increase in the percentage of proteins involved in development, regulation of biological processes, and transport.

According to Ingenuity Pathway Analysis, the molecular and cellular functions associated with the largest number of candidate proteins are small molecule biochemistry, molecular transport, lipid metabolism, protein degradation, and protein synthesis. The diseases and disorders associated with the largest number of candidate proteins are neurological disease, cancer, endocrine disorders, metabolic disease, and reproductive system disease. The top canonical pathways most strongly represented by the upregulated candidates are acute phase response signaling, the complement system, and the coagulation system.

Figure 7:
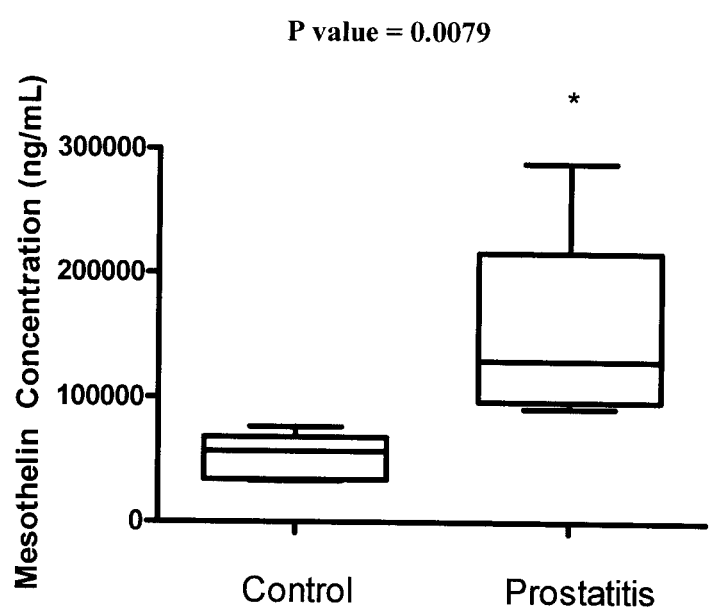
FIG. 7 is a box plot representing ELISA candidate validation of a) mesothelin isoform 2; and b) cystatin C. * denotes significance (p<0.05) as determined by two-tailed Mann Whitney test.
Figure 7:
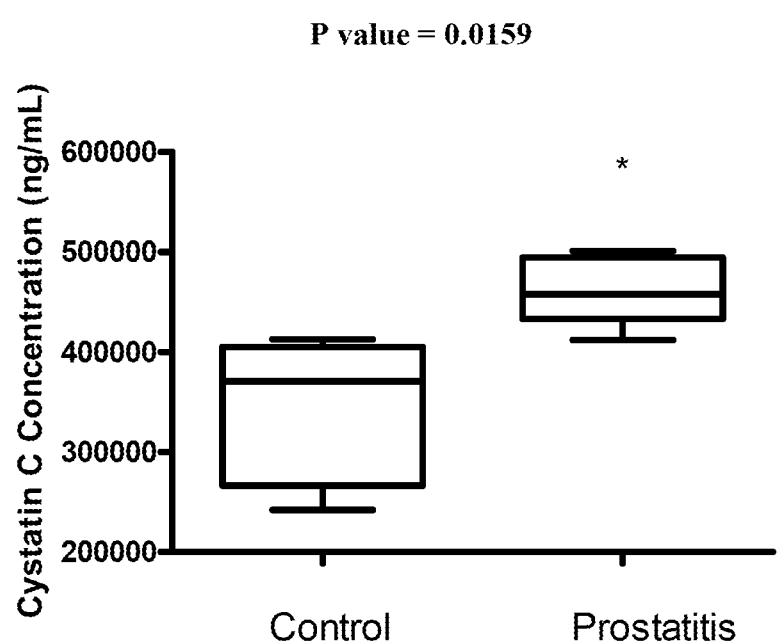

Candidate Validation. Two candidate protein biomarkers were arbitrarily chosen based on fold differences, putative roles in the pathogenesis of prostatitis, and the availability of assay reagents for validation using the gold standard in protein quantification, the enzyme-linked immunosorbent assay (ELISA) (Table 8). The proteins selected were mesothelin isoform 2 and cystatin C, both of which were upregulated in prostatitis samples compared to controls. Seminal plasma from each patient who contributed a sample to the mass spectrometric analysis was analyzed individually for mesothelin isoform 2 and cystatin C concentrations (FIG. 7). For mesothelin isoform 2, every sample from the Prostatitis group had a higher concentration than every sample from the Control group, and a mean concentration nearly 3 times greater in the Prostatitis group as compared to the Control group. Statistical analysis using a two-tailed Mann Whitney test found this difference to be significant (p=0.0079). Similarly, Cystatin C was significantly increased in concentration in the seminal plasma of patients with prostatitis (p=0.0159), although the difference was not as drastic. These results support the data obtained through mass spectrometric analysis, and suggest that the other candidates identified are likely upregulated or downregulated in prostatitis as compared to healthy fertile males. The discrepancy in fold change may be a consequence of the semi-quantitative nature of spectral counting with mass spectrometry, and reflects the need for future validation of other candidate biomarkers, using multiple reaction monitoring (MRM) or ELISA.

Proteins Increased in Prostatitis. Of the 33 proteins increased in prostatitis, 26 were determined to be expressed in the prostate gland, according to at least one of three databases searched (UniGene, BioGPS, and the Human Protein Atlas). The 7 proteins that were not expressed in the prostate according to these databases included cystatin-S, cystatin-SA and lipocalin-1. However, cystatin-S gene expression in the prostate gland, as well as in other tissues of the male genitourinary system, has been reported [Dickinson, D. P., et al, 2002]. As well, lipocalin-1, the major protein found in human tear fluid, has similarly been shown to be expressed in the prostate [Redl, B., 2000]. Thus, out of 33 candidate proteins from seminal plasma found to be increased in prostatitis, 28 are known to be produced in the prostate gland.

Protease inhibitors form a large proportion of the proteins found to be increased in the seminal fluid of prostatitis patients. The majority of these are members of the cystatin superfamily of secreted cysteine protease inhibitors, specifically the type 2 cystatin family. The type 2 cystatins found to be upregulated in prostatitis patients in this study are cystatin S, cystatin C, cystatin M, and cystatin SA. Other type 2 cystatins were previously found to be involved in processes such as spermatogenesis in the male reproductive tract, but those cystatins were not identified in this study [Li, Y., et al, 2003]. While previous work on type 2 cystatins classifies their function as anti-inflammatory, and indicates that they are downregulated in inflammatory responses, conflicting evidence suggests that their regulation may not be so simple. Cystatin-C, a cysteine protease inhibitor, has been shown to be upregulated in Sjogren's syndrome, which is a paradigm of autoimmunity and inflammation [Ryu, O. H. et al, 2006]. Studies on inflammatory skin disorders also found increased levels of cystatin M/E in the spinous cell layers of inflammatory lesions, which, they speculated, might help control increased levels of cysteine proteases during inflammation and infection [Zeeuwen, P. L., et al, 2002]. Similarly, production of cystatin-SA is enhanced by nuclear factor κ-light-chain enhancer of activated B cells (NFκB), an intracellular signaling molecule activated by pro-inflammatory cytokines [Kato, T. et al, 2002]. Cystatin-SA, in turn, increases interleukin-6 production, which is a pleiotropic cytokine with many pro-inflammatory functions. One potential explanation for the upregulation of anti-inflammatory type 2 cystatin proteins in prostatitis is the body's attempt to regulate the inflammatory response and prevent excessive tissue destruction, similar to the case of activation of hemostatic pathways, which activate fibrinolytic proteins to prevent excessive clotting. Notably, none of the type 2 cystatins has previously been investigated as a biomarker of prostatitis.

Other protease inhibitors found to be increased in the seminal plasma of prostatitis patients in this study include SERPINA1 (alpha-1-antitrypsin), SERPINA5, SERPING1, SERPINF1, Lipocalin-1, and TIMP3. As with the type 2 cystatins, the literature generally characterizes these proteins as anti-inflammatory; however, this does not preclude their upregulation during inflammation. Lipocalin-1, for example, is another cysteine protease inhibitor that has been documented to be overexpressed during periods of stress, inflammation, or infection [Wojnar, P. et al, 2001]. With the exception of SERPINA1, which has been found in histopathological studies of granulomatous prostatitis [Dhundee, J. and Maciver, A. G., 1991], none of these protease inhibitors have been studied in the context of prostatitis.

Other candidate biomarker proteins found in these experiments have functions more consistent with those expected to be upregulated during inflammation. Olfactomedin-4, for example, has been shown to be upregulated in crypt epithelial cells during inflammatory bowel disease [Shinozaki. S., et al, 2001], and is also induced by NFκB in myeloid precursor cells, suggesting that it forms part of a pro-inflammatory signaling network [Chin, K. L. et al, 2008]. Alpha-2-macroglobulin and fibrinogen beta chain are acute phase proteins, which are known to be strongly upregulated during inflammation and other stresses [Pang, W. W. et al, 2010]. Complement component C3 is a central player in the complement system, which is one of the major enzyme cascades activated during infection and inflammation [Dunkelberger, J. R. and Song, W. C., 2010]. Sphingomyelin phosphodiesterase isoform 1 has been described as strongly pro-inflammatory [Sakata, A. et al, 2007]. Mesothelin isoform 2, while not associated with inflammation in the literature, has been proposed as a biomarker to distinguish pancreatitis from pancreatic cancer [Watanabe, H., et al, 2005]. Such a protein would be invaluable in differentiating other inflammatory and neoplastic processes (i.e. prostatitis and prostate cancer).

Of the 33 candidate biomarkers that were increased in prostatitis, only 5 have previously been studied for prostatitis diagnosis. Complement component C3 levels in seminal plasma were found to help distinguish chronic prostatitis and leukocytospermia from controls [Ludwig, M., et al, 1998]. Urinary alpha-2-macroglobulin and albumin were investigated for possible utility in diagnosing acute prostatitis, and the ratio of alpha-2-macroglobulin:albumin was found to be a highly sensitive diagnostic test for acute prostatitis [Everaert, K. et al, 2003]. Furthermore, including other urinary parameters in a stepwise multinomial logistic regression analysis provides optimal differentiation between acute pyelonephritis and acute prostatitis [Everaert, K. et al, 2003]. Both SERPINA1 [Dhundee, J. and Maciver, A. G., 1991] and fibrinogen beta chain [Doble, A. et al, 1990] have been found to be increased in prostatitis tissue obtained through biopsy, but the invasiveness of such a procedure is precisely what was aimed to be avoided, by searching for a seminal plasma diagnostic biomarker. All of these previously investigated proteins are all quintessential pro-inflammatory proteins, which reflect the current understanding of prostatitis as an inflammatory disease of the prostate. By using a mass spectrometry approach to identify large numbers of proteins of diverse function, it is possible to find proteins whose functions may be unrelated to inflammation, or are as yet unknown, but which still may function as biomarkers of prostatitis.

Comparing the candidates upregulated in prostatitis to the overall seminal plasma proteome in healthy fertile controls, reveals a striking 3-fold increase in the percentage of proteins annotated as possessing enzyme regulator activity, which is consistent with the number of candidates that regulate the inflammatory response. In terms of subcellular localization, the upregulated prostatitis candidates show an almost 3-fold increase in percentage of extracellular proteins, with a concomitant decrease in the number of cytoskeletal, cytosolic, and membrane proteins. Notably, while the percentage of membrane proteins in prostatitis patients' seminal plasma is decreased, compared to normal seminal plasma, it is still over 40% of the prostatitis candidates, which may reflect the cellular destruction in prostatitis and the release of membrane proteins into the seminal plasma. The biological processes of the seminal plasma proteomes from prostatitis vs control patients show a 3-fold increase in proteins involved in the defense response and coagulation, which supports the understanding of prostatitis as an inflammatory process. A moderate decrease (15%) in the percentage of proteins involved in cell organization and biogenesis is also noted, which may reflect the changing priorities of cells during an inflammatory response as compared to normal.

Proteins Decreased in Prostatitis. A prostatitis biomarker could also be a protein that is decreased in the seminal plasma of prostatitis patients as compared to controls. Of the 59 candidate biomarkers, 26 were decreased in the seminal plasma of men with prostatitis. 25 of these were expressed in the prostate gland, according to at least one of three databases searched (UniGene, BioGPS, and the Human Protein Atlas). The one remaining protein is CACNA2D1, a voltage-dependent calcium channel subunit, which is not expressed in the prostate but is expressed in the testes (Unigene).

Candidate proteins which bear mention include SOD3 extracellular superoxide dismutase, which has been shown to be highly anti-inflammatory, inhibiting inflammatory cell migration by preventing fragmentation of hyaluronic acid [Gao, F., et al, 2008]. Thus, the downregulation of SOD3 is consistent with prostatitis being a disease of inflammation. Moreover, previous studies have demonstrated that SOD3 levels in the seminal plasma are constant between fertile controls and vasectomized men, indicating that it originates proximal to the site of ligation of the vas deferens, likely the prostate [Williams, K. et al, 1998]. Taken together, this suggests that SOD3 has potential in the diagnosis and monitoring of inflammatory diseases of the prostate.

Several other downregulated candidate proteins have been previously described as possessing pro-inflammatory properties. The most plausible explanation for this observation is the complex interplay between pro- and anti-inflammatory factors, resulting in a response that is carefully regulated and controlled. It is possible that the downregulated pro-inflammatory proteins are responding to regulatory signals, ensuring that the inflammation does not spiral out of control. Such pro-inflammatory proteins found in this study include Mucin-5b, which has been shown to be upregulated in inflamed nasosinus mucosa [Ali, M. 2009] and in chronic rhinosinusitis [Viswanathan, H et al, 2006]. As well, Filamin-B, which functions to recruit inflammatory cells to the site of inflammation, was found to be decreased in expression [Kanters, E. et al, 2008].

Other noteworthy proteins include NOV and L-xylulose reductase, both of which are decreased in prostatitis, but which previous investigations have found to be increased in prostate cancer [Maillard, M. et al, 2001; Cho-Vega, J. H. et al, 2007]. Both of these proteins could potentially be invaluable in distinguishing prostate cancer from prostatitis, which is currently a major confounder in the diagnosis of cancer.

Comparing the GO annotations of candidates downregulated in prostatitis to the normal seminal plasma proteome produced less striking results than the upregulated prostatitis candidates. This may reflect the fact that cells downregulate proteins of varying functions and localization during an inflammatory response, while upregulating proteins of a single function (i.e. defense). Compared to the normal seminal plasma proteome, the down-regulated prostatitis candidates had moderate increases in the percentage of proteins involved in catalytic activity and protein binding. Downregulated prostatitis candidates also had increased percentages of proteins involved in regulation of biological processes, suggesting that while some regulatory proteins increase during prostatitis, others decrease. Notably, none of the downregulated prostatitis candidates were involved in the defense response, suggesting that prostatitis causes defensive proteins to be upregulated, not down-regulated.

59 proteins were identified as potential prostatits biomarkers because of their significantly differential expression in the seminal plasma of prostatitis patients. Such proteins would have application in the diagnosis of prostatitis, as well as in monitoring response to treatment. Furthermore, improved methods of diagnosing prostatitis would better distinguish prostatitis from more serious causes of elevated PSA, such as prostate cancer, and reduce the need for unnecessary anxiety and invasive investigations. As well, diagnosing prostatitis could help better elucidate the cause of a patient's infertility. Many of the candidate biomarkers have previously been reported to be involved in inflammatory pathways, which correlate with the understanding of prostatitis as a disease of inflammation.

EXAMPLE 4

2048 proteins in seminal plasma from men presented with NOA were catalogued. Using spectral-counting, the NOA proteome was compared to proteomes of fertile control men and post-vasectomy (PV) men, and proteins at differential abundance levels amongst these clinical groups were identified. In order to verify spectral counting ratios for candidate proteins, extracted ion current (XIC) intensities were also used to calculate abundance ratios. The Pearson correlation coefficient between spectral counting and XIC ratios for the Control-NOA and NOA-PV datasets is 0.83 and 0.80, respectively. Proteins that showed inconsistent spectral counting and XIC ratios were removed from analysis. There are 32 proteins elevated in Control relative to NOA, 18 decreased in Control relative to NOA, 59 elevated in NOA relative to PV and 16 decreased in NOA relative to PV.

The following materials and methods were used in the study.

Sample Preparation and Mass Spectrometry: Samples were prepared and analyzed as described above. Briefly, semen from five men diagnosed with NOA was collected after 3 or more days of sexual abstinence. Samples were left to liquefy at room temperature and centrifuged to remove sperm and obtain seminal plasma (supernatant). NOA pools containing 3 mg of total protein were prepared such that each individual patient contributed 0.6 mg of total protein. Three NOA pools were further reduced with dithiothreitol (DDT), alkylated with iodoacetamide and digested with porcine trypsin overnight. Protein digests were then fractionated using strong-cation exchange (SCX) chromatography into 60 fractions. Out of the 60 fractions, 21 (some fractions were pooled) were desalted and microextracted with $C_{18}$ tips. 40 µL of sample was then loaded onto an in-house packed 3 cm long 5 µM particle $C_{18}$ trap-column from a 96-well microplate autosampler using the EASY-nLC system (Thermo Fisher Scientific, San Jose, Calif.) and an increasing concentration of acetonitrile was used to elute peptides from the trap-column onto an in-house packed 5 cm long 3 µm particle $C_{18}$ analytical column. This liquid chromatography setup was coupled online to LTQ-Orbitrap XL (Thermo Fisher Scientific) mass spectrometer using a nanoelectrospray ionization source (Proxeon Biosystems, now Thermo Fisher Scientific). Pooled fractions 26-30 and individual fractions 31 to 39 were analyzed using an 88 min liquid chromatography gradient, whereas fractions 40 to 49 and pooled 50-54 were analyzed with a 55 min gradient. The full $MS^1$ scan was acquired in the Orbitrap with subsequent $MS^2$ scans on the top six parent ions in the linear ion trap (LTQ) in data-dependent mode. Dynamic exclusion, monoisotopic precursor selection and charge state screening were enabled. Unassigned charge states, as well as charges +1 and ≥+4 were rejected from $MS^2$ fragmentation. The resulting XCalibur RAW files were uploaded into Mascot Daemon (v.2.2) and extract_msn was used to generate Mascot Generic Files (MGF). MGF files were searched with Mascot (Matrix Science, London, UK; version 2.2) and X!Tandem (Global Proteome Machine Manager, version 2006.06.01) against the concatenated (forward and reverse) non-redundant IPI.Human v.3.54 database with a parent and fragment tolerances of 7 ppm and 0.4 Da, respectively. Data was searched with trypsin as the digestion enzyme with one missed cleavage allowed, fixed carbamidomethylation of cysteines and the following variable modifications: oxidation of methionines, deamidation of asparagines and glutamines, cyclization of N-terminal glutamines and glutamic acids (pyro-Glu), and protein N-terminal acetylation. Program Scaffold (Proteome Software Inc., Portland, Oreg.; v.2.0) was used to merge Mascot DAT and X!Tandem search result files and filter the data to achieve a false-positive rate (FPR) of 1.2%. ProteinCenter (Proxeon Biosystems, now Thermo Fisher Scientific) was used to retrieve Genome Ontology annotations and pathway analysis from Kyoto Encyclopedia of Genes and Genomes (KEGG). Pathways were also investigated using Ingenuity Pathway Analysis (Ingenuity Systems, Inc., Redwood, Calif.). For a detailed procedure refer to Example 1.

Label-Free Quantitation by Spectral Counting: Normalized spectral counts were used to select proteins at different abundances in NOA relative to Control and PV datasets. The selection criteria was the same as that described earlier, but in short required the proteins to be elevated or decreased by at least 2-fold (see Example 1). Upon normalization of spectral counts using the combined NOA, Control and PV datasets, a small number of proteins had their spectral counts significantly elevated due to protein ambiguity (shared peptides with other proteins). These proteins were removed from the list.

Label-Free Quantitation Using Extracted Ion Current (XIC): RAW files corresponding to Control, NOA and PV datasets was uploaded into MaxQuant [Cox, J. and Mann, M, 2008] v.1.1.1.25 (www.maxquant.org) and searched with Andromeda [Cox, J. et al, 2011] (built into MaxQuant) against the nonredundant IPI.Human v.3.54 database. The search parameters included a fixed carbamidomethylation of cysteines and variable modifications were oxidation of methionine and N-terminal protein acetylation. Data was initially searched against a 'human first search' database with a parent tolerance of 20 ppm and a fragment tolerance of 0.5 Da in order to calculate and set the correct parent tolerance of 7 ppm for the search against the IPI.Human fasta file. During the search, the IPI.Human fasta database was randomized and FPR was set to 1% at the peptide and protein levels. Data was analysed with 'Label-free quantification' checked and 'Match between runs' interval set to 2 min. The resulting MaxQuant 'proteinGroups' file contained 2700 identified proteins, of which 32 were reverse hits and 39 contaminant protein hits. Reverse and contaminant protein hits were removed from the analysis, yielding 2629 proteins. 'LFQ Intensity' columns corresponding to each protein in replicate Control, NOA and PV groups were averaged. Averaged 'LFQ Intensity' values were used to calculate Control/NOA and NOA/PV ratios.

Spectral count and XIC comparison: Spectral counting fold changes were initially used to select proteins at differential abundances in Control-NOA and NOA-PV datasets. For these same proteins, XIC fold changes were extracted. Spectral counting and XIC fold changes, for Control-NOA and NOA-PV datasets, were log 10 transformed. The log 10 values corresponding to spectral count and XIC were plotted using an x-y scatter plot and the Pearson correlation coefficient was calculated (For Control/NOA: Pearson correlation coefficient=0.83, 95% confidence interval=0.75-0.89; For NOA/PV: Pearson correlation coefficient=0.80; 95% confidence interval=0.72-0.87). Proteins that according to spectral counting, were uniquely identified in one clinical group, could not be log transformed and were omitted from the plot. Only proteins with XIC ratios 2 or greater and those that showed consistent up- or down-regulation relative to spectral counting ratios were used for further analysis.

Public database searches: Differentially expressed proteins were checked for tissue specificity using UniProtKB, UniGene, BioGPS and Human Protein Atlas databases. Genes that were shown to have restricted, exclusive, dominant or above average expression in the testis, epididymis, seminal vesicle and the prostate were marked as originating from the above mentioned tissues. Since expression profiles using the above mentioned databases are represented in different formats, in order for proteins to be annotated used the following criteria were used: in UniGene, expression had to be 'restricted' or the tissue was required to have a dominant/major contribution relative to other tissues; in BioGPS, expression had to be 'exclusive' or had to exceed the average expression by at least 3-fold; and in Human Protein Atlas, expression had to be 'strong'. Furthermore, UniGene and BioGPS do not have epididymis and seminal vesicles in their tissue list, therefore, proteins that were expressed in the epididymis were considered to be originating from the testis.

The following are the results of the study.

2048 proteins were identified in the NOA seminal plasma pool, with 1732, 1756 and 1765 proteins in each replicate. The false-positive rate (FPR) of 1.2% was achieved by adjusting Mascot and X!Tandem peptide thresholds in Scaffold 2.0. FPR was calculated as 2×FP/(TP+FP), where FP (false positive) is the number of proteins matching the reverse database and TP (true positive) is the number of proteins matching the forward database.

Just as in Control and PV datasets (see Example 1) protein localization, function and process distribution is very similar. The majority of the proteins are cytoplasmic, membrane and extracellular. The large proportion of intracellular proteins can be attributed due to presence of epididymosomes [Thimon, V. et al, 2008] (from the epididymis) and prostasomes [Poliakov, A.; et al, 2009] (from the prostate) in seminal plasma. These are exosome-like vesicles that take up many intracellular proteins during their formation in the cytoplasmic domain. In addition, leakage from epithelial cells in contact with seminal fluid can also contribute many intracellular proteins. In terms of function, the majority of the proteins are involved in catalytic activity, followed by protein binding. Four-hundred thirty eight proteins are categorized as enzymes. Relative to the human IPI database containing 86 719 proteins, glycosidases, hydrolases and glycosylates are overrepresented with 28, 365 and 30 proteins respectively. This finding is consistent with the knowledge that seminal plasma liquefaction requires many enzymes acting in cascades and agrees with work by Pilch et al (2006). The underrepresented enzyme categories include transferases consisting of 156 proteins, transferring phosphorus-containing group proteins with 59 members, and 30 serine/threonine kinases. In terms of biological processes, the top categories are metabolism, regulation, cell organisation and biogenesis, response to stimulus, cell communication and transport. Cell communication and transport have been shown to be important in successful capacitation of spermatozoa [Baldi, E. et al, 2002]. There are also 198 proteins involved in reproduction.

Comparison of NOA to Control and PV protein lists. Comparison of the NOA protein list to previously published seminal plasma from fertile Control and post-vasectomy (PV) men using normalized spectral counts allowed identification of proteins unique to NOA and at different abundance levels in NOA. Upon merging NOA, Control and PV datasets into Scaffold, 2500 proteins in seminal plasma were identified (at an FPR of 1.2%) in three datasets, 1489 are common in all three, 1595 are shared between NOA and Control, and 1670 between NOA and PV.

Control and NOA comparison Using the spectral count cut-offs, 96 proteins were identified at differential abundance levels between NOA and Control datasets. For proteins to be selected, they needed to be elevated or decreased by at least 2-fold, or be uniquely identified in one clinical group. Upon comparing these 96 proteins to their XIC ratios, the Pearson correlation coefficient is 0.83 (95% confidence interval 0.75-0.89). There are 13 proteins, GMPPB, LIPA, UGCGL1, SLC2A5, RNASE4, APLP2, CTSH, UNC13B, GMPR, SPON2, OAF, C4B, and CYFIP1 that do not correlate as their XIC ratios are opposite to the spectral counting ratios. The 13 proteins that did not correlate originally belonged to the list at higher concentration in NOA relative to Control. In addition to the 13 proteins with XIC ratios being opposite of spectral counting ratios, there are also 33 proteins with XIC ratios that do not satisfy the criteria of being elevated or decreased by at least 2-fold in one clinical group relative to the other. For these proteins, XIC ratios range between 1 and 2. Of the 33 proteins, 30 belong to the group of proteins that are elevated in NOA. By comparing spectral count ratios to XIC ratios, the original list of 96 proteins has been reduced to 50. Out of 50 proteins that correlate and according to spectral counting, 15 are found only in Control and 17 are at a lower concentration in NOA relative to Control, 2 are found only in NOA and 16 are found at a higher concentration in NOA relative to Control. There are 13 proteins showing expression in testis/epididymis in at least 2 databases, DPEP3, TEX101, PGK2, SLC2A14, ASRGL1, SPACA3, SLC1A1, ZPBP, PTGDS, CRISP2, HIST1H2BA, GPR64 and SPARC. Similarly, PTGDS is produced by the prostate. Proteins found only in Control and those more abundant in Control relative to NOA are enriched for extracellular localization, followed by membrane and cytoplasmic components according to Genome Ontology analysis within ProteinCenter. This is in contrast to complete NOA and Control proteomes, where the percentage of cytoplasmic proteins is greater than those of extracellular origin by nearly 2-fold. Furthermore, in Protein Center this same group of proteins over represents the carbohydrate catabolic process and glycolytic pathway in Kyoto Encyclopedia of Genes and Genomes (KEGG). A short list of proteins, up to 10 from each category is presented in Table 10. Upon comparing these proteins to those selected in the earlier Control-PV analysis (see Example 1), 31 out of 50 protein candidates from this study were also identified to be at different abundance levels in Control-PV work.

NOA and PV comparison Comparison of NOA and PV datasets utilising spectral counts identified 109 proteins to be differentially expressed. The correlation of spectral counting and XIC ratios is 0.80 (95% confidence interval 0.72-0.87). There are 7 proteins, GMPPB, CSE1L, UNC45A, NANS, GMPR, FAM129A and NAGA that do not correlate, as their ratios are opposite to those from spectral counting. There are also 27 proteins that have XIC ratios >1 but <2, with 25 belonging to those at higher abundance in NOA. Verification of spectral count ratios with XIC ratios reduced the list of 109 proteins down to 75: according to spectral counts 8 proteins to be uniquely found in NOA, 51 at lower level in PV relative to NOA, 5 found only in PV and 11 at higher level in PV. Proteins LDHC, ADAM7, AKAP4, ELSPBP1, SPINT3, FAM12B, RNASE1, NPC2 and CRISP1 have been previously identified to have expression in the testis/epididymis according to two or more gene or protein databases. In addition to these, PATE4 and OR51E2 are found in the prostate. According to Genome Ontology analysis within Protein Center, proteins unique to NOA and those at higher abundance in NOA relative to PV are mostly of extracellular, followed by cytoplasmic and membrane origin. A similar pattern is observed for proteins unique to PV and those at higher level in PV relative to NOA. Proteins short-listed down to 10 in each category are shown in Table 11. Out of 75 differentially expressed proteins, 47 are in common with candidates identified in the Control-PV study described in Example 1.

A number of proteins have been verified quantitatively in many samples using selective-reaction monitoring (SRM) as described in Example 2. In the study described in Example 2, the relative abundance levels of 31 proteins, out of 79 which were at higher concentration (according to spectral counting) in Control relative to PV, have been measured in Control, NOA and PV seminal plasma samples. For the majority of these proteins, SRM data correlated well with the semi-quantitative spectral-counting results. Out of 31 proteins investigated, Control/PV fold changes did not agree with spectral-counting data for six proteins, PTGDS, CAMP, FAM12B, PATE4, GPR64 and ABP1. For these proteins, the discrepancy between SRM and spectral-counting ratios was greater than 3-fold. However, even in these cases, the fold change was in the same direction, having Control/PV ratios greater than 1.

Of the proteins verified in all three clinical groups, SRM and spectral-counting Control/NOA fold changes did not correlate for MGAM, ECM1, CD177, ABP1, NPC2, CRISP1, SERPINA1, PTGDS, LDHC, GPR64 and CA4. Note, that of these, only PTGDS, LDHC, CA4 and GPR64 have been selected in this study to have differential to expression between Control and NOA. In the case of PTGDS, LDHC and CA4, the SRM Control/NOA ratio was 3.5, 1728 and 1.3, respectively, versus 11.7, 7.4 and 5.3 for spectral-counting data. For the remaining proteins, SRM and spectral-counting fold changes were in the opposite direction, however, since these ratios fall in the range 1-2, they are of little statistical significance. The reason the lower fold-change limit of at least 2 and not a greater cutoff for candidate selections was chosen, is because of concern about eliminating proteins that are expressed in the testis or epididymis. Testis/epididymis only contribute about 10% of the fluid to the total seminal plasma volume, rendering many of these proteins of low abundance with few spectra and difficult to detect [Robert, M. et al, 1994].

It should be noted that despite SRM assays being performed on the same Control, PV and NOA seminal plasma pools, samples were subjected to a different trypsin-digestion protocol and SCX fractionation was not performed. Due to these sample preparation differences as well as due to the inherent semi-quantitative nature of spectral-counting methodology [Liu, H., et al, 2004; Duncan, M. W. et al, 2010; Mitchell, P., 2010] disagreement between spectral-counting and SRM data for a fraction of proteins was to be expected.

2048 proteins were identified in NOA seminal plasma with a false-positive rate (FPR) of 1.2%. Upon comparison of the NOA proteome to the seminal plasma work by Pilch et al. (2006), 667 proteins in common were found. In the study described in Example 1 the proteome of seminal plasma from Control and PV seminal plasma were compared and a number of proteins with origin in the reproductive tract were identified. Now, seminal plasma from men diagnosed with NOA was analyzed and the dataset was compared to Control and PV with the aim of identifying proteins that may be characteristic of NOA. Since the experimental design of examining NOA samples was identical in every respect to the Control and PV work, from sample processing to analysis by MS and to data interpretation, it was possible to directly compare these three datasets. In order to ensure that the mass spectrometer was at the same level of sensitivity with the previous NOA dataset Control and PV, several SCX fractions from the Control were re-run and re-analyzed, and a similar number of peptides and proteins was found.

In this study, spectral counting was used to identify proteins that were elevated or decreased amongst Control-NOA and NOA-PV datasets in order to have an analogous comparison to the Control-PV work described in Example 1. Since spectral counting is a semi-quantitative method that is not remarkably sensitive to small abundance changes, especially with low abundance proteins identified by few spectra, another label-free approach that utilises extracted-ion current (XIC) intensities in order to verify the spectral counting ratios, was implemented. A more reliable protein candidate list was generated by combining the quantitative results of both spectral counting and XIC which are label-free strategies [Duncan, M. W. et al, 2010; Mitchell, P., 2010; Mallick, P. and Kuster, B., 2010]. As observed from the Pearson correlation coefficient the results from the two methods correlate well. Generally, the XIC ratios are smaller than the SC ratios. The average ratio of XIC/SC ratios for proteins at different abundances in the Control-NOA dataset is 0.73, whereas for the NOA-PV dataset it is 0.93. Spectral counting ratios may be overestimated in cases where only one of three replicates contains spectral counts. Proteins with XIC ratios >1 but <2 and those with ratios opposite of spectral counting ratios were removed from analysis. A number of candidate proteins found in this analysis are in common with the earlier Control-PV work.

Control and NOA comparison. Out of 50 proteins selected to be at differential abundance levels in Control and NOA, 29 belong to those that were at a higher concentration in Control relative to PV. These same 29 proteins are also at higher concentration in Control relative to NOA. Many of these 29 proteins originate in the testis, epididymis or the prostate according to UniProtKB, UniGene, BioGPS and Human Protein Atlas databases. In addition to the previously identified proteins, according to two or more databases, ASRGL1 and SPARC are expressed in the testis. All together, there are 13 proteins with expression in testis and 1 in the prostate according to at least 2 databases. ASRGL1 is localized to the midpiece region of sperm and its antibodies are found in postvasectomy sera [Bush, L. A. et al, 2002]. SPARC is a matricellular protein with a significant role in testis development [Wilson, M. J. et al, 2006]. SPARC expression is elevated in fetal testis cords, it is also abundantly found in Sertoli and Leydig cells [Wilson, M. J. et al, 2006; Howe, C. C. et al, 1988; Vernon, R. B.; Sage, H. et al, 1989]. Several of the proteins at differential abundance levels concur with the SRM study of Example 2. For example, TEX101, which is unique to Control according to spectral counting and elevated over 20,000× in Control relative to NOA using XIC, was elevated over 300× in Control according to SRM. PTGDS, also elevated 11.5× and 15.3× in Control relative to NOA according to spectral counting and XIC ratios, respectively, was shown to be elevated 3.5× using the SRM methodology. PTGDS has previously been studied using ELISA methods to determine protein levels in normal and azoospermic patients [Diamandis, E. P. et al, 1999; Heshmat, S. M. et al, 2008]. These studies have shown that the median PTGDS concentration in 10 normal men and 14 men diagnosed with NOA was 800 µg/L and 18.5 µg/L, respectively, a 40-fold decrease in NOA.

Proteins found only in Control, and those more abundant in Control relative to NOA (32 in total), in addition to being enriched for extracellular component are also enriched for biological processes involved in fertility. According to ProteinCenter analysis of this group of proteins in relation to IPI human database that contains 89,422 protein sequences, biological processes being over-represented by these proteins include sexual reproduction, single fertilization and sperm-egg recognition. The proteins belonging to these processes include ZPBP, ELSBPB1, PGAM2, SPACA3, GPR64 and SLC2A14. The majority of these proteins are not exclusive to one biological process, but are involved in more than one process. SLC2A14 (GLUT3), having strong expression in the testis, belongs to the sugar transporter family and is involved in glucose transport. Since spermatogonia require substantial amounts of glucose in order to maintain motility, decreased levels of this protein in NOA seminal plasma is highly plausible. The carbohydrate catabolic process is also overexpressed and includes LDHC, PGK2, PGAM2, SPACA3 and CALR. Using the Kyoto Encyclopedia of Genes and Genomes (KEGG) in Protein Center for pathway analysis, shows that relative to the 86 719 human proteins in IPI database, the glycolysis (glyconeogenesis) pathway is upregulated in this group of proteins (unique and elevated in Control). The proteins belonging to this pathway are LDHC, PGK2 and PGAM2. These glycolytic proteins are involved in the development of spermatozoa and generating ATP molecules required for movement of sperm flagellum. According to Ingenuity Pathway Analysis, proteins A2M and CDH2 belong to Germ Cell-Sertoli Cell Junction Signalling. Sertoli cells are known to provide a supportive and nourishing environment in the testis for the development of sperm from primordial germ cells. Absence or decreased levels of these proteins could lead to breakdown of the signalling cascade between the Sertoli cell and the maturing germ cell resulting in detrimental effects on successful production of spermatozoa. In cases of Sertoli-cell only syndrome (SCOS), absence of germ cells could potentially lead to lowered production of these proteins. A2M is synthesized by the Sertoli cell and complexed by PSA, resulting in a conformational change thereby allowing it to bind spermatozoa [Cheng, C. Y. et al, 1990; Birkenmeier, G. et al, 1998]. There is positive correlation between A2M and sperm motility and seminal plasma levels from vasectomised men shows a 12-fold reduction relative to controls [Glander, H. J. et al, 1996].

In a gene expression study of caput epididymides of non-obstructive azoospermic men by Dubé et al, 414 proteins were found to be down-regulated in NOA men relative to fertile control men [Dube, E. et al, 2008]. In that study, there were 10 proteins down-regulated and 7 upregulated in NOA men by at least a 4-fold. Of these 17 proteins, CRISP 1 and AKAP4 are on the list of candidates, however, in this case, these do not differentiate NOA from Control, but rather NOA from PV. A testicular gene expression study by Feig et al., of tissues from normal men and men with spermatogenic defects (Sertoli-cell only syndrome (SCOS), hypospermatogenesis, meiotic arrest) identified over 1100 genes differentially expressed [Feig, C., et al, 2007]. Proteins DPEP3, PGAM2, ASRGL1, SPACA3, ZPBP, CRISP2, and LDHC are in common with Feig's list and are elevated or unique in the Control relative to NOA. Fox et al. utilizing gene expression studies of testicular biopsies from men with SCOS and men with normal spermatogenesis yet having an obstruction of the reproductive tract due to vasectomy or infection, identified 682 genes overexpressed in normal (obstructed) testis relative to NOA SCOS cases [Fox, M. et al, 2003]. Amongst these 682 proteins, ZPBP, CRISP2, LDHC are also found to be elevated in the Control group relative to NOA. In genetic expression profiling of NOA and OA testis samples, Okada et al. identified 2611 genes differentially expressed with a fold change 2 or greater [Okada, et al, 2008]. Out of these 2611 genes, 149 showed differential expression between three NOA subclasses (differentiated using the non-negative matrix factorization method). Upon comparison of 50 proteins to 149 genes identified by Okada et al., TEX101 and HIST1H2BA are in common. According to Okada et al., these genes were underexpressed in NOA relative to OA, and in the present finding they were also underexpressed in NOA relative to Control. In gene expression studies, testicular biopsies from OA (or PV) men could be treated as fertile controls. The proteins found to be decreased in NOA relative to PV in seminal plasma could merely arise from obstruction of the vas deferens in PV men, and not necessarily from decreased expression of these proteins in testis or epididymis. For this reason, it is believed that it is correct to compare data from PV (or OA) and NOA gene expression studies to proteins differently expressed in Control and NOA, as long as the PV (or OA) group in the gene expression study had normal spermatogenesis.

There are 18 proteins out of 50 that show lower concentration (including unique to NOA) in Control relative to NOA. Of these, only COL6A2 has been previously identified to be at lower abundance in Control relative to PV. GGT7, according to spectral counting is found uniquely in NOA and is part of the glutathione metabolism pathway. Along with PTGDS, glutathione is required for conversion of prostaglandin $H_2$ (PGH2) to prostaglandin $D_2$ (PGD2) [Lu, S. C., 2000]. Furthermore, glutathione is important for antioxidant defense and has a role in spermatogenesis and sperm maturation [Sies, H., 1999]. Rockett et al. also identified 5 proteins involved in glutathione metabolism in microarray studies of fertile and infertile mice [Rockett, J. C. et al, 2004]. The study has shown that glutathione transferases are found in Leydig and Sertoli cells of human testis and glutathione reductases are found in germ and Sertoli cells of rat testis [Klys, H. S. et al 1992; Kaneko, T., et al, 2002]. Based on these findings, it has been hypothesized that the presence of glutathione reductases in germ cells is rationalized by high levels of cysteines in these cells. This finding supports the notion that glutathione metabolism pathway is important in male fertility. An additional protein that is involved in the glycolytic mechanism and is identified in only NOA seminal plasma is SORD. It is an enzyme that converts sorbitol to fructose and increases tyrosine phosphorylation in sperm proteins [Cao, W. et al 2009]. This suggests that in addition to providing energy molecules, SORD is also involved in sperm capacitation. SORD is found on sperm and can originate from progenitor germ cells or be carried by epididymosomes, membraneous vesicles secreted by the epididymis [Cao, W. et al, 2009; Frenette, G. et al 2004] but it is also expressed in the prostate [Szabo, Z. et al, 2010]. Overexpression of these proteins in NOA that are involved in fructose metabolism reinforces the possibility that upregulation of this pathway could be a result of events associated with hypospermatogenesis or maturation arrest. Since spermatogenesis is a complex process and the exact cause of NOA is unknown, it is possible that certain proteins in seminal plasma become elevated due to aberrant cellular processes.

Proteomic analysis of seminal plasma from asthenoazoospermic (AS) patients and fertile men by Wang et al. identified 45 proteins upregulated and 56 proteins downregulated in AS relative to fertile men [Wang, J. et al, 2009]. From their list of downregulated proteins in AS, A2M is also present at higher abundance in the Control relative to NOA. In addition to A2M, MPO and ORM1, have been identified as differentially expressed in Wang's study.

NOA and PV comparison The group of proteins found to have a variation in expression between PV and NOA are of great interest as these may be useful in differentiating the two cases of azoospermia. There are 75 proteins that according to spectral counting and XIC have differential abundances in NOA and PV datasets: 8 that are unique to NOA, 52 at lower abundance in PV relative to NOA, 6 proteins that are unique to PV and 12 at lower abundance in NOA relative to PV. Forty-seven out of 75 proteins have been previously recognized as differentially expressed in the Control-PV data analysis.

Many of the proteins in this category have been shown to be involved in male fertility and several have already been discussed in Example 1. Underexpression or undersulfation of MFGE8 in mice renders them subfertile, despite normal spermatogenesis and normal sperm motility [Hoffhines, A. J. et al, 2009]. Sperm lacking this protein have a reduced ability to bind zona pellucida. Other proteins, such as BSPH1, being a sperm binding protein expressed in the epididymis, is involved in sperm capacitation [Lefebvre, J. et al, 2009]. SORD is the only protein that is uniquely found in NOA and not in Control or PV and has been discussed earlier. In a study of obstructive azoospermia patients with congenital bilateral absence of vas deferens, several genes have been shown to have genomic copy number variations [Lee, C. H. et al, 2009].

One such gene that is also elevated in NOA relative to PV is COL18A1. GAS6 protein expressed in Leydig and Sertoli cells acts as a ligand in activating protein-tyrosine kinases, TYRO3 family, AXL and MER [Lu, Q. et al, 1999]. Generally, tyrosine kinases are involved in intracellular signalling and this specific group of proteins is implicated in regulation of phagycytotic activity of Sertoli cells. It has been reported that Sertoli cells have the ability to degrade apoptotic spermatogenic cells, a requirement for proper spermatogenesis [Russell, L. D. and Clermont, Y., 1977; Chemes, H., 1986; Pineau, C. et al, 1991; Miething, A., 1992]. In this process, GAS6 promotes binding of Sertoli cells to apoptotic spermatogenic cells [Xiong, W. et al, 2008]. Maturation arrest of spermatogenic cells in NOA may result in elevated numbers of apoptotic cells. This in turn could induce production of GAS6 at higher levels in NOA than in PV in order to signal degradation of these cells.

In comparison to the list of proteins at different levels in seminal plasma from normal and AS men presented by Wang et al. [Wang, J. et al, 2009], proteins CD177, MXRA5, ABP1, WFDC2, MPO and ORM1 are in common. Of these, CD177, WFDC2 and MPO are upregulated in AS and are also elevated in NOA relative to PV. Out of 75 proteins differentially expressed, 3 are in common with Feig's testicular gene expression study [Feig, C. et al, 2007]. These proteins include, LDHC, AKAP4, and MGAM, all found to be elevated in NOA relative to PV.

Control, NOA and PV comparison There are a number of proteins according to spectral counts showing differential expression in Control-NOA comparison as well as NOA-PV comparison. Comparative analysis of three datasets reveals several proteins in NOA having spectral counts and XIC values intermediate to Control and PV. These proteins include LDHC, ELSPBP1, CES7, A2M, OVCH2, PTGDS, GPR64 and ALDH1A1. As discussed in Example 2, LDHC and PTGDS concur with the findings disclosed herein, while GPR64 and ALDHA1 show a minor decrease in NOA relative to PV. Proteins HIST1H4H, LDHC, SORD, ELSPBP1, GMPR, CTS2 and A2M show differential expression in Control-NOA dataset as well as in NOA-PV comparison.

EXAMPLE 5

By comparing the semen proteomes of men with OA, NOA and normal fertility, over 80 semen proteins were identified as potential markers for OA and NOA. Validation was performed on a subset of 43 different proteins in this group that were amenable to a multiple reaction monitoring (MRM) assay on a group of 30 men (fertile controls, men with OA and NOA). From this initial validation, a total of 20 semen proteins were found to be potentially excellent markers for the differentiation of OA and NOA.

Figure 8:
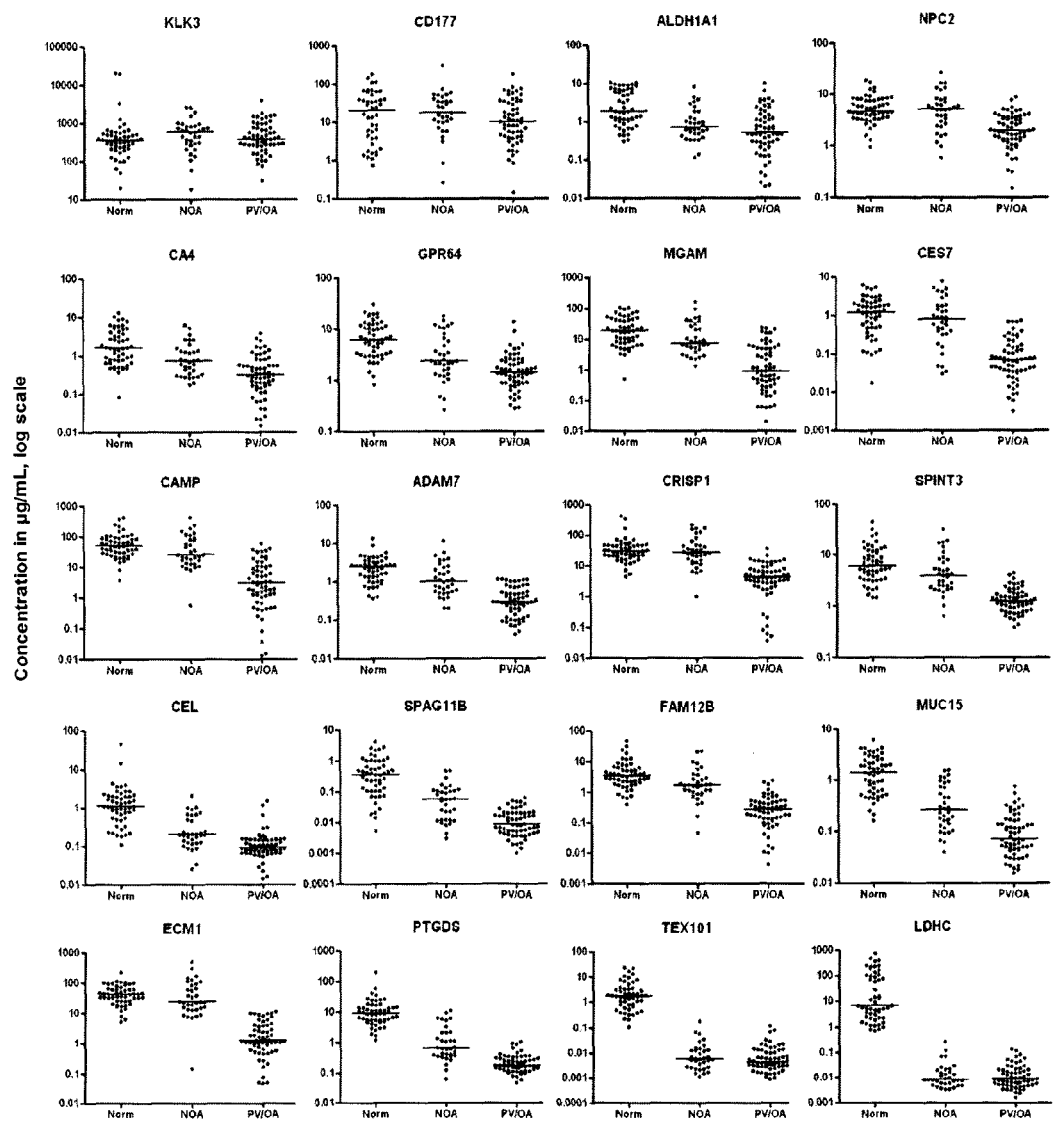
FIG. 8 shows the concentration of 20 proteins measured with a stable-isotope dilution SRM assay in normal (n=12), NOA (n=10) and PV (n=8) seminal plasma samples.

To validate these markers, MRM assays were performed for the 20 semen proteins on a total of 148 semen samples from men (fertile controls (n=53), and men with NOA (High FISH, some sperm by microTESE, no sperm by microTESE) (n=34) or OA (n=61)). As can be seen on Table 12, some of the proteins had >10,000× fold difference in the semen concentrations in fertile men compared to men with OA or NOA (TEX101, LDHC). Proteins were identified with 100% sensitivity and >95% specificity to differentiate OA from fertile controls and NOA from fertile controls. The most clinically relevant issue is the differentiation of OA from NOA: with the use of 2 biomarker proteins OA could be differentiated from NOA with >90% sensitivity and >95% specificity (FIG. 8, Table 13). With one marker alone (ECM1), there was 87% sensitivity to identify OA from NOA with >95% specificity.

These results validate these markers as sensitive and specific markers to differentiate OA from NOA.

EXAMPLE 6

High-throughput proteomic analysis was performed on the conditioned media of the androgen-dependent cell lines LNCaP and VCaP, androgen-independent cell lines LNCaP-SF, DU-145, PC3, PPC1, 22Rv1, as well as a normal prostate cell line (RWPE). A comprehensive data set was compiled, permitting identification of differentially secreted proteins that could serve as potential markers for androgen-independent cancers. Quantitative real-time PCR, as well as in vitro wound healing assays were used to corroborate the proteomic analysis results. The anti-coagulant factor, Protein S (PROS1) was identified as a potential modulator and marker of androgen-independence. Based on spectral counts, PROS 1 was found highly secreted in all the androgen-independent cell lines, with no detectable secretion in the normal or androgen-dependent cell lines. The gene expression profile of the androgen-independent cell lines also maintained the over-expression of PROS1, when compared to the normal and androgen-dependent cell lines, while only prostate cancer tissue samples showed an up regulation of PROS1. Tissue expression of PROS 1 and its putative receptor TYRO3 was determined in normal (n=8) and prostate cancer tumour (n=36) samples. Both genes were found to be significantly over-expressed in prostate cancer specimens (p<0.05). Further, recombinant PROS1-treated LNCaP cells demonstrated an increase in wound repair and invasive growth potential, implying that PROS1 may have functional roles outside of the coagulation pathway. The results indicate that PROS 1 is involved in the progression of androgen-independent prostate cancers.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the antibodies, methodologies etc. which are reported therein which might be used in connection with the invention. Nothing herein is to be construed as an admission that the invention is not entitled to antedate such disclosure by virtue of prior invention.

TABLE 1

Proteins found uniquely in Control seminal plasma (absent in post-vasectomy (PV) seminal plasma) according to spectral counting.

| Gene Name | Average Spectral Count | | Protein origin** | Reference *** |
|---|---|---|---|---|
| | Control | PV* | | |
| LDHC (lactate dehydrogenase C) NCBI Gene ID NO. 3948 | 54 | 0 | testis | 16, 17, 18 |
| DPEP3 (dipeptidase 3) NCBI Gene ID NO. 64180 | 16 | 0 | testis | |
| TEX101 (testis expressed gene 101) NCBI Gene ID NO. 83639 | 17 | 0 | Testis | 19, 20, 21 |
| CEL (carboxyl ester lipase precursor) NCBI Gene ID NO. 1056 | 15 | 0 | | |
| ADAM7 (a disintegrin and metalloprotease domain (ADAM) 7) NCBI Gene ID NO. 8756 | 10 | 0 | testis | 22 |
| LIPI (lipase, member I) NCBI Gene ID NO. 149998 | 9 | 0 | | 135 |
| BSPH1 (binder of sperm protein homolog 1, bovine seminal plasma protein homolog 1) NCBI Gene ID NO. 100131137 | 14 | 0 | | 127 |
| OVCH2 (ovochymase 2) NCBI Gene ID NO. 341277 | 10 | 0 | | |
| MFGE8 (milk fat globule-EGF factor 8 protein, lactadherin) NCBI Gene ID NO. 4240 | 9 | 0 | | 33 |
| PGK2 (phosphoglycerate kinase 2) NCBI Gene ID NO. 5232 | 17 | 0 | Testis | 23, 136 |
| ACRBP (acrosin binding protein) NCBI Gene ID NO. 84519 | 8 | 0 | Testis | 32 |
| HIST1H2BA (histone cluster 1, H2ba histone H2B type 1-A) NCBI Gene ID NO. 255626 | 9 | 0 | Testis | 28, 27 |
| PGAM2 (phosphoglycerate mutase 2) Gene ID NO. 5224 | 7 | 0 | | |
| CDH2 (cadherin 2) NCBI Gene ID NO. 1000 | 6 | 0 | | 34 |
| MFAP4 (microfibrillar-associated protein 4) NCBI Gene ID NO. 4239 | 4 | 0 | | |
| SLC2A14 (solute carrier family 2 (facilitated glucose transporter), member 14, isoform 1) NCBI Gene ID NO. 144195 | 4 | 0 | Testis | 29 |
| REG3G (regenerating islet-derived 3 gamma) NCBI Gene ID NO. 130120 | 6 | 0 | | 137 |
| PTPRG (protein tyrosine phosphatase, receptor type, G, isoform 1) NCBI Gene ID NO. 5793 | 4 | 0 | | 138 |
| HSPA4L (heat shock 70 kDa protein 4-like) NCBI Gene ID NO. 22824 | 4 | 0 | | 35, 36, 37 |
| THBS2 (thrombospondin 2) NCBI Gene ID NO. 7058 | 4 | 0 | | 38 |
| RNASE13 (ribonuclease, RNase A family, 13) NCBI Gene ID NO. 440163 | 4 | 0 | | |
| VASN (vasorin) NCBI Gene ID NO. 114990 | 3 | 0 | | |
| LRRC37A3 (leucine rich repeat containing 37, member A3) NCBI Gene ID NO. 374819 | 2 | 0 | | |
| SI (sucrase-isomaltase (alpha-glucosidase)) NCBI Gene ID NO. 6476 | 7 | 0 | | |
| SPACA3 (sperm acrosome membrane-associated 3) NCBI Gene ID NO. 124912 | 3 | 0 | Testis | 30 |
| GAPDHS (glyceraldehyde-3-phosphate dehydrogenase, spermatogenic) NCBI Gene ID NO. 26330 | 3 | 0 | Testis | 24, 25 |

TABLE 1-continued

Proteins found uniquely in Control seminal plasma (absent in post-vasectomy (PV) seminal plasma) according to spectral counting.

| Gene Name | Average Spectral Count Control | PV* | Protein origin** | Reference *** |
|---|---|---|---|---|
| SLC1A1 (solute carrier family 1 (neuronal/epithelial high affinity glutamate transporter, system Xag), member 1, excitatory amino acid transporter 3) NCBI Gene ID NO. 6505 | 3 | 0 | Testis | |
| C16orf89 (chromosome 16 open reading frame 89, hypothetical protein LOC146556 isofrom 2) NCBI Gene ID NO. 146556 | 3 | 0 | | |
| DEFB121 (defensin, beta 121, ESC42-RELC) NCBI Gene ID NO. 245934 | 3 | 0 | | |
| BSG (basigin) NCBI Gene ID NO. 682 | 3 | 0 | | |
| ZPBP (zona pellucida binding protein) NCBI Gene ID NO. 11055 | 3 | 0 | Testis | 31 |
| AKAP4 (kinase (PRKA) anchor protein 4) NCBI Gene ID NO. 8852 | 3 | 0 | Testis | 26 |

*PV—post-vasectomy
**For protein origin to be annotated, the corresponding gene name needed to be found in testis, epididymis or prostate in at least two out of four databases.
*** Linked to urogenital tract

TABLE 2

Proteins found at lower abundance in post-vasectomy (PV) seminal plasma relative to Control seminal plasma according to spectral counting.

| Gene Name | Average Spectral Count Control | PV* | Fold Change** Control/PV | Protein origin*** | References**** |
|---|---|---|---|---|---|
| MUC5B (mucin 5B, oligomeric mucus/gel-forming) NCBI Gene ID 727897 | 30 | 0.3 | 89.0 | | 139 |
| PTGDS (prostaglandin D2 synthase 21 kDa, prostaglandin-H2 D-isomerase) NCBI Gene ID 5730 | 52 | 1 | 39.3 | testis, epididymis, prostate | 41, 43, 42 |
| CPVL (carboxypeptidase, vitellogenic-like) NCBI Gene ID 54504 | 10 | 0.3 | 29.0 | | |
| ELSPBP1 (epididymal sperm binding protein 1) NCBI Gene ID 64100 | 22 | 1 | 22.0 | testis | 47, 48 |
| GPR64 (G protein-coupled receptor 64, isoform 1) NCBI Gene ID 10149 | 14 | 1 | 20.5 | testis | 49, 50 |
| C20orf114 (BPI fold containing family B, member 1) NCBI Gene ID 92747 | 7 | 0.3 | 20.0 | | |
| CA4 (carbonic anhydrase IV) NCBI Gene ID 762 | 6 | 0.3 | 18.0 | | 140, 141 |
| STOM (stomatin) NCBI Gene ID 2040 | 6 | 0.3 | 17.0 | | |
| BGN (biglycan) NCBI Gene ID 633 | 9 | 1 | 14.0 | | |
| CES7 (carboxylesterase 7) NCBI Gene ID 221223 | 23 | 2 | 13.8 | | 142 |
| PFKP (phosphofructokinase, platelet) NCBI Gene ID 5214 | 4 | 0.3 | 13.0 | | |
| LOC642103 (similar to Maltase-glucoamylase, intestinal) | 29 | 3 | 10.9 | | |
| SPINT3 (serine peptidase inhibitor, Kunitz type, 3) NCBI Gene ID 10816 | 21 | 2 | 10.3 | testis | |
| MGAM (maltase-glucoamylase (alpha-glucosidase)) NCBI Gene ID 8972 | 28 | 3 | 8.4 | | |
| COL18A1 (collagen, type XVIII, alpha 1) NCBI Gene ID 80781 | 15 | 2 | 7.7 | | 128 |
| NID1 (nidogen 1) NCBI Gene ID 4811 | 12 | 2 | 7.4 | | |
| CRISP2 (cysteine-rich secretory protein 2,) NCBI Gene ID 7180 | 7 | 1 | 7.3 | testis | 51, 55, 56 |
| FAM12B (epididymal protein 3B) NCBI Gene ID 64184 | 19 | 3 | 7.3 | testis, epididymis | 73 |
| BCAN (brevican) NCBI Gene ID 63827 | 15 | 2 | 6.6 | | |
| ECM1 (extracellular matrix protein 1) NCBI Gene ID 1893 | 114 | 18 | 6.3 | | |
| A2M (alpha-2-macroglobulin) NCBI Gene ID 2 | 47 | 8 | 6.1 | | 44, 45, 7 |
| PATE4 (prostate and testis expressed 4) NCBI Gene ID 399968 | 5 | 1 | 5.3 | prostate | |
| SERPINA6 (serpin peptidase inhibitor, clade A (alpha-1 antiproteinase, antitrypsin), member 6, corticosteroid-binding globulin) NCBI Gene ID 866 | 5 | 1 | 5.0 | | |
| APCS (amyloid P component, serum) NCBI Gene ID 325 | 10 | 2 | 4.3 | | |
| EEF1G (eukaryotic translation elongation factor 1 gamma) NCBI Gene ID 1937 | 10 | 2 | 4.1 | | |
| AK1 (adenylate kinase 1) NCBI Gene ID 203 | 10 | 3 | 3.8 | | 143 |
| ALDH1A1 (aldehyde dehydrogenase 1 family, member A1, retinal dehydrogenase 1) NCBI Gene ID 216 | 17 | 5 | 3.7 | | 144 |
| PDGFA (platelet-derived growth factor alpha polypeptide) NCBI Gene ID 5154 | 5 | 1 | 3.5 | | 145 |

TABLE 2-continued

Proteins found at lower abundance in post-vasectomy (PV) seminal plasma relative to Control seminal plasma according to spectral counting.

| Gene Name | Average Spectral Count Control | PV* | Fold Change** Control/PV | Protein origin*** | References**** |
|---|---|---|---|---|---|
| NPC2 (Niemann-Pick disease, type C2; epididymal secretory protein E1) NCBI Gene ID 10577 | 234 | 68 | 3.4 | testis, epididymis | 46, 6 |
| CRISP1 (cysteine-rich secretory protein 1) NCBI Gene ID 167 | 59 | 17 | 3.4 | testis | 51, 52, 53, 54 |
| ABP1 (amiloride binding protein 1 (amine oxidase (copper-containing)) NCBI Gene ID 26 | 71 | 21 | 3.4 | | 7 |
| CFI (complement factor I) NCBI Gene ID 3426 | 9 | 3 | 3.4 | | |
| CAMP (cathelicidin antimicrobial peptide) NCBI Gene ID 820 | 11 | 4 | 3.1 | | |
| CALR (calreticulin) NCBI Gene ID 811 | 14 | 5 | 3.0 | | |
| CPAMD8 (C3 and PZP-like, alpha-2-macroglobulin domain containing 8) NCBI Gene ID 27151 | 13 | 5 | 2.7 | | |
| PPA1 (pyrophosphatase (inorganic) 1) NCBI Gene ID 5464 | 10 | 4 | 2.6 | | |
| CD177 (CD177 molecule) NCBI Gene ID 57126 | 82 | 32 | 2.5 | | 7 |
| SERPINA1 (serpin peptidase inhibitor, clade A (alpha-1 antiproteinase, antitrypsin), member 1) NCBI Gene ID 5265 | 155 | 62 | 2.5 | | 146 |
| BPIL1 (BPI fold containing family B, member 2, bactericidal/permeability-increasing protein-like 1) NCBI Gene ID 80341 | 17 | 7 | 2.5 | | |
| FBLN2 (fibulin 2) NCBI Gene ID 2199 | 17 | 7 | 2.3 | | 147 |
| DAG1 (dystroglycan 1 (dystrophin-associated glycoprotein 1) NCBI Gene ID 1605 | 12 | 5 | 2.3 | | |
| FAM3C (family with sequence similarity 3, member C) NCBI Gene ID 10447 | 10 | 4 | 2.3 | | |
| PGLYRP2 (peptidoglycan recognition protein 2, isoform 1 of N-acetylmuramoyl-L-alanine amidase) NCBI Gene ID 114770 | 11 | 5 | 2.3 | | |
| CHGB (chromogranin B (secretogranin 1)) NCBI Gene ID 1114 | 12 | 5 | 2.3 | | |
| GAS6 (growth arrest-specific 6) NCBI Gene ID 2621 | 34 | 15 | 2.2 | | 129 |
| NP (cDNA FLJ25678 fis, clone TST04067, highly similar to purine nucleoside phosphorylase) Accession No. IPI00017672 | 16 | 7 | 2.2 | | |
| RNASE1 (ribonuclease, RNase A family, 1 (pancreatic)) NCBI Gene ID 6035 | 58 | 28 | 2.1 | testis | |
| CD14 (CD14 molecule, monocyte differentiation antigen CD14) NCBI Gene ID 929 | 32 | 16 | 2.0 | | |
| MXRA5 (matrix-remodelling associated 5) NCBI Gene ID 25878 | 56 | 28 | 2.0 | | 7 |

*PV—post-vasectomy
**Fold changes may be overestimated especially in cases where only one out of three replicates contains spectral counts.
***For protein origin to be annotated, the protein needed to be found in testis, epididymis or prostate in at least two out of four databases.
****Linked to urogenital tract

TABLE 3

List of proteins found at higher abundance in post-vasectomy (PV) seminal plasma relative to Control seminal plasma according to spectral counting.

| Gene Name | Average Spectral Count Control | PV* | Fold Change** Control/PV | References*** |
|---|---|---|---|---|
| ELA2 (elastase, neutrophil expressed) NCBI Gene ID 1991 | 1 | 15 | −15.0 | |
| AZU1 (azurocidin 1) NCBI Gene ID 566 | 1 | 6 | −6.0 | |
| HIST1H2BL (histone cluster 1, H2bl) NCBI Gene ID 8340 | 3 | 18 | −5.5 | |
| PRELP (proline/arginine-rich end leucine-rich repeat protein) NCBI Gene ID 5549 | 1 | 5 | −5.5 | |
| FGB (fibrinogen beta chain) NCBI Gene ID 2244 | 5 | 26 | −5.3 | |
| MPO (myeloperoxidase, isoform H17 of myeloperoxidase) NCBI Gene ID 4353 | 9 | 37 | −4.2 | |
| AGL (amylo-alpha-1, 6-glucosidase, 4-alpha-glucanotransferase) NCBI Gene ID 178 | 2 | 7 | −4.0 | |
| HIST1H4H (histone cluster 1, H4h) NCBI Gene ID 8365 | 4 | 14 | −3.6 | |
| GSTT2 (glutathione S-transferase theta 2) NCBI Gene ID 2953 | 3 | 10 | −3.3 | |
| COL6A2 (collagen, type VI, alpha 2) NCBI Gene ID 1292 | 3 | 8 | −3.1 | |
| MYO1C (myosin 1C) NCBI Gene ID 4641 | 3 | 9 | −3.0 | |
| FMOD (fibromodulin) NCBI Gene ID 2331 | 5 | 16 | −2.9 | |
| SYTL1 (synaptotagmin-like 1) NCBI Gene ID 84958 | 5 | 11 | −2.4 | |
| PAEP (progestagen-associated endometrial protein) NCBI Gene ID 5047 | 57 | 134 | −2.4 | 148, 149 |

TABLE 3-continued

List of proteins found at higher abundance in post-vasectomy (PV) seminal plasma relative to Control seminal plasma according to spectral counting.

| Gene Name | Average Spectral Count | | Fold Change** | References*** |
|---|---|---|---|---|
| | Control | PV* | Control/PV | |
| FLJ58816 (highly similar to *Homo sapiens* nephronectin (NPNT), (EMBL-CDS: BAG63765.1)) | 4 | 10 | −2.3 | |
| ALDH7A1 (aldehyde dehydrogenase 7 family, member A1) NCBI Gene ID 501 | 4 | 10 | −2.3 | |
| MYH9 (myosin, heavy chain 9, non-muscle) NCBI Gene ID 4627 | 28 | 63 | −2.3 | |
| C11orf54 (chromosome 11 open reading frame 54) NCBI Gene ID28970 | 5 | 12 | −2.2 | |
| ORM2 (orosomucoid 2) NCBI Gene ID 5005 | 111 | 241 | −2.2 | |
| STAT3 (signal transducer and activator of transcription 3 (acute-phase response factor)) NCBI Gene ID 6774 | 8 | 16 | −2.1 | 150 |
| ORM1 (orosomucoid 1, alpha-1-acid glycoprotein 1) NCBI Gene ID 5004 | 225 | 467 | −2.1 | |
| PYGB (phosphorylase, glycogen; brain) NCBI Gene ID 5834 | 16 | 34 | −2.1 | |
| APOA1 (apolipoprotein A-I) NCBI Gene ID 335 | 18 | 36 | −2.1 | |
| ACAT2 (acetyl-CoA acetyltransferase 2) NCBI Gene ID 39 | 8 | 16 | −2.0 | |
| C3 (complement component 3) NCBI Gene ID 718 | 36 | 70 | −2.0 | |

*PV—post-vasectomy
**Fold changes may be overestimated especially in cases where only one out of three replicates contains spectral counts.
***Linked to urogenital tract

TABLE 4

List of proteins at different abundances in seminal plasma from Control and post-vasectomy (PV) men according to spectral counting that are expressed in the testis/epididymis or the prostate in at least three out of four databases.

| Gene Name | Average Spectral Count | | Fold Change** | Protein origin |
|---|---|---|---|---|
| | Control | PV* | Control/PV | |
| Unique to Control | | | | |
| TEX101 | 17.0 | 0 | PV<<Control | testis |
| PGK2 | 16.7 | 0 | PV<<Control | testis |
| HIST1H2BA | 8.7 | 0 | PV<<Control | testis |
| SLC2A14 [1] | 4.3 | 0 | PV<<Control | testis |
| SPACA3 [2] | 3.3 | 0 | PV<<Control | testis |
| GAPDHS [3] | 3.0 | 0 | PV<<Control | testis |
| AKAP4 | 2.7 | 0 | PV<<Control | testis |
| ↓in PV | | | | |
| PTGDS | 52.3 | 1 | 39.3 | testis |
| ELSPBP1 [4] | 22.0 | 1 | 22.0 | testis |
| SPINT3 | 20.7 | 2 | 10.3 | testis |
| CRISP2 | 7.3 | 1 | 7.3 | testis |
| FAM12B | 19.3 | 3 | 7.3 | testis |
| PATE4 | 5.3 | 1 | 5.3 | prostate |
| NPC2 | 234.0 | 68 | 3.4 | testis |
| CRISP1 | 59.0 | 17 | 3.4 | testis |

*PV—post-vasectomy
**Fold changes may be overestimated especially in cases where only one out of three replicates contains spectral counts
[1] solute carrier family 2 (facilitated glucose transporter), member 14; NCBI Gene ID 144195
[2] sperm acrosome associated 3, NCBI Gene ID 124912
[3] glyceraldehyde-3-phosphate dehydrogenase, spermatogenic, NCBI Gene ID 26330
[4] epididymal sperm binding protein 1, NCBI Gene ID 64100

TABLE 5

Proteins and peptides selected for a 32-peptide label-free SRM assay.

| Protein | Proteotypic peptide | 2D-LC-MS/MS spectral counting Pool of 5 samples, ratio Normal/PV[2] | LC-SRM Pool of 5 samples, ratio Normal/PV[2] | LC-SRM Individual samples, ratio of medians Normal/PV[2,3] |
|---|---|---|---|---|
| LDHC | EELFLSIPCVLGR [SEQ ID NO. 7] | $\infty$[1] | 6400[1] | 1100[1] |
| SPAG11B[a] | ICVDFLGPR [SEQ ID NO. 8] | $\infty$[1] | 55[1] | 149[1] |
| TEX101 | LMSGILAVGPMFVR [SEQ ID NO. 9] | $\infty$[1] | 1200[1] | 143[1] |
| MUC15[b] | DGIPMDDIPPLR [SEQ ID NO. 10] | $\infty$[1] | 140[1] | 142[1] |

TABLE 5-continued

Proteins and peptides selected for a 32-peptide label-free SRM assay.

| Protein | Proteotypic peptide | 2D-LC-MS/MS spectral counting Pool of 5 samples, ratio Normal/PV | LC-SRM Pool of 5 samples, ratio Normal/PV[2] | LC-SRM Individual samples, ratio of medians Normal/PV[2,3] |
|---|---|---|---|---|
| CES7 | DAGAPVYFYEFR[SEQ ID NO. 11] | 14 | 15[1] | 100[1] |
| PTGDS | AQGFTEDTIVFLPQTDK [SEQ ID NO. 12] | 39 | 190 | 66 |
| ECM1 | ELLALIQLER [SEQ ID NO. 13] | 6.3 | 9.1 | 47 |
| MGAM | AYVAFPDFFR[SEQ ID NO. 14] | 8.4 | 6.4 | 31 |
| CEL | LGLLGDSVDIFK[SEQ ID NO. 15] | ∞[1] | 41[1] | 26[1] |
| CAMP | FALLGDFFR[SEQ ID NO. 16] | 3.1 | 9.7 | 19 |
| ADAM7 | TYEEELLYEIK[SEQ ID NO. 17] | ∞[1] | 9.4[1] | 15[1] |
| FAM12B | NAYVWVQNPLK[SEQ ID NO. 18] | 7.3 | 30 | 15 |
| CRISP1 | YCDMTESNPLER[SEQ ID NO. 19] | 3.4 | 5.7 | 12 |
| PATE4 | ENELCSTTAYFR[SEQ ID NO. 20] | 5.3 | 30 | 5.6 |
| SPINT3 | DLLPNVCAFPMEK[SEQ ID NO. 21] | 10 | 7.0 | 5.3 |
| GPR64 | GEIMFQYDK[SEQ ID NO. 22] | 21 | 3.5 | 4.8 |
| ALDH1A1 | TIPIDGNFFTYTR[SEQ ID NO. 23] | 3.7 | 3.5 | 3.6 |
| CA4 | ASISGGGLPAPYQAK[SEQ ID NO.24] | 18 | 6.7 | 2.5 |
| NPC2 | LVVEWQLQDDK[SEQ ID NO. 25] | 3.4 | 2.0 | 1.9 |
| ABP1 | GGFNFYAGLK[SEQ ID NO. 26] | 3.4 | 1.1 | 1.5 |
| LGALS3BP[c] | SDLAVPSELALLK[SEQ ID NO. 27] | 1.5 | 2.1 | 1.1 |
| DAG1 | VTIPTDLIASSGDIIK[SEQ ID NO. 28] | 2.3 | 2.1 | 1.0 |
| GAS6 | LVAEFDFR[SEQ ID NO. 29] | 2.2 | 1.4 | 1.0 |
| LTBP3 | NQCLCPPDFTGR[SEQ ID NO. 30] | 1.9 | 2.1 | 0.9 |
| SERPINA1 | SVLGQLGITK[SEQ ID NO. 31] | 2.5 | 3.1 | 0.8 |
| CD177 | GGGIFSNLR[SEQ ID NO. 32] | 2.5 | 2.0 | 0.8 |
| GSTM3[d] | LDLDFPNLPYLLDGK[SEQ ID NO. 33] | 1.5 | 0.6 | 0.7 |
| DEFB118[e] | ACCIPSNEDHR[SEQ ID NO. 34] | ∞ | 2.3 | 0.7 |
| MXRA5[f] | FSILSSGWLR[SEQ ID NO. 35] | 2.0 | 1.5 | 0.6 |
| KLK3 | LSEPAELTDAVK[SEQ ID NO. 36] | 0.6 | 0.7 | 0.5 |
| SERPINA5[g] | TLYLADTFPTNFR[SEQ ID NO. 5] | 1.1 | 1.1 | 0.5 |

[1] In PV samples, protein was not identified or its peptide level measured by SRM was below LOQ
[2] Peptide abundances were normalized to the internal standard (spiked-in heavy peptide of KLK3)
[3] Based on 12 normal and 8 PV samples
[a] sperm associated antigen 11B, NCBI Gene ID 10407
[b] mucin 15, cell surface associated; NCBI Gene ID 143662
[c] lectin, galactoside-binding, soluble, 3 binding protein, NCBI Gene ID 3959
[d] glutathione S-transferase mu 3 (brain), NCBI Gene ID 2947
[e] defensin, beta 118, NCBI Gene ID 117285
[f] matrix-remodelling associated 5, NCBI Gene ID 25878
[g] serpin peptidase inhibitor, Glade A (alpha-1 antiproteinase, antitrypsin), member 5, NCBI Gene ID 5104

TABLE 6

Concentration of 20 proteins in 30 seminal plasma samples measured with a 40-peptide stable-isotope dilution SRM assay

| Protein | MW, kDa | Concentration in seminal plasma, median (IQR[1]), µg/mL | | | Median CV of SRM assay[2] |
|---|---|---|---|---|---|
| | | Normal (n = 12) | NOA (n = 10) | PV (n = 8) | |
| KLK3 | 28.7 | 330 (240-480[1]) | 620 (420-900) | 490 (280-970) | 0.7% |
| CAMP | 19.3 | 37 (17-62) | 33 (16-125) | 1.5 (1.0-4.9) | 0.9% |
| ECM1 | 60.7 | 34 (19-58) | 28 (14-98) | 1.1 (0.8-3.1) | 0.7% |
| CRISP1 | 28.5 | 30 (15-52) | 24 (17-91) | 3.7 (3.1-7.1) | 1.3% |
| PTGDS | 21.0 | 9.0 (5.5-15) | 2.1 (0.4-5.5) | 0.2 (0.1-0.2) | 1.2% |
| MGAM | 210.0 | 8.1 (4.8-17) | 7.1 (5.3-40) | 0.5 (0.3-0.8) | 1.3% |
| SPINT3 | 10.3 | 7.0 (3.0-8.2) | 3.7 (2.3-14) | 1.1 (0.8-1.4) | 0.9% |
| GPR64 | 112.0 | 5.2 (2.6-6.5) | 7.5 (2.8-11) | 1.1 (0.9-1.9) | 1.5% |
| NPC2 | 22.0 | 4.2 (3.4-6.2) | 5.4 (3.7-7.7) | 4.0 (2.7-4.5) | 0.9% |
| CD177 | 46.4 | 3.8 (1.7-20) | 13 (9.8-34) | 12 (4.3-25) | 7.9% |
| FAM12B | 17.6 | 2.3 (1.6-5.9) | 1.8 (1.0-6.1) | 0.23 (0.17-0.35) | 1.1% |
| LDHC | 36.3 | 1.8 (1.2-5.3) | <0.09[3] | <0.09[3] | 1.1% |
| CEL | 79.3 | 1.5 (0.9-2.1) | 0.20 (0.14-0.59) | <0.07[3] | 1.7% |
| ADAM7 | 85.7 | 1.4 (0.8-2.7) | 1.3 (0.5-2.8) | <0.2[3] | 2.9% |
| CES7 | 63.9 | 1.3 (0.8-3.1) | 1.2 (0.5-2.1) | <0.05[3] | 2.8% |
| ALDH1A1 | 54.9 | 1.2 (1.0-1.9) | 0.59 (0.45-1.8) | 0.45 (0.37-0.72) | 0.5% |
| TEX101 | 26.7 | 1.1 (0.8-1.9) | <0.07[3] | <0.07[3] | 1.1% |
| MUC15 | 36.3 | 0.93 (0.53-1.1) | 0.48 (0.13-1.3) | <0.03[3] | 1.4% |
| CA4 | 35.0 | 0.80 (0.50-1.4) | 0.60 (0.31-1.4) | 0.34 (0.20-0.47) | 1.2% |
| SPAG11B | 11.4 | 0.23 (0.10-0.38) | 0.10 (0.02-0.11) | <0.01[3] | 1.3% |

[1]interquartile range
[2]median CV of normal samples based on analysis of duplicates
[3]limit of quantification of protein calculated based on the limit of quantification of a synthetic peptide in the seminal plasma digest

TABLE 7

Groups of proteins for differential diagnosis of azoospermia based on concentrations of proteins in seminal plasma samples.

| Protein | Statistical significance of difference of groups[1] | ROC area[2] | % sensitivity at ≥ 95% specificity | Exclusive tissue specificity | Testis cell specificity |
|---|---|---|---|---|---|
| Normal (n = 12) vs PV (n = 8) | | | | | |
| LDHC | <0.001 | 1.00 | 100 | Testis | Sertoli, Leydig, germ |
| SPAG11B | <0.001 | 1.00 | 100 | Testis | Leydig |
| TEX101 | <0.001 | 1.00 | 100 | Testis | Sertoli, Leydig, germ |
| MUC15 | <0.001 | 1.00 | 100 | Testis | Leydig |
| PTGDS | <0.001 | 1.00 | 100 | | Sertoli, Leydig, germ |
| ECM1 | <0.001 | 1.00 | 100 | | |
| CEL | <0.001 | 1.00 | 100 | | |
| FAM12B | <0.001 | 1.00 | 100 | Testis | Leydig, germ |
| CAMP | <0.01 | 0.97 | 88 | | Germ |
| SPINT3 | <0.01 | 0.96 | 75 | Testis | Germ |
| CES7 | <0.01 | 0.95 | 75 | | |
| MGAM | <0.01 | 0.94 | 88 | | |
| ADAM7 | <0.01 | 0.92 | 50 | Testis | Leydig |
| CRISP1 | <0.05 | 0.91 | 75 | Testis | Leydig, Germ |
| GPR64 | <0.05 | 0.89 | 63 | Testis | Leydig |
| CA4 | <0.05 | 0.89 | 63 | | |
| Normal (n = 12) vs NOA (n = 10) | | | | | |
| TEX101 | <0.01 | 0.99 | 90 | Testis | Sertoli, Leydig, germ |
| LDHC | <0.01 | 0.93 | 90 | Testis | Sertoli, Leydig, germ |
| CEL | <0.05 | 0.85 | 50 | | |
| NOA (n = 10) vs PV (n = 8) | | | | | |
| ECM1 | <0.01 | 0.96 | 75 | | |
| CAMP | <0.01 | 0.96 | 88 | | |
| MGAM | <0.01 | 0.95 | 88 | | |
| MUC15 | <0.05 | 0.94 | 63 | Testis | Leydig |
| CES7 | <0.01 | 0.94 | 75 | | |
| NOA (n = 10) vs PV (n = 8) | | | | | |
| SPINT3 | <0.01 | 0.93 | 50 | Testis | Germ |
| FAM12B | <0.01 | 0.91 | 13 | Testis | Leydig, germ |
| CRISP1 | <0.01 | 0.90 | 75 | Testis | Leydig, germ |
| SPAG11B | <0.05 | 0.89 | 63 | Testis | Leydig |
| ADAM7 | <0.05 | 0.88 | 13 | | |
| GPR64 | <0.05 | 0.83 | 10 | Testis | Leydig |

[1]nonparametric one-way ANOVA Kruskal-Wallis test followed by Dunn's multiple-comparisons test for differences between three groups
[2]area under receiver operating characteristic curve

TABLE 8

List of candidate biomarker proteins found at higher abundance in prostatitis compared to control, according to spectral counting.

| Gene Name | Average Spectral Count Control | Average Spectral Count Prostatitis | Fold Change* | Prostatic Origin** |
|---|---|---|---|---|
| ALB (albumin) NCBI Gene ID 213 | 1441 | 3079 | 2.1 | |
| SERPINA1 | 149 | 382 | 2.6 | Yes |
| CST4 (cystatin S) NCBI Gene ID 1472 | 83 | 468 | 5.7 | |
| CST3 (cystatin C) NCBI Gene ID 1471 | 65 | 202 | 3.1 | Yes |
| PAEP cDNA FLJ52183 (progestagen-associated endometrial protein)NCBI Gene ID 5047 | 52 | 144 | 2.8 | |
| C4A (complement component 4A (Rodgers blood group)) NCBI Gene ID 720 | 38 | 131 | 3.5 | Yes |
| A2M (alpha-2-macroglobulin) NCBI Gene ID 2 | 44 | 103 | 2.3 | Yes |
| SERPINA5 | 37 | 122 | 3.3 | |
| C3 (complement component 3) NCBI Gene ID 718 | 34 | 104 | 3 | Yes |
| LPL (lipoprotein lipase) NCBI Gene ID 4023 | 30 | 66 | 2.2 | |
| IGHG2 (immunoglobulin heavy constant gamma 2 (G2m marker)) NCBI Gene ID 3501 | 17 | 46 | 2.6 | |
| A1BG (alpha-1-B glycoprotein) NCBI Gene ID 1 | 25 | 50 | 2 | |
| MSLN (mesothelin) NCBI Gene ID 10232 | 16 | 33 | 2 | |
| SERPING1 (serpin peptidase inhibitor, clade G (C1 inhibitor), member 1) NCBI Gene ID 710 | 17 | 48 | 2.9 | |
| SCPEP1 (serine carboxypeptidase 1) NCBI Gene ID 59342 | 17 | 44 | 2.6 | Yes |
| GLA (galactosidase, alpha) NCBI Gene ID 2717 | 21 | 43 | 2 | Yes |
| OLFM4 (olfactomedin 4) NCBI Gene ID 10562 | 15 | 41 | 2.7 | Yes |
| SMPD1 (sphingomyelin phosphodiesterase 1, acid lysosomal) NCBI Gene ID 6609 | 9 | 20 | 2.2 | Yes |
| CTSF (cathepsin F) NCBI Gene ID 8722 | 9 | 24 | 2.5 | Yes |
| SERFINF1 (serpin peptidase inhibitor, clade F (alpha-2 antiplasmin, pigment epithelium derived factor), member 1) NCBI Gene ID 5176 | 10 | 33 | 3.4 | Yes |
| MINPP1 (multiple inositol-polyphosphate phosphatase 1) NCBI Gene ID 9562 | 9 | 19 | 2.1 | Yes |
| CFI (complement factor I) NCBI Gene ID 3426 | 9 | 18 | 2.1 | |
| CTSC (cathepsin C) NCBI Gene ID 1075 | 5 | 10 | 2.2 | |
| CST6 (cystatin E/M) NCBI Gene ID 1474 | 7 | 15 | 2.2 | Yes |
| TXNDC16 (thioredoxin domain containing 16) NCBI Gene ID 57544 | 8 | 18 | 2.3 | Yes |
| LCN1 (lipocalin 1 (tear prealbumin)) NCBI Gene ID 3933 | 2 | 15 | 6.3 | |
| COL6A2 (collagen, type VI, alpha 2) NCBI Gene ID 1292 | 3 | 15 | 5.5 | Yes |
| A4GALT (alpha 1,4-galactosyltransferase) NCBI Gene ID 53947 | 4 | 15 | 4 | Yes |
| PATE4 | 4 | 13 | 3 | Yes |
| TIMP3 (TIMP metallopeptidase inhibitor 3) NCBI Gene ID 7078 | 5 | 11 | 2.1 | |
| CST2 (cystatin SA) NCBI Gene ID 1470 | 2 | 16 | 9.6 | |
| FGB (fibrinogen beta chain) NCBI Gene ID 2244 | 4 | 11 | 2.6 | |
| COMP (cartilage oligomeric matrix protein) NCBI Gene ID 1311 | 4 | 12 | 2.9 | |

*Fold change = average prostatitis/average control
**Protein/gene name annotated as expressed in the prostate in at least 2 out of 3 databases (BioGPS; Unigene, Protein Atlas)

TABLE 9

List of candidate biomarker proteins found at higher abundance in control compared to prostatitis, according to spectral counting.

| Gene Name | Average Spectral Count Control | Average Spectral Count Prostatitis | Fold Change* | Prostatic Origin** |
|---|---|---|---|---|
| CPM (carboxypeptidase M) NCBI Gene ID 1368 | 31 | 10 | 3 | Yes |
| DYNC1H1 (dynein, cytoplasmic 1, heavy chain 1) NCBI Gene ID 1778 | 29 | 13 | 2.3 | |
| MUC5B (mucin 5B, oligomeric mucus/gel-forming) NCBI Gene ID 727897 | 29 | 7 | 4.2 | |
| RAB27B (member RAS oncogene family) NCBI Gene ID 5874 | 21 | 11 | 2 | Yes |
| PHGDH (phosphoglycerate dehydrogenase) NCBI Gene ID 26227 | 20 | 10 | 2.1 | Yes |

TABLE 9-continued

List of candidate biomarker proteins found at higher abundance in
control compared to prostatitis, according to spectral counting.

| Gene Name | Average Spectral Count Control | Average Spectral Count Prostatitis | Fold Change* | Prostatic Origin** |
|---|---|---|---|---|
| CA2 (carbonic anhydrase II) NCBI Gene ID 760 | 19 | 9 | 2 | |
| ACO1 (aconitase 1, soluble) NCBI Gene ID 48 | 14 | 6 | 2.3 | Yes |
| ANXA6 (annexin A6) NCBI Gene ID 309 | 19 | 5 | 3.5 | |
| CACNA2D1 (calcium channel, voltage-dependent, alpha 2/delta subunit 1) NCBI Gene ID 781 | 19 | 5 | 4 | |
| FAM129A (family with sequence similarity 129, member A) NCBI Gene ID 116496 | 10 | 4 | 2.4 | Yes |
| CDC42 (cell division cycle 42 (GTP binding protein, 25 kDa)) NCBI Gene ID 998 | 12 | 4 | 2.7 | Yes |
| RHOC (ras homolog gene family, member C) NCBI Gene ID 389 | 13 | 4 | 3.2 | Yes |
| HGD (homogentisate 1,2-dioxygenase) NCBI Gene ID 3081 | 14 | 5 | 2.9 | |
| RAB2A (member RAS oncogene family) NCBI Gene ID 5862 | 11 | 5 | 2.1 | Yes |
| DCXR (dicarbonyl/L-xylulose reductase) NCBI Gene ID 51181 | 12 | 6 | 2.1 | Yes |
| LAMP1 (lysosomal-associated membrane protein 1) NCBI Gene ID 3916 | 10 | 4 | 2.3 | Yes |
| ALDH9A1 (aldehyde dehydrogenase 9 family, member A1) NCBI Gene ID 223 | 11 | 5 | 2 | Yes |
| CMPK1 (cytidine monophosphate (UMP-CMP) kinase 1, cytosolic) NCBI Gene ID 51727 | 13 | 5 | 2.5 | |
| NOV (nephroblastoma overexpressed gene) NCBI Gene ID 4856 | 13 | 5 | 2.4 | Yes |
| NAPA (N-ethylmaleimide-sensitive factor attachment protein, alpha) NCBI Gene ID 8775 | 12 | 4 | 2.8 | Yes |
| SOD3 (superoxide dismutase 3, extracellular) NCBI Gene ID 6649 | 12 | 5 | 2.3 | Yes |
| LIFR (leukemia inhibitory factor receptor alpha) NCBI Gene ID 3977 | 11 | 5 | 2.3 | Yes |
| RNPEP (arginyl aminopeptidase (aminopeptidase B) NCBI Gene ID 6051 | 12 | 5 | 2.2 | Yes |
| FLNB (filamin B, beta) NCBI Gene ID 2317 | 13 | 4 | 3.2 | Yes |
| DDAH1 (dimethylarginine dimethylaminohydrolase 1) NCBI Gene ID 23576 | 12 | 5 | 2.3 | Yes |
| KIF5B (kinesin family member 5B) NCBI Gene ID 3799 | 11 | 4 | 3.1 | Yes |

*Fold change = average control/average prostatitis
**Protein/gene name annotated as expressed in the prostate in at least 2 out of 3 databases (BioGPS; Unigene, Protein Atlas)

TABLE 10

Proteins at different abundances in NOA relative to Control seminal plasma according to spectral counting. Respective ratios from extracted ion current (XIC) intensities are also provided. Only up to top 10 proteins for each category are listed.

| Gene name | Control/NOA[a] Ratios SC[b] | Control/NOA[a] Ratios XIC[c] | Protein Origin[d] |
|---|---|---|---|
| *Unique to NOA[a]* | | | |
| SORD[1] | NOA>>Control | NOA>>Control | |
| GGT7[2] | NOA>>Control | 0.2 | |
| *Unique to Control* | | | |
| HIST1H4H[3] | NOA<<Control | 13.6 | |
| DPEP3[4] | NOA<<Control | NOA<<Control | testis* (2) |
| TEX101 | NOA<<Control | 20220.0 | testis* (3) |
| CEL | NOA<<Control | 189.1 | |
| PGK2 | NOA<<Control | 533.7 | testis* (3) |
| PRKACA[5] | NOA<<Control | 2.8 | |
| PGAM2[6] | NOA<<Control | 3509.5 | |
| SLC2A14[7] | NOA<<Control | 17.0 | testis* (3) |
| CDH2[8] | NOA<<Control | NOA<<Control | |
| ASRGL1[9] | NOA<<Control | 6.6 | testis (3) |
| *↓ in NOA[a]* | | | |
| STOM[10] | 15.0 | 6.8 | |
| OVCH2 | 13.5 | 14.2 | |
| PTGDS | 11.7 | 15.3 | testis (2), epididymis (2), prostate (2) |
| CRISP2 | 10.0 | 16.8 | testis* (3) |
| LIPI | 7.7 | 7.2 | |
| LDHC | 7.4 | 112.7 | |
| SERPINA6 | 7.0 | 3.6 | |
| CA4 | 5.3 | 3.4 | |
| HIST1H2BA | 4.2 | 8.3 | testis (3) |
| MPO[11] | 3.4 | 3.8 | |
| *↑ in NOA[a]* | | | |
| VAV2[12] | 0.04 | 0.4 | |
| TGM2[13] | 0.04 | 0.4 | |

TABLE 10-continued

Proteins at different abundances in NOA relative to Control seminal plasma according to spectral counting. Respective ratios from extracted ion current (XIC) intensities are also provided. Only up to top 10 proteins for each category are listed.

| Gene name | Control/NOA[a] Ratios SC[b] | XIC[c] | Protein Origin[d] |
|---|---|---|---|
| SPARC [14] | 0.05 | 0.2 | testis (2) |
| KIAA0368[15] | 0.05 | 0.2 | |
| EPS8L2[16] | 0.1 | 0.4 | |
| SPARCL1[17] | 0.1 | 0.4 | |
| COL6A2[18] | 0.2 | 0.3 | |
| DDX1[19] | 0.2 | 0.5 | |
| CST2[20] | 0.2 | 0.1 | |
| CST4[21] | 0.2 | 0.4 | |

[a]NOA—non-obstructive azoospermia
[b]SC—spectral counts. Fold changes may be overestimated especially in cases where only one out of three replicates contains spectral counts
[c]XIC— extracted ion current ratios. XICs were calculated using MaxQuant
[d]For protein origin to be annotated, the protein needed to be found in testis, epididymis or prostate in at least two out of four databases. The number in bracket indicates number of databases showing above average expression in the tissue.
*indicates restricted (UniGene) and exclusive (BioGPS) expression
[1]sorbitol dehydrogenase, 11 kDa protein, NCBI Gene ID 6652
[2]gamma-glutamyltransferase 7, isofrom 1, NCBI Gene ID 2686
[3]histone cluster 1, H4h, histone H4, NCBI Gene ID 8365
[4]dipeptidase 3, NCBI Gene ID 64180
[5]protein kinase, cAMP-dependent, catalytic, alpha, NCBI Gene ID 5566
[6]phosphoglycerate mutase 2 (muscle), NCBI Gene ID 5224
[7]solute carrier family 2 (facilitated glucose transporter), member 14, NCBI Gene ID 144195
[8]cadherin 2, type 1, N-cadherin (neuronal), NCBI Gene ID 1000
[9]asparaginase like 1, NCBI Gene ID 80150
[10]stomatin, NCBI Gene ID 2040
[11]myeloperoxidase, NCBI Gene ID 4353
[12]vav 2 guanine nucleotide exchange factor, NCBI Gene ID 7410
[13] transglutaminase 2 (C polypeptide, protein-glutamine-gamma-glutamyltransferase), NCBI Gene ID 7052
[14] secreted protein, acidic, cysteine-rich (osteonectin), NCBI Gene ID 6678
[15]ECM29 homolog, proteasome accessory protein; NCBI Gene ID 23392
[16]EPS8-like 2, NCBI Gene ID 64787
[17]SPARC-like 1 (hevin), NCBI Gene ID 8404
[18]collagen, type VI, alpha 2, NCBI Gene ID 1292
[19]DEAD (Asp-Glu-Ala-Asp) box polypeptide 1, NCBI Gene ID 1653
[20]cystatin SA, NCBI Gene ID 1470
[21]cystatin S, NCBI Gene ID 1472

TABLE 11

Proteins at different abundances in NOA relative to post-vasectomy (PV) seminal plasma according to spectral counting. Respective ratios from extracted ion current (XIC) intensities are also provided. Only up to top 10 proteins for each category are listed.

| Gene name | NOA[a]/PV[b] ratios SC[c] | XIC[d] | Protein Origin[e] |
|---|---|---|---|
| *Unique to PV[b]* | | | |
| HIST1H4H | PV>>NOA | 0.02 | |
| ELA2 | PV>>NOA | 0.01 | |
| MMP9[1] | PV>>NOA | 0.002 | |
| CORO1A[2] | PV>>NOA | 0.01 | |
| SAA2[3]; SAA1[4] | PV>>NOA | 0.02 | |
| *Unique to NOA[a]* | | | |
| LDHC | PV<<NOA | 55.2 | testis* (2) |
| BSPH1 | PV<<NOA | 761.2 | |
| ADAM7 | PV<<NOA | 56.9 | testis* (2) |
| MFGE8 | PV<<NOA | 10.0 | |
| REG3G | PV<<NOA | 7.4 | |
| MFAP4 | PV<<NOA | 18.6 | |
| AKAP4 | PV<<NOA | 18.2 | testis* (3) |
| SORD | PV<<NOA | PV<<NOA | |
| ↑in NOA[a] | | | |
| MUC5B | 83.0 | 50.2 | |
| CPVL | 20.0 | 3.9 | |
| CRIM2 | 16.0 | 6.4 | |
| SLC2A5 | 14.4 | 2.3 | |
| ELSPBP1 | 13.5 | 11.4 | testis* (3) |
| PATE4 | 13.0 | 112.6 | prostate* (3) |
| LOC642103 | 12.6 | 7.5 | |
| SPINT3 | 12.0 | 11.8 | testis* (3) |
| COL18A1 | 9.6 | 4.6 | |
| BGN | 9.0 | 3.5 | |
| ↓in NOA[a] | | | |
| HIST1H2BL | 0.04 | 0.06 | |
| FGG | 0.05 | 0.2 | |
| AZU1 | 0.07 | 0.005 | |
| MPO | 0.07 | 0.07 | |
| GSTM2 | 0.07 | 0.5 | |
| PRELP | 0.1 | 0.5 | |
| ORM1 | 0.2 | 0.1 | |
| FLJ11151 | 0.2 | 0.5 | |
| FGB | 0.3 | 0.1 | |
| PAEP | 0.5 | 0.5 | |

[a]NOA—non-obstructive azoospermia
[b]PV—post-vasectomy
[c]Fold changes may be overestimated especially in cases where only one out of three replicates contains spectral counts
[d]XIC—extracted ion current ratios. XICs were calculated using MaxQuant
[e]For protein origin to be annotated, the protein needed to be found in testis, epididymis or prostate in at least two out of four databases. The number in bracket indicates number of databases showing above average expression in the tissue.
*indicates restricted (UniGene) and exclusive (BioGPS) expression
[1]matrix metallopeptidase 9, NCBI Gene ID 4318
[2]coronin, actin binding protein, 1 A, NCBI Gene ID 11151
[3]serum amyloid A2, NCBI Gene ID 6289
[4]serum amyloid A1, NCBI Gene ID 6288

TABLE 12

Absolute concentration of 20 proteins in 148 seminal plasma samples measured with a 40-peptide stable-isotope dilution SRM assay

| Protein | MW, kDa | Concentration in seminal plasma, median (IQR[1]), μg/mL | | | Median CV of SRM assay[2] |
|---|---|---|---|---|---|
| | | Normal (n = 53) | NOA (n = 34) | PV/OA (n = 61) | |
| ADAM7 | 85.7 | 2.3 (1.3-3.2) | 0.99 (0.55-2.2) | 0.28 (0.16-0.53) | 2.7% |
| ALDH1A1 | 54.9 | 1.8 (1.0-6.6) | 0.67 (0.46-1.2) | 0.49 (0.27-1.2) | 1.4% |
| CA4 | 35.0 | 1.6 (0.7-4.0) | 0.72 (0.33-1.3) | 0.32 (0.16-0.56) | 1.1% |
| CAMP | 19.3 | 50 (27-88) | 25 (14-85) | 3 (1.1-9.7) | 0.5% |

TABLE 12-continued

Absolute concentration of 20 proteins in 148 seminal plasma samples measured with a 40-peptide stable-isotope dilution SRM assay

| Protein | MW, kDa | Concentration in seminal plasma, median (IQR[1]), µg/mL | | | Median CV of SRM assay[2] |
|---|---|---|---|---|---|
| | | Normal (n = 53) | NOA (n = 34) | PV/OA (n = 61) | |
| CD177 | 46.4 | 19 (3.7-43) | 17 (9.5-37) | 9.6 (4-34) | 7.7% |
| CEL | 79.3 | 1.1 (0.55-2.0) | 0.20 (0.12-0.48) | 0.091 (0.071-0.15) | 1.7% |
| CES7 | 63.9 | 1.2 (0.48-2.1) | 0.79 (0.34-1.7) | 0.068 (<0.04-0.15) | 2.8% |
| CRISP1 | 28.5 | 30 (20-47) | 26 (14-46) | 4 (2.5-7.7) | 1.4% |
| ECM1 | 60.7 | 41 (24-61) | 23 (14-80) | 1.24 (0.64-3.61) | 0.5% |
| FAM12B | 17.6 | 3.2 (2.0-6.0) | 1.6 (0.94-2.7) | 0.27 (0.13-0.48) | 0.8% |
| GPR64 | 112.0 | 6.3 (3.4-12) | 2.4 (1.4-6.4) | 1.4 (0.89-2.4) | 1.5% |
| KLK3 | 28.7 | 350 (220-500) | 560 (290-800) | 350 (240-700) | 0.6% |
| LDHC | 36.3 | 6.7 (2.3-100) | <0.09[3] | <0.09[3] | 0.7% |
| MGAM | 210.0 | 18 (7.5-43) | 7.1 (4.8-2.4) | 0.88 (0.33-4.74) | 1.2% |
| MUC15 | 36.3 | 1.4 (0.60-2.5) | 0.26 (0.13-0.73) | 0.071 (0.045-0.16) | 1.6% |
| NPC2 | 22.0 | 4.6 (3.5-7.9) | 5.0 (2.7-7.4) | 1.9 (1.3-3.6) | 0.9% |
| PTGDS | 21.0 | 9 (5.4-15) | 0.64 (0.38-2.1) | 0.18 (0.14-0.31) | 1.1% |
| SPAG11B | 11.4 | 0.35 (0.11-1.0) | 0.055 (0.012-0.11) | <0.01[3] | 1.1% |
| SPINT3 | 10.3 | 6 (3.6-12) | 3.9 (2.3-7.7) | 1.22 (0.84-1.7) | 1.4% |
| TEX101 | 26.7 | 1.7 (0.67-3.4) | <0.07[3] | <0.07[3] | 1.0% |

[1]interquartile range
[2]median CV of normal samples based on analysis of duplicates
[3]limit of quantification of protein calculated based on the limit of quantification of a synthetic peptide in the seminal plasma digest

TABLE 13

Groups of proteins for differential diagnosis of azoospermia based on absolute concentrations of proteins in seminal plasma samples

| Protein | Statistical significance of difference of groups[1] | ROC area[2] | % sensitivity at ≥95% specificity | Ratio of medians | Exclusive tissue specificity | Testis cell specificity |
|---|---|---|---|---|---|---|
| Normal vs PV/OA | | | | | | |
| LDHC | <0.001 | 1.00 | 100 | >74 | Testis | Sertoli, Leydig, germ |
| TEX101 | <0.001 | 1.00 | 100 | >25 | Testis | Sertoli, Leydig, germ |
| PTGDS | <0.001 | 1.00 | 100 | 51 | | Sertoli, Leydig, germ |
| ECM1 | <0.001 | 0.99 | 90 | 33 | | |
| MUC15 | <0.001 | 0.98 | 85 | 20 | Testis | Leydig |
| FAM12B | <0.001 | 0.97 | 84 | 12 | Testis | Leydig, germ |
| SPAG11B | <0.001 | 0.97 | 70 | >35 | Testis | Leydig |
| CEL | <0.001 | 0.97 | 90 | 12 | | |
| SPINT3 | <0.001 | 0.96 | 72 | 4.9 | Testis | Germ |
| CRISP1 | <0.001 | 0.96 | 74 | 7.3 | Testis | Leydig, Germ |
| ADAM7 | <0.001 | 0.95 | 66 | 8.3 | Testis | Leydig |
| CAMP | <0.001 | 0.95 | 80 | 17 | | Germ |
| CES7 | <0.001 | 0.93 | 67 | 17 | | |
| MGAM | <0.001 | 0.91 | 69 | 21 | | |
| GPR64 | <0.001 | 0.90 | 51 | 4.4 | Testis | Leydig |
| CA4 | <0.001 | 0.86 | 59 | 5.0 | | |
| NPC2 | <0.001 | 0.84 | 36 | 2.4 | | Leydig |
| ALDH1A1 | <0.001 | 0.79 | 38 | 3.7 | | |
| Normal vs NOA | | | | | | |
| LDHC | <0.001 | 1.00 | 100 | >74 | Testis | Sertoli, Leydig, germ |
| TEX101 | <0.001 | 1.00 | 100 | >25 | Testis | Sertoli, Leydig, germ |
| PTGDS | <0.001 | 0.92 | 71 | 14 | | Sertoli, Leydig, germ |
| CEL | <0.001 | 0.86 | 41 | 5.4 | | |
| MUC15 | <0.001 | 0.85 | 50 | 5.5 | Testis | Leydig |
| SPAG11B | <0.001 | 0.84 | 29 | 6.4 | Testis | Leydig |
| ALDH1A1 | <0.01 | 0.75 | 24 | 2.7 | | |
| GPR64 | <0.01 | 0.73 | 26 | 2.7 | Testis | Leydig |
| CA4 | <0.05 | 0.71 | 35 | 2.2 | | |
| ADAM7 | <0.05 | 0.70 | 15 | 2.3 | Testis | Leydig |

TABLE 13-continued

Groups of proteins for differential diagnosis of azoospermia based on absolute concentrations of proteins in seminal plasma samples

| Protein | Statistical significance of difference of groups[1] | ROC area[2] | % sensitivity at ≥95% specificity | Ratio of medians | Exclusive tissue specificity | Testis cell specificity |
|---|---|---|---|---|---|---|
| NOA vs PV/OA | | | | | | |
| ECM1 | <0.001 | 0.96 | 87 | 18 | | |
| CRISP1 | <0.001 | 0.91 | 62 | 6.5 | Testis | Leydig, germ |
| FAM12B | <0.001 | 0.90 | 33 | 6.1 | Testis | Leydig, germ |
| SPINT3 | <0.001 | 0.89 | 31 | 3.2 | Testis | Germ |
| CAMP | <0.001 | 0.88 | 70 | 8.3 | | Germ |
| PTGDS | <0.001 | 0.87 | 21 | 3.6 | | Sertoli, Leydig, germ |
| CES7 | <0.001 | 0.87 | 21 | 12 | | |
| ADAM7 | <0.001 | 0.84 | 33 | 3.5 | Testis | Leydig |
| MGAM | <0.001 | 0.84 | 62 | 8.1 | | |
| SPAG11B | <0.001 | 0.81 | 48 | 6.7 | Testis | Leydig |
| MUC15 | <0.001 | 0.80 | 44 | 3.7 | Testis | Leydig |
| CEL | <0.01 | 0.78 | 7 | 2.2 | | |
| NPC2 | <0.001 | 0.78 | 15 | 2.6 | | Leydig |
| CA4 | <0.01 | 0.72 | 33 | 2.3 | | |
| GPR64 | <0.01 | 0.69 | 8 | 1.7 | Testis | Leydig |

[1]nonparametric one-way ANOVA Kruskal-Wallis test followed by Dunn's multiple- comparisons test for differences between three groups
[2]area under receiver operating characteristic curve Below are full citations for publications mentioned herein.
1. Pilch, B.; Mann, M. Large-scale and high-confidence proteomic analysis of human seminal plasma. *Genome Biol.* 2006, 7 (5), R40
2. Robert, M.; Gagnon, C. Sperm motility inhibitor from human seminal plasma: presence of a precursor molecule in seminal vesicle fluid and its molecular processing after ejaculation. *Int. J. Androl* 1994, 17 (5), 232-240.
3. Edwards, J. J.; Tollaksen, S. L.; Anderson, N. G. Proteins of human semen. I. Two-dimensional mapping of human seminal fluid. *Clin. Chem.* 1981, 27 (8), 1335-1340.
4. Martinez-Heredia, J.; de Mateo, S.; Vidal-Taboada, J. M.; Ballesca, J. L.; Oliva, R. Identification of proteomic differences in asthenozoospermic sperm samples. *Hum. Reprod.* 2008, 23 (4), 783-791.
5. Fung, K. Y.; Glode, L. M.; Green, S.; Duncan, M. W. A comprehensive characterization of the peptide and protein constituents of human seminal fluid. *Prostate* 2004, 61 (2), 171-181.
6. Yamakawa, K.; Yoshida, K.; Nishikawa, H.; Kato, T.; Iwamoto, T. Comparative analysis of interindividual variations in the seminal plasma proteome of fertile men with identification of potential markers for azoospermia in infertile patients. *J Androl* 2007, 28 (6), 858-865.
7. Wang, J.; Wang, J.; Zhang, H. R.; Shi, H. J.; Ma, D.; Zhao, H. X.; Lin, B.; Li, R. S. Proteomic analysis of seminal plasma from asthenozoospermia patients reveals proteins that affect oxidative stress responses and semen quality. *Asian J Androl* 2009, 11 (4), 484-491.
8. Lilja, H.; Oldbring, J.; Rannevik, G.; Laurell, C. B. Seminal vesicle-secreted proteins and their reactions during gelation and liquefaction of human semen. *J. Clin. Invest* 1987, 80 (2), 281-285.
9. Searle, B. C.; Turner, M.; Nesvizhskii, A. I. Improving sensitivity by probabilistically combining results from multiple MS/MS search methodologies. *J. Proteome. Res.* 2008, 7 (1), 245-253.
10. Elias, J. E.; Gygi, S. P. Target-decoy search strategy for increased confidence in large-scale protein identifications by mass spectrometry. *Nat. Methods* 2007, 4 (3), 207-214.
11. Choi, H.; Nesvizhskii, A. I. False discovery rates and related statistical concepts in mass spectrometry-based proteomics. *J. Proteome. Res.* 2008, 7 (1), 47-50.
12. Sardana, G.; Jung, K.; Stephan, C.; Diamandis, E. P. Proteomic analysis of conditioned media from the PC3, LNCaP, and 22Rv1 prostate disease cell lines: discovery and validation of candidate prostate disease biomarkers. *J. Proteome. Res.* 2008, 7 (8), 3329-3338.
13. Poliakov, A.; Spilman, M.; Dokland, T.; Amling, C. L.; Mobley, J. A. Structural heterogeneity and protein composition of exosome-like vesicles (prostasomes) in human semen. *Prostate* 2009, 69 (2), 159-167.
14. Thimon, V.; Frenette, G.; Saez, F.; Thabet, M.; Sullivan, R. Protein composition of human epididymosomes collected during surgical vasectomy reversal: a proteomic and genomic approach. *Hum. Reprod.* 2008, 23 (8), 1698-1707.
15. Sullivan, R.; Frenette, G.; Girouard, J. Epididymosomes are involved in the acquisition of new sperm proteins during epididymal transit. *Asian J. Androl* 2007, 9 (4), 483-491.
16. Virji, N.; Naz, R. K. The role of lactate dehydrogenase-C4 in testicular function and infertility. *Int. J. Androl* 1995, 18 (1), 1-7.
17. Odet, F.; Duan, C.; Willis, W. D.; Goulding, E. H.; Kung, A.; Eddy, E. M.; Goldberg, E. Expression of the gene for mouse lactate dehydrogenase C (Ldhc) is required for male fertility. *Biol. Reprod.* 2008, 79 (1), 26-34.
18. Sawane, M. V.; Kaore, S. B.; Gaikwad, R. D.; Patil, P. M.; Patankar, S. S.; Deshkar, A. M. Seminal LDH-C4 isoenzyme and sperm mitochondrial activity: a study in male partners of infertile couples. *Indian J. Med. Sci.* 2002, 56 (11), 560-566.
19. Takayama, T.; Mishima, T.; Mori, M.; Jin, H.; Tsukamoto, H.; Takahashi, K.; Takizawa, T.; Kinoshita, K.; Suzuki, M.; Sato, I.; Matsubara, S.; Araki, Y.; Takizawa, T. Sexually dimorphic expression of the novel germ cell antigen TEX101 during mouse gonad development. *Biol. Reprod.* 2005a, 72 (6), 1315-1323.

20. Takayama, T.; Mishima, T.; Mori, M.; Ishikawa, T.; Takizawa, T.; Goto, T.; Suzuki, M.; Araki, Y.; Matsubara, S.; Takizawa, T. TEX101 is shed from the surface of sperm located in the caput epididymidis of the mouse. *Zygote.* 2005b, 13 (4), 325-333.
21. Yoshitake, H.; Shirai, Y.; Mochizuki, Y.; Iwanari, H.; Tsubamoto, H.; Koyama, K.; Takamori, K.; Ogawa, H.; Hasegawa, A.; Kodama, T.; Hamakubo, T.; Araki, Y. Molecular diversity of TEX101, a marker glycoprotein for germ cells monitored with monoclonal antibodies: variety of the molecular characteristics according to subcellular localization within the mouse testis. *J. Reprod. Immunol.* 2008, 79 (1), 1-11.
22. Oh, J.; Woo, J. M.; Choi, E.; Kim, T.; Cho, B. N.; Park, Z. Y.; Kim, Y. C.; Kim, D. H.; Cho, C. Molecular, biochemical, and cellular characterization of epididymal ADAMs, ADAMs and ADAM28. *Biochem. Biophys. Res. Commun.* 2005, 331 (4), 1374-1383.
23. Yoshioka, H.; Geyer, C. B.; Hornecker, J. L.; Patel, K. T.; McCarrey, J. R. In vivo analysis of developmentally and evolutionarily dynamic protein-DNA interactions regulating transcription of the Pgk2 gene during mammalian spermatogenesis. *Mol. Cell. Biol.* 2007, 27 (22), 7871-7885.
24. Krisfalusi, M.; Miki, K.; Magyar, P. L.; O'Brien, D. A. Multiple glycolytic enzymes are tightly bound to the fibrous sheath of mouse spermatozoa. *Biol. Reprod.* 2006, 75 (2), 270-278.
25. Miki, K.; Qu, W.; Goulding, E. H.; Willis, W. D.; Bunch, D. O.; Strader, L. F.; Perreault, S. D.; Eddy, E. M.; O'Brien, D. A. Glyceraldehyde 3-phosphate dehydrogenase-S, a sperm-specific glycolytic enzyme, is required for sperm motility and male fertility. *Proc. Natl. Acad. Sci. U.S.A.* 2004, 101 (47), 16501-16506.
26. Miki, K.; Willis, W. D.; Brown, P. R.; Goulding, E. H.; Fulcher, K. D.; Eddy, E. M. Targeted disruption of the Akap4 gene causes defects in sperm flagellum and motility. *Dev. Biol.* 2002, 248 (2), 331-342.
27. Zalensky, A. O.; Siino, J. S.; Gineitis, A. A.; Zalenskaya, I. A.; Tomilin, N. V.; Yau, P.; Bradbury, E. M. Human testis/sperm-specific histone H2B (hTSH2B). Molecular cloning and characterization. *J. Biol. Chem.* 2002, 277 (45), 43474-43480.
28. Gineitis, A. A.; Zalenskaya, I. A.; Yau, P. M.; Bradbury, E. M.; Zalensky, A. O. Human sperm telomere-binding complex involves histone H2B and secures telomere membrane attachment. *J. Cell Biol.* 2000, 151 (7), 1591-1598.
29. Wu, X.; Freeze, H. H. GLUT14, a duplicon of GLUT3, is specifically expressed in testis as alternative splice forms. *Genomics* 2002, 80 (6), 553-557.
30. Mandal, A.; Klotz, K. L.; Shetty, J.; Jayes, F. L.; Wolkowicz, M. J.; Bolling, L. C.; Coonrod, S. A.; Black, M. B.; Diekman, A. B.; Haystead, T. A.; Flickinger, C. J.; Herr, J. C. SLLP1, a unique, intra-acrosomal, non-bacteriolytic, c lysozyme-like protein of human spermatozoa. *Biol. Reprod.* 2003, 68 (5), 1525-1537.
31. Lin, Y. N.; Roy, A.; Yan, W.; Burns, K. H.; Matzuk, M. M. Loss of zona pellucida binding proteins in the acrosomal matrix disrupts acrosome biogenesis and sperm morphogenesis. *Mol. Cell. Biol.* 2007, 27 (19), 6794-6805.
32. Gaboriau, D.; Howes, E. A.; Clark, J.; Jones, R. Binding of sperm proacrosin/beta-acrosin to zona pellucida glycoproteins is sulfate and stereodependent. Synthesis of a novel fertilization inhibitor. *Dev. Biol.* 2007, 306 (2), 646-657.
33. Hoffhines, A. J.; Jen, C. H.; Leary, J. A.; Moore, K. L. Tyrosylprotein sulfotransferase-2 expression is required for sulfation of RNase 9 and Mfge8 in vivo. *J. Biol. Chem.* 2009, 284 (5), 3096-3105.
34. Sarkar, O.; Mathur, P. P.; Cheng, C. Y.; Mruk, D. D. Interleukin 1 alpha (IL1A) is a novel regulator of the blood-testis barrier in the rat. *Biol. Reprod.* 2008, 78 (3), 445-454.
35. Held, T.; Paprotta, I.; Khulan, J.; Hemmerlein, B.; Binder, L.; Wolf, S.; Schubert, S.; Meinhardt, A.; Engel, W.; Adham, I. M. Hspa4l-deficient mice display increased incidence of male infertility and hydronephrosis development. *Mol. Cell. Biol.* 2006, 26 (21), 8099-8108.
36. Rockett, J. C.; Patrizio, P.; Schmid, J. E.; Hecht, N. B.; Dix, D. J. Gene expression patterns associated with infertility in humans and rodent models. *Mutat. Res.* 2004, 549 (1-2), 225-240.
37. Nonoguchi, K.; Tokuchi, H.; Okuno, H.; Watanabe, H.; Egawa, H.; Saito, K.; Ogawa, O.; Fujita, J. Expression of Apg-1, a member of the Hsp110 family, in the human testis and sperm. *Int. J. Urol.* 2001, 8 (6), 308-314.
38. Kyriakides, T. R.; Zhu, Y. H.; Yang, Z.; Bornstein, P. The distribution of the matricellular protein thrombospondin 2 in tissues of embryonic and adult mice. *J. Histochem. Cytochem.* 1998, 46 (9), 1007-1015.
39. Igakura, T.; Kadomatsu, K.; Kaname, T.; Muramatsu, H.; Fan, Q. W.; Miyauchi, T.; Toyama, Y.; Kuno, N.; Yuasa, S.; Takahashi, M.; Senda, T.; Taguchi, O.; Yamamura, K.; Arimura, K.; Muramatsu, T. A null mutation in basigin, an immunoglobulin superfamily member, indicates its important roles in peri-implantation development and spermatogenesis. *Dev. Biol.* 1998, 194 (2), 152-165.
40. Saxena, D. K.; Oh-Oka, T.; Kadomatsu, K.; Muramatsu, T.; Toshimori, K. Behaviour of a sperm surface transmembrane glycoprotein basigin during epididymal maturation and its role in fertilization in mice. *Reproduction.* 2002, 123 (3), 435-444.
41. Diamandis, E. P.; Arnett, W. P.; Foussias, G.; Pappas, H.; Ghandi, S.; Melegos, D. N.; Mullen, B.; Yu, H.; Srigley, J.; Jarvi, K. Seminal plasma biochemical markers and their association with semen analysis findings. *Urology* 1999, 53 (3), 596-603.
42. Tokugawa, Y.; Kunishige, I.; Kubota, Y.; Shimoya, K.; Nobunaga, T.; Kimura, T.; Saji, F.; Murata, Y.; Eguchi, N.; Oda, H.; Urade, Y.; Hayaishi, O. Lipocalin-type prostaglandin D synthase in human male reproductive organs and seminal plasma. *Biol. Reprod.* 1998, 58 (2), 600-607.
43. Heshmat, S. M.; Mullen, J. B.; Jarvi, K. A.; Soosaipillai, A.; Diamandis, E. P.; Hamilton, R. J.; Lo, K. C. Seminal plasma lipocalin-type prostaglandin D synthase: a potential new marker for the diagnosis of obstructive azoospermia. *J. Urol.* 2008, 179 (3), 1077-1080.
44. Birkenmeier, G.; Usbeck, E.; Schafer, A.; Otto, A.; Glander, H. J. Prostate-specific antigen triggers transformation of seminal alpha2-macroglobulin (alpha2-M) and its binding to alpha2-macroglobulin receptor/low-density lipoprotein receptor-related protein (alpha2-M-R/LRP) on human spermatozoa. *Prostate* 1998, 36 (4), 219-225.
45. Glander, H. J.; Kratzsch, J.; Weisbrich, C.; Birkenmeier, G. Insulin-like growth factor-I and alpha 2-macroglobulin in seminal plasma correlate with semen quality. *Hum. Reprod.* 1996, 11 (11), 2454-2460.

46. Legare, C.; Thabet, M.; Gatti, J. L.; Sullivan, R. HE1/NPC2 status in human reproductive tract and ejaculated spermatozoa: consequence of vasectomy. *Mol. Hum. Reprod.* 2006, 12 (7), 461-468.

47. Sahin, E.; Petrunkina, A. M.; Ekhlasi-Hundrieser, M.; Hettel, C.; Waberski, D.; Harrison, R. A.; Topfer-Petersen, E. Fibronectin type II-module proteins in the bovine genital tract and their putative role in cell volume control during sperm maturation. *Reprod. Fertil. Dev.* 2009, 21 (3), 479-488.

48. Ekhlasi-Hundrieser, M.; Schafer, B.; Philipp, U.; Kuiper, H.; Leeb, T.; Mehta, M.; Kirchhoff, C.; Topfer-Petersen, E. Sperm-binding fibronectin type II-module proteins are genetically linked and functionally related. *Gene* 2007, 392 (1-2), 253-265.

49. Osterhoff, C.; Ivell, R.; Kirchhoff, C. Cloning of a human epididymis-specific mRNA, HE6, encoding a novel member of the seven transmembrane-domain receptor superfamily. *DNA Cell Biol.* 1997, 16 (4), 379-389.

50. Davies, B.; Baumann, C.; Kirchhoff, C.; Ivell, R.; Nubbemeyer, R.; Habenicht, U. F.; Theuring, F.; Gottwald, U. Targeted deletion of the epididymal receptor HE6 results in fluid dysregulation and male infertility. *Mol. Cell. Biol.* 2004, 24 (19), 8642-8648.

51. Gibbs, G. M.; O'Bryan, M. K. Cysteine rich secretory proteins in reproduction and venom. *Soc. Reprod. Fertil. Suppl* 2007, 65 261-267.

52. Da Ros, V. G.; Maldera, J. A.; Willis, W. D.; Cohen, D. J.; Goulding, E. H.; Gelman, D. M.; Rubinstein, M.; Eddy, E. M.; Cuasnicu, P. S. Impaired sperm fertilizing ability in mice lacking Cysteine-RIch Secretory Protein 1 (CRISP1). *Dev. Biol.* 2008, 320 (1), 12-18.

53. Cohen, D. J.; Da Ros, V. G.; Busso, D.; Ellerman, D. A.; Maldera, J. A.; Goldweic, N.; Cuasnicu, P. S. Participation of epididymal cysteine-rich secretory proteins in sperm-egg fusion and their potential use for male fertility regulation. *Asian J. Androl* 2007, 9 (4), 528-532.

54. Cohen, D. J.; Rochwerger, L.; Ellerman, D. A.; Morgenfeld, M. M.; Busso, D.; Cuasnicu, P. S. Relationship between the association of rat epididymal protein "DE" with spermatozoa and the behavior and function of the protein. *Mol. Reprod. Dev.* 2000, 56 (2), 180-188.

55. Jamsai, D.; Reilly, A.; Smith, S. J.; Gibbs, G. M.; Baker, H. W.; McLachlan, R. I.; de Kretser, D. M.; O'Bryan, M. K. Polymorphisms in the human cysteine-rich secretory protein 2 (CRISP2) gene in Australian men. *Hum. Reprod.* 2008, 23 (9), 2151-2159.

56. Busso, D.; Cohen, D. J.; Hayashi, M.; Kasahara, M.; Cuasnicu, P. S. Human testicular protein TPX1/CRISP-2: localization in spermatozoa, fate after capacitation and relevance for gamete interaction. *Mol. Hum. Reprod.* 2005, 11 (4), 299-305.

57. Thimon, V.; Calvo, E.; Koukoui, O.; Legare, C.; Sullivan, R. Effects of vasectomy on gene expression profiling along the human epididymis. *Biol. Reprod.* 2008, 79 (2), 262-273.

58. Picotti, P.; Rinner, O.; Stallmach, R.; Dautel, F.; Farrah, T.; Domon, B.; Wenschuh, H.; Aebersold, R., High-throughput generation of selected reaction-monitoring assays for proteins and proteomes. *Nat Meth* 2009, 7, (1), 43-46.

59. Kiyonami, R.; Schoen, A.; Prakash, A.; Peterman, S.; Zabrouskov, V.; Picotti, P.; Aebersold, R.; Huhmer, A.; Domon, B., Increased selectivity, analytical precision, and throughput in targeted proteomics. *Mol Cell Proteomics* 2010, (2), M110 002931.

60. Wang, T. J.; Rittenhouse, H. G.; Wolfert, R. L.; Lynne, C. M.; Brackett, N. L., PSA concentrations in seminal plasma. *Clin Chem* 1998, 44, (4), 895-6.

61. Craig, R.; Cortens, J. P.; Beavis, R. C., Open source system for analyzing, validating, and storing protein identification data. *J Proteome Res* 2004, 3, (6), 1234-42.

62. Deutsch, E. W.; Lam, H.; Aebersold, R., PeptideAtlas: a resource for target selection for emerging targeted proteomics workflows. *EMBO Rep* 2008, 9, (5), 429-34.

63. Yin, L.; Chung, C. M.; Huo, R.; Liu, H.; Zhou, C.; Xu, W.; Zhu, H.; Zhang, J.; Shi, Q.; Wong, H. Y.; Chen, J.; Lu, Y.; Bi, Y.; Zhao, C.; Du, Y.; Ma, M.; Cai, Y.; Chen, W. Y.; Fok, K. L.; Tsang, L. L.; Li, K.; Ni, Y.; Chung, Y. W.; Zhou, Z.; Sha, J.; Chan, H. C., A sperm GPI-anchored protein elicits sperm-cumulus cross-talk leading to the acrosome reaction. *Cell Mol Life Sci* 2009, 66, (5), 900-8.

64. Goldberg, E.; Eddy, E. M.; Duan, C.; Odet, F., LDHC: the ultimate testis-specific gene. *J Androl* 2010, 31, (1), 86-94.

65. Urade, Y.; Hayaishi, O., Biochemical, structural, genetic, physiological, and pathophysiological features of lipocalin-type prostaglandin D synthase. *Biochim Biophys Acta* 2000, 1482, (1-2), 259-71.

66. Eguchi, Y.; Eguchi, N.; Oda, H.; Seiki, K.; Kijima, Y.; Matsu-ura, Y.; Urade, Y.; Hayaishi, O., Expression of lipocalin-type prostaglandin D synthase (beta-trace) in human heart and its accumulation in the coronary circulation of angina patients. *Proc Natl Acad Sci USA* 1997, 94, (26), 14689-94.

67. Leone, M. G.; Abdel, H. H.; Gennaro, G.; Amici, S.; Conte, D.; Romanelli, F.; Latini, M.; Isidori, A.; Saso, L.; Silvestrini, B., Changes of lipocalin type prostaglandin D-synthase in the seminal plasma of subfertile man. *Res Commun Mol Pathol Pharmacol* 2001, 110, (1-2), 17-25.

68. Huang, J.; Che, M. I.; Huang, Y. T.; Shyu, M. K.; Huang, Y. M.; Wu, Y. M.; Lin, W. C.; Huang, P. H.; Liang, J. T.; Lee, P. H.; Huang, M. C., Overexpression of MUC15 activates extracellular signal-regulated kinase 1/2 and promotes the oncogenic potential of human colon cancer cells. *Carcinogenesis* 2009, 30, (8), 1452-8.

69. von Horsten, H. H.; Derr, P.; Kirchhoff, C., Novel antimicrobial peptide of human epididymal duct origin. *Biol Reprod* 2002, 67, (3), 804-13.

70. Avellar, M. C.; Honda, L.; Hamil, K. G.; Yenugu, S.; Grossman, G.; Petrusz, P.; French, F. S.; Hall, S. H., Differential expression and antibacterial activity of epididymis protein 2 isoforms in the male reproductive tract of human and rhesus monkey (Macaca mulatta). *Biol Reprod* 2004, 71, (5), 1453-60.

71. Kirchhoff, C.; Pera, I.; Rust, W.; Ivell, R., Major human epididymis-specific gene product, HE3, is the first representative of a novel gene family. *Mol Reprod Dev* 1994, 37, (2), 130-7.

72. Lasserre, A.; Barrozo, R.; Tezon, J. G.; Miranda, P. V.; Vazquez-Levin, M. H., Human epididymal proteins and sperm function during fertilization: un update. *Biol Res* 2001, 34, (3-4), 165-78.

73. Dube, E.; Hermo, L.; Chan, P. T.; Cyr, D. G., Alterations in gene expression in the caput epididymides of nonobstructive azoospermic men. *Biol Reprod* 2008, 78, (2), 342-51.

74. Oh, J. S.; Han, C.; Cho, C., ADAM7 is associated with epididymosomes and integrated into sperm plasma membrane. *Mol Cells* 2009, 28, (5), 441-6.

75. Cornwall, G. A.; Hsia, N., ADAM7, a member of the ADAM (a disintegrin and metalloprotease) gene family is specifically expressed in the mouse anterior pituitary and epididymis. *Endocrinology* 1997, 138, (10), 4262-72.

76. Li, J. Y.; Wang, H. Y.; Liu, J.; Liu, Q.; Zhang, J. S.; Wan, F. C.; Liu, F. J.; Jin, S. H.; Zhang, Y. L., Transcriptome analysis of a cDNA library from adult human epididymis. *DNA Res* 2008, 15, (3), 115-22.

77. Ota, T.; et al, Complete sequencing and characterization of 21,243 full-length human cDNAs. *Nat Genet.* 2004, 36, (1), 40-5.

78. Levitin, F.; Weiss, M.; Hahn, Y.; Stern, O.; Papke, R. L.; Matusik, R.; Nandana, S. R.; Ziv, R.; Pichinuk, E.; Salame, S.; Bera, T.; Vincent, J.; Lee, B.; Pastan, I.; Wreschner, D. H., PATE gene clusters code for multiple, secreted TFP/Ly-6/uPAR proteins that are expressed in reproductive and neuron-rich tissues and possess neuromodulatory activity. *J Biol Chem* 2008, 283, (24), 16928-39.

79. Uhlen, M.; Oksvold, P.; Fagerberg, L.; Lundberg, E.; Jonasson, K.; Forsberg, M.; Zwahlen, M.; Kampf, C.; Wester, K.; Hober, S.; Wernerus, H.; Bjorling, L.; Ponten, F., Towards a knowledge-based Human Protein Atlas. *Nat. Biotechnol* 2010, 28, (12), 1248-50.

80. 99. Nickel, J. C., Downey, J., Hunter, D., Clark, J., Prevalence of prostatitis-like symptoms in a population based study using the National Institutes of Health chronic prostatitis symptom index. *J. Urol.* 2001, 165, 842-845.

81. Christopoulos, T. K., Diamandis, E. P., Enzymatically amplified time-resolved fluorescence immunoassay with terbium chelates. *Anal. Chem.* 1992, 64, 342-346.

82. Mitchell, P., Proteomics retrenches. *Nat. Biotechnol.* 2010, 28, 665-670.

83. Liu, H., Sadygov, R. G., Yates, J. R. III., A model for random sampling and estimation of relative protein abundance in shotgun proteomics. *Anal. Chem.* 2004, 76, 4193-4201.

84. Dickinson, D. P., Thiesse, M., Hicks, M. J., Expression of type 2 cystatin genes CST1-CST5 in adult human tissues and the developing submandibular gland. *DNA Cell. Biol.* 2002, 21, 47-65.

85. Redl, B., Human tear lipocalin. *Biochim. Biophys. Acta* 2000, 1482, 241-248.

86. Li, Y., Friel, P. J., McLean, D. J., Griswold, M. D., Cystatin E1 and E2, new members of male reproductive tract subgroup within cystatin type 2 family. *Biol. Reprod.* 2003, 69, 489-500.

87. Ryu, O. H., Atkinson, J. C., Hoehn, G. T., Illei, G. G., Hart, T. C., Identification of parotid salivary biomarkers in Sjogren's syndrome by surface-enhanced laser desorption/ionization time-of-flight mass spectrometry and two-dimensional difference gel electrophoresis. *Rheumatology (Oxford)* 2006, 45, 1077-1086.

88. Zeeuwen, P. L., Vlijmen-Willems, I. M., Egami, H., Schalkwijk, J., Cystatin M/E expression in inflammatory and neoplastic skin disorders. *Br. J. Dermatol.* 2002, 147, 87-94.

89. Kato, T., Imatani, T., Minaguchi, K., Saitoh, E., Okuda, K., Salivary cystatins induce interleukin-6 expression via cell surface molecules in human gingival fibroblasts. *Mol. Immunol.* 2002, 39, 423-430.

90. Wojnar, P., van't H of, W., Merschak, P., Lechner, M., Redl, B., The N-terminal part of recombinant human tear lipocalin/von Ebner's gland protein confers cysteine proteinase inhibition depending on the presence of the entire cystatin-like sequence motifs. *Biol. Chem.* 2001, 382, 1515-1520.

91. Dhundee, J., Maciver, A. G., An immunohistological study of granulomatous prostatitis. *Histopathology* 1991, 18, 435-441.

92. Shinozaki, S., Nakamura, T., Iimura, M., Kato, Y., et al., Upregulation of Reg 1alpha and GW112 in the epithelium of inflamed colonic mucosa. *Gut.* 2001, 48, 623-629.

93. Chin, K. L., Aerbajinai, W., Zhu, J., Drew, L., et al., The regulation of OLFM4 expression in myeloid precursor cells relies on NF-kappaB transcription factor. *Br. J. Haematol.* 2008, 143, 421-432.

94. Pang, W. W., Abdul-Rahman, P. S., Wan-Ibrahim, W. I., Hashim, O. H., Can the acute-phase reactant proteins be used as cancer biomarkers? *Int. J. Biol. Markers* 2010, 25, 1-11.

95. Dunkelberger, J. R., Song, W. C., Complement and its role in innate and adaptive immune responses. *Cell Res.* 2010, 20, 34-50.

96. Sakata, A., Ochiai, T., Shimeno, H., Hikishima, S., et al., Acid sphingomyelinase inhibition suppresses lipopolysaccharide-mediated release of inflammatory cytokines from macrophages and protects against disease pathology in dextran sulphate sodium-induced colitis in mice. *Immunology* 2007, 122, 54-64.

97. Watanabe, H., Okada, G., Ohtsubo, K., Yamaguchi, Y., et al., Expression of mesothelin mRNA in pure pancreatic juice from patients with pancreatic carcinoma, intraductal papillary mucinous neoplasm of the pancreas, and chronic pancreatitis. *Pancreas* 2005, 30, 349-354.

98. Ludwig, M., Kummel, C., Schroeder-Printzen, I., Ringert, R. H., Weidner, W., Evaluation of seminal plasma parameters in patients with chronic prostatitis or leukocytospermia. *Andrologia* 1998, 30, Suppl 1:41-47.

99. Everaert, K., Delanghe, J., Vanderkelen, M., Cornelis, K., et al., Urinary plasma protein patterns in acute prostatitis. *Clin. Chem. Lab. Med.* 2003, 41, 79-84.

100. Doble, A., Walker, M. M., Harris, J. R., Taylor-Robinson, D., Witherow, R. O., Intraprostatic antibody deposition in chronic abacterial prostatitis. *Br. J. Urol.* 1990, 65, 598-605.

101. Gao, F., Koenitzer, J. R., Tobolewski, J. M., Jiang, D., et al., Extracellular superoxide dismutase inhibits inflammation by preventing oxidative fragmentation of hyaluronan. *J. Biol. Chem.* 2008, 283, 6058-6066.

102. Williams, K., Frayne, J., McLaughlin, E. A., Hall, L., Expression of extracellular superoxide dismutase in the human male reproductive tract, detected using antisera raised against a recombinant protein. *Mol. Hum. Reprod.* 1998, 4, 235-242.

103. Ali, M., Nasosinus mucin expression in normal and inflammatory conditions. *Curr. Opin Allergy Clin. Immunol.* 2009, 9, 10-15.

104. Viswanathan, H., Brownlee, I. A., Pearson, J. P., Carrie, S., MUC5B secretion is up-regulated in sinusitis compared with controls. *Am. Rhinol.* 2006, 20, 554-557.

105. Kanters, E., van Rijssel, J., Hensbergen, P. J., Hondius, D., et al., Filamin B mediates ICAM-1-driven leukocyte transendothelial migration. *J. Biol. Chem.* 2008, 283, 31830-31839.

106. Maillard, M., Cadot, B., Ball, R. Y., Sethia, K., et al., Differential expression of the ccn3 (nov) proto-oncogene in human prostate cell lines and tissues. *Mol. Pathol.* 2001, 54, 275-280.

107. Cho-Vega, J. H., Tsavachidis, S., Do, K. A., Nakagawa, J., et al., Dicarbonyl/L-xylulose reductase: a potential biomarker identified by laser-capture microdissection-micro serial analysis of gene expression of human prostate adenocarcinoma. *Cancer Epidemiol. Biomarkers Prev.* 2007, 16, 15-2622.

108. Cox, J.; Mann, M. MaxQuant enables high peptide identification rates, individualized p.p.b.-range mass accuracies and proteome-wide protein quantification. *Nat. Biotechnol.* 2008, 26 (12), 1367-1372.

109. Cox, J.; Neuhauser, N.; Michalski, A.; Scheltema, R. A.; Olsen, J. V.; Mann, M. Andromeda: A Peptide Search Engine Integrated into the MaxQuant Environment. *J. Proteome. Res.* 2011, 10(4), 1794-805

110. Baldi, E.; Luconi, M.; Bonaccorsi, L.; Forti, G. Signal transduction pathways in human spermatozoa. *J. Reprod. Immunol.* 2002, 53 (1-2), 121-131.

111. Duncan, M. W.; Aebersold, R.; Caprioli, R. M. The pros and cons of peptide-centric proteomics. *Nat. Biotechnol.* 2010, 28 (7), 659-664.

112. Mallick, P.; Kuster, B. Proteomics: a pragmatic perspective. *Nat. Biotechnol.* 2010, 28 (7), 695-709.

113. Bush, L. A.; Herr, J. C.; Wolkowicz, M.; Sherman, N. E.; Shore, A.; Flickinger, C. J. A novel asparaginase-like protein is a sperm autoantigen in rats. *Mol. Reprod. Dev.* 2002, 62 (2), 233-247.

114. Wilson, M. J.; Bowles, J.; Koopman, P. The matricellular protein SPARC is internalized in Sertoli, Leydig, and germ cells during testis differentiation. *Reprod. Dev.* 2006, 73 (5), 531-539.

115. Howe, C. C.; Overton, G. C.; Sawicki, J.; Solter, D.; Stein, P.; Strickland, S. Expression of SPARC/osteonectin transcript in murine embryos and gonads. *Differentiation* 1988, 37 (1), 20-25.

116. Vernon, R. B.; Sage, H. The calcium-binding protein SPARC is secreted by Leydig and Sertoli cells of the adult mouse testis. *Biol. Reprod.* 1989, 40 (6), 1329-1340.

117. Cheng, C. Y.; Grima, J.; Stahler, M. S.; Guglielmotti, A.; Silvestrini, B.; Bardin, C. W. Sertoli cell synthesizes and secretes a protease inhibitor, alpha 2-macroglobulin. *Biochemistry* 1990, 29 (4), 1063-1068.

118. Feig, C.; Kirchhoff, C.; Ivell, R.; Naether, O.; Schulze, W.; Spiess, A. N. A new paradigm for profiling testicular gene expression during normal and disturbed human spermatogenesis. *Mol. Hum. Reprod.* 2007, 13 (1), 33-43.

119. Fox, M. S.; Ares, V. X.; Turek, P. J.; Haqq, C.; Reijo Pera, R. A. Feasibility of global gene expression analysis in testicular biopsies from infertile men. *Mol. Reprod. Dev.* 2003, 66 (4), 403-421.

120. Okada, H.; Tajima, A.; Shichiri, K.; Tanaka, A.; Tanaka, K.; Inoue, I. Genome-wide expression of azoospermia testes demonstrates a specific profile and implicates ART3 in genetic susceptibility. *PLoS. Genet.* 2008, 4 (2), e26

121. Lu, S. C. Regulation of glutathione synthesis. *Curr. Top. Cell Regul.* 2000, 36 95-116.

122. Sies, H. Glutathione and its role in cellular functions. *Free Radic. Biol. Med.* 1999, 27 (9-10), 916-921.

123. Klys, H. S.; Whillis, D.; Howard, G.; Harrison, D. J. Glutathione S-transferase expression in the human testis and testicular germ cell neoplasia. *Br. J. Cancer* 1992, 66 (3), 589-593.

124. Kaneko, T.; Iuchi, Y.; Kobayashi, T.; Fujii, T.; Saito, H.; Kurachi, H.; Fujii, J. The expression of glutathione reductase in the male reproductive system of rats supports the enzymatic basis of glutathione function in spermatogenesis. *Eur. J. Biochem.* 2002, 269 (5), 1570-1578.

125. Cao, W.; Aghajanian, H. K.; Haig-Ladewig, L. A.; Gerton, G. L. Sorbitol can fuel mouse sperm motility and protein tyrosine phosphorylation via sorbitol dehydrogenase. *Biol. Reprod.* 2009, 80 (1), 124-133.

126. Frenette, G.; Lessard, C.; Sullivan, R. Polyol pathway along the bovine epididymis. *Mol. Reprod. Dev.* 2004, 69 (4), 448-456.

127. Szabo, Z.; Hamalainen, J.; Loikkanen, I.; Moilanen, A. M.; Hirvikoski, P.; Vaisanen, T.; Paavonen, T. K.; Vaarala, M. H. Sorbitol dehydrogenase expression is regulated by androgens in the human prostate. *Oncol. Rep.* 2010, 23 (5), 1233-1239.

128. Lefebvre, J.; Boileau, G.; Manjunath, P. Recombinant expression and affinity purification of a novel epididymal human sperm-binding protein, BSPH 1. *Mol. Hum. Reprod.* 2009, 15 (2), 105-114.

129. Lee, C. H.; Wu, C. C.; Wu, Y. N.; Chiang, H. S. Gene copy number variations in Asian patients with congenital bilateral absence of the vas deferens. *Hum. Reprod.* 2009, 24 (3), 748-755.

130. Lu, Q.; Gore, M.; Zhang, Q.; Camenisch, T.; Boast, S.; Casagranda, F.; Lai, C.; Skinner, M. K.; Klein, R.; Matsushima, G. K.; Earp, H. S.; Goff, S. P.; Lemke, G. Tyro-3 family receptors are essential regulators of mammalian spermatogenesis. *Nature* 1999, 398 (6729), 723-728.

131. Russell, L. D.; Clermont, Y. Degeneration of germ cells in normal, hypophysectomized and hormone treated hypophysectomized rats. *Anat. Rec.* 1977, 187 (3), 347-366.

132. Chemes, H. The phagocytic function of Sertoli cells: a morphological, biochemical, and endocrinological study of lysosomes and acid phosphatase localization in the rat testis. *Endocrinology* 1986, 119 (4), 1673-1681.

133. Pineau, C.; Le Magueresse, B.; Courtens, J. L.; Jegou, B. Study in vitro of the phagocytic function of Sertoli cells in the rat. *Cell Tissue Res.* 1991, 264 (3), 589-598.

134. Miething, A. Germ-cell death during prespermatogenesis in the testis of the golden hamster. *Cell Tissue Res.* 1992, 267 (3), 583-590.

135. Xiong, W.; Chen, Y.; Wang, F L; Wang, H.; Wu, H.; Lu, Q.; Han, D. Gas6 and the Tyro 3 receptor tyrosine kinase subfamily regulate the phagocytic function of Sertoli cells. *Reproduction.* 2008, 135 (1), 77-87.

136. Foell, J. L.; Hesse, M.; Volkmer, I.; Schmiedel, B. J.; Neumann, I.; Staege, M. S. Membrane-associated phospholipase A1 beta (LIPI) Is an Ewing tumour-associated disease/testis antigen. *Pediatr. Blood Disease* 2008, 51 (2), 228-234.

137. VandeBerg, J. L.; Cooper, D. W.; Close, P. J. Mammalian testis phosphoglycerate kinase. *Nat. New Biol.* 1973, 243 (123), 48-50.

138. Nata, K.; Liu, Y.; Xu, L.; Ikeda, T.; Akiyama, T.; Noguchi, N.; Kawaguchi, S.; Yamauchi, A.; Takahashi, I.; Shervani, N. J.; Onogawa, T.; Takasawa, S.; Okamoto, H. Molecular cloning, expression and chromosomal localization of a novel human REG family gene, REG III. *Gene* 2004, 340 (1), 161-170.
139. Gonzalez-Fernandez, L.; Ortega-Ferrusola, C.; Macias-Garcia, B.; Salido, G. M.; Pena, F. J.; Tapia, J. A. Identification of protein tyrosine phosphatases and dual-specificity phosphatases in mammalian spermatozoa and their role in sperm motility and protein tyrosine phosphorylation. *Biol. Reprod.* 2009, 80 (6), 1239-1252.
140. Russo, C. L.; Spurr-Michaud, S.; Tisdale, A.; Pudney, J.; Anderson, D.; Gipson, I. K. Mucin gene expression in human male urogenital tract epithelia. *Hum. Reprod.* 2006, 21 (11), 2783-2793.
141. Kaunisto, K.; Fleming, R. E.; Kneer, J.; Sly, W. S.; Rajaniemi, H. Regional expression and androgen regulation of carbonic anhydrase IV and II in the adult rat epididymis. *Biol. Reprod.* 1999, 61 (6), 1521-1526.
142. Ekstedt, E.; Holm, L.; Ridderstrale, Y. Carbonic anhydrase in mouse testis and epididymis; transfer of isozyme IV to spermatozoa during passage. *J. Mol. Histol.* 2004, 35 (2), 167-173.
143. Zhang, L.; Liu, Q.; Zhou, Y.; Zhang, Y. Baculo-expression and enzymatic characterization of CES7 esterase. *Acta Biochim. Biophys. Sin.* (*Shanghai*) 2009, 41 (9), 731-736.
144. Cao, W.; Haig-Ladewig, L.; Gerton, G. L.; Moss, S. B. Adenylate kinases 1 and 2 are part of the accessory structures in the mouse sperm flagellum. *Biol. Reprod.* 2006, 75 (4), 492-500.
145. Bowles, J.; Feng, C. W.; Knight, D.; Smith, C. A.; Roeszler, K. N.; Bagheri-Fam, S.; Harley, V. R.; Sinclair, A. H.; Koopman, P. Male-specific expression of Aldh1a1 in mouse and chicken fetal testes: implications for retinoid balance in gonad development. *Dev. Dyn.* 2009, 238 (8), 2073-2080.
146. Basciani, S.; Mariani, S.; Arizzi, M.; Ulisse, S.; Rucci, N.; Jannini, E. A.; Della, R. C.; Manicone, A.; Carani, C.; Spera, G.; Gnessi, L. Expression of platelet-derived growth factor-A (PDGF-A), PDGF-B, and PDGF receptor-alpha and -beta during human testicular development and disease. *J. Clin. Endocrinol. Metab* 2002, 87 (5), 2310-2319.
147. Schiff, W. B. Quantitative determination of high molecular weight serum proteinase inhibitors in human semen. *Andrologia* 1976, 8 (4), 359-364.
148. Loveland, K.; Schlatt, S.; Sasaki, T.; Chu, M. L.; Timpl, R.; Dziadek, M. Developmental changes in the basement membrane of the normal and hypothyroid postnatal rat testis: segmental localization of fibulin-2 and fibronectin. *Biol. Reprod.* 1998, 58 (5), 1123-1130.
149. Piludu, M.; Cossu, M.; De Lisa, A.; Piras, M.; Lantini, M. S. Ultrastructural localization of glycodelin oligosaccharides Le-x and Le-y in human seminal vesicles by immunogold staining. *J. Anat.* 2007, 210 (3), 352-356.
150. Yeung, W. S.; Lee, K. F.; Koistinen, R.; Koistinen, H.; Seppala, M.; Ho, P. C.; Chiu, P. C. Roles of glycodelin in modulating sperm function. *Mol. Cell. Endocrinol.* 2006, 250 (1-2), 149-156.
151. Murphy, K.; Carvajal, L.; Medico, L.; Pepling, M. Expression of Stat3 in germ cells of developing and adult mouse ovaries and testes. *Gene Expr. Patterns.* 2005, 5 (4), 475-482.

What is claimed is:

1. A method for diagnosis of a urogenital condition in a subject comprising:
   (a) contacting a sample of seminal plasma from the subject with an antibody capable of detecting a urogenital marker ECM1 in the sample using an enzyme linked immunosorbent assay (ELISA); and
   (b) diagnosing the urogenital condition by detecting a change in the amount or status of the urogenital marker as compared to the amount or status of the same urogenital marker obtained from a control subject who does not suffer from the urogenital condition or a post-vasectomy subject,
   wherein the urogenital condition is non-obstructive azoospermia (NOA) or obstructive azoospermia (OA).

2. A method of claim 1 wherein the contacting step further comprises an antibody capable of detecting urogenital marker TEX101 and an antibody capable of detecting urogenital marker LDHC and the method differentiates NOA from OA.

3. A method of claim 1, wherein the contacting step further comprises at least one additional antibody, each antibody capable of detecting one of the urogenital markers PTGDS, CEL, MUC15, SPAG11B, ALDH1A1, GPR64, CA4 and ADAM7.

4. A method of claim 1, wherein the contacting step further comprises at least one additional antibody, each antibody capable of detecting one of the urogenital markers CRISP1, FAM12B, SPINT3, CAMP, PTGDS, CES7, ADAM7, MGAM, SPAG11B, MUC15, CEL, NPC2, CA4 and GPR64.

5. A method of claim 1, wherein the contacting step further comprises at least one additional antibody, each antibody capable of detecting one of the urogenital markers ADAM7, ALDH1A1, CA4, CAMP, CD177, CEL, CES7, CRISP1, FAM12B, GPR64, MGAM, MUC15, NPC2, PTGDS, SPAG11B and SPINT3.

6. A method of claim 1, wherein the contacting step further comprises an antibody capable of detecting the urogenital marker TEX101.

7. A method of claim 1, wherein the contacting step further comprises an antibody capable of detecting the urogenital marker LDHC.

8. A method for diagnosing non-obstructive azoospermia (NOA) or obstructive azoospermia (OA) in a male subject, the method comprising:
analyzing, in vitro, the level of expression of ECM1 in a sample from a human subject in an enzyme-linked immunosorbent assay;
and correlating a diagnosis of NOA or OA with a change in the level of expression of ECM1 in the sample relative to a level of expression of ECM1 in a control subject who does not suffer from NOA or a post-vasectomy subject.

9. A method of claim 8, further comprising:
analyzing the level of expression of TEX101 in the sample and correlating a diagnosis of NOA or OA with a change in the level of expression each of TEX101 and ECM1 in the sample relative to a level of expression each of TEX101 and ECM1 in the control subject.

10. A method for diagnosis of a urogenital condition in a male subject, wherein the urogenital condition is characterized by the presence of ECM1 biomarker comprising:
   (a) obtaining a biological sample from the subject;
   (b) applying an antibody specific for ECM1 to the sample, wherein the presence of ECM1 biomarker creates an antibody-ECM1 biomarker complex;
   (c) applying a detection agent that detects the antibody-ECM1 biomarker complex; and
   (d) diagnosing the urogenital condition by detecting a change in the amount of antibody-ECM1 biomarker complex as compared to the amount of antibody-ECM1 biomarker complex in a sample obtained from a control subject who does not suffer from the urogenital condition or a post-vasectomy subject,
   wherein the urogenital condition is non-obstructive azoospermia (NOA) or obstructive azoospermia (OA).

11. A method of claim 10, further comprising:
applying an antibody specific for TEX101 to the sample, wherein the presence of TEX101 biomarker creates an antibody-TEX101 biomarker complex;
applying a second detection agent that detects the antibody-TEX101 biomarker complex; and
diagnosing the urogenital condition by detecting a change in the amount of antibody-TEX101 biomarker complex as compared to the amount of antibody-TEX101 biomarker complex in the control sample and a change in the amount of antibody-ECM1 biomarker complex as compared to the amount of antibody-ECM1 biomarker complex in the control sample.

* * * * *